(12) United States Patent
Rasmussen

(10) Patent No.: US 8,168,381 B2
(45) Date of Patent: May 1, 2012

(54) TEMPLATE DIRECTED SPLIT AND MIX SYSTHESIS OF SMALL MOLECULE LIBRARIES

(76) Inventor: Peter Birk Rasmussen, Valby (DK)

( * ) Notice: Subject to any disclaimer, the term of this patent is extended or adjusted under 35 U.S.C. 154(b) by 619 days.

(21) Appl. No.: 11/719,846

(22) PCT Filed: Nov. 22, 2005

(86) PCT No.: PCT/DK2005/000747
§ 371 (c)(1),
(2), (4) Date: Apr. 29, 2009

(87) PCT Pub. No.: WO2006/053571
PCT Pub. Date: May 26, 2006

(65) Prior Publication Data
US 2009/0209430 A1 Aug. 20, 2009

(51) Int. Cl.
*C12Q 1/68* (2006.01)
*C12P 19/34* (2006.01)
*C07H 21/04* (2006.01)
*C40B 40/06* (2006.01)

(52) U.S. Cl. ......... 435/6; 435/91.1; 536/23.1; 536/24.3; 506/16

(58) Field of Classification Search ............... 536/23.1, 536/24.3; 435/6, 91.1; 506/16
See application file for complete search history.

(56) References Cited

FOREIGN PATENT DOCUMENTS

| | | |
|---|---|---|
| EP | 0 604 552 B1 | 2/1997 |
| EP | 0 643 778 B1 | 5/2000 |
| WO | WO 93/06121 | 4/1993 |
| WO | WO 93/20242 | 10/1993 |
| WO | WO 02/074929 A2 | 9/2002 |
| WO | WO 02/103008 A2 | 12/2002 |
| WO | WO 03/078625 A2 | 9/2003 |
| WO | WO 2004/016767 A2 | 2/2004 |
| WO | WO 2004/039825 A2 | 5/2004 |
| WO | WO 2004/083427 A2 | 9/2004 |
| WO | WO 2005/058479 A2 | 6/2005 |

OTHER PUBLICATIONS

Bruick, Richard K., "Template-directed ligation of peptides of oligonucleotides," Chemistry & Biology, Jan. 1996, 3:49-56.
Doyon, Jeffrey B., "Highly Sensitive in Vitro Selections for DNA-Linked Synthetic Small Molecules with Protein Binding Affinity and Specificity," J. Am. Chem. Soc., 2003, 125:12372-12373.
Walder, Joseph A., "Complementary carrier peptide synthesis: General strategy and implications for prebiotic origin of peptide synthesis," Proc. Natl. Acad. Sci. USA, 1979, 7:51-55.

*Primary Examiner* — Jezia Riley
(74) *Attorney, Agent, or Firm* — Knobbe, Martens, Olson & Bear LLP

(57) ABSTRACT

The present invention provides a method for combining the advantages of encoded molecule fragments made by split and mix synthesis with the advantages of template directed synthesis of molecules. The method provided in the invention comprises the steps of: Adding a linker molecule L to one or more reaction wells; Adding a molecule fragment to each of said reaction wells; Adding an oligonucleotide identifier to each of said reaction wells; Subjecting said wells to conditions sufficient to allow said molecule fragments and said oligonucleotie identifiers to become attached to said linker molecule, or conditions sufficient for said molecule fragments to bind to other molecule fragments and sufficient for said oligonucleotide identifiers to bind to other oligonucleotide identifiers; Combining the contents of said one or more reaction wells; Optionally, distributing the combined product to one or more new reaction wells; Optionally, repeating steps b) to e) one or more times; Contacting the resulting bifunctional molecule(s) of step e) or g) with one or more Contacting the resulting bifunctional molecule(s) of step e) or g) with one or more (oligonucleotide) templates each capable of hybridizing to at least one of the oligonucleotide identifiers added in step c).

46 Claims, 36 Drawing Sheets

Figure 1:
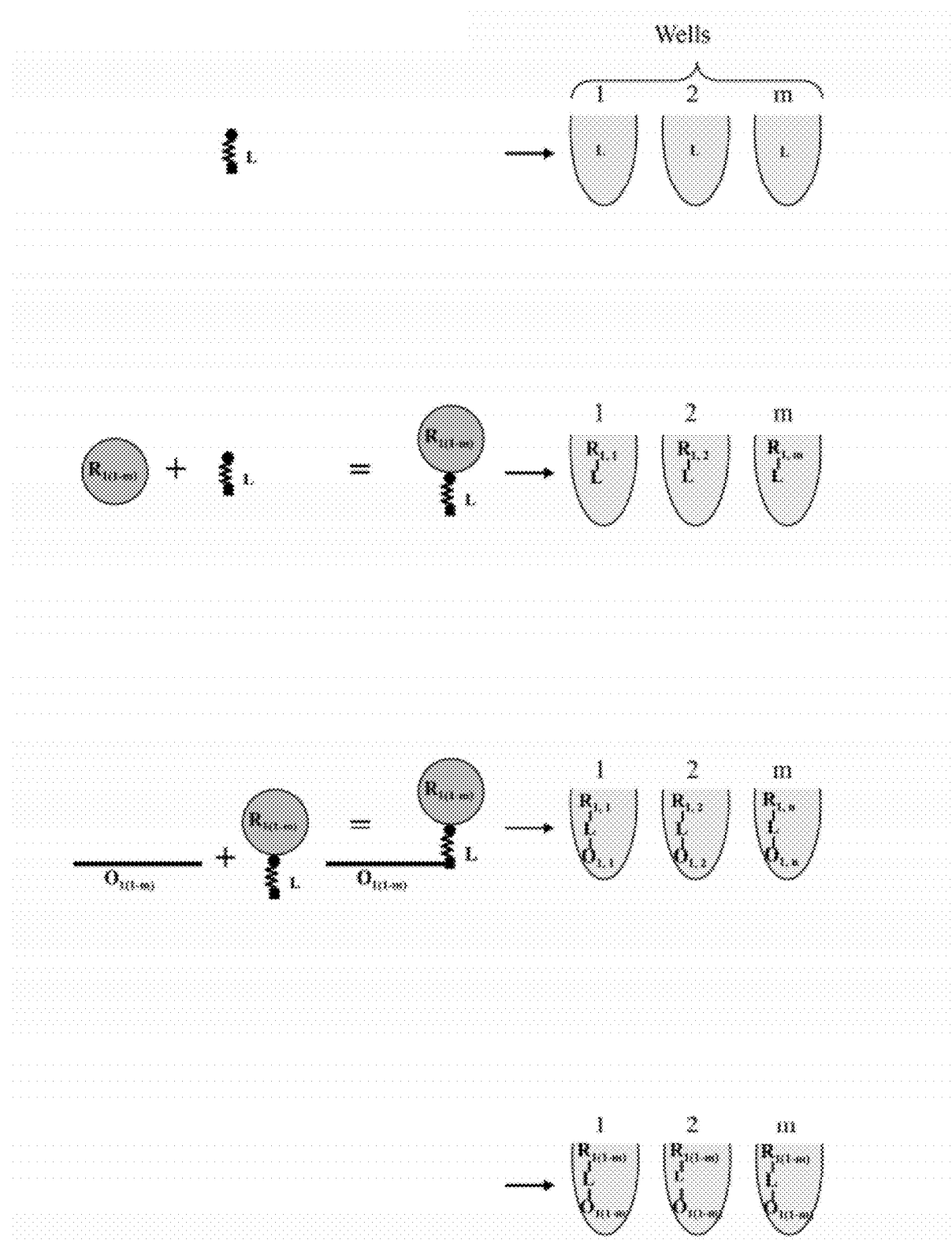

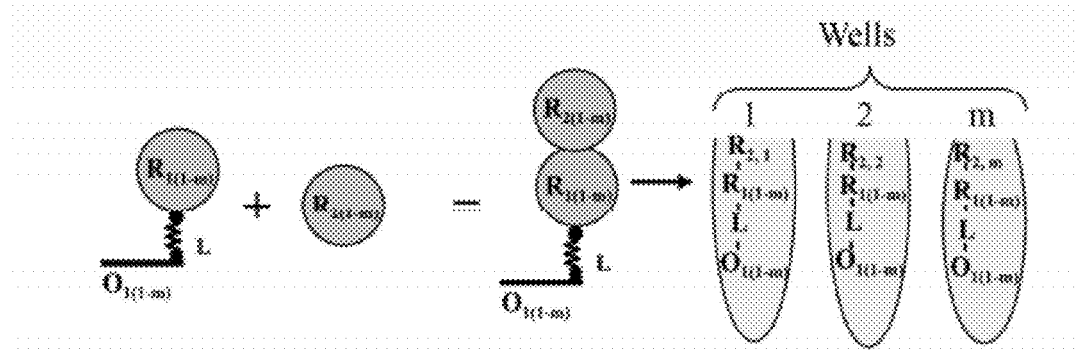
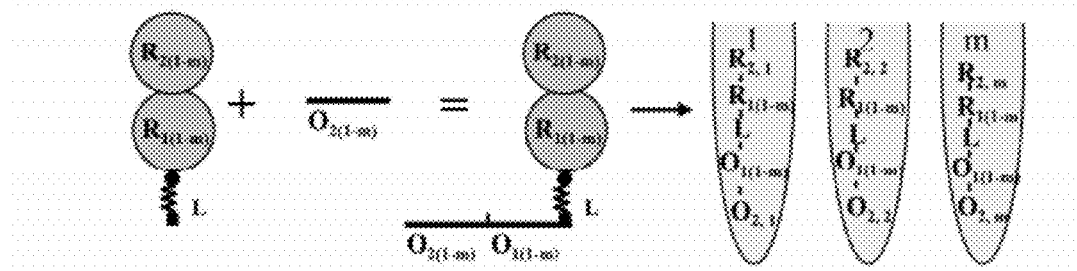
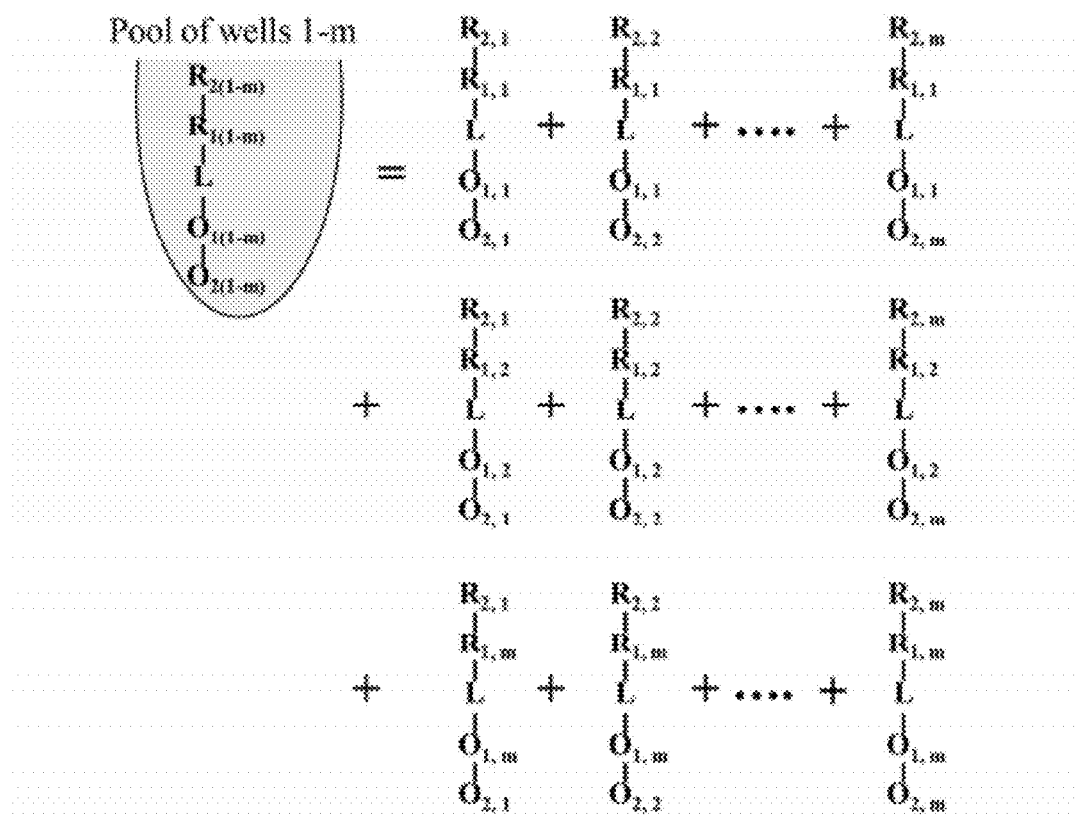
Fig. 1 cont.

A. Direct transfer reaction
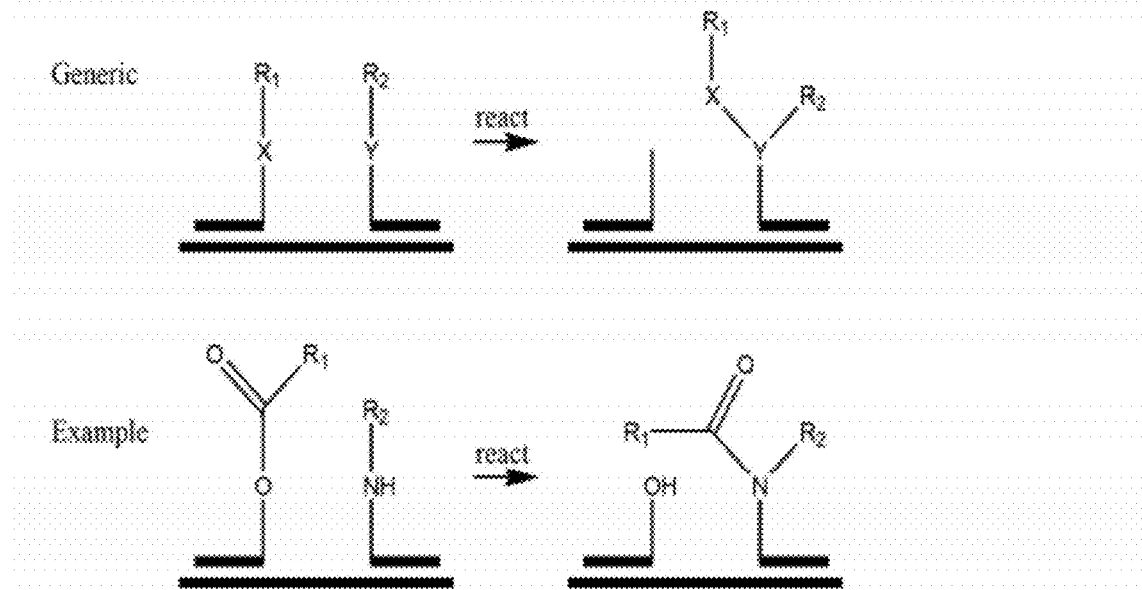
B. Indirect transfer reaction (reaction followed by cleavage)
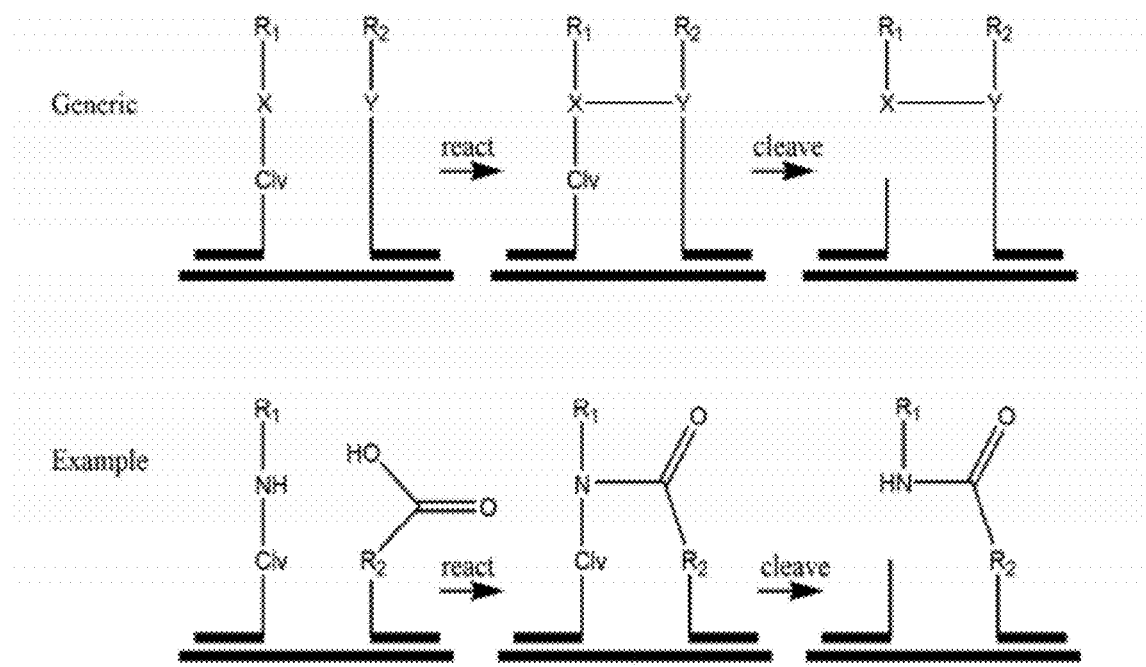
Fig. 3

Example 1:
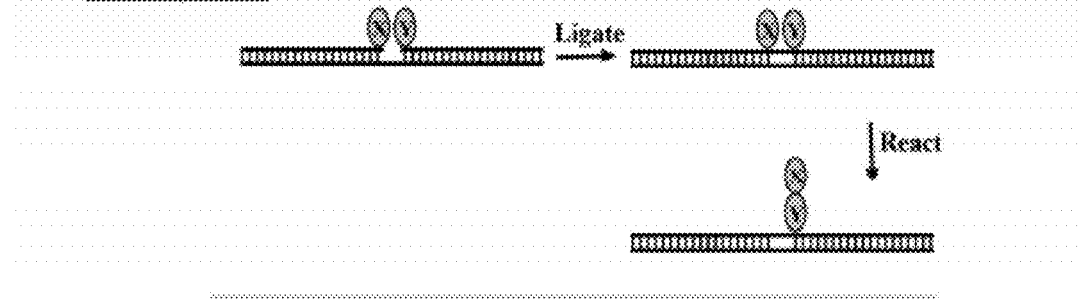
Example 2:
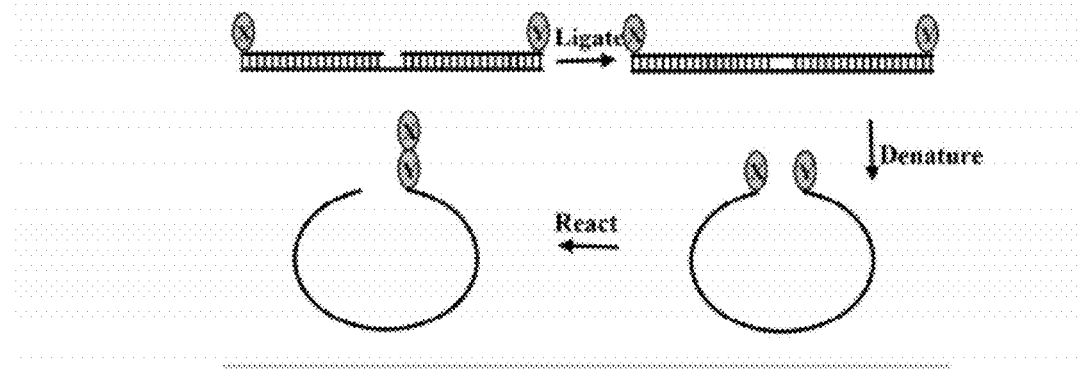
Example 3:
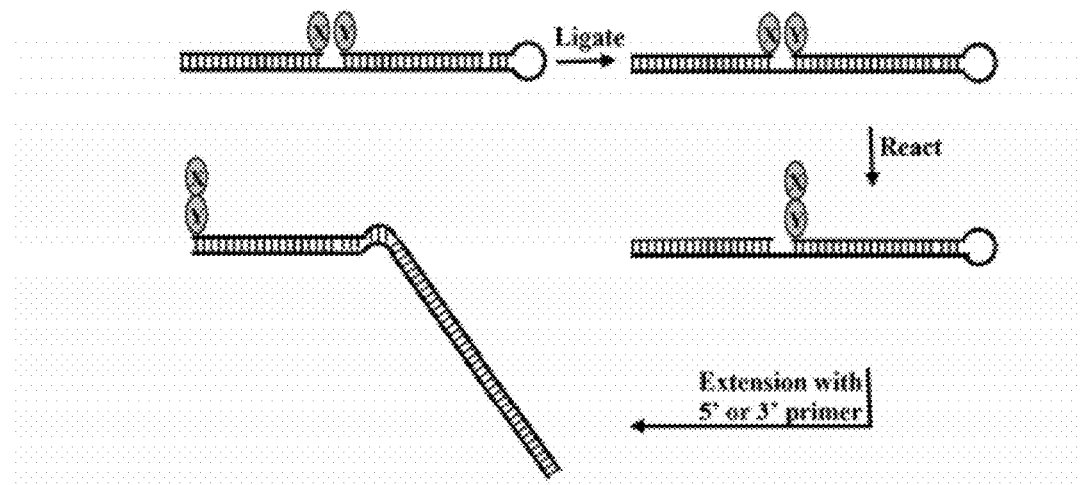
Example 4:
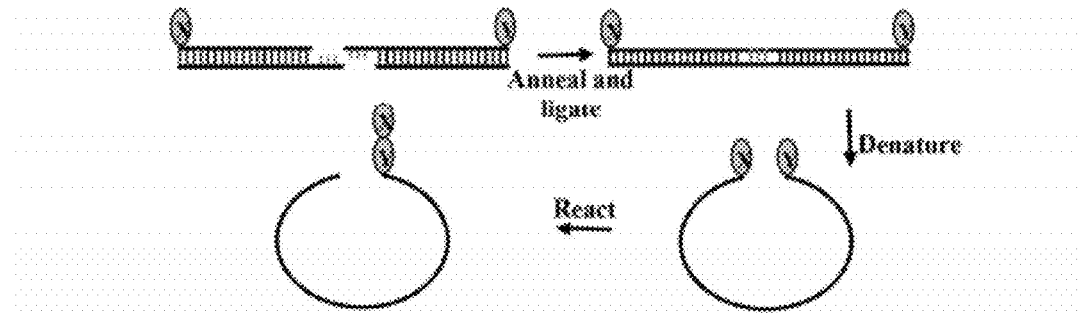
Fig. 4

Example 5:
Step 1:
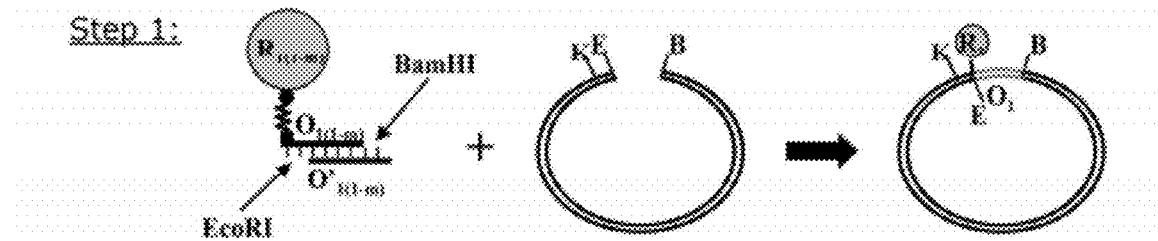
Step 2:
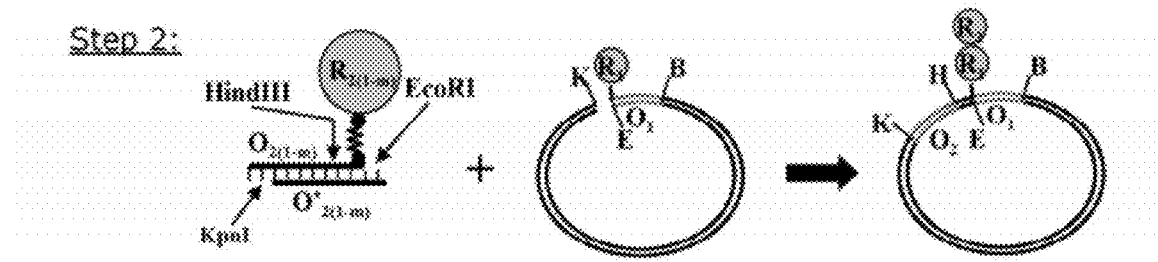
Step 3:
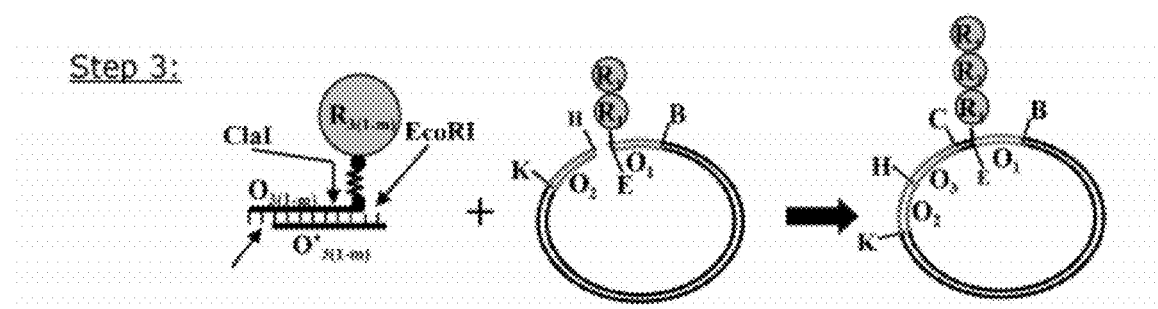
Step 4:
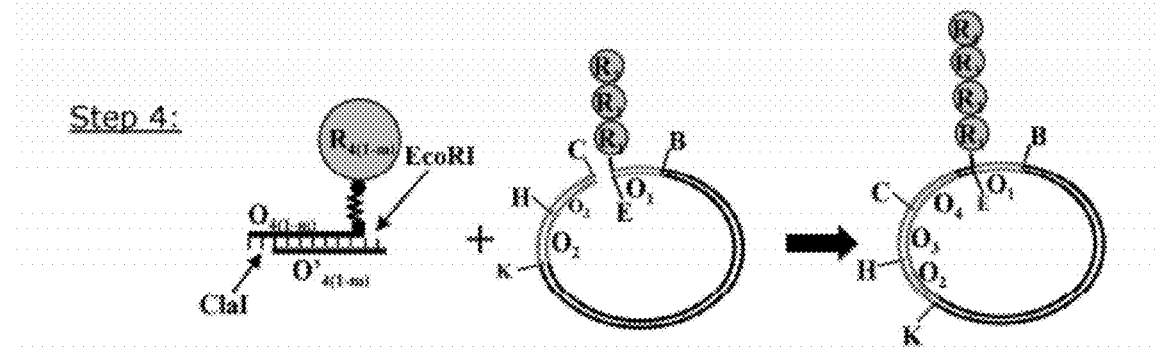
Fig. 4 cont.

Nucleophilic substitution by activation of electrophiles

A. Acylation - principle

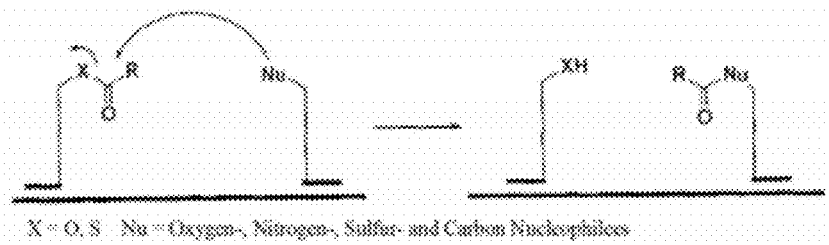

X = O, S   Nu = Oxygen-, Nitrogen-, Sulfur- and Carbon Nucleophiles

B. Acylation
Amide formation by reaction of amines with activated esters

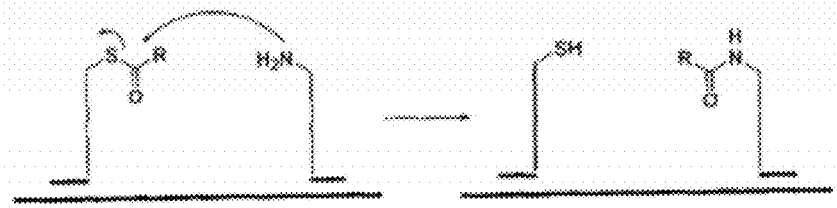

C. Acylation
Pyrazolone formation by reaction of hydrazines with β-ketoesters

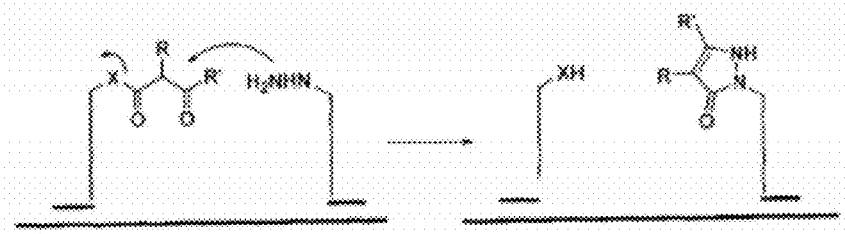

D. Acylation
Isoxazolone formation by reaction of hydroxyl-amines with β-ketoesters

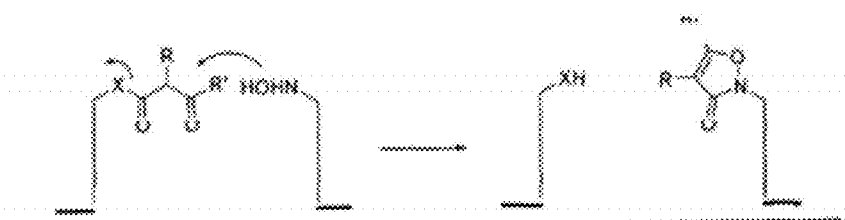

Fig. 6

E. Acylation
Pyrimidine formation by reaction of thioureas with β-Ketoesters

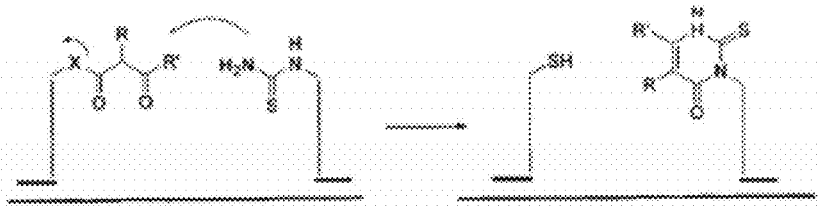

F. Acylation
Pyrimidine formation by reaction of ureas with Malonates

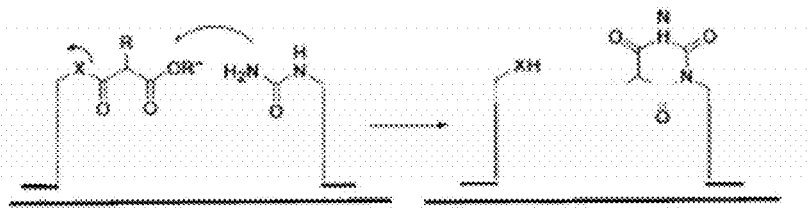

G. Acylation
Coumarine or quinolinon formation by a Heck reaction followed by a nucleophilic substitution

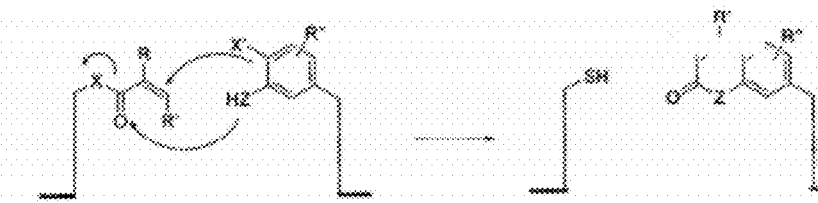

X = O, S    X' = Halogen, OTf, OMs    Z = O, NH

H. Acylation
Phthalhydrazide formation by reaction of Hydrazines and Phtalimides

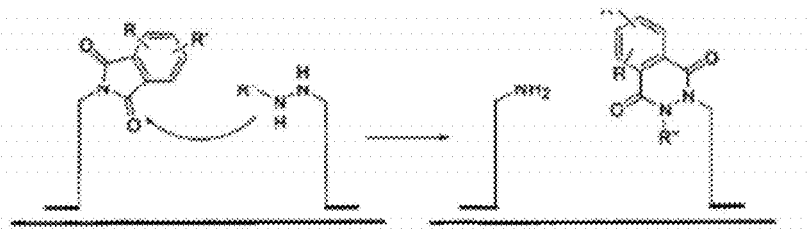

Fig. 6 cont.

I. Acylation
Diketopiperazine formation by reaction of Amino Acid Esters

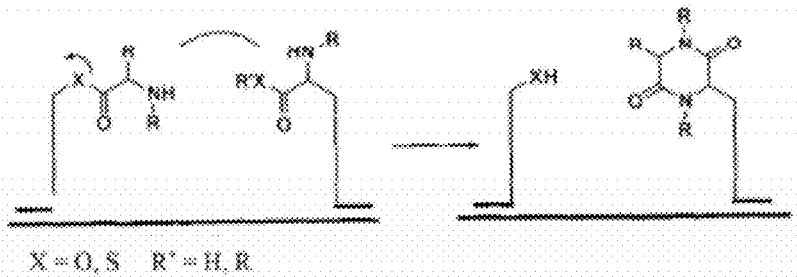

X = O, S   R' = H, R

J. Acylation
Hydantoin formation by reaction of Urea and α-substituted Esters

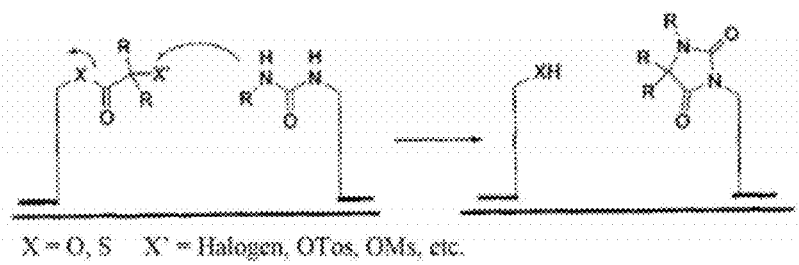

X = O, S   X' = Halogen, OTos, OMs, etc.

K. Alkylation - principle
Alkylated compounds by reaction of Sulfonates with Nucleophiles

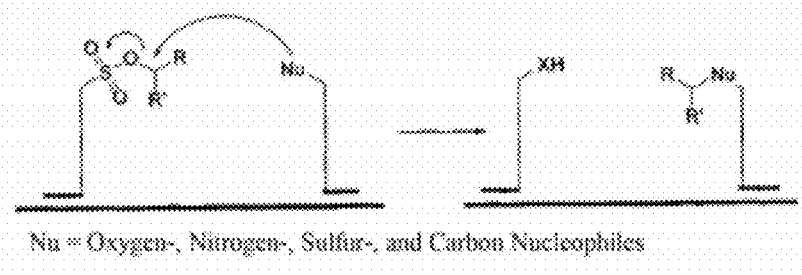

Nu = Oxygen-, Nitrogen-, Sulfur-, and Carbon Nucleophiles

L. Vinylation - principle

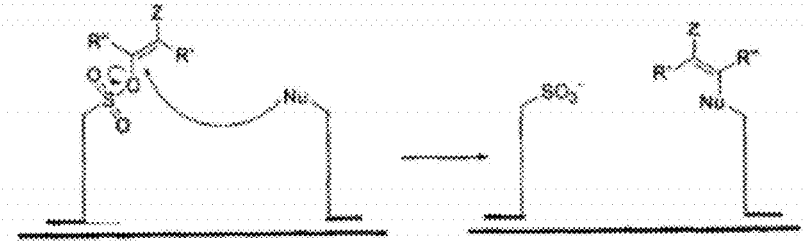

Z = CN, COOR, COR, $NO_2$, $SO_2R$, S(=O)R, $SO_2NR_2$, F
Nu = Oxygen-, Nitrogen-, Sulfur- and Carbon Nucleophiles

Fig. 6 cont.

M. Heteroatom electrophiles
Disulfide formation by reaction of Pyridyl disulfide with Mercaptanes

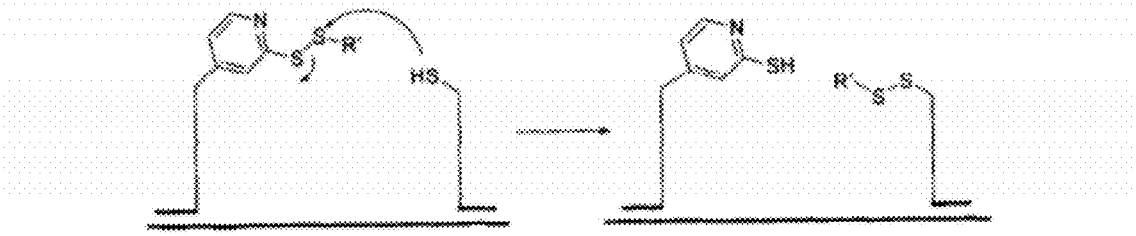

N. Acylation
Benzodiazepinone formation by reaction of Amino Acid Esters and Amino Ketones

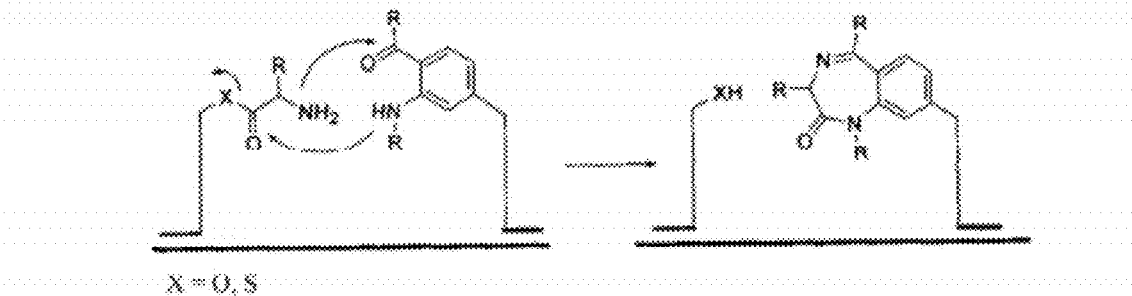

X = O, S

Addition to carbon-hetero multiple bonds

O. Wittig/Horner-Wittig-Emmon reagents
Substituted alkene formation by reaction of Phosphonates with Aldehydes or Ketones

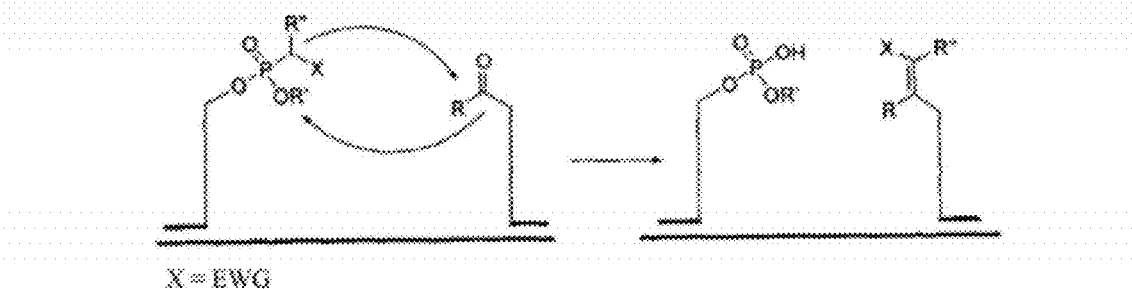

X = EWG

Fig. 6 cont.

Figure 6:
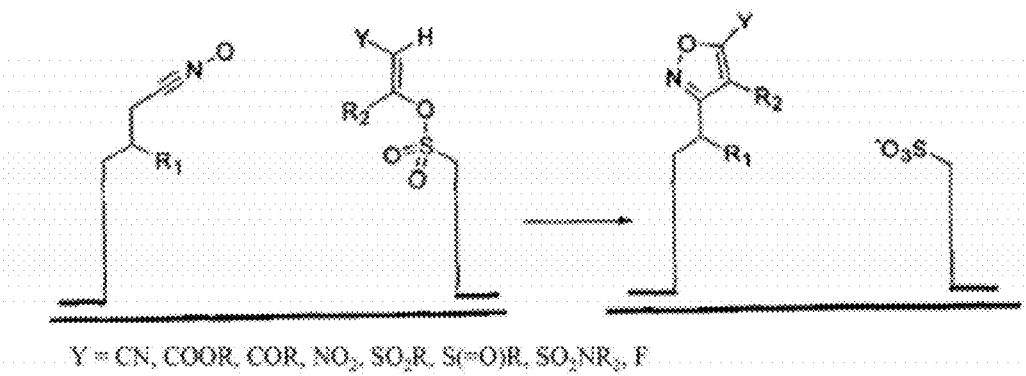

Transition metal catalyzed reactions
P. Arylation
Biaryl formation by reaction of Boronates with Aryls or Heteroaryls
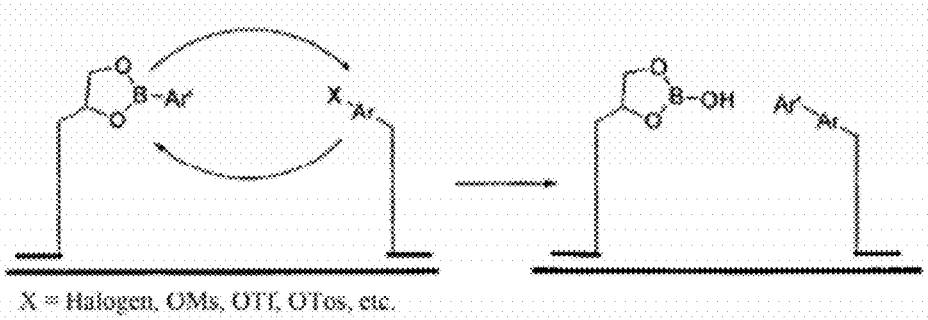
X = Halogen, OMs, OTf, OTos, etc.
Q. Arylation
Biaryl formation by reaction of Boronates with Aryls or Heteroaryls
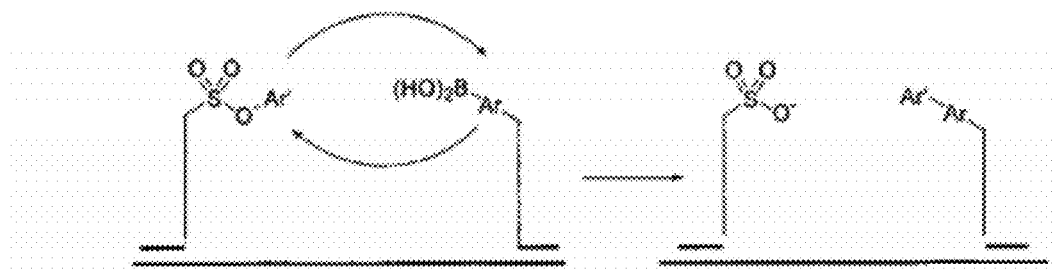
R. Arylation
Vinylarene formation by reaction of alkenes with Aryls or Heteroaryls
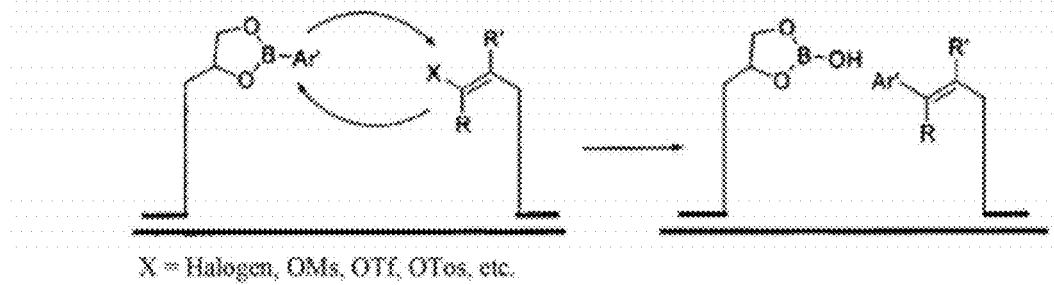
X = Halogen, OMs, OTf, OTos, etc.
Fig. 6 cont.

S. Alkylation
Alkylation of arenes/hetarenes by reaction with Alkyl boronates

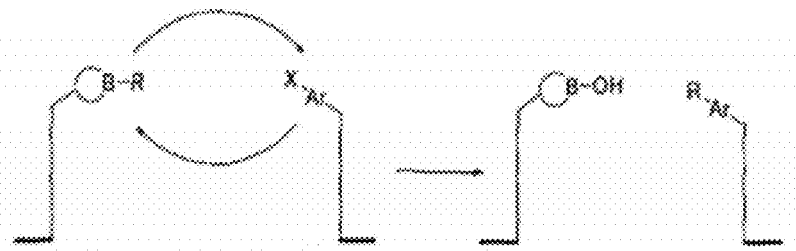

X = Halogen, OMs, OTf, OTos, etc.

T. Alkylation
Alkylation of arenes/hetarenes by reaction with Enolethers

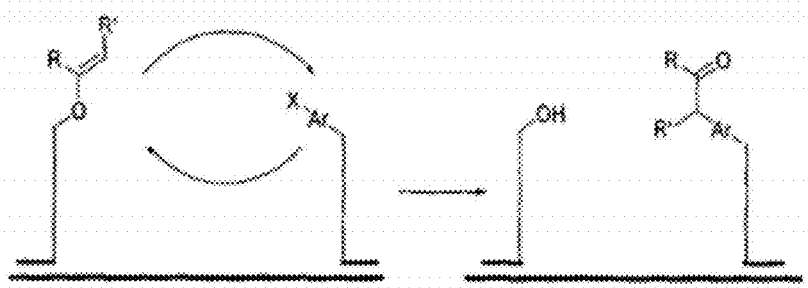

X = Halogen, OMs, OTf, OTos, etc.

Nucleophilic substitution using activation of nucleophiles

• Condensations
Alkylation of Aldehydes with Enolethers or Enamines

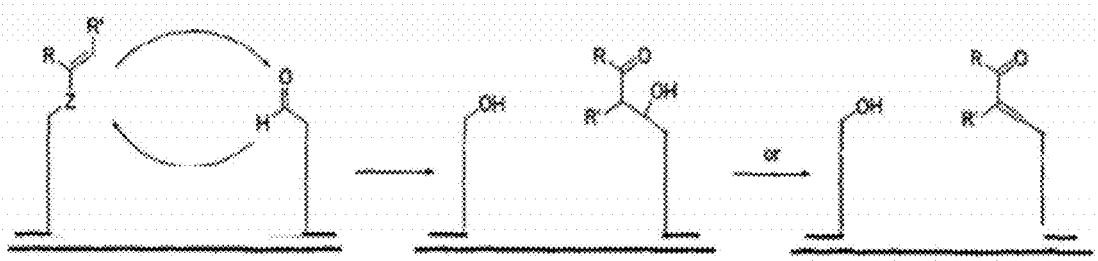

Z = NR, O     X = Halogen, OMs, OTf, OTos, etc.

Fig. 6 cont.

V. Alkylation
Alkylation of aliphatic halides or tosylates with Enolethers or enamines
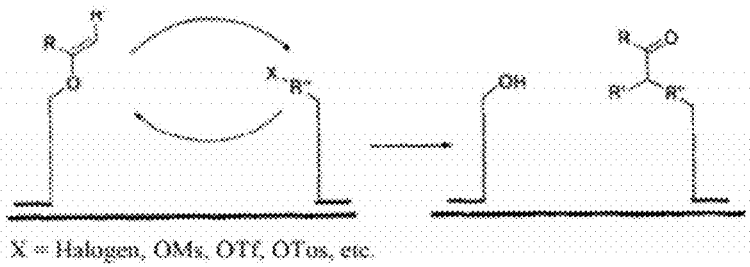
X = Halogen, OMs, OTf, OTos, etc.
Cycloadditions
W. [2+4] Cycloadditions
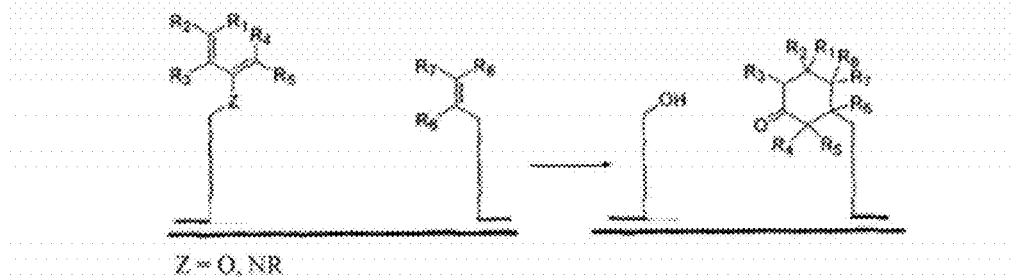
Z = O, NR
X. [2+4] Cycloadditions
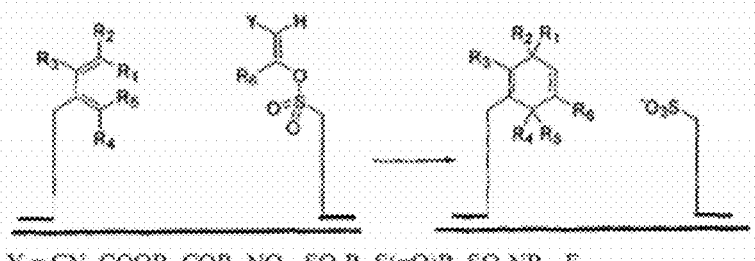
Y = CN, COOR, COR, $NO_2$, $SO_2R$, S(=O)R, $SO_2NR_2$, F
Y. [3+2] Cycloadditions
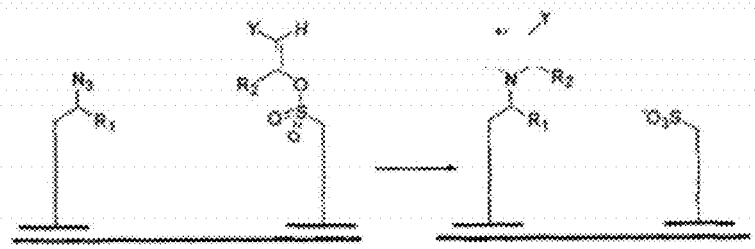
Y = CN, COOR, COR, $NO_2$, $SO_2R$, S(=O)R, $SO_2NR_2$, F
Fig. 6 cont.

Figure 7:
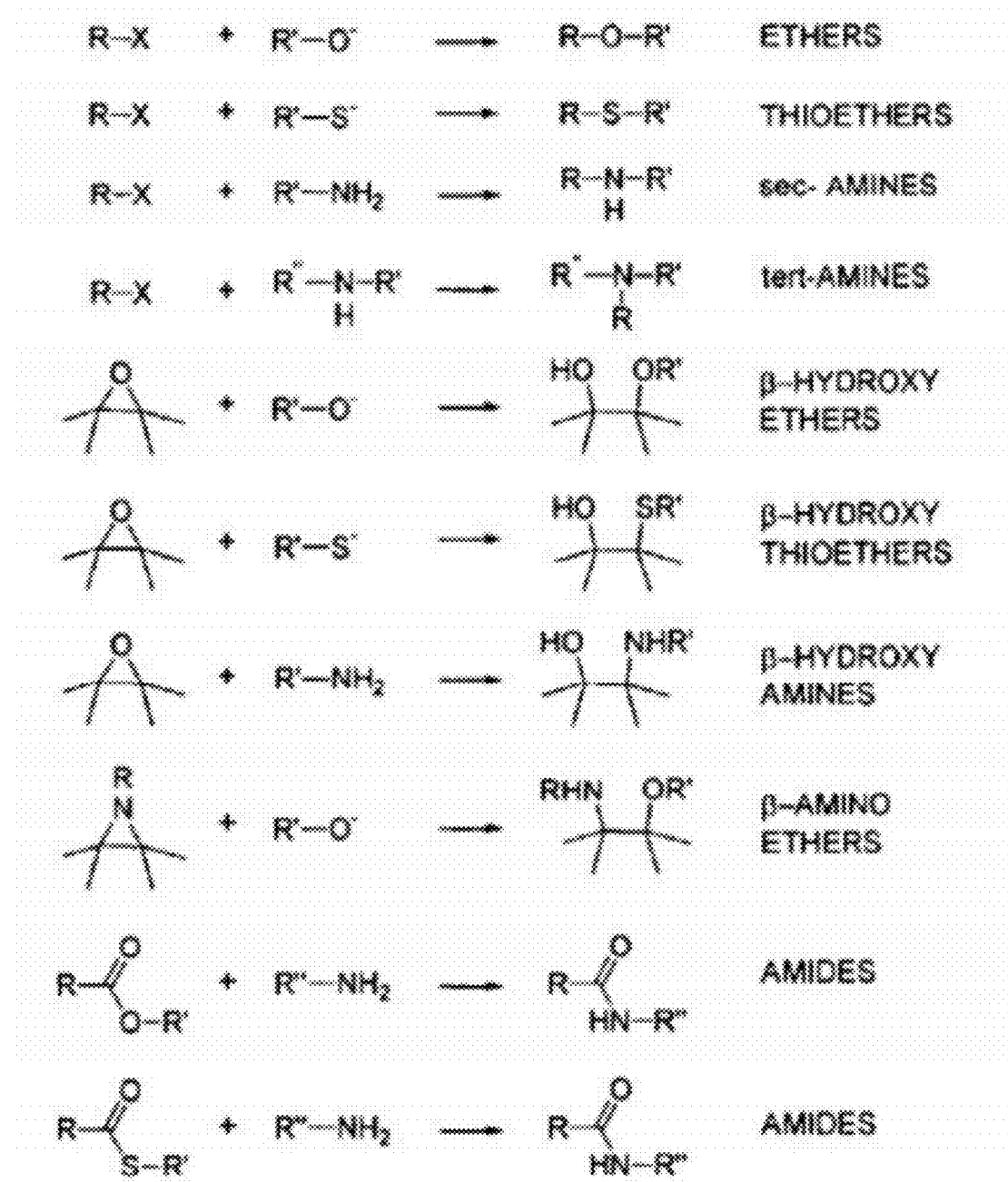
Figure 7:
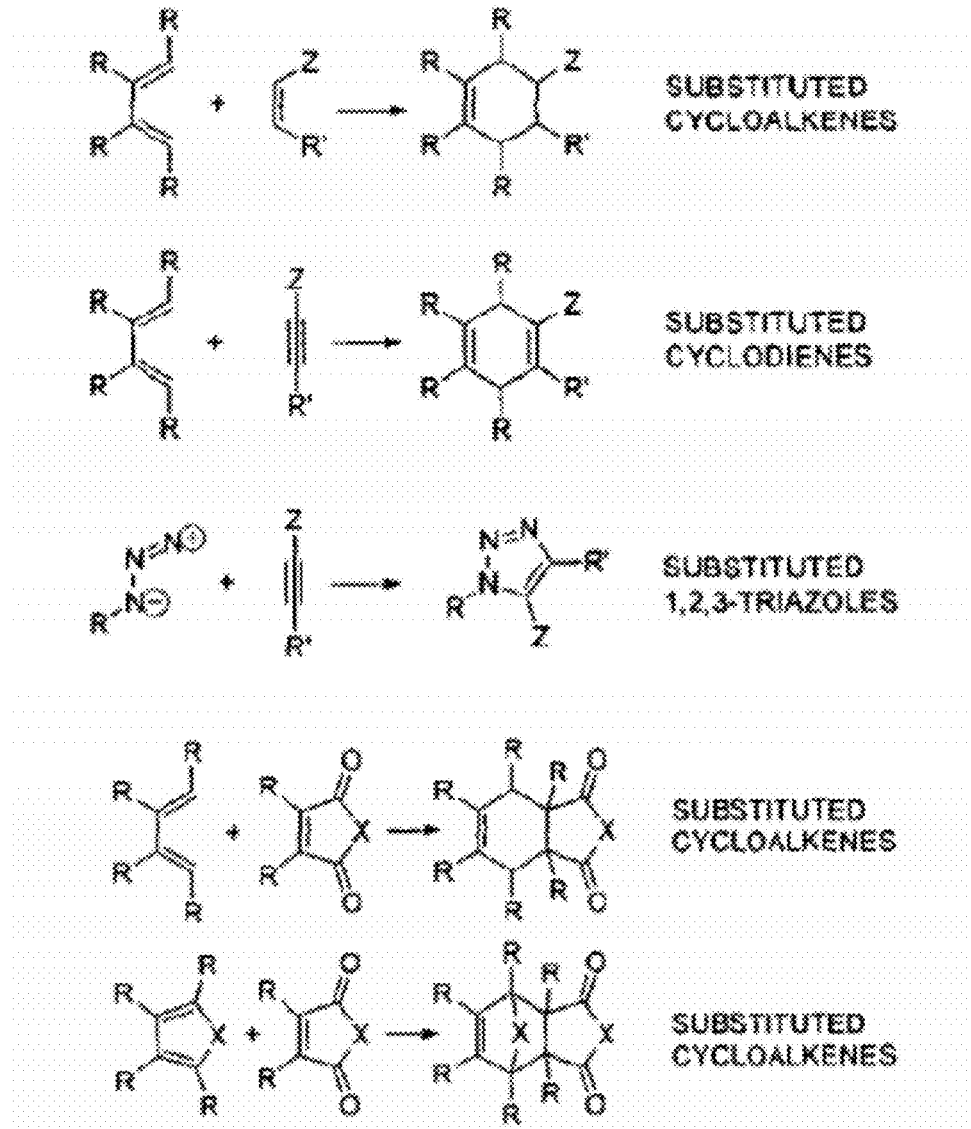
Figure 7:
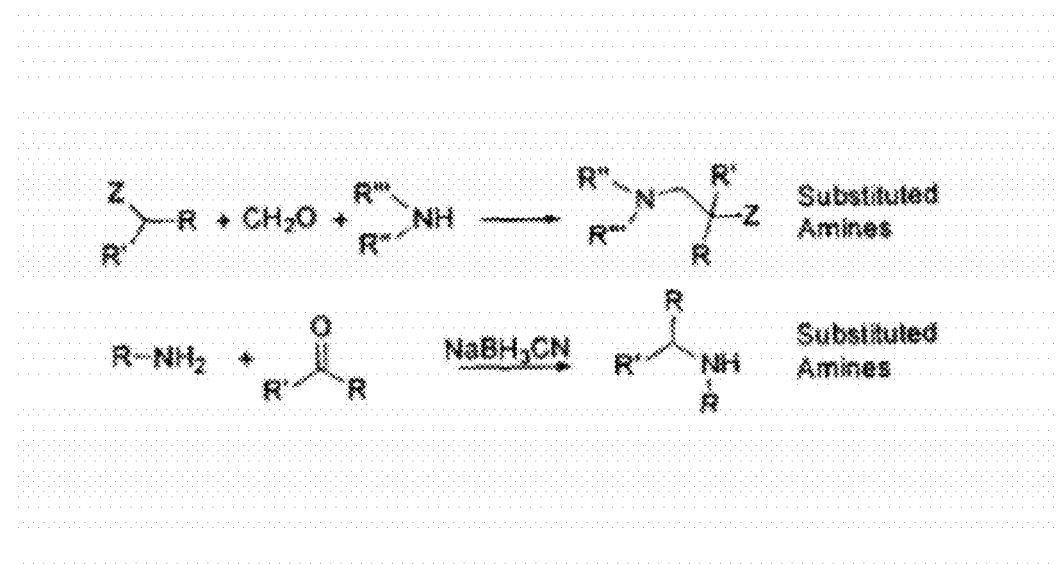

Nucleophilic substitution reaction
 THIOAMIDES
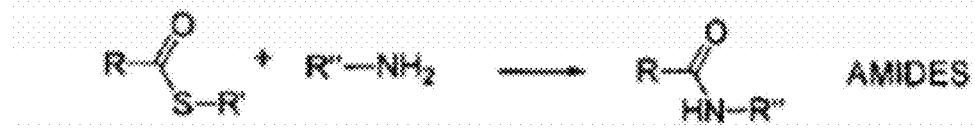 AMIDES
 THIOAMIDES
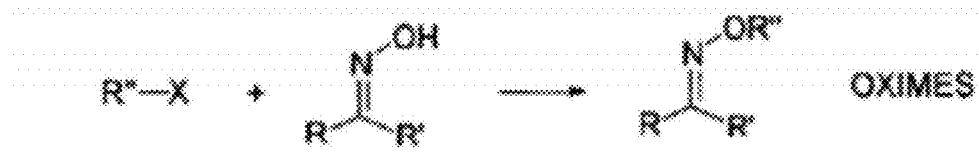 OXIMES
 SULFONAMIDES
 DI- AND TRI-FUNCTIONAL COMPOUNDS
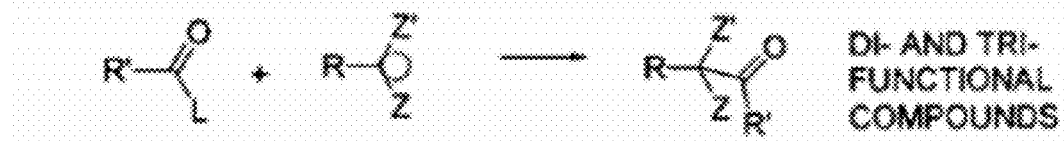 DI- AND TRI-FUNCTIONAL COMPOUNDS
$Z, Z$ = COOR, CHO, COR, CONR"$_2$, COO⁻, NO$_2$, SOR, SO$_2$R, SO$_2$NR"$_2$, CN, ect.
Fig. 7 cont.

Aromatic nucleophilic substitution

SUBSTITUTED AROMATIC COMPOUNDS

Nu = Oxygen- , Nitrogen- , Sulfur- and Carbon Nucleophiles
X = F, Cl, Br, I, $OSO_2CH_3$, $OSO_2CF_3$, $OSO_2TOL$, .. etc.
Z',Z = COOR , CHO , COR , $CONR"_2$, $COO^-$, CN ,
$NO_2$ , SOR , $SO_2R$ , $SO_2NR"_2$ .. ect.

Transition metal catalysed reactions

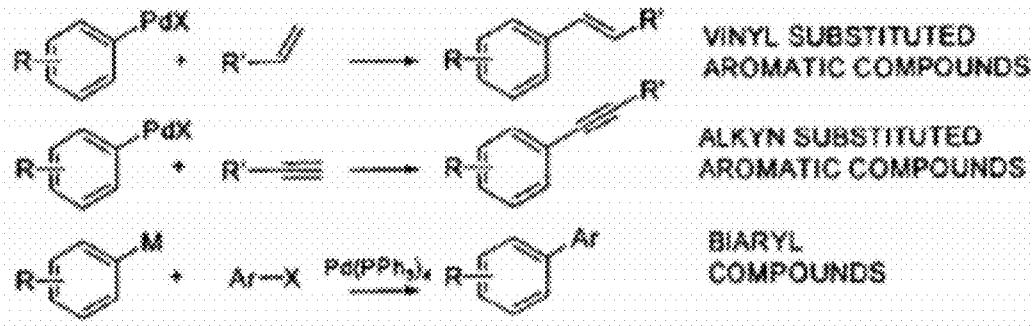

VINYL SUBSTITUTED AROMATIC COMPOUNDS

ALKYN SUBSTITUTED AROMATIC COMPOUNDS

BIARYL COMPOUNDS

Fig. 7 cont.

Addition to carbon-carbon multiplebonds
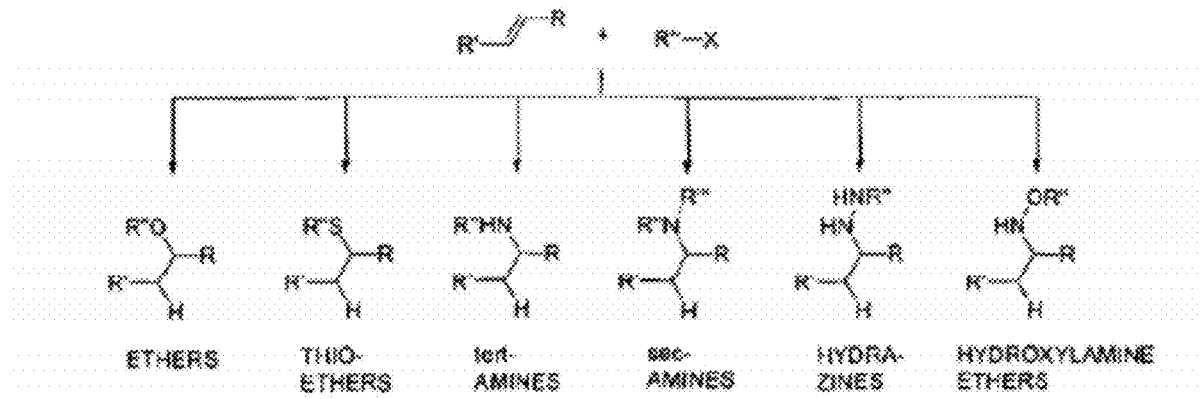
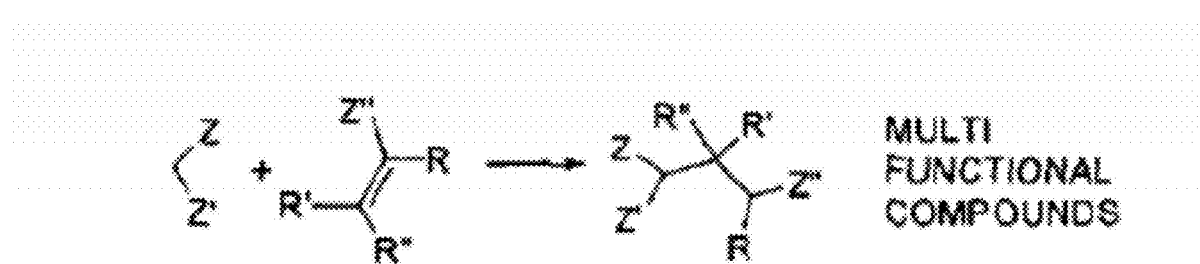
MULTI FUNCTIONAL COMPOUNDS
$Z = H$, Alkyl, $Z'$, Ar
$Z'' = COOR$, $CHO$, $COR$, $CONR''_2$, $CN$, $NO_2$, $SOR$, $SO_2R$, $SO_2NR''_2$, ect.
$Z' = Z''$    $R = R'$, $= R''$, $= Z$
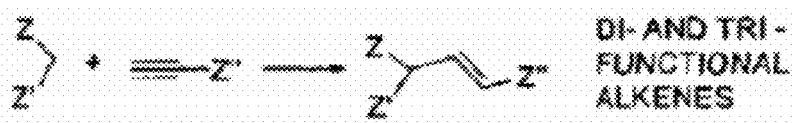
DI- AND TRI- FUNCTIONAL ALKENES
$Z = H$, Alkyl, Ar,
$Z'' = Z'$, Alkyl, Ar,
$Z' = COOR$, $CHO$, $COR$, $CONR''_2$, $CN$, $NO_2$, $SOR$, $SO_2R$, $SO_2NR''_2$, ect.
Fig. 7 cont.

Addition to carbon-hetero multiple bonds
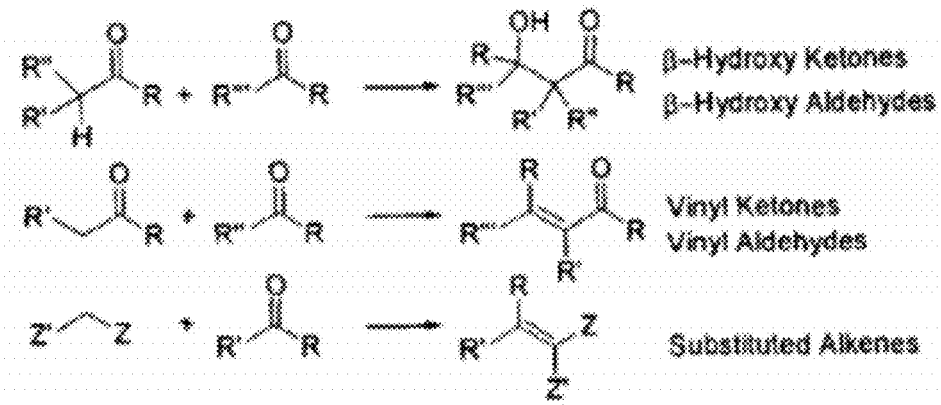
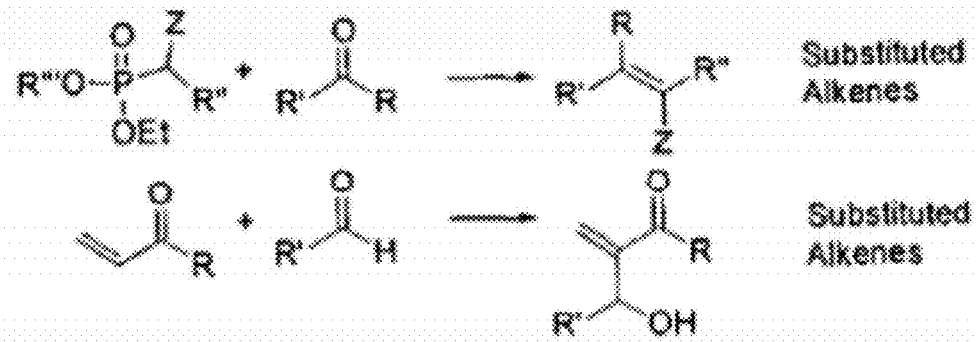
Z, Z' = COOR, CHO, COR, CONR''$_2$, CN, NO$_2$, SOR, SO$_2$R, SO$_2$NR''$_2$, ect.   R'' = H, Alkyl, Aryl
Z = COOR, CHO, COR, SOR, SO$_2$R, CN, NO$_2$, ect.
R = R', H, Alkyl, Ar,
R'' = R''', H, Alkyl, COR,
Fig. 7 cont.

Addition to carbon-hetero multiple bonds $Z$ = COOR, CHO, COR, SOR, $SO_2R$, CN, $NO_2$, ect.

$R$ = $R'$, H, Alkyl, Ar, $R''$ = $R'''$, H, Alkyl, COR,

A. Linker for the formation of Ketones, Aldehydes, Amides and Acids
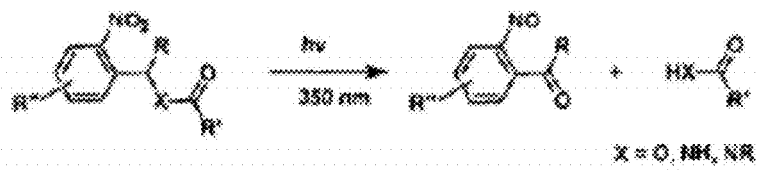
X = O, NH, NR
B. Linker for the formation of Ketones, Amides and Acids
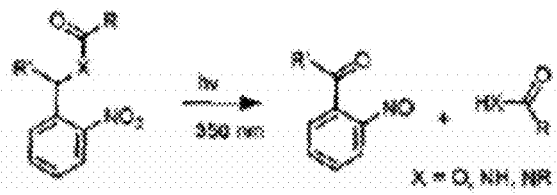
X = O, NH, NR
C. Linker for the formation of Aldehydes and Ketones
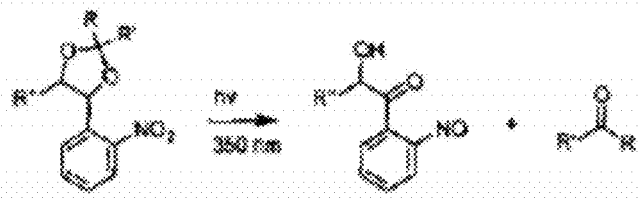
D. Linker for the formation of Alcohols and Acids
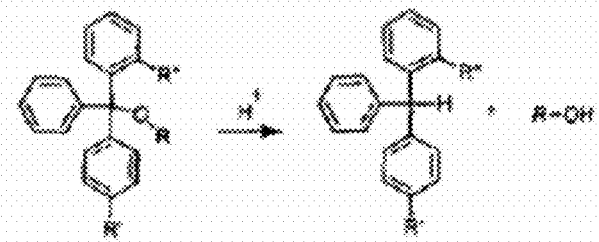
E. Linker for the formation of Amines and Alcohols
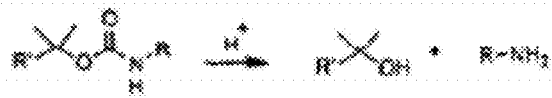
Fig. 8

F. Linker for the formation of Esters, Thioesters, Amides and Alcohols
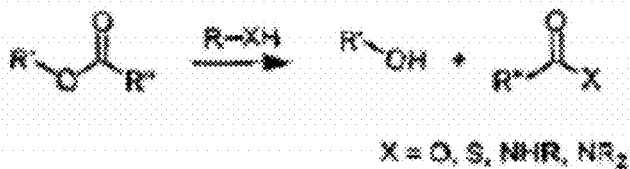
X = O, S, NHR, NR$_2$
G. Linker for the formation of Sulfonamides and Alcohols
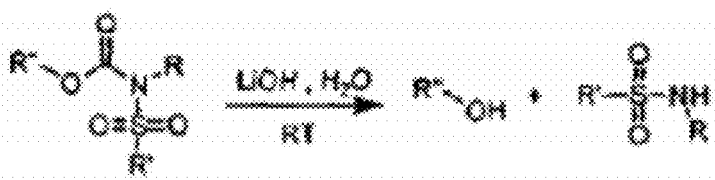
H. Linker for the formation of Ketones, Amines and Alcohols
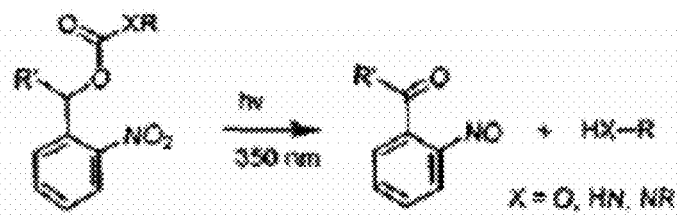
X = O, HN, NR
I. Linker for the formation of Ketones, Amines, Alcohols and Mercaptanes
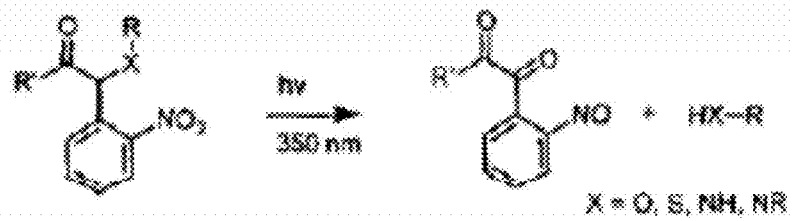
X = O, S, NH, NR
Fig. 8 cont.

J. Linker for the formation of Biaryl and Biheteryl

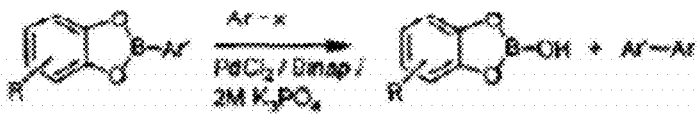

K. Linker for the formation of Benzyles, Amines, Anilins Alcohols and Phenoles

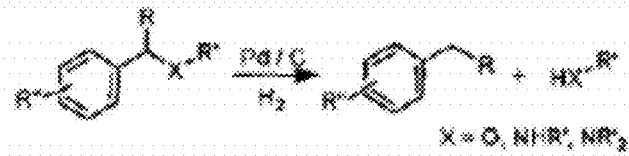

L. Linker for the formation of Mercaptanes

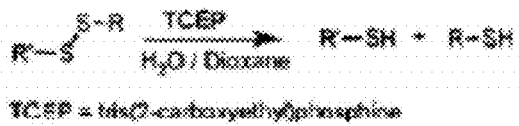

TCEP = tris(2-carboxyethyl)phosphine

M. Linker for the formation of Glycosides

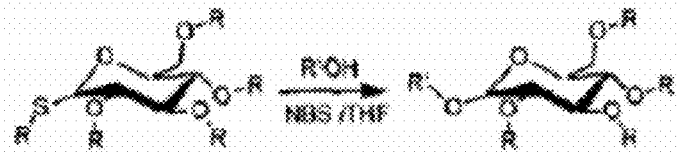

N. Linker for the formation of Aldehydes and Glyoxylamides

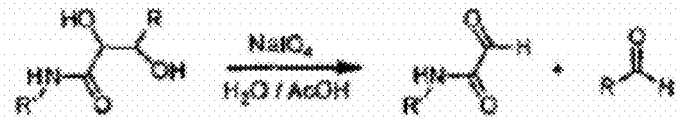

O. Linker for the formation of Aldehydes, Ketones and Aminoalcohols

Fig. 8 cont.

- In vivo and in vitro amplification, recombination and mutagenesis
- Kunkel site-directed mutagenesis, using one or multiple (e.g., 50) different mutagenic oligos at below-saturating concentrations, i.e., generating a combinatorial library
- USE (Unique Site-directed Elimination), using one or multiple (e.g., 50 different mutagenic oligos) at below-saturating concentrations, i.e., generating a combinatorial library
- PCR (Polymerase Chain Reaction)
- LCR (Ligase Chain Reaction)
- PCR shuffling, including family shuffling (shuffling sequences containing blocks with particular homology), and directed shuffling where oligos are spiked into the reaction to direct the shuffling process in a certain direction
- Other types of shuffling, e.g. homologous recombination in yeast; shuffling protocols as developed at the companies Phylos, Energy Biosystems, Diversa and by Frances Arnold.
- Cassette mutagenesis
- Other polymerase- or PCR-based methods, e.g., overlap extension, gene synthesis, and error-prone PCR
- Chemical or UV-induced mutagenesis
- Wildtype or variant template synthesis and translation into templated polymer (wildtype in this respect means the template sequence that will template the synthesis of the known ("wildtype") polymer; variant in this respect means a partly randomised or spiked template sequence that will template the synthesis of a variant of the known polymer)
- Specific cleavage by restriction enzymes
- Ligation by DNA or RNA ligases; "gene splicing"
- Affinity selections (using the template-templated polymer complex)
- Sequencing
- Arraying the polymers on "DNA chips", by using the template as a tag that binds a DNA array

Fig. 10

Figure 11:
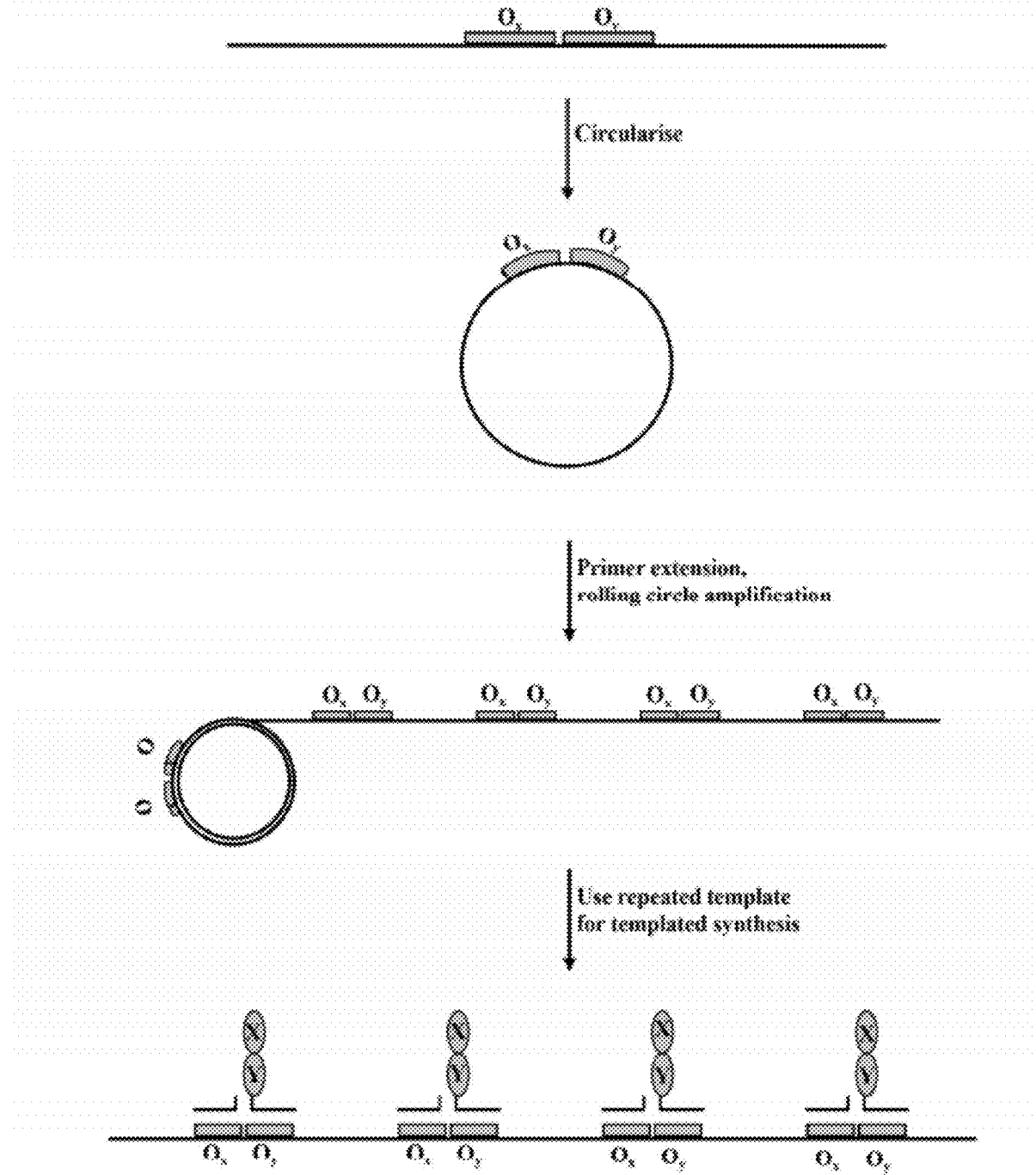

Example B:
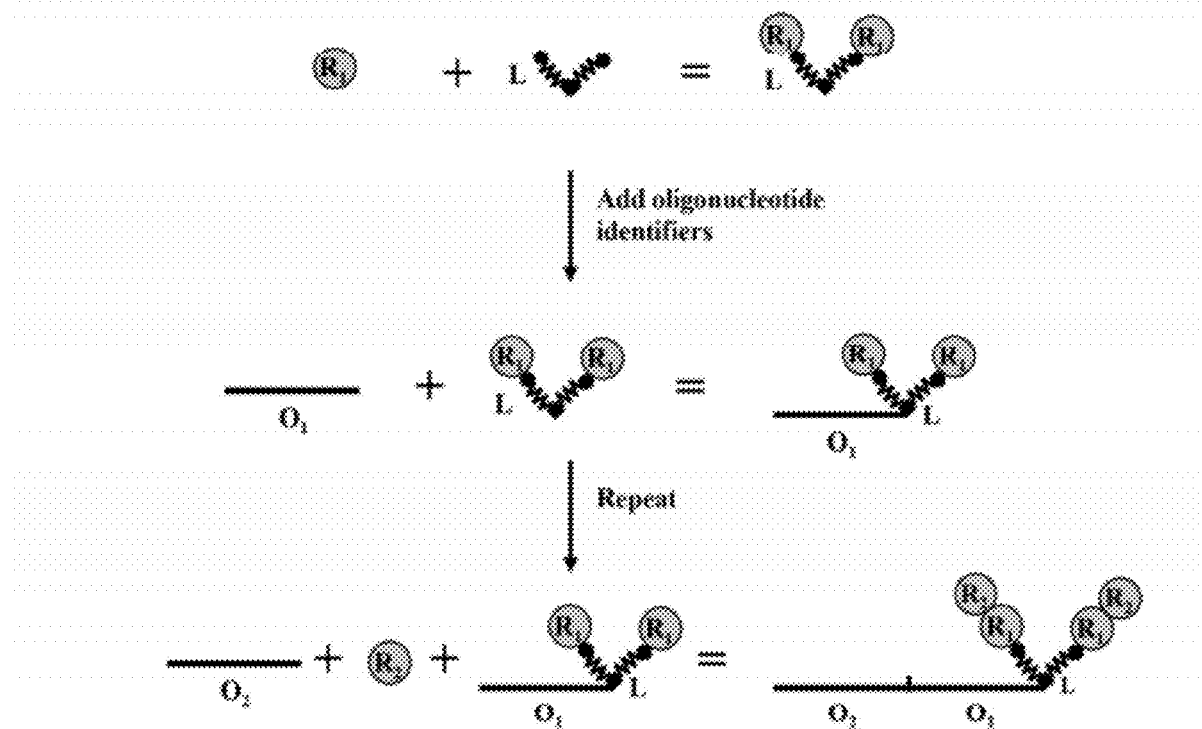
Example C:
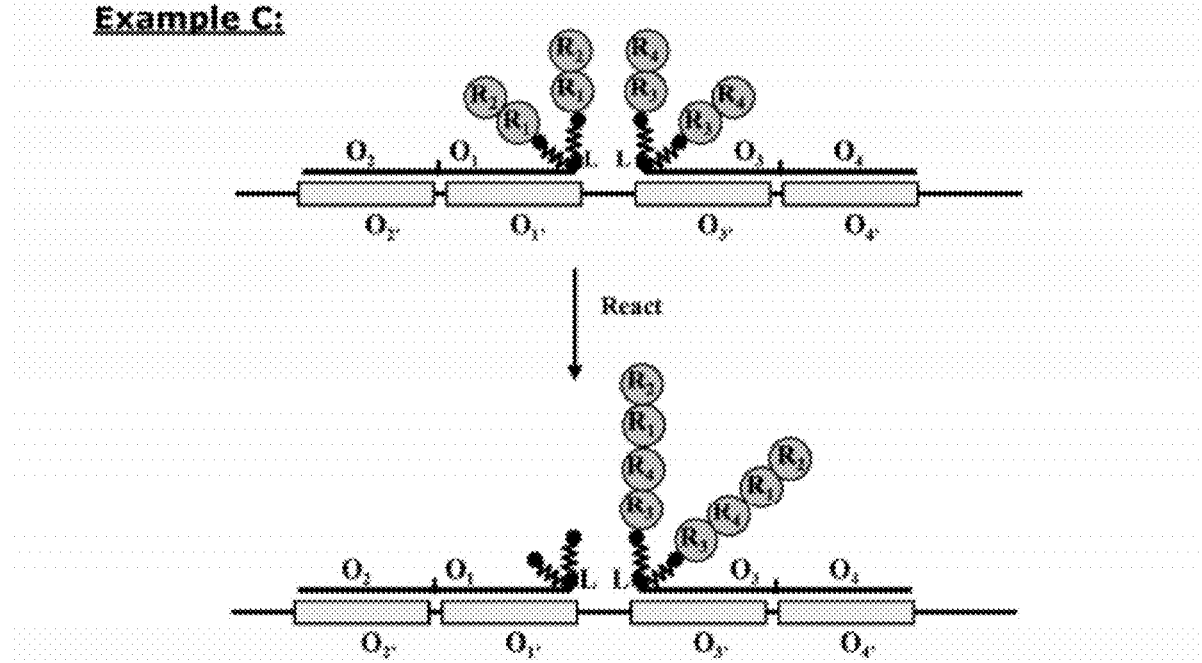
Fig. 11 cont.

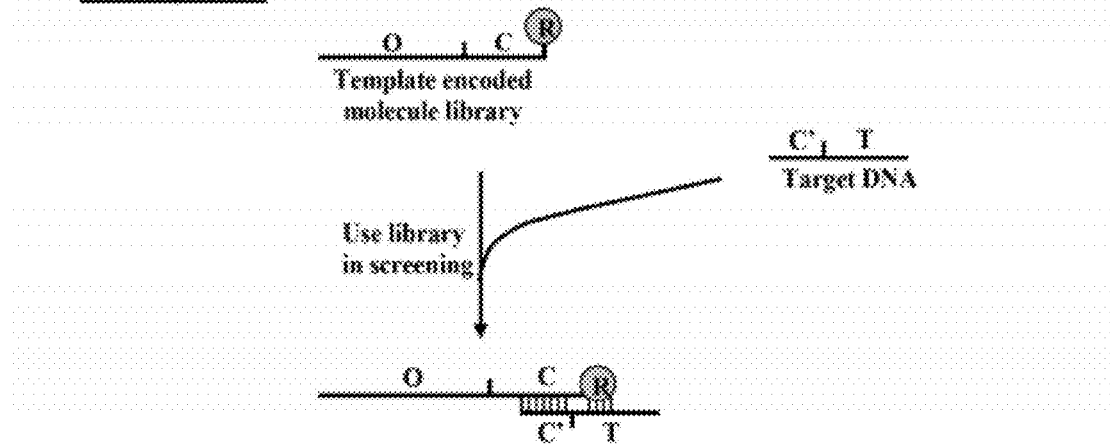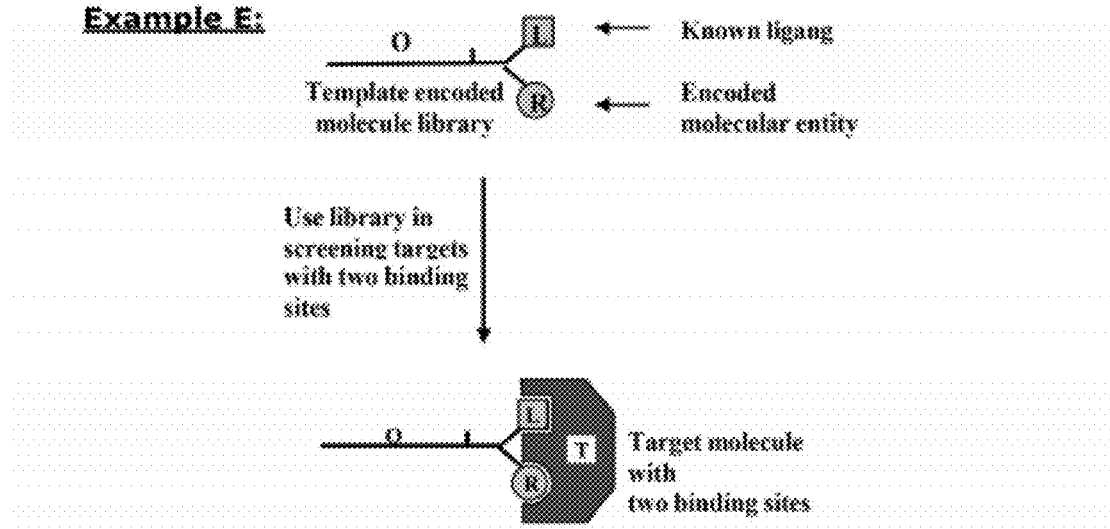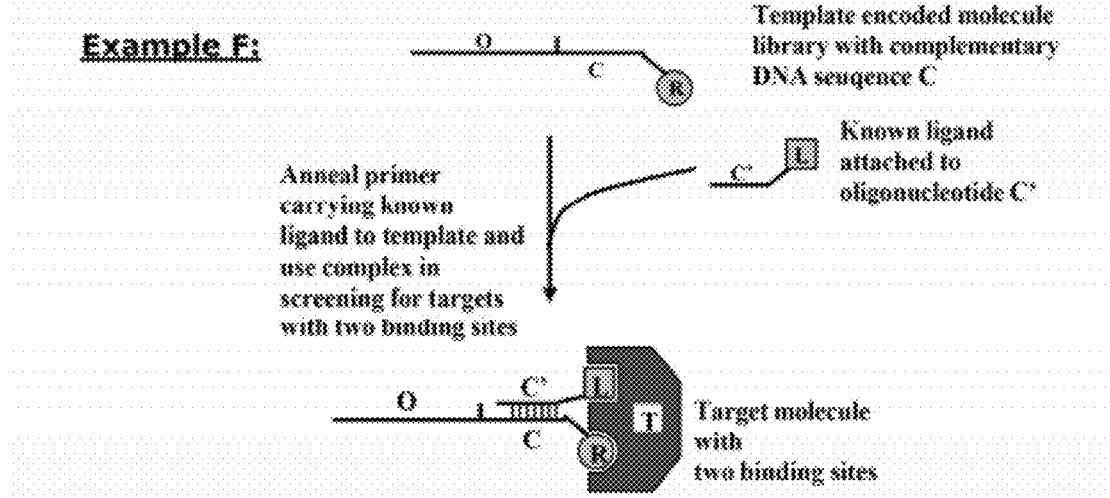
Fig.11 cont.

Example G:
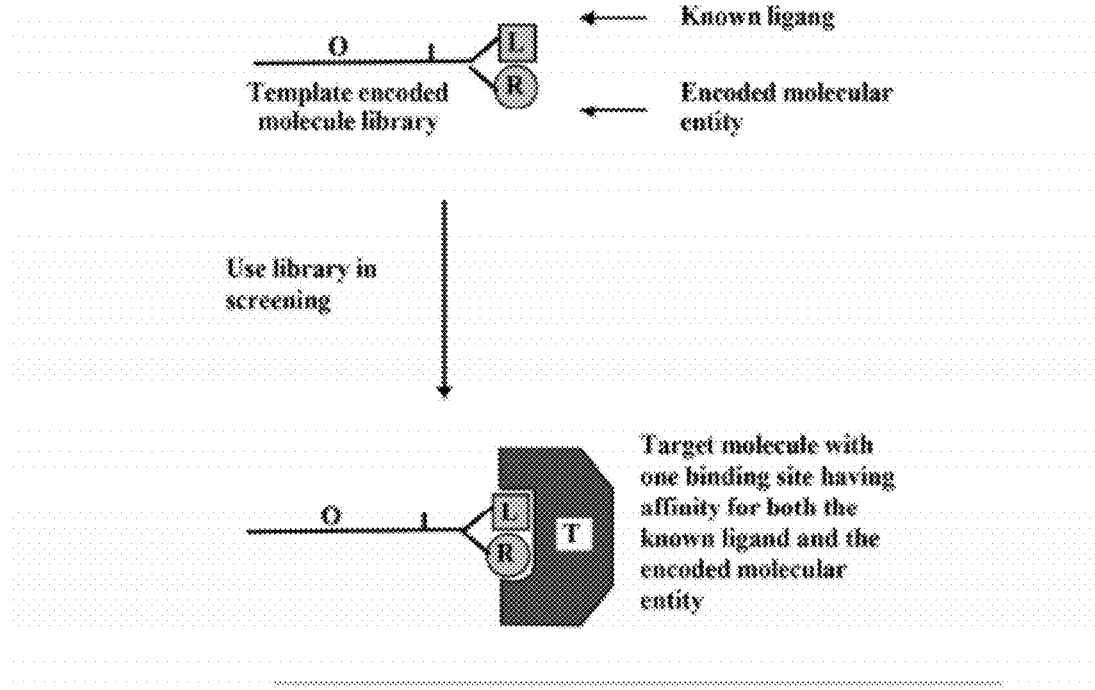
Example H:
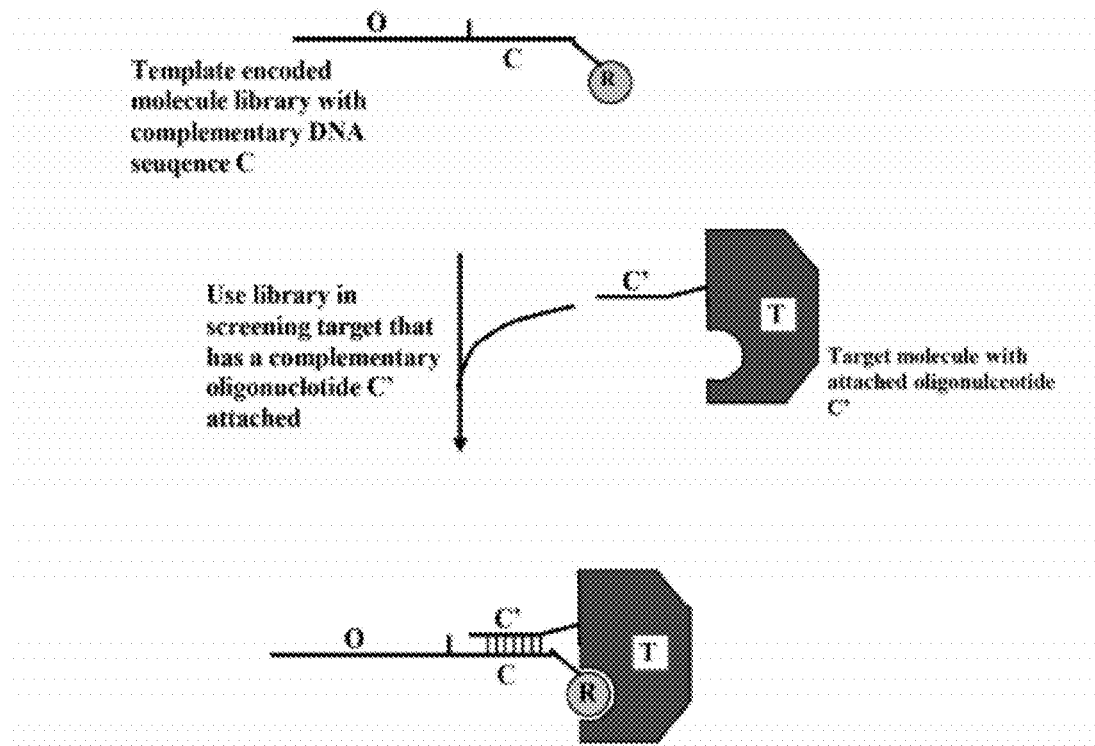
Fig. 11 cont.

Example A:
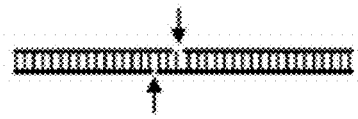
Example B:
Example C:
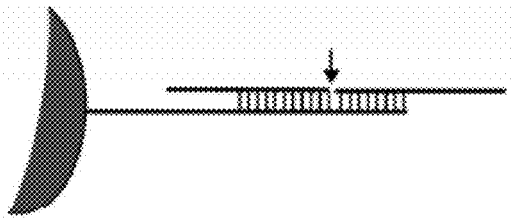
Example D:
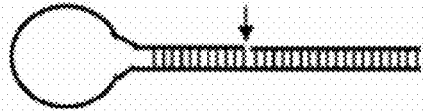
Example E:
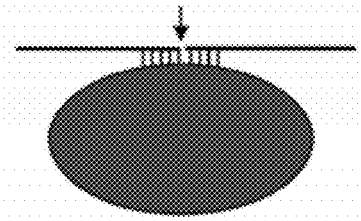
Fig. 12

SEQUENCE LISTING

<160> NUMBER OF SEQ ID NOS: 88

<210> SEQ ID NO 1
<211> LENGTH: 14
<212> TYPE: DNA
<213> ORGANISM: Artificial Sequence
<220> FEATURE:
<223> OTHER INFORMATION: Primer

<400> SEQUENCE: 1
atgctcgaga cgcg                                                         14

<210> SEQ ID NO 2
<211> LENGTH: 14
<212> TYPE: DNA
<213> ORGANISM: Artificial Sequence
<220> FEATURE:
<223> OTHER INFORMATION: Primer

<400> SEQUENCE: 2
tagctgtagg cgcg                                                         14

<210> SEQ ID NO 3
<211> LENGTH: 14
<212> TYPE: DNA
<213> ORGANISM: Artificial Sequence
<220> FEATURE:
<223> OTHER INFORMATION: Primer

<400> SEQUENCE: 3
agagctctga cgcg                                                         14

<210> SEQ ID NO 4
<211> LENGTH: 14
<212> TYPE: DNA
<213> ORGANISM: Artificial Sequence
<220> FEATURE:
<223> OTHER INFORMATION: Primer

<400> SEQUENCE: 4
cgtcgtcgta cgcg                                                         14

<210> SEQ ID NO 5
<211> LENGTH: 14
<212> TYPE: DNA
<213> ORGANISM: Artificial Sequence
<220> FEATURE:
<223> OTHER INFORMATION: Primer

<400> SEQUENCE: 5
atcgtcgaga cgcg                                                         14

<210> SEQ ID NO 6
<211> LENGTH: 14
<212> TYPE: DNA
<213> ORGANISM: Artificial Sequence
<220> FEATURE:
<223> OTHER INFORMATION: Primer

<400> SEQUENCE: 6
cacaagtacg aacg                                                         14

<210> SEQ ID NO 7
<211> LENGTH: 14
<212> TYPE: DNA

```
<213> ORGANISM: Artificial Sequence
<220> FEATURE:
<223> OTHER INFORMATION: Primer

<400> SEQUENCE: 7
cacatagtct cctc                                                   14

<210> SEQ ID NO 8
<211> LENGTH: 14
<212> TYPE: DNA
<213> ORGANISM: Artificial Sequence
<220> FEATURE:
<223> OTHER INFORMATION: Primer

<400> SEQUENCE: 8
cacatacatc gttc                                                   14

<210> SEQ ID NO 9
<211> LENGTH: 14
<212> TYPE: DNA
<213> ORGANISM: Artificial Sequence
<220> FEATURE:
<223> OTHER INFORMATION: Primer

<400> SEQUENCE: 9
cacatccagt gcaa                                                   14

<210> SEQ ID NO 10
<211> LENGTH: 14
<212> TYPE: DNA
<213> ORGANISM: Artificial Sequence
<220> FEATURE:
<223> OTHER INFORMATION: Primer

<400> SEQUENCE: 10
cacaagcatc acta                                                   14

<210> SEQ ID NO 11
<211> LENGTH: 15
<212> TYPE: DNA
<213> ORGANISM: Artificial Sequence
<220> FEATURE:
<223> OTHER INFORMATION: Primer

<400> SEQUENCE: 11
gaccaccagg acgag                                                  15

<210> SEQ ID NO 12
<211> LENGTH: 15
<212> TYPE: DNA
<213> ORGANISM: Artificial Sequence
<220> FEATURE:
<223> OTHER INFORMATION: Primer

<400> SEQUENCE: 12
gaccatcacc agctc                                                  15

<210> SEQ ID NO 13
<211> LENGTH: 15
<212> TYPE: DNA
<213> ORGANISM: Artificial Sequence
<220> FEATURE:
<223> OTHER INFORMATION: Primer

<400> SEQUENCE: 13
gaccatcctt cgtgc                                                  15
```

```
<210> SEQ ID NO 14
<211> LENGTH: 15
<212> TYPE: DNA
<213> ORGANISM: Artificial Sequence
<220> FEATURE:
<223> OTHER INFORMATION: Primer

<400> SEQUENCE: 14
gaccagctgt ggtcc                                                    15

<210> SEQ ID NO 15
<211> LENGTH: 15
<212> TYPE: DNA
<213> ORGANISM: Artificial Sequence
<220> FEATURE:
<223> OTHER INFORMATION: Primer

<400> SEQUENCE: 15
gaccaggagc agctc                                                    15

<210> SEQ ID NO 16
<211> LENGTH: 14
<212> TYPE: DNA
<213> ORGANISM: Artificial Sequence
<220> FEATURE:
<223> OTHER INFORMATION: Primer

<400> SEQUENCE: 16
gcaagcatga ttcc                                                     14

<210> SEQ ID NO 17
<211> LENGTH: 14
<212> TYPE: DNA
<213> ORGANISM: Artificial Sequence
<220> FEATURE:
<223> OTHER INFORMATION: Primer

<400> SEQUENCE: 17
gaaaggcaca ttcc                                                     14

<210> SEQ ID NO 18
<211> LENGTH: 14
<212> TYPE: DNA
<213> ORGANISM: Artificial Sequence
<220> FEATURE:
<223> OTHER INFORMATION: Primer

<400> SEQUENCE: 18
tcgatcatcg ttcc                                                     14

<210> SEQ ID NO 19
<211> LENGTH: 14
<212> TYPE: DNA
<213> ORGANISM: Artificial Sequence
<220> FEATURE:
<223> OTHER INFORMATION: Primer

<400> SEQUENCE: 19
agccttaagg ttcc                                                     14

<210> SEQ ID NO 20
<211> LENGTH: 14
<212> TYPE: DNA
<213> ORGANISM: Artificial Sequence
<220> FEATURE:
<223> OTHER INFORMATION: Primer
```

```
<400> SEQUENCE: 20
aggtaccatg ttcc                                                       14

<210> SEQ ID NO 21
<211> LENGTH: 14
<212> TYPE: DNA
<213> ORGANISM: Artificial Sequence
<220> FEATURE:
<223> OTHER INFORMATION: Primer

<400> SEQUENCE: 21
atbctcgaga cgcg                                                       14

<210> SEQ ID NO 22
<211> LENGTH: 11
<212> TYPE: DNA
<213> ORGANISM: Artificial Sequence
<220> FEATURE:
<223> OTHER INFORMATION: Primer

<400> SEQUENCE: 22
tctcgagcat g                                                          11

<210> SEQ ID NO 23
<211> LENGTH: 34
<212> TYPE: DNA
<213> ORGANISM: Artificial Sequence
<220> FEATURE:
<223> OTHER INFORMATION: Primer

<400> SEQUENCE: 23
cacaagtacg aacgtatgcg ttggccaaac actg                                 34

<210> SEQ ID NO 24
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 8
<223> OTHER INFORMATION: n=t

<400> SEQUENCE: 24
cagtgttngg gccaacgcat acgttcgtac ttgtgcgcg                            39

<210> SEQ ID NO 25
<211> LENGTH: 16
<212> TYPE: DNA
<213> ORGANISM: Artificial Sequence
<220> FEATURE:
<223> OTHER INFORMATION: Primer

<400> SEQUENCE: 25
gaccaccagg acgagc                                                     16

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
ctcgtcctgg tggtcggaa                                                  19
```

```
<210> SEQ ID NO 27
<211> LENGTH: 34
<212> TYPE: DNA
<213> ORGANISM: Artificial Sequence
<220> FEATURE:
<223> OTHER INFORMATION: Primer

<400> SEQUENCE: 27
ttggttgact agagacgagc gcaagcatga ttcc                               34

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
tcatgcttgc gctcgtctct agtcaaccaa                                    30

<210> SEQ ID NO 29
<211> LENGTH: 36
<212> TYPE: DNA
<213> ORGANISM: Artificial Sequence
<220> FEATURE:
<223> OTHER INFORMATION: Primer

<400> SEQUENCE: 29
tatgcgttgg ccaaacactg gcagatagag gtctgc                             36

<210> SEQ ID NO 30
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 1
<223> OTHER INFORMATION: n=a,t,c, or g

<400> SEQUENCE: 30
ncgtaacgac tgaatgacgt                                               20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
cgctcgatac acagctgagg                                               20

<210> SEQ ID NO 32
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 1
<223> OTHER INFORMATION: n=a,t,c or g

<400> SEQUENCE: 32
ntgctgataa ccgacggctg c                                             21
```

```
<210> SEQ ID NO 33
<211> LENGTH: 27
<212> TYPE: DNA
<213> ORGANISM: Artificial Sequence
<220> FEATURE:
<223> OTHER INFORMATION: Primer

<400> SEQUENCE: 33
aattccggaa catactagtc aacatga                                         27

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
cgatggtacg tccaggtcgc a                                               21

<210> SEQ ID NO 35
<211> LENGTH: 15
<212> TYPE: DNA
<213> ORGANISM: Artificial Sequence
<220> FEATURE:
<223> OTHER INFORMATION: Primer

<400> SEQUENCE: 35
atcgtgctgc gacct                                                      15

<210> SEQ ID NO 36
<211> LENGTH: 23
<212> TYPE: DNA
<213> ORGANISM: Artificial Sequence
<220> FEATURE:
<223> OTHER INFORMATION: Primer

<400> SEQUENCE: 36
gcacgatatg tacgatacac tga                                             23

<210> SEQ ID NO 37
<211> LENGTH: 14
<212> TYPE: DNA
<213> ORGANISM: Artificial Sequence
<220> FEATURE:
<223> OTHER INFORMATION: Primer

<400> SEQUENCE: 37
gtgccattca gtgt                                                       14

<210> SEQ ID NO 38
<211> LENGTH: 14
<212> TYPE: DNA
<213> ORGANISM: Artificial Sequence
<220> FEATURE:
<223> OTHER INFORMATION: Primer

<400> SEQUENCE: 38
tgtatgcgca ttac                                                       14

<210> SEQ ID NO 39
<211> LENGTH: 14
<212> TYPE: DNA
<213> ORGANISM: Artificial Sequence
<220> FEATURE:
<223> OTHER INFORMATION: Primer
```

```
<400> SEQUENCE: 39
tgtatgcgca ttac                                                    14

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
gcatacaaat cgataatgca c                                            21

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
cgatggtacg tccaggtcga c                                            21

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
gtgcattatc gatttgtatg c                                            21

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
ggcacattga tttgggagtc a                                            21

<210> SEQ ID NO 44
<211> LENGTH: 19
<212> TYPE: DNA
<213> ORGANISM: Artificial Sequence
<220> FEATURE:
<223> OTHER INFORMATION: Primer

<400> SEQUENCE: 44
tgactcccaa atcaatgtg                                               19

<210> SEQ ID NO 45
<211> LENGTH: 30
<212> TYPE: DNA
<213> ORGANISM: Artificial Sequence
<220> FEATURE:
<223> OTHER INFORMATION: Primer

<400> SEQUENCE: 45
ggtacgaatt cgactcggga ataccacctt                                   30

<210> SEQ ID NO 46
<211> LENGTH: 48
<212> TYPE: DNA
```

```
<213> ORGANISM: Artificial Sequence
<220> FEATURE:
<223> OTHER INFORMATION: Primer

<400> SEQUENCE: 46
cgcgagcgta cgctcgcggg tacgaattcg actcgggaat accacctt          48

<210> SEQ ID NO 47
<211> LENGTH: 29
<212> TYPE: DNA
<213> ORGANISM: Artificial Sequence
<220> FEATURE:
<223> OTHER INFORMATION: Primer

<400> SEQUENCE: 47
ggtacgaatt cgaccgggaa taccacctt                                29

<210> SEQ ID NO 48
<211> LENGTH: 10
<212> TYPE: DNA
<213> ORGANISM: Artificial Sequence
<220> FEATURE:
<223> OTHER INFORMATION: Primer

<400> SEQUENCE: 48
aattcgtacc                                                     10

<210> SEQ ID NO 49
<211> LENGTH: 10
<212> TYPE: DNA
<213> ORGANISM: Artificial Sequence
<220> FEATURE:
<223> OTHER INFORMATION: Primer

<400> SEQUENCE: 49
tcccgagtcg                                                     10

<210> SEQ ID NO 50
<211> LENGTH: 10
<212> TYPE: DNA
<213> ORGANISM: Artificial Sequence
<220> FEATURE:
<223> OTHER INFORMATION: Primer

<400> SEQUENCE: 50
aaggtggtat                                                     10

<210> SEQ ID NO 51
<211> LENGTH: 10
<212> TYPE: DNA
<213> ORGANISM: Artificial Sequence
<220> FEATURE:
<223> OTHER INFORMATION: Primer

<400> SEQUENCE: 51
tcccgtatcg                                                     10

<210> SEQ ID NO 52
<211> LENGTH: 13
<212> TYPE: DNA
<213> ORGANISM: Artificial Sequence
<220> FEATURE:
<223> OTHER INFORMATION: Primer

<400> SEQUENCE: 52
tcccgagtcg acc                                                 13
```

```
<210> SEQ ID NO 53
<211> LENGTH: 14
<212> TYPE: DNA
<213> ORGANISM: Artificial Sequence
<220> FEATURE:
<223> OTHER INFORMATION: Primer

<400> SEQUENCE: 53
tcccgagtcg tacc                                                        14

<210> SEQ ID NO 54
<211> LENGTH: 15
<212> TYPE: DNA
<213> ORGANISM: Artificial Sequence
<220> FEATURE:
<223> OTHER INFORMATION: Primer

<400> SEQUENCE: 54
tcccgagtcg gtacc                                                       15

<210> SEQ ID NO 55
<211> LENGTH: 13
<212> TYPE: DNA
<213> ORGANISM: Artificial Sequence
<220> FEATURE:
<223> OTHER INFORMATION: Primer

<400> SEQUENCE: 55
aaggtggtat acc                                                         13

<210> SEQ ID NO 56
<211> LENGTH: 14
<212> TYPE: DNA
<213> ORGANISM: Artificial Sequence
<220> FEATURE:
<223> OTHER INFORMATION: Primer

<400> SEQUENCE: 56
aaggtggtat tacc                                                        14

<210> SEQ ID NO 57
<211> LENGTH: 15
<212> TYPE: DNA
<213> ORGANISM: Artificial Sequence
<220> FEATURE:
<223> OTHER INFORMATION: Primer

<400> SEQUENCE: 57
aaggtggtat gtacc                                                       15

<210> SEQ ID NO 58
<211> LENGTH: 13
<212> TYPE: DNA
<213> ORGANISM: Artificial Sequence
<220> FEATURE:
<223> OTHER INFORMATION: Primer

<400> SEQUENCE: 58
tcccgtatcg acc                                                         13

<210> SEQ ID NO 59
<211> LENGTH: 14
<212> TYPE: DNA
<213> ORGANISM: Artificial Sequence
<220> FEATURE:
<223> OTHER INFORMATION: Primer
```

-continued

<400> SEQUENCE: 59
tccctgatcg tacc                                                                                14

<210> SEQ ID NO 60
<211> LENGTH: 15
<212> TYPE: DNA
<213> ORGANISM: Artificial Sequence
<220> FEATURE:
<223> OTHER INFORMATION: Primer

<400> SEQUENCE: 60
tccctgatcg gtacc                                                                               15

<210> SEQ ID NO 61
<211> LENGTH: 7
<212> TYPE: DNA
<213> ORGANISM: Artificial Sequence
<220> FEATURE:
<223> OTHER INFORMATION: Primer

<400> SEQUENCE: 61 attcccg                                                                                         7

<210> SEQ ID NO 62
<211> LENGTH: 10
<212> TYPE: DNA
<213> ORGANISM: Artificial Sequence
<220> FEATURE:
<223> OTHER INFORMATION: Primer

<400> SEQUENCE: 62
tggtattccc                                                                                     10

<210> SEQ ID NO 63
<211> LENGTH: 10
<212> TYPE: DNA
<213> ORGANISM: Artificial Sequence
<220> FEATURE:
<223> OTHER INFORMATION: Primer

<400> SEQUENCE: 63
gtggtattcc                                                                                     10

<210> SEQ ID NO 64
<211> LENGTH: 10
<212> TYPE: DNA
<213> ORGANISM: Artificial Sequence
<220> FEATURE:
<223> OTHER INFORMATION: Primer

<400> SEQUENCE: 64
ggtggtattc                                                                                     10

<210> SEQ ID NO 65
<211> LENGTH: 10
<212> TYPE: DNA
<213> ORGANISM: Artificial Sequence
<220> FEATURE:
<223> OTHER INFORMATION: Primer

<400> SEQUENCE: 65
aggtggtatt                                                                                     10

<210> SEQ ID NO 66
<211> LENGTH: 10
<212> TYPE: DNA

<213> ORGANISM: Artificial Sequence
<220> FEATURE:
<223> OTHER INFORMATION: Primer

<400> SEQUENCE: 66
gtcgaattcg                                                              10

<210> SEQ ID NO 67
<211> LENGTH: 10
<212> TYPE: DNA
<213> ORGANISM: Artificial Sequence
<220> FEATURE:
<223> OTHER INFORMATION: Primer

<400> SEQUENCE: 67
aattcgtagc                                                              10

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
tggtacgaat tcgactcggg                                                   20

<210> SEQ ID NO 69
<211> LENGTH: 16
<212> TYPE: DNA
<213> ORGANISM: Artificial Sequence
<220> FEATURE:
<223> OTHER INFORMATION: Primer

<400> SEQUENCE: 69
gagtcgaatt cgtacc                                                       16

<210> SEQ ID NO 70
<211> LENGTH: 16
<212> TYPE: DNA
<213> ORGANISM: Artificial Sequence
<220> FEATURE:
<223> OTHER INFORMATION: Primer

<400> SEQUENCE: 70
gggctcagct tcccca                                                       16

<210> SEQ ID NO 71
<211> LENGTH: 30
<212> TYPE: DNA
<213> ORGANISM: Artificial Sequence
<220> FEATURE:
<223> OTHER INFORMATION: Primer

<400> SEQUENCE: 71
ggtacgaatt cgactcggga ataccacctt                                        30

<210> SEQ ID NO 72
<211> LENGTH: 10
<212> TYPE: DNA
<213> ORGANISM: Artificial Sequence
<220> FEATURE:
<223> OTHER INFORMATION: Primer

<400> SEQUENCE: 72
tcccgagtcg                                                              10

```
<210> SEQ ID NO 73
<211> LENGTH: 10
<212> TYPE: DNA
<213> ORGANISM: Artificial Sequence
<220> FEATURE:
<223> OTHER INFORMATION: Primer

<400> SEQUENCE: 73
aattcgtacc                                                          10

<210> SEQ ID NO 74
<211> LENGTH: 10
<212> TYPE: DNA
<213> ORGANISM: Artificial Sequence
<220> FEATURE:
<223> OTHER INFORMATION: Primer

<400> SEQUENCE: 74
tcacctagca                                                          10

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
ggtacgaatt cgactcggga                                               20

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
tcccgagtcg aattcgtacc                                               20

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
gggctcagct tccccataat                                               20

<210> SEQ ID NO 78
<211> LENGTH: 10
<212> TYPE: DNA
<213> ORGANISM: Artificial Sequence
<220> FEATURE:
<223> OTHER INFORMATION: Primer

<400> SEQUENCE: 78
aattcgtacc                                                          10

<210> SEQ ID NO 79
<211> LENGTH: 10
<212> TYPE: DNA
<213> ORGANISM: Artificial Sequence
<220> FEATURE:
<223> OTHER INFORMATION: Primer
```

```
<400> SEQUENCE: 79
tcgtattcca                                                            10

<210> SEQ ID NO 80
<211> LENGTH: 30
<212> TYPE: DNA
<213> ORGANISM: Artificial Sequence
<220> FEATURE:
<223> OTHER INFORMATION: Primer

<400> SEQUENCE: 80
tagcgattac ggtacgaatt cgactcggga                                      30

<210> SEQ ID NO 81
<211> LENGTH: 98
<212> TYPE: DNA
<213> ORGANISM: Artificial Sequence
<220> FEATURE:
<223> OTHER INFORMATION: ligation product

<400> SEQUENCE: 81
ttggttgact agagacgagc gcaagcatga ttccgaccac caggacgagc atgctcgaga     60
cgcgcacaag tacgaacgta tgcgttggcc aaacactg                             98

<210> SEQ ID NO 82
<211> LENGTH: 97
<212> TYPE: DNA
<213> ORGANISM: Artificial Sequence
<220> FEATURE:
<223> OTHER INFORMATION: ligation product

<400> SEQUENCE: 82
cagtgtttgg caacgcatac gttcgtactt gtgcgcgtct cgagcatgct cgtcctggtg     60
gtcggaatca tgcttgcgct cgtctctagt acaccaa                              97

<210> SEQ ID NO 83
<211> LENGTH: 11
<212> TYPE: DNA
<213> ORGANISM: Artificial Sequence
<220> FEATURE:
<223> OTHER INFORMATION: Primer

<400> SEQUENCE: 83
tatctacaga g                                                          11

<210> SEQ ID NO 84
<211> LENGTH: 17
<212> TYPE: DNA
<213> ORGANISM: Artificial Sequence
<220> FEATURE:
<223> OTHER INFORMATION: Primer

<400> SEQUENCE: 84
tatctacaga gtagtct                                                    17

<210> SEQ ID NO 85
<211> LENGTH: 23
<212> TYPE: DNA
<213> ORGANISM: Artificial Sequence
<220> FEATURE:
<223> OTHER INFORMATION: Primer

<400> SEQUENCE: 85
tatctacaga gtagtctaat gac                                             23
```

```
<210> SEQ ID NO 86
<211> LENGTH: 14
<212> TYPE: DNA
<213> ORGANISM: Artificial Sequence
<220> FEATURE:
<223> OTHER INFORMATION: Primer

<400> SEQUENCE: 86
cagcctctgt agat                                                         14

<210> SEQ ID NO 87
<211> LENGTH: 16
<212> TYPE: DNA
<213> ORGANISM: Artificial Sequence
<220> FEATURE:
<223> OTHER INFORMATION: Primer

<400> SEQUENCE: 87
ctcagcctct gtagat                                                       16

<210> SEQ ID NO 88
<211> LENGTH: 18
<212> TYPE: DNA
<213> ORGANISM: Artificial Sequence
<220> FEATURE:
<223> OTHER INFORMATION: Primer

<400> SEQUENCE: 88
ggctcagcct ctgtagat                                                     18
```

TEMPLATE DIRECTED SPLIT AND MIX SYSTHESIS OF SMALL MOLECULE LIBRARIES

CROSS REFERENCE TO RELATED APPLICATIONS

This application claims priority to and is a U.S. National Phase filing of PCT International Application Number PCT/DK2005/000747, filed on Nov. 22, 2005, designating the United States of America and published in the English language, which claims priority under 35 U.S.C. §119 to Denmark Patent Application Number PA 2004 01809, filed on Nov. 22, 2004. The disclosures of the above-described applications are hereby expressly

FIELD OF INVENTION

The present invention relates to a method for synthesizing an encoded molecule. Furthermore the invention pertains to a method for identifying a molecule with desired characteristics and in certain aspects to a library of encoded molecules obtained by a method according to the invention.

GENERAL BACKGROUND AND PRIOR ART

Methods are desired for increasing the efficiency of production and screening of chemical libraries with the purpose of generation and isolation of new compounds that can be used for applications in medicine, agriculture and other areas. Active molecules, for example for use in medicine, have been identified by screening of natural materials (such as plant extracts) or chemical libraries of synthesised molecules in assays that identify molecules with the desired properties. The outcome of such screens usually only is low affinity leads, i.e. molecules that are identified in the assay, (e.g. by binding to a target molecule or by another function), but which have insufficient affinity and specificity for the target. Further improvement of the leads is therefore required, which can be done empirically or by chemical design. In either case, the process of lead optimisation is time-consuming and expensive and in many cases it does still not provide molecules with sufficient affinity and specificity for the target molecule to exert the desired function with high efficiency and without unwanted reactions to occur. Methods are required that increase the size of the compound libraries, in order to increase the diversity in the pool of molecules that is used for screening, and as the size of the libraries increase improved methods are required to identify the molecules that have the desired properties in the screening assay.

DNA-encoding of compounds provides a means to perform more efficient screens or selections where the isolated compound-DNA complexes can be identified at the end by PCR-amplification, cloning and sequencing of the DNA portion (Lerner et al., EP0643778B1). In these DNA-encoded libraries, each compound in the library is attached to a unique identifier that "encodes" the chemical structure of the molecule to which it is attached. This way, the structure of a molecule that is selected in the screening assay can easily be decoded by the attached unique identifier. DNA-encoded libraries have also been generated by means of DNA-templating. In this approach, DNA templates direct the synthesis of the encoded compounds (Walder et al., Proc. Natl. Acad. Sci. USA (1979), 76, 51-55; Bruick et al., Chemistry and Biology (1996), 3: 49-56; Liu et al., WO02/074929A2; Pedersen et al., WO02/103008A2). Moreover, when these libraries are used in affinity selection experiments, the DNA of the recovered DNA-compound complexes can be amplified by PCR, and subsequently used in a new DNA-templated synthesis round, which directly amplifies the recovered compounds.

SUMMARY OF THE INVENTION

The present invention combines the non-templated technique of Lerner with the templated technique of Walder and thereby provides an improved method for the generation of oligonucleotide-encoded libraries.

In a primary aspect the invention pertains to a method for synthesizing an encoded molecule comprising the steps of:
a) Adding a linker molecule L to one or more reaction wells;
b) Adding a molecule fragment to each of said reaction wells;
c) Adding an oligonucleotide identifier to each of said reaction wells;
d) Subjecting said wells to conditions sufficient to allow said molecule fragments and said oligonucleotide identifiers to become attached to said linker molecule, or conditions sufficient for said molecule fragments to bind to other molecule fragments and sufficient for said oligonucleotide identifiers to bind to other oligonucleotide identifiers;
e) Combining the contents of said one or more reaction wells;
f) Optionally, distributing the combined product to one or more new reaction wells;
g) Optionally, repeating steps b) to f) one or more times;
h) Contacting the resulting bifunctional molecule(s) of step e) or g) with one or more (oligonucleotide) templates each capable of hybridizing to at least one of the oligonucleotide identifiers added in step c); wherein the linker molecule L contains at least one reactive group capable of reacting with a reactive group in the molecule fragments and at least one reactive group capable of reacting with a reactive group in the oligonucleotide; the molecule fragments each contain at least one reactive group capable of reacting with a reactive group in the linker molecule L or a reactive group in another molecule fragment, and the reactive groups of each molecule fragment may be the same or different;

the oligonucleotide identifiers each contain at least one reactive group capable of reacting with a reactive group in the linker L or a reactive group in another oligonucleotide identifier, and the reactive groups of each oligonucleotide identifier may be the same or different;

the oligonucleotide identifier added to each well in step c) identifies the molecule fragment added to the same well in step b);

the steps a) to d) may be performed in any order;
the steps b) to d) in step f) may also be performed in any order;
the number of wells in steps a) and f) may be the same or different;
the oligonucleotide template optionally is associated with a reactive group.

In another aspect, the invention relates to a method for identifying a molecule with desired characteristics, said method comprising synthesizing a library of encoded molecules by a method according to the invention.

In a further aspect, the invention pertains to a library of encoded molecules obtained or obtainable by a method according to the invention.

DEFINITIONS

As used herein, the term Bi-functional molecule means a bi-functional molecule consisting of an encoded molecule (e.g. a low molecular weight organic molecule) and an oligonucleotide (e.g. a single- or double-stranded DNA molecule), where the oligonucleotide sequence uniquely identifies the identity (structure) of the encoded molecule. The encoded molecule and the identifier are physically connected through a linker moiety. In certain embodiments, several oligonucleotides encode the same encoded molecule, or several encoded molecules are encoded by one oligonucleotide (see below under "Library of bi-functional molecules").

The bi-functional molecule can have one or more molecule fragments encoded by one or more oligonucleotide identifiers depending on the number of rounds of stage 1 split and mix synthesis used to generated the molecule.

Carrier molecule: Used interchangeably with carrier and bi-functional carrier molecule. A carrier molecule is a bi-functional molecule that is employed in a Stage 2 templated synthesis, and may be generated by e.g. stage 1 synthesis. It thus consists of an encoded molecule (made up of one or more molecule fragments) and an oligonucleotide identifier (made up of one or more oligonucleotide identifiers) that uniquely identifies (encodes) the molecule fragment to which it is attached. The bi-functional carrier molecule can have one or more molecule fragments encoded by one or more oligonucleotide identifiers (depending on the number of rounds of stage 1 split and mix synthesis used to generate the carrier molecule).

Encoded molecule: The portion of the bi-functional molecule that is encoded by the oligonucleotide identifier of the bi-functional molecule. The encoded molecule is typically an organic molecule, typically of relatively low molecular weight compared to the oligonucleotide identifier to which it is attached. The encoded molecule may be released from the identifier after its synthesis, to obtain the "free encoded molecule". The encoded molecule is typically attached to the identifier through a flexible linker.

Identifier: An oligonucleotide that encodes (specifies) the identity of the molecule fragment or encoded molecule to which it is attached. For the purpose of this invention, three kinds of identifiers are described:

Unit identifier, which is the oligonucleotide used in stage 1 synthesis to describe the identity of the molecule fragment that it becomes attached to, through the nascent bi-functional molecule, during a synthesis round in stage 1 synthesis.

Carrier identifier, which is the oligonucleotide component of a carrier molecule, i.e., the carrier identifier encodes the molecule fragment to which it is attached.

Template identifier, also termed identifier template, encodes the encoded molecule attached to it after templated synthesis, or in cases where no templated synthesis is performed prior to the screening of the bi-functional molecules, encodes and identifies the encoded molecule attached to it.

Library of bi-functional molecules: A library of bi-functional molecules consists of a number of bi-functional molecules, each of which consists of an encoded molecule (e.g. low molecular weight organic molecules), attached to an identifier oligonucleotide (e.g. a single- or double-stranded DNA molecule), where the oligonucleotide sequence uniquely identifies the identity (structure) of the encoded molecule to which it is attached. In certain embodiments, several oligonucleotides encode the same encoded molecule (i.e. several bi-functional molecules in the library carry the same encoded molecule but different oligonucleotide identifiers. In other embodiments, several different encoded molecules are attached to the same oligonucleotide identifier.

Ligase enzyme: An enzyme that ligates together oligonucleotides. Ligase enzymes may also be non-protein-based catalysts that mediate the ligation of oligonucleotides, on single- or double-stranded form.

Ligation: A ligation reaction covalently links together molecules. It is primarily used here to describe the ligation of two oligonucleotides to produce one molecule, consisting of the two oligonucleotide sequences.

Linker L: The linker L is a molecule comprising a reactive group X, which is adapted for reaction with a molecule fragment, and a reactive group Z, which is adapted for ligation to an oligonucleotide fragment, and a linker Y, which connects X and Z.

Molecule fragment: A molecule fragment contains one or more reactive groups that may react with reactive groups of other molecule fragments.

Molecular Entity: Used interchangeably with encoded molecule.

Nucleic acid: Used interchangeably with oligonucleotide.

Nucleic acid analog: Used interchangeably with oligonucleotide analog and unnatural oligonucleotide.

Nucleotide: Nucleotides as used herein refers to both natural and unnatural nucleotides. Oligonucleotides made up of nucleotides are thus capable of sequence-specific hybridisation to natural oligonucleotides such as DNA and RNA. Nucleotides may differ from natural nucleotides by having a different phosphate moiety, sugar moiety, and/or base moiety.

Oligonucleotide: Oligonucleotides comprise a number of nucleotides as defined above, i.e., oligonucleotides may comprise natural as well as unnatural nucleotides. Example oligonucleotides are thus DNA, RNA, PNA, morpholinos, and LNA, and may involve unnatural bases as well.

Reactive group: Reactive groups are capable of reacting with other reactive groups to form a chemical bond. Reactive groups include —$NH_2$, —COOH, —CHO, —OH, —NHR, —$CSO_2OH$, phenylchloride, —SH, —SS, and many others. Example pairs of reactive groups, and the resulting bonds formed, are shown in FIGS. 6 and 7. The reaction between two reactive groups may be spontaneous under the conditions used, or can be catalyzed by enzymes, ribozymes or other organic or inorganic catalysts such as metals. Furthermore, additional reagents may be added that reacts with the reactive groups, in order to covalently link molecule fragments. The linkage between molecule fragments are thus typically of covalent character. However, it may also be of non-covalent character. An example of such non-covalent bond between molecule fragments of an encoded molecule is the bond formed when adding a molecule fragment comprising a metal-chelate complex (e.g., NTA-$Zn^{++}$) to a nascent bi-functional molecule comprising an imidazole functionality.

Reactive units: Used herein interchangeably with reactive groups.

As used herein the term "well" defines a physical containment of reagents, molecule fragments etc. in a localized space. A "well" thus include the well of a microtiter plate, any container, a spot of a solution on a glass plate, or other type of solid support (microarray), a reagent tube, a bead to which the reagents and molecules to be kept separated are attached, and any other type of well that separates different compositions of reagents, molecule fragments etc. as desired. The separation does not have to be absolute, but should preferably ensure that the major components of a given well are the desired components. A nanocompartment where the molecule fragment to be attached to the nascent bi-functional molecule is held in the vicinity of the reactive group of the bi-functional molecule, by hybridisation of oligonucleotide strands, also is considered a "well", since the hybridisation of the oligonucleotides keeps one reactive group (e.g., of the incoming molecule fragment) in localised space as seen from the other reactive group (e.g., of the bi-functional molecule). The complex of the bi-functional molecule and the incoming oligonucleotide-molecule fragment is therefore considered a nanocompartment and hence, under this invention, a "well".

The terms 'nucleic acid', 'nucleic acid molecule' and 'nucleic acid sequence' as used herein refer to an oligomer or polymer of ribonucleic acid (RNA) or deoxyribonucleic acid (DNA) or mimics/mimetics thereof. This term includes molecules composed of naturally-occurring nucleobases, sugars and covalent internucleoside (backbone) phosphodiester bond linkages as well as molecules having non-naturally occurring nucleobases, sugars and covalent internucleoside (backbone) linkages which function similarly or combinations thereof. Such modified or substituted nucleic acids are often preferred over native forms because of desirable properties such as, for example, enhanced cellular uptake, enhanced affinity for nucleic acid target and increased stability in the presence of nucleases and other enzymes, and are in the present context described by the terms "nucleic acid analogues" or "nucleic acid mimics". Preferred examples of nucleic acid mimics/mimetics are peptide nucleic acid (PNA-), Locked Nucleic Acid (LNA-), xylo-LNA-, phosphorothioate-, 2'-methoxy-, 2'-methoxyethoxy-, morpholino- and phosphoramidate-containing molecules or the like.

The nucleic acid, nucleic acid molecule or nucleic acid sequence may, for instance, be composed entirely of deoxyribonucleotides, entirely of ribonucleotides, entirely of nucleic acid mimics or analogues or chimeric mixtures thereof. The monomers are typically linked by internucleotide phosphodiester bond linkages. Nucleic acids typically range in size from a few monomeric units, e.g., 5-40, when they are commonly referred to as oligonucleotides, to several thousands of monomeric units. Whenever a nucleic acid or a nucleic acid sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

In the present context 'complementary sequence' or 'complement' refers to nucleotide sequences which will anneal to a nucleic acid molecule of the invention under stringent conditions. The term "stringent conditions" refers to general conditions of high, weak or low stringency. The term "stringency" is well known in the art and is used in reference to the conditions (temperature, ionic strength and the presence of other compounds such as organic solvents) under which nucleic acid hybridisations are conducted. With "high stringency" conditions, nucleic acid base pairing will occur only between nucleic acid fragments that have a high frequency of complementary base sequences, as compared to conditions of "weak" or "low" stringency.

As an example, high stringency hybridisation conditions comprise (1) low ionic strength and high temperature for washing, such as 0.015 M NaCl/0.0015 M sodium citrate, pH 7.0 (0.1×SSC) with 0.1% sodium dodecyl sulfate (SDS) at 50° C.; (2) hybridisation in 50% (vol/vol) formamide with 5×Denhardt's solution (0.1% (wt/vol) highly purified bovine serum albumin/0.1% (wt/vol) Ficoll/0.1% (wt/vol) polyvinylpyrrolidone), 50 mM sodium phosphate buffer at pH 6.5 and 5×SSC at 42° C.; or (3) hybridisation in 50% formamide, 5×SSC, 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C. with washes at 42° C. in 0.2×SSC and 0.1% SDS.

When referring to 'identical sequences' herein, again it is meant sequences having a certain degree of sequence identity. The sequences may thus be from 1-100%, such as at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 99% or 100% identical.

The term 'sequence identity' indicates a quantitative measure of the degree of homology between two nucleic acid sequences of equal length. If the two sequences to be compared are not of equal length they must be aligned to give the best possible fit, allowing the insertion of gaps or, alternatively, truncation at the ends of the polypeptide sequences or nucleotide sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$).

In all polypeptide or amino acid based embodiments of the invention the percentage of sequence identity between one or more sequences is based on alignment of the respective sequences as performed by clustalW software (http:/www.e-bi.ac.uk/clustalW/index.html) using the default settings of the program. With respect to the nucleotide-based embodiments of the invention, the percentage of sequence identity between one or more sequences is also based on alignments using the clustalW software with default settings. For nucleotide sequence alignments these settings are: Alignment=3Dfull, Gap Open 10.00, Gap Ext. 0.20, Gap separation Dist. 4, DNA weight matrix: identity (IUB).

In the present context, by 'amplification reaction' is meant a reaction that produces one or more copies of a sequence of nucleic acids by repeated extension of a probe or primer.

'Extension' may occur by virtue of polymerisation of individual nucleotide monomers, as in PCR, or it may occur by the addition of prefabricated oligonucleotide segments, as in LCR, or by a combination of these as in gap LCR or Repair Chain Reaction (RCR). Though not essential to the invention, ideally the extension reactions are performed repeatedly and the extension products themselves may serve as templates to produce an exponential generation of products.

'$T_m$' can be defined as the temperature at which 50% of a nucleic acid and its perfect complement are in duplex. The denaturation of double stranded nucleic acids causes a shift in the absorbance of UV light at 260 nm wavelength, an effect which can be assayed by determining the optical density at 260 nm ($OD_{260}$). $T_m$ is defined as the temperature corresponding to 50% denaturation, i.e. where the ($OD_{260}$) is midway between the value expected for double stranded nucleic acids and the value expected for single stranded nucleic acids. The $T_m$ of perfectly complementary duplexes can be calculated as follows:

DNA: $T_m = 81.5 + 16.6(\log_{10}[Na^+]) + 0.41(\% \, GC) - 500/\text{length}$

-continued

| | |
|---|---|
| RNA; RNA-DNA: | $T_m = 79.8 + 18.5(\log_{10}[Na^+]) +$ $0.58(\% \text{ GC}) + 11.8(\% \text{ GC})^2 - 820/\text{length}$ |
| Oligonucleotides: | $T_m = 2(\text{no. of AT pairs}) + 4(\text{no. of GC pairs})$ |

As used herein, 'nucleic acid analogue' is understood to mean a structural analogue of DNA or RNA, designed to hybridise to complementary nucleic acid sequences (1). Through modification of the internucleotide linkage(s), the sugar, and/or the nucleobase, nucleic acid analogues may attain any or all of the following desired properties: 1) optimised hybridisation specificity or affinity, 2) nuclease resistance, 3) chemical stability, 4) solubility, 5) membrane-permeability, and 6) ease or low costs of synthesis and purification. Examples of nucleic acid analogues include, but are not limited to, peptide nucleic acids (PNA), locked nucleic acids "LNA", 2'-O-methyl nucleic acids, 2'-fluoro nucleic acids, phosphorothioates, and metal phosphonates. Nucleic acid analogues are described in (2) and (3).

Abbreviations

L=Linker molecule.

$R_{1(1-m)}$=Molecule fragments from repertoire 1. The repertoire used in the corresponding round thus comprises m different molecule fragments.

$R_{2(1-m)}$=Molecule fragments from repertoire 2. The repertoire used in the corresponding round thus comprises m different molecule fragments.

$O_{1(1-m)}$=Oligonucleotides coding for molecule fragments of repertoire 1. m different oligonucleotide sequences are thus used to encode the m different molecule fragments.

$O_{1(1-m)}$=Oligonucleotides coding for molecule fragments of repertoire 2. m different oligonucleotide sequences are thus used to encode the m different molecule fragments.

$R_{1,1}$ thus is molecule fragment no. 1 of repertoire 1; $R_{1,2}$ is molecule fragment no. 2 of repertoire 2; $R_{2,17}$ thus is molecule fragment no. 17 of repertoire 2; etc.

Oligo $O_{1,1}$ codes for molecule fragment $R_{1,1}$; oligo $O_{1,2}$ codes for molecule fragment $R_{1,2}$; oligo $O_{2,m}$ codes for molecule fragment $R_{2,m}$ etc.

DETAILED DESCRIPTION OF THE INVENTION

The invention provides a method for combining the advantages of encoded molecule fragments made by split and mix synthesis with the advantages of template directed synthesis of molecules. The method provided in the invention further has the advantage that molecules in the library after selection in a screening assay can be easily identified and amplified for use in subsequent screening procedures.

In outline, the invention combines methods for producing encoded molecule fragments with methods for template directed synthesis of molecules. In the first step unique identifiers are attached to different molecule fragments, so that each different molecule fragment is "encoded" by a unique identifier. In the next step, a second molecule fragment and thereafter a second identifier are attached. Like in the first step the identifier encodes the newly attached molecule fragment. This process can be continued until the desired number and diversity of encoded molecules have been made. The resulting molecules are termed carrier molecules, where a given carrier molecule contains organic molecule fragments that are linked together, and where the linked molecule fragments are also linked to the identifiers that have also been linked together.

These carrier molecules are hereafter brought together two-and-two by complementary binding of the identifier molecules to a template that directs which two carrier molecules are brought together. Thus, each template binds two carriers. In certain embodiments, the number of carriers that bind to the same template may be 3, 4, 5, 6, 7 or more. The proximity of the molecule fragments, once they are juxtaposed on the template, allows for high fidelity chemical transfer reactions to occur in which one molecule fragment is transferred to the other and linked. In this way, the encoded molecule fragments produced by the first methods can be linked in all possible combinations to create very large libraries of molecules. Since each molecule is defined by a template the identity of the molecule, after it for example has been selected in a screening assay, can easily be determined. Furthermore, the templates of the selected molecules can easily be amplified and used for amplification of the selected molecule fragments, which can then be subjected to further rounds of screening and selection. Each round of screening will thus enrich the pool of selected molecules with molecules having the highest affinity or best function in the screening assay.

In a first aspect the invention pertains to a method for synthesizing an encoded molecule comprising the steps of:
a) Adding a linker molecule L to one or more reaction wells;
b) Adding a molecule fragment to each of said reaction wells;
c) Adding an oligonucleotide identifier to each of said reaction wells;
d) Subjecting said wells to conditions sufficient to allow said molecule fragments and said oligonucleotide identifiers to become attached to said linker molecule, or conditions sufficient for said molecule fragments to bind to other molecule fragments and sufficient for said oligonucleotide identifiers to bind to other oligonucleotide identifiers;
e) Combining the contents of said one or more reaction wells;
f) Optionally, distributing the combined product to one or more new reaction wells;
g) Optionally, repeating steps b) to f) one or more times;
h) Contacting the resulting bifunctional molecule(s) of step e) or g) with one or more (oligonucleotide) templates each capable of hybridizing to at least one of the oligonucleotide identifiers added in step c); wherein the linker molecule L contains at least one reactive group capable of reacting with a reactive group in the molecule fragment and at least one reactive group capable of reacting with a reactive group in the oligonucleotide;

the molecule fragments each contain at least one reactive group capable of reacting with a reactive group in the linker molecule L or a reactive group in another molecule fragment, and the reactive groups of each molecule fragment may be the same or different;

the oligonucleotide identifiers each contain at least one reactive group capable of reacting with a reactive group in the linker L or a reactive group in another oligonucleotide identifier, and the reactive groups of each oligonucleotide identifier may be the same or different;

the oligonucleotide identifier added to each well in step c) identifies the molecule fragment added to the same well in step b);

the steps a) to d) may be performed in any order;

the steps b) to d) in step f) may also be performed in any order;

the number of wells in steps a) and f) may be the same or different;

the oligonucleotide template optionally is associated with a reactive group.

The process outlined above may be seen as a combination of a stage 1 synthesis and a stage 2 synthesis, wherein the stage 1 synthesis comprises the steps a) to g) and the stage 2 synthesis is carried out in step h.

As mentioned, steps b) to e) may be repeated one or more times. It is to be understood, however, that when step d) is performed for the first time the conditions must allow for the molecule fragments and said oligonucleotide identifiers to become attached to said linker molecule. Accordingly, in the first round of stage 1 synthesis, the conditions must be so that the molecule fragments do not only bind to other molecule fragments.

The present invention thus provides a method for the fast generation of very large libraries of DNA-encoded molecules in an amplifiable system. In the invention the synthesis of a library is carried out in two stages by combination of two different methods. In stage 1 a repertoire of different bi-functional molecules are generated. These bi-functional molecules are called "bi-functional carrier molecules", "carrier molecules" or simply "carriers". Each bi-functional molecule consists of a molecular entity and a unique identifier that codes for the molecular entity. In one embodiment of the invention the molecular entity is a polypeptide and the identifier encoding the polypeptide is a DNA oligonucleotide.

In stage 2, the carrier molecules produced in stage 1 are used in a templated synthesis reaction, in order to create very large libraries of molecule fragments each attached to a unique identifier and each with the ability of being amplified. In one embodiment the templates are DNA oligonucleotides that are complementary to the oligonucleotide identifiers of the bi-functional carrier molecules produced in stage 1.

Stage 1:

In principle any method could be used for producing the bi-functional carrier molecules. In one embodiment this is done by split and mix synthesis of the molecular entities and identifier molecules. In a further embodiment this is done using the method in the example described below and illustrated in FIG. 1.

Example of Split and Mix Synthesis of Carriers:

The following example of split and mix synthesis of carriers is a modification of the method described by Lerner et al (Lerner, R. et al. (1993), European Patent Specification, "EP 064377881").

The example is outlined in FIG. 1. In round 1, a linker molecule is first added to wells in a microtitre plate. Repertoires of different amino acids (R, 1 through m) are hereafter added to the wells, one type of amino acid per well (i.e., a specific amino acid to each well), and operatively linked to the linker molecule. Other types of molecule fragments can be used as well, but in the present example amino acids are used. Furthermore, a unique identifier (O, 1 through m), here a DNA oligonucleotide, is added to each well and operatively linked to the linker molecule. Each well now contains a bi-functional molecule that consists of a linker molecule linked to an amino acid and an identifier oligonucleotide. Each well has a different amino acid and each amino acid is linked, via the linker, to a unique DNA oligo. The sequence of the oligo encodes the type of amino acid added to that well. The oligonucleotide can be of any length depending on the number of different amino acids that must be encoded. In the present example a DNA oligo of 12 nucleotides is used.

The content of all the wells are hereafter pooled, and then split into wells on a new microtitre plate. Each well on the new plate will now contain all the different species of bi-functional molecules generated by the above reactions. A new round of synthesis (round 2) that is similar to round 1 can hereafter be applied: first an amino acid is added to each well, one species of amino acid for each well, and linked to the amino group of the amino acids of the bi-functional molecules in the well (instead of linking to the amino group of the linker as in round 1). Likewise, different DNA oligos are added to each well and linked to the DNA-portion of the bi-functional molecules in the wells. Like in the first round, the oligos in each well have different sequences so that each newly added amino acid is uniquely encoded by the sequence of the newly added oligo. Each well now contains a bi-functional molecule consisting of a di-peptide (two amino acids) linked to an oligonucleotide through a linker molecule. The oligonucleotide, which in the present example is now 24 nucleotides long, uniquely identifies the di-peptide to which it is linked. The sequence of the first 12 nucleotides encodes the species of the first amino acid in the di-peptide and the sequence of the next 12 nucleotides encodes the identity of the second amino acid.

The amino acids used in the second round can be from the same repertoire as used in round 1, or it can be a different set of amino acids or other completely different types of molecule fragments. In the present example they are from a different repertoire of amino acids in order to increase the diversity of the molecules.

The desired coupling reactions of the reactive groups are ensured by protecting and de-protecting the relevant reactive groups of the molecules during the process.

The content of each well is hereafter pooled as after round 1. A new round of synthesis can hereafter be applied by splitting the pooled bi-functional molecules into wells on a new plate and repeating round 2, which would create bi-functional molecules consisting of tri-peptides (or other kinds of compounds made up of three molecule fragments) attached to 36-mer identifier oligos through a linker. Principally the molecules could be increased in size and diversity by applying new rounds of synthesis until the desired compound is obtained. In the present example the synthesis is terminated after round 2. The pool of bi-functional molecules that is obtained will have a diversity that depends on the number of amino acids (or other molecule fragments) used for the synthesis in round 1 and 2. If 1000 different molecule fragments are used in both rounds the number of different bi-functional molecules in the pool will be one million (1000 times 1000). The length of the attached oligos (which is in this example 24 nucleotides) is more than enough to uniquely encode the one million different compounds formed.

Thus, using this split and mix approach a repertoire of bi-functional carrier molecules have been generated. This repertoire of bi-functional carrier molecules are then used in Stage 2 to generate, through a DNA-templating approach, an even bigger repertoire of bi-functional molecules.

Stage 2:

The next stage of the library synthesis uses the bi-functional carrier molecules generated in stage 1 in DNA templated synthesis reactions, which essentially links together the bi-functional carrier molecules provided by stage 1 in different combinations. The molecules generated this way are all uniquely identifiably by attached templates that encode the bi-functional carrier molecules that were combined by the reaction. One advantage of the templated carrier synthesis reaction is that the template, in addition to being a unique identifier that encodes the carrier molecules that are linked together by the reaction, also brings the molecules into close proximity and thereby essentially eliminates the likelihood of reactions to occur with other template-carrier complexes. Another advantage, important for the present invention, is that the DNA template can easily be amplified (e.g. by PCR using appropriate primer binding sites included in the template) and serve for the amplification of molecules that are isolated in a screening assay, even if only a small number of each molecule is present in the isolated samples. The amplification allows for the execution of further rounds of screening and selection, until molecules with desired characteristics (e.g., affinity, specificity, or catalytic activity) are identified.

Several different methods of templated synthesis have been proposed as described in the background of the invention. In principle any of these methods could be used to carry out the reaction set in stage 2. In one embodiment of the invention the templated synthesis is done using the method described below and illustrated in FIG. 2.

Figure 2:
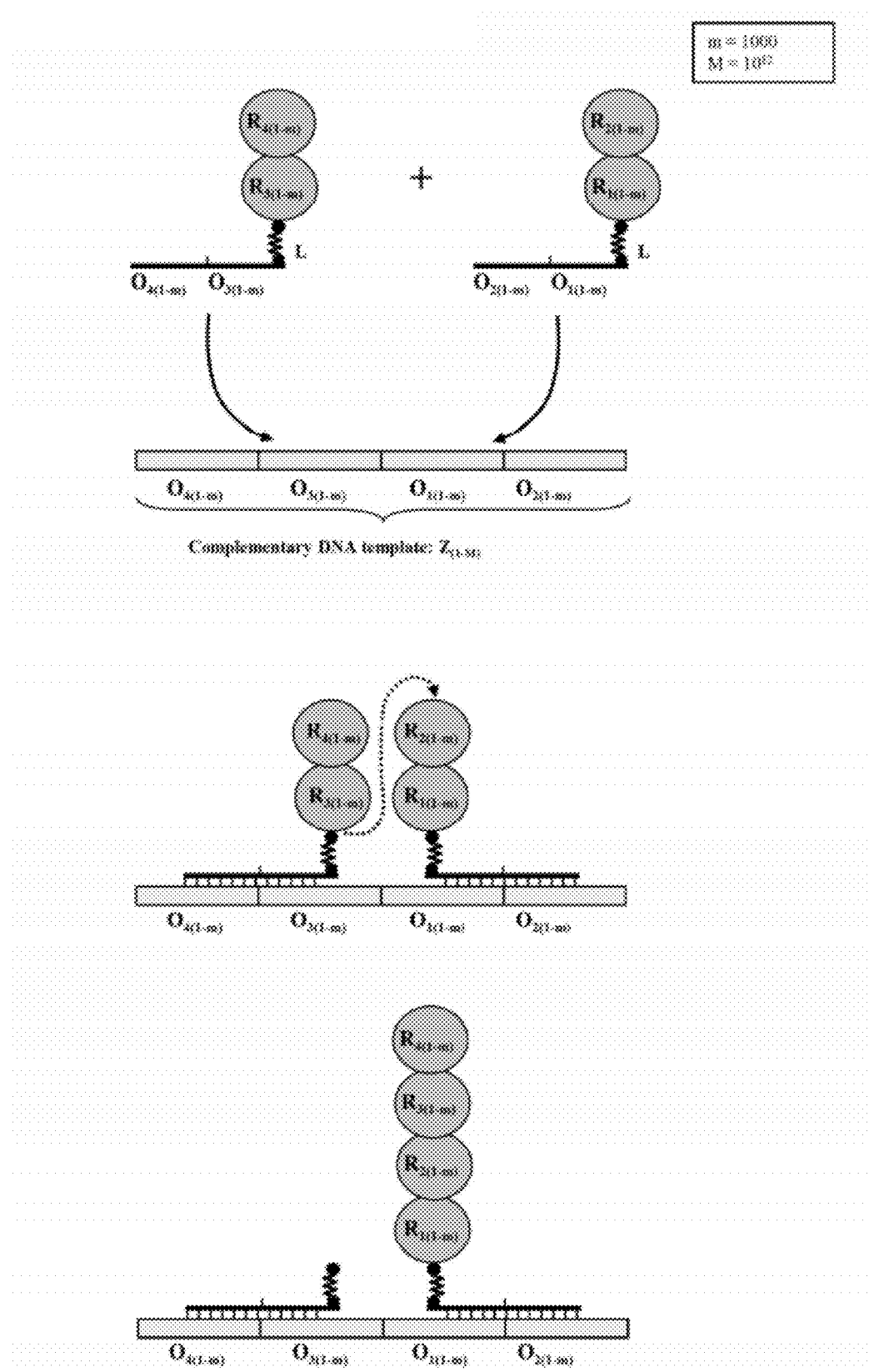

Example of Template Directed Synthesis Using Bi-Functional Carrier Molecules Generated in Stage 1 Above:

The following example is a modification of the method described by Walder et al (Walder, J. A. et al. (1979) *Proc. Natl. Acad. Sci.,* 76; 51-55). FIG. 2 shows an example of templated synthesis using templates that are complementary to pairs of bi-functional carrier molecules generated in step 1. Thus, two bi-functional carrier molecules, each comprising an encoded molecule generated in Stage 1 above (thus, in this example, a di-peptide) that is linked to a unique DNA oligonucleotide identifier (in this example, a 24-nucleotide DNA oligo), are brought into close proximity through hybridisation of the carriers' DNA portion to a complementary DNA template. The sequence of the DNA template thus determines which carrier molecules bind to the template. A reaction between the reactive groups of the two carriers hybridised to the same template may now be induced. In the present example, the design of the molecule fragments in Stage 1 led to carrier molecules that can react through an acylation reaction in Stage 2. Thus, an acyl transfer reaction (see e.g., FIGS. 3 and 6A) leads to the transfer of the encoded molecule (here, a di-peptide) of one carrier onto the encoded molecule (here, a di-peptide) of the other carrier, resulting in the generation of a bi-functional molecule where the encoded molecule (here, a tetra-peptide) is linked, covalently or non-covalently (in this example non-covalently) to a template that encodes the combination of the di-peptides and thus, ultimately encodes the tetrapeptide.

The acyl transfer leaves the donor carrier as an "empty" oligonucleotide without encoded molecule. Both the empty donor carrier and the acceptor carrier molecule (now carrying the full encoded molecule, here the tetrapeptide) may be attached to the DNA template throughout the acyl transfer reaction. In order to keep the encoded molecule (tetrapeptide) physically associated with a DNA that encodes it, the two carriers must be linked together, or alternatively the carrier that carries the encoded molecule (the tetra-peptide) must be linked covalently or non-covalently to the DNA template. Several ways to ensure the association of the encoded molecule with a DNA molecule that encodes it can be envisioned, some of which are shown in the section "alternative methods for templated synthesis using carriers".

In a simple embodiment, the link to the DNA template is kept by conducting the subsequent screening of the library under conditions that does not disrupt the hybridisation of the oligonucleotide identifiers of the carriers to the template.

In the present invention, as shown in the example in FIG. 2, the carrier molecules used in the templated synthesis in stage 2 originate from the repertoire of different bi-functional di-peptide carrier molecules generated by the reactions in stage 1. These are di-peptides attached through a linker to a 24-mer oligonucleotide, where the first 12 nucleotides encode the first amino acid of the di-peptide and the next 12 nucleotides encode the second amino acid. A library of DNA templates is therefore synthesised where each template consists of a coding sequence of 48 nucleotides; the first 24 nucleotides are complementary to the 24-mer identifier oligonucleotide of one di-peptide carrier molecule from stage 1 and the last 24 nucleotides are complementary to another 24-mer oligo from the repertoire of carrier molecules. Thus, the sequence of the template encodes which di-peptide carriers can bind and thereby it encodes and uniquely identifies the four amino acid polypeptides that result from the transfer of one di-peptide onto the other in the acyl transfer reaction. The two carrier molecules from stage 1 that are encoded by the template can be from the same repertoire or from two different sets of bi-functional carriers. In the present example they originate from different repertoires.

If one million different bi-functional carrier molecules were generated in stage 1 in the example and combined in stage 2 with another set of one million different bi-functional carriers, the diversity of the resulting library of molecules generated in stage 2 would be $10^{12}$ (1 million times 1 million) different four amino acid polypeptides. If different repertoires of amino acids and carriers are used in stage 1 and 2, respectively, a total of up to 4000 different amino acids would be required to carry out the synthesis as in the present example. If the same repertoire of amino acids was used only 1000 different amino acids would be required, but the resulting library would be less complex although it would still contain $10^{12}$ different molecules.

During Stage 1, the oligonucleotide identifiers may be linked to the linker or to the oligonucleotide portion of the nascent bi-functional molecule by enzymatic means, e.g. by ligases (e.g. T4 DNA ligase, *E. coli* DNA ligase, or T7 DNA ligase for double stranded DNA fragments, or T4 RNA ligase for single-stranded DNA fragments), or by chemical ligation. Several methods for chemical ligation are known in the art, such as the 5'-phosphoimidazolid method (Visscher, J., Shwartz, A. W. *Journal of Molecular Evolution* (1988), 28, 3-6; Zhao, Y., Thorson, J. S. *Journal of Organic Chemistry* (1998), 63, 7568-7572), or the 3'-phosphothioate method (Alvarez et al., *Journal of Organic Chemistry* (1999), 64, 6319-28; Pirrung et al., *Journal of Organic Chemistry* (1998) 63, 241-46). Other means of ligating together two oligonucleotides include the use of CNBr as a condensating agent for chemical ligation (Sokolova, N. I., et al., *FEBS Letters* (1988), 232, 153-155; Dolinnaya, N. G. et al., *Nucl. Acids. Res.* (1993), 21, 5403-5407); reductive amination between juxtaposed amine and aldehyde groups (Goodwin, J. T., and Lynn, D. G., *J. Am. Chem. Soc.* (1992), 114, 9197-9198); disulfide bond formation (e.g. reaction of a thiol and an activated disulfide such as pyridyl disulfide); reaction between pyrophosphate-activated 5'-phosphate and 3'-hydroxyl, to form a phosphodiester bond (Rohatgi, R., et al., *J. Am. Chem. Soc.* (1996), 118, 3332-3339); a tosyl displacement reaction (Herrlein, M. K., et al, *J. Am. Chem. Soc.* (1995), 117, 10151-10152); and reaction of 5'-iodonucleoside and 3-phosphothioate (Yanzheng, X., and Kool, E. T., *Tetrahedron Letters* (1997), 38, 5595-5598.

Some of the ligation reactions generate natural phosphodiester bonds, while other ligation reactions generate non-natural bonds between the ligated oligonucleotides. Some of the more effective methods for forming natural phosphodiester bonds utilise activation of a phosphoryl group with CNBr, cyanoimidazole or water soluble carbodiimide, described in the following papers: Wang, E., Yanagawa, H. *Biochemistry* (1986), 25, 7423-7430; Shabarova, Z. A., *Biochemie* (1988), 70, 1323-1334; Dolinnaya, N. G., Merenkova, I. N., Shabarova, Z. A. *Nucleosides Nucleotides* (1994), 13, 2169-2183; Kool, E. T. *J. Am. Chem. Soc.* (1991), 113, 6265-6266; Ashley, G. W., Kushlan, D. M. *Biochemistry* (1991), 30, 2927-2933; Luebke, K. J., Dervan, P. B., *J. Am. Chem. Soc.* (1991), 113, 7447-7448; Luebke, K. J., Dervan, P. B. *Nucl. Acids Res.* (1992), 20, 3005-3009; Gao, H., et al., *Bioconjugate Chem.* (1994), 5, 445-453. In particular, 3'-OH and 5'-phosphate groups, or functional derivatives thereof, have been used to ligate together oligonucleotides, to form a natural phosphodiester bond. Other examples of reactions that may be used to link together identifiers, and the bonds resulting from those reactions, are shown in FIGS. 6 and 7.

The standard phosphoramidite method for oligonucleotide synthesis may also be applied for chemical ligation. For both enzymatic and chemical ligation it is preferable that the DNA fragments to be ligated are on double-stranded form and with overhangs. In stage 1 synthesis, the identifier may be attached as a double stranded oligonucleotide or a single stranded oligonucleotide, and likewise, the identifier of the nascent bi-functional molecule may be on double- or single-stranded form. The incoming oligonucleotide may be attached by ligation (chemical or enzymatic) of one or two strands, or may be attached by non-covalent interaction of the incoming identifier and the oligonucleotide of the bi-functional molecule, e.g. by annealing of complementary oligonucleotide regions of the incoming oligonucleotide and the bi-functional molecule, or by a third oligonucleotide and the incoming identifier/bi-functional molecule.

In a preferred embodiment the oligonucleotide identifiers are not de-protected (after the phosphoramidite synthesis of individual identifiers), prior to their linking in the Stage 1 synthesis. This will allow conditions to be applied in the linking of molecule fragments and linking of oligonucleotide identifiers during the stage 1 process that could not otherwise easily have been applied, such as the use of certain organic solvents. As an example, if the reaction that is used for linking two unit identifiers together during a stage 1 synthesis require relatively strong acidic conditions, and the use of an organic solvent such as DMF, it may be desirable to use oligonucleotides, for which the nucleic acid bases have not been deprotected, as this will make them less vulnerable to acidic conditions, and also, will make them more soluble in organic solvents such as DMF. Then, after the stage 1 synthesis of the carrier molecule, the oligonucleotide component may be deprotected, to allow efficient sequence specific interaction between the carrier and the template in a stage 2 synthesis.

Finally, the ligation of unit identifiers may lead to linear as well as branched products.

An alternative method for performing stage 1 synthesis involves the hybridisation between the bi-functional molecule and the incoming oligonucleotide, where then an extension reaction is performed using e.g. a polymerase to extend from the 3'-end of the bi-functional molecule, to add an identifier sequence (Freskgård et al., WO 2004/039825 A2, Enzymatic Encoding). Polymerases that may be used in this approach include Reverse transcriptase, DNA polymerase, RNA polymerase, Taq polymerase, Pfu polymerase, Vent polymerase, Klenow fragment, and many others.

During templated synthesis in stage 2 the oligonucleotide portions of the carrier molecules may be ligated together by enzymatic or chemical ligation.

During both stage 1 and stage 2, the bi-functional molecules may be immobilised to solid support, allowing simple and efficient removal of reagents and by-products, as well as allowing the use of organic solvents that might otherwise precipitate molecule fragments, oligonucleotides or bi-functional molecules.

A wide range of conditions may be applied to mediate the reaction between the nascent bi-functional molecule and the molecule fragment. These include the addition of catalysts, base, acid, or reagents that take part in the reaction. The latter may react with both the nascent bi-functional molecule and the molecule fragment, and thus may end up as a bridge or linker that links the nascent bi-functional molecule and the molecule fragment. Such linking moeties include di-carboxylic acids (where for example the reactive groups to become linked are two amines), or di-amines (where two carboxylic acids become linked through the linking moiety).

Reactive groups of the present invention include aldehydes, hydroxyls, isocyanate, thiols, amines, esters, thioesters, carboxylic acids, triple bonds, double bonds, ethers, acid chlorides, phosphates, imidazoles, halogenated aromatic rings, any precursors thereof, or any protected reactive groups. Examples of reactive groups that can be employed during stage 1, and the bonds resulting from these reactions, are shown in FIGS. 6 and 7. Reactions that may be employed during stage 1 synthesis include acylation (formation of amide, pyrazolone, isoxazolone, pyrimidine, comarine, quinolinon, phthalhydrazide, diketopiperazine, benzodiazepinone, and hydantoin), alkylation, vinylation, disulfide formation, Wittig reaction, Horner-Wittig-Emmans reaction, arylation (formation of biaryl or vinylarene), condensation reactions, cycloadditions ((2+4), (3+2)), addition to carbon-carbon multiplebonds, cycloaddition to multiple bonds, addition to carbon-hetero multiple bonds, nucleophilic aromatic substitution, transition metal catalyzed reactions, as well as the reaction types listed below, and may involve formation of ethers, thioethers, secondary amines, tertiary amines, beta-hydroxy ethers, beta-hydroxy thioethers, beta-hydroxy amines, beta-amino ethers, amides, thioamides, oximes, sulfonamides, di- and tri-functional compounds, substituted aromatic compounds, vinyl substituted aromatic compounds, alkyn substituted aromatic compounds, biaryl compounds, hydrazines, hydroxylamine ethers, substituted cycloalkenes, substituted cyclodienes, substituted 1, 2, 3 triazoles, substituted cycloalkenes, beta-hydroxy ketones, beta-hydroxy aldehydes, vinyl ketones, vinyl aldehydes, substituted alkenes, substituted alkenes, substituted amines, and many others.

Molecule Fragments, Identifiers and Reagents.

In stage 1 synthesis, any number of molecule fragments may be linked to the nascent bi-functional molecule during a synthesis round. Thus, 0, 1, 2, 3 or more molecule fragments may be linked to the nascent bi-functional molecule in a given synthesis round. In the same synthesis round an identifier encoding the molecule fragment(s) that were linked to the nascent bi-functional molecule is linked to the nascent oligonucleotide of the bi-functional molecule. Thus, one identifier may encode a combination of several molecule fragments, and also, may encode molecule fragment(s), reagent(s), catalyst(s) and conditions employed. In such cases, two different identifiers may encode the same molecule fragment but different reaction conditions. If desired, more than one identifier may be linked to the nascent oligonucleotide. For example, if two molecule fragments are reacted with the nascent bi-functional molecule, one may choose to also link two identifiers to the nascent oligonucleotide. However, in most cases one identifier is used to encode all the molecule fragments added in a given synthesis round.

In a given synthesis round, the attachment of the molecule fragment(s) to the nascent bi-functional molecule can be performed before, simultaneously with, or after the attachment of the identifier(s) encoding said molecule fragments.

In stage 2 synthesis, any number of carriers may be added simultaneously, in order to transfer 0, 1, 2, 3, 4 or more molecule fragments to the nascent bi-functional molecule. Alternatively, carriers are added sequentially or partly sequentially (e.g. two carriers at a time), and therefore, the molecule fragments of the final bi-functional molecule are made up of molecule fragments that have been transferred simultaneously, partly sequentially or fully sequentially (i.e., one at a time).

During the templated synthesis of stage 2, the molecule fragments are attached to the oligonucleotide identifiers prior to reaction between carriers. During the templated synthesis, the molecule fragment of one carrier is transferred to another carrier. This may involve a direct transfer in which the reaction between two reactive groups directly leads to a transfer of one molecule fragment from one carrier to another (FIG. 3A). Reactions that mediate the direct transfer of one molecule fragment from one carrier to another carrier include the reactions listed in FIG. 6. Alternatively, a transfer may involve first a reaction between the reactive groups, followed by cleavage of the bond linking one molecule fragment to the carrier, which will result in the transfer of that molecule fragment onto the other carrier (FIG. 3B). Types of direct and indirect transfer reactions, as well as the bonds resulting from the reaction of reactive groups, are shown in FIGS. 6 and 7. A number of reactions for stage 1 and stage 2 synthesis are listed below.

In certain embodiments the molecule fragments remain associated with both carriers after the reaction step of Stage 2, i.e., it is not a requirement in the present invention that the molecule fragments are transferred from one carrier to another.

Reaction Conditions Compatible with Stage 1 and Stage 2 Synthesis of Bifunctional Molecules.

Stage 1 and stage 2 reactions can occur in aqueous or non-aqueous (i.e., organic) solutions, or a mixture of one or more aqueous and non-aqueous solutions. In aqueous solutions, reactions can be performed at pH ranges from about 2 to about 12, or preferably from about 2 to about 10, or more preferably from about 4 to about 10. The reactions used in DNA-templated chemistry preferably should not require very basic conditions (e.g., pH>13, pH>10), or very acidic conditions (e.g., pH<1, pH<2, pH<4), because extreme conditions may lead to degradation or modification of the nucleic acid template and/or encoded molecule being synthesized. The aqueous solution can contain one or more inorganic salts, including, but not limited to, NaCl, $Na_2SO_4$, KCl, $Mg^{+2}$, $Mn^{+2}$, etc., at various concentrations.

Organic solvents suitable for stage 1 and stage 2 reactions include, but are not limited to, methylene chloride, chloroform, dimethylformamide, and organic alcohols, including methanol and ethanol. To permit quantitative dissolution of reaction components in organic solvents, quaternized ammonium salts, such as, for example, long chain tetraalkylammonium salts, can be added (Jost et al. (1989) NUCLEIC ACIDS RES. 17:2143; Melnikov et al. (1999) LANGMUIR 15: 1923-1928).

Stage 1 or stage 2 reactions may require a catalyst, such as, for example, homogeneous, heterogeneous, phase transfer, and asymmetric catalysis. In other embodiments, a catalyst is not required. The presence of additional, accessory reagents not linked to a nucleic acid are preferred in some embodiments. Useful accessory reagents can include, for example, oxidizing agents (e.g., $NaIO_4$; reducing agents (e.g., NaC-$NBH_3$); activating reagents (e.g., EDC, NHS, and sulfo-NHS); transition metals such as nickel (e.g., $Ni(NO_3)_2$), rhodium (e.g. $RhCl_3$), ruthenium (e.g. $RuCl_3$), copper (e.g. $Cu(NO_3)_2$), cobalt (e.g. $COCl_2$), iron (e.g. $Fe_(NO_3)_3$), osmium (e.g. $OsO_4$), titanium (e.g. $TiCl_4$ or titanium tetraisopropoxide), palladium (e.g. $NaPdCl_4$), or Ln; transition metal ligands (e.g., phosphines, amines, and halides); Lewis acids; and Lewis bases.

Reaction conditions preferably are optimized to suit the nature of the reactive units and oligonucleotides used.

Reaction Types Compatible with Stage 1 and Stage 2 Synthesis.

Known chemical reactions for synthesizing polymers, small molecules, or other chemical compounds can be used in stage 1 and stage 2 synthesis reactions. Thus, reactions such as those listed in *March's Advanced Organic Chemistry, Organic Reactions, Organic Syntheses*, organic text books, journals such as *Journal of the American Chemical Society, Journal of Organic Chemistry, Tetrahedron, etc.*, and Carruther's *Some Modern Methods of Organic Chemistry* can be used. The chosen reactions preferably are compatible with nucleic acids such as DNA or RNA or are compatible with the modified nucleic acids used as the template.

Reactions useful in stage 1 and stage 2 synthesis include, for example, substitution reactions, carbon-carbon bond forming reactions, elimination reactions, acylation reactions, and addition reactions. An illustrative but not exhaustive list of aliphatic nucleophilic substitution reactions useful in the present invention includes, for example, $S_N2$ reactions, $S_N1$ reactions, $S_Ni$ reactions, allylic rearrangements, nucleophilic substitution at an aliphatic trigonal carbon, and nucleophilic substitution at a vinylic carbon.

Specific aliphatic nucleophilic substitution reactions with oxygen nucleophiles include, for example, hydrolysis of alkyl halides, hydrolysis of gen-dihalides, hydrolysis of 1,1,1-trihalides, hydrolysis of alkyl esters or inorganic acids, hydrolysis of diazo ketones, hydrolysis of acetal and enol ethers, hydrolysis of epoxides, hydrolysis of acyl halides, hydrolysis of anhydrides, hydrolysis of carboxylic esters, hydrolysis of amides, alkylation with alkyl halides (Williamson Reaction), epoxide formation, alkylation with inorganic esters, alkylation with diazo compounds, dehydration of alcohols, transetherification, alcoholysis of epoxides, alkylation with onium salts, hydroxylation of silanes, alcoholysis of acyl halides, alcoholysis of anhydrides, esterfication of carboxylic acids, alcoholysis of carboxylic esters (transesterfication), alcoholysis of amides, alkylation of carboxylic acid salts, cleavage of ether with acetic anhydride, alkylation of carboxylic acids with diazo compounds, acylation of carboxylic adds with acyl halides; acylation of carlpoxylic adds with carboxylic acids, formation of oxoniiim salts, preparation of peroxides arid hydroperoxides, preparation of inorganic esters (e.g., nitrites, nitrates, sulfonates), preparation of alcohols from amines, arid preparation of mixed organic-inorganic anhydrides.

Specific aliphatic nucleophilic substitution reactions with sulfur nucleophiles, which tend to be better nucleophiles than their oxygen analogs, include, for example, attack by SH at an alkyl carbon to form thiols, attack by S at an alkyl carbon to form thioethers, attack by SH or SR at an acyl carbon, formation of disulfides, formation of Bunte salts, alkylation of sulfuric acid salts, and formation of alkyl thiocyanates.

Aliphatic nucleophilic substitution reactions with nitrogen nucleophiles include, for example, alkylation of amines, N-arylation of amines, replacement of a hydroxy by an amino group, transamination, transamidation, alkylation of amines with diazo compounds, animation of epoxides, amination of oxetanes, amination of aziridines, amination of alkanes, formation of isocyanides, acylation of amines by acyl halides, acylation of amines by anhydrides, acylation of amines by carboxylic adds, acylation of amines by carboxylic esters, acylation of amines by amides, acylation of amines by other acid derivatives, N-alkylation or N-arylation of amides and imides, N-acylation of amides and imides, formation of aziridines from epoxides, formation of nitro compounds, formation of azides, formation of isocyanates and isothiocyanates, and formation of azoxy compounds.

Aliphatic nucleophilic substitution reactions with halogen nucleophiles include, for example, attack at an alkyl carbon, halide exchange, formation of alkyl halides from esters of sulfuric and sulfonic acids, formation of alkyl halides from alcohols, formation of alkyl halides from ethers, formation of halohydrins from epoxides, cleavage of carboxylic esters with lithium iodide, conversion of diazo ketones to alpha-halo ketones, conversion of amines to halides, conversion of tertiary amines to cyanamides (the von Braun reaction), formation of acyl halides from carboxylic adds, and formation of acyl halides from acid derivatives.

Aliphatic nucleophilic substitution reactions using hydrogen as a nucleophile include, for example, reduction of alkyl halides, reduction of tosylates, other sulfonates, and similar compounds, hydrogenolysis of alcohols, hydrogenolysis of esters (Barton-McCombie reaction), hydrogenolysis of nitriles, replacement of alkoxyl by hydrogen, reduction of epoxides, reductive cleavage of carboxylic esters, reduction of a C—N bond, desulfurization, reduction of acyl halides, reduction of carboxylic acids, esters, and anhydrides to aldehydes, and reduction of amides to aldehydes.

Although certain carbon nucleophiles may be too nucleophilic and/or basic to be used in certain embodiments of the invention, aliphatic nucleophilic substitution reactions using carbon nucleophiles include, for example, coupling with silanes, coupling of alkyl halides (the Wurtz reaction), the reaction of alkyl halides and sulfonate esters with Group I (I A), and II (II A) organometallic reagents, reaction of alkyl halides and sulfonate esters with organocuprates, reaction of alkyl halides and sulfonate esters with other organometallic reagents; allylic and propargylic coupling with a halide substrate, coupling of organometallic reagents with esters of sulfuric and sulfonic acids, sulfoxides, and sulfones, coupling involving alcohols, coupling of organometallic reagents with carboxylic esters, coupling of organometallic reagents with compounds containing an ester linkage, reaction of organometallic reagents with epoxides, reaction of organometallics with aziridine, alkylation at a carbon bearing an active hydrogen, alkylation of ketones, nitriles, and carboxylic esters, alkylation of carboxylic acid salts, alkylation at a position alpha to a heteroatom (alkylation of 1,3-dithianes), alkylation of dihydro-1,3-oxazine (the Meyers synthesis of aldehydes, ketones, and carboxylic acids), alkylation with trialkylboranes, alkylation at an alkynyl carbon, preparation of nitriles, direct conversion of alkyl halides to aldehydes and ketones, conversion of alkyl halides, alcohols, or alkanes to carboxylic acids and their derivatives, the conversion of acyl halides to ketones with organometallic compounds, the conversion of anhydrides, carboxylic esters, or amides to ketones with organometallic compounds, the coupling of acyl halides, acylation at a carbon bearing an active hydrogen, acylation of carboxylic esters by carboxylic esters (the Claisen and Dieckmann condensation), acylation of ketones and nitriles with carboxylic esters, acylation of carboxylic acid salts, preparation of acyl cyanides, and preparation of diazo ketones, ketonic decarboxylation.

Reactions which involve nucleophilic attack at a sulfonyl sulfur atom may also be used in the present invention and include, for example, hydrolysis of sulfonic acid derivatives (attack by OH), formation of sulfonic esters (attack by OR), formation of sulfonamides (attack by nitrogen), formation of sulfonyl halides (attack by halides), reduction of sulfonyl chlorides (attack by hydrogen), and preparation of sulfones (attack by carbon).

Aromatic electrophilic substitution reactions may also be used in stage 1 and stage 2 synthesis schemes. Hydrogen exchange reactions are examples of aromatic electrophilic substitution reactions that use hydrogen as the electrophile. Aromatic electrophilic substitution, reactions which use nitrogen electrophiles include, for example, nitration and nitro-dehydrogenation, nitrosation of nitroso-de-hydrogenation, diazonium coupling, direct introduction of the diazonium group, and amination or amino-dehydrogenation. Reactions of this type with sulfur electrophiles include, for example, sulfonation, sulfo-dehydrogenation, halosulfonation, halosulfo-dehydrogenation, sulfurization, and sulfonylation. Reactions using halogen electrophiles include, for example, halogenation, and halo-dehydrogenation. Aromatic electrophilic substitution reactions with carbon electrophiles include, for example, Friedel-Crafts alkylation, alkylation, alkyl-dehydrogenation, Friedel-Crafts arylation (the Scholl reaction), Friedel-Crafts acylation, formylation with disubstituted formamides, formylation with zinc cyanide and HCl (the Gatterman reaction), formylation with chloroform (the Reimer-Tiemami reaction), other formylations, formyl-dehydrogenation, carboxylation with carbonyl halides, carboxylation with carbon dioxide (the Kolbe-Schmitt reaction), amidation with isocyanates, N-alkylcarbamoyl-dehydrogenation, hydroxyalkylation, hydroxyalkyl-dehydrogenation, cyclodehydration of aldehydes and ketones, haloalkylation, halo-dehydrogenation, aminoalkylation, amidoalkylation, dialkylaminoalkylation, dialkylamino-dehydrogenation, thioalkylation, acylation with nitriles (the Hoesch reaction), cyanation, and cyano-de hydrogenation. Reactions using oxygen electrophiles include, for example, hydroxylation and hydroxy-dehydrogenation.

Rearrangement reactions include, for example, the Fries rearrangement, migration of a nitro group, migration of a nitroso group (the Fischer-Hepp Rearrangement), migration of an arylazo group, migration of a halogen (the Orton rearrangement), migration of an alkyl group, etc. Other reaction on an aromatic ring include the reversal of a Friedel-Crafts alkylation, decarboxylation of aromatic aldehydes, decarboxylation of aromatic acids, the Jacobsen reaction, deoxygenation, desulfonation, hydro-desulfonation, dehalogenation, hydro-dehalogenation, and hydrolysis of organometallic compounds.

Aliphatic electrophilic substitution reactions are also useful. Reactions using the $S_E I$, $S_E 2$ (front), $S_E 2$ (back), $S_E i$, addition-elimination, and cyclic mechanisms can be used in the present invention. Reactions of this type with hydrogen as the leaving group include, for example, hydrogen exchange (deuterio-de-hydrogenation, deuteriation), migration of a double bond, and keto-enol tautomerization. Reactions with halogen electrophiles include, for example, halogenation of aldehydes and ketones, halogenation of carboxylic adds and acyl halides, and halogenation of sulfoxides and sulfones. Reactions with nitrogen electrophiles include, for example, aliphatic diazonium coupling, nitrosation at a carbon bearing an active hydrogen, direct formation of diazo compounds, conversion of amides to alpha-azido amides, direct amination at an activated position, and insertion by nitrenes. Reactions with sulfur or selenium electrophiles include, for example, sulfenylation, sulfonation, and selenylation of ketones and carboxylic esters. Reactions with carbon electrophiles include, for example, acylation at an aliphatic carbon, conversion of aldehydes to beta-keto esters or ketones, cyanation, cyano-de-hydrogenation, alkylation of alkanes, the Stork enamine reaction, and insertion by carbenes. Reactions with metal electrophiles include, for example, metalation with organometallic compounds, metalation with metals and strong bases, and conversion of enolates to silyl enol ethers. Aliphatic electrophilic substitution reactions with metals as leaving groups include, for example, replacement of metals by hydrogen, reactions between organometallic reagents and oxygen, reactions between organometallic reagents and peroxides, oxidation of trialkylboranes to borates, conversion of Grignard reagents to sulfur compounds, halo-demetalation, the conversion of organometallic compounds to amines, the conversion of organometallic compounds to ketones, aldehydes, carboxylic esters and amides, cyano-de-metalation, transmetalation with a metal, transmetalation with a metal halide, transmetalation with an organometallic compound, reduction of alkyl halides, metallo-de-halogenation, replacement of a halogen by a metal from an organometallic compound, decarboxylation of aliphatic acids, cleavage of alkoxides, replacement of a carboxyl group by an acyl group, basic cleavage of beta-keto esters and beta-diketones, haloform reaction, cleavage of non-enolizable ketones, the Haller-Bauer reaction, cleavage of alkanes, decyanation, and hydro-de-cyanation. Electrophilic substitution reactions at nitrogen include, for example, diazotization, conversion of hydrazines to azides, N-nitrosation, N-nitroso-de-hydrogenation, conversion of amines to azo compounds, N-halogenation, N-halo-de-hydrogenation, reactions of amines with carbon monoxide, and reactions of amines with carbon dioxide.

Aromatic nucleophilic substitution reactions may also be used in the present invention. Reactions proceeding via the $S_NAr$ mechanism, the $S_N1$ mechanism, the benzyne mechanism, the $S_{RN}1$ mechanism, or other mechanism, for example, can be used. Aromatic nucleophilic substitution reactions with oxygen nucleophiles include, for example, hydroxy-de-halogenation, alkali fusion of sulfonate salts, and replacement of OR or OAr. Reactions with sulfur nucleophiles include, for example, replacement by SH or SR. Reactions using nitrogen nucleophiles include, for example, replacement by $NH_2$, NHR, or $NR_2$, and replacement of a hydroxy group by an amino group: Reactions with halogen nucleophiles include, for example, the introduction halogens. Aromatic nucleophilic substitution reactions with hydrogen as the nucleophile include, for example, reduction of phenols and phenolic esters and ethers, and reduction of halides and nitro compounds. Reactions with carbon nucleophiles include, for example, the Rosenmund-von Braun reaction, coupling of organometallic compounds with aryl halides, ethers, and carboxylic esters, arylation at a carbon containing an active hydrogen, conversions of aryl substrates to carboxylic acids, their derivatives, aldehydes, and ketones, and the Ullmann reaction. Reactions with hydrogen as the leaving group include, for example, alkylation, arylation, and amination of nitrogen heterocycles. Reactions with $N_2^+$ as the leaving group include, for example, hydroxy-de-diazoniation, replacement by sulfur-containing groups, iodo-de-diazoniation, and the Schiemann reaction. Rearrangement reactions include, for example, the von Richter rearrangement, the Sommelet-Hauser rearrangement, rearrangement of aryl hydroxylamines, and the Smiles rearrangement. Reactions involving free radicals can also be used, although the free radical reactions used in nucleotide-templated chemistry should be carefully chosen to avoid modification or cleavage of the nucleotide template. With that limitation, free radical substitution reactions can be used in the present invention. Particular free radical substitution reactions include, for example, substitution by halogen, halogenation at an alkyl carbon, allylic halogenation, benzylic halogenation, halogenation of aldehydes, hydroxylation at an aliphatic carbon, hydroxylation at an aromatic carbon, oxidation of aldehydes to carboxylic adds, formation of cyclic ethers, formation of hydroperoxides, formation of peroxides, acyloxylation, acyloxy-de-hydrogenation, chlorosulfonation, nitration of alkanes, direct conversion of aldehydes to amides, amidation and amination at an alkyl carbon, simple coupling at a susceptible position, coupling of alkynes, arylation of aromatic compounds by diazonium salts, arylation of activated alkenes by diazonium salts (the Meerwein arylation), arylation and alkylation of alkenes by organopalladium compounds (the Heck reaction), arylation and alkylation of alkenes by vinyltin compounds (the Stille reaction), alkylation and arylation of aromatic compounds by peroxides, photochemical arylation of aromatic compounds, alkylation, acylation, and carbalkoxylation of nitrogen heterocycles. Particular reactions in which $N_2^+$ is the leaving group include, for example, replacement of the diazonium group by hydrogen, replacement of the diazonium group by chlorine or bromine, nitro-de-diazoniation, replacement of the diazonium group by sulfur-containing groups, aryl dimerization with diazonium salts, methylation of diazonium salts, vinylation of diazonium salts, arylation of diazonium salts, and conversion of diazonium salts to aldehydes, ketones, or carboxylic acids. Free radical substitution reactions with metals as leaving groups include, for example, coupling of Grignard reagents, coupling of boranes, and coupling of other organometallic reagents. Reaction with halogen as the leaving group are included. Other free radical substitution reactions with various leaving groups include, for example, desulfurization with Raney Nickel, conversion of sulfides to organolithium compounds, decarboxylative dimerization (the Kolbe reaction), the Hunsdiecker reaction, decarboxylative allylation, and decarbonylation of aldehydes and acyl halides.

Reactions involving additions to carbon-carbon multiple bonds are also used in the stage 1 and stage 2 synthesis schemes. Any mechanism may be used in the addition reaction including, for example, electrophilic addition, nucleophilic addition, free radical addition, and cyclic mechanisms. Reactions involving additions to conjugated systems can also be used. Addition to cyclopropane rings can also be utilized. Particular reactions include, for example, isomerization, addition of hydrogen halides, hydration of double bonds, hydration of triple bonds, addition of alcohols, addition of carboxylic acids, addition of $H_2S$ and thiols, addition of ammonia and amines, addition of amides, addition of hydrazoic acid, hydrogenation of double and triple bonds, other reduction of double and triple bonds, reduction of the double and triple bonds of conjugated systems, hydrogenation of aromatic rings, reductive cleavage of cyclopropanes, hydroboration, other hydrometalations, addition of alkanes, addition of alkenes and/or alkynes to alkenes and/or alkynes (e.g., pi-cation cyclization reactions, hydro-alkenyl-addition), ene reactions, the Michael reaction, addition of organometallics to double and triple bonds not conjugated to carbonyls, the addition of two alkyl groups to an alkyne, 1,4-addition of organometallic compounds to activated double bonds, addition of boranes to activated double bonds, addition of tin and mercury hydrides to activated double bonds, acylation of activated double bonds and of triple bonds, addition of alcohols, amines, carboxylic esters, aldehydes, etc., carbonylation of double and triple bonds, hydrocarboxylation, hydroformylation, addition of aldehydes, addition of HCN, addition of silanes, radical addition, radical cyclization, halogenation of double and triple bonds (addition of halogen, halogen), halolactonization, halolactamization, addition of hypohalous acids and hypohalites (addition of halogen, oxygen), addition of sulfur compounds (addition of halogen, sulfur), addition of halogen and an amino group (addition of halogen, nitrogen), addition of NOX and $NO_2X$ (addition of halogen, nitrogen), addition of $XN_3$ (addition of halogen, nitrogen), addition of alkyl halides (addition of halogen, carbon), addition of acyl halides (addition of halogen, carbon), hydroxylation (addition of oxygen, oxygen) (e.g., asymmetric dihydroxylation reaction with $OSO_4$), dihydroxylation of aromatic rings, epoxidation (addition of oxygen, oxygen) (e.g., Sharpless asymmetric epoxidation), photooxidation of dienes (addition of oxygen, oxygen), hydroxysulfenylation (addition of oxygen, sulfur), oxyamination (addition of oxygen, nitrogen), diamination (addition of nitrogen, nitrogen), formation of aziridines (addition of nitrogen), aminosulferiylation (addition of nitrogen, sulfur), acylacyloxylation and acylamidation (addition of oxygen, carbon or nitrogen, carbon), 1,3-dipolar addition; (addition of oxygen, nitrogen, carbon), Diels-Alder reaction, heteroatom Diels-Alder reaction, all carbon 3+2 cycloadditions, dimerization of alkenes, the addition of carbenes and carbenoids to double and triple bonds, trimerization and tetramerization of alkynes, and other cycloaddition reactions.

In addition to reactions involving additions to carbon-carbon multiple bonds, addition reactions to carbon-hetero multiple bonds can be used in nucleotide-templated chemistry. Exemplary reactions include, for example, the addition of water to aldehydes and ketones (formation of hydrates), hydrolysis of carbon-nitrogen double bond, hydrolysis of aliphatic nitro compounds, hydrolysis of nitriles, addition of alcohols and thiols to aldehydes and ketones, reductive alkylation of alcohols, addition of alcohols to isocyanates, alcoholysis of nitriles, formation of xanthates, addition of $H_2S$ and thiols to carbonyl compounds, formation of bisulfite addition products, addition of amines to aldehydes and ketones, addition of amides to aldehydes, reductive alkylation of ammonia or amines, the Mannich reaction, the addition of amines to isocyanates, addition of ammonia or amines to nitriles, addition of amines to carbon disulfide and carbon dioxide, addition of hydrazine derivative to carbonyl compounds, formation of oximes, conversion of aldehydes to nitriles, formation of gem-dihalides from aldehydes and ketones, reduction of aldehydes and ketones to alcohols, reduction of the carbon-nitrogen double bond, reduction of nitriles to amines, reduction of nitriles to aldehydes, addition of Grignard reagents and organolithium reagents to aldehydes and ketones, addition of other organometallics to aldehydes and ketones, addition of trialkylallylsilanes to aldehydes and ketones, addition of conjugated alkenes to aldehydes (the Baylis-Billmah reaction), the Reformatsky reaction, the conversion of carboxylic acid salts to ketones with organometallic compounds, the addition of Grignard reagents to add derivatives, the addition of Organometallic compounds to $CO_2$ and $CS_2$, addition of organometallic compounds to C=N compounds, addition of carbenes and diazoalkanbs to C=N compounds, addition of Grignard reagents to nitriles and isocyanates, the Aldol reaction, Mukaiyama Aldol and related reactions, Aldol-type reactions between carboxylic esters or amides and aldehydes or ketones, the Knoevenagel reaction (e.g., the Nef reaction, the Favorskii reaction), the Peterson alkenylation reaction, the addition of active hydrogen compounds to $CO_2$ and $CS_2$, the Perkin reaction, Darzens glycidic ester condensation, the Tollens reaction, the Wittig reaction, the Tebbe alkenylation, the Petasis alkenylation, alternative alkenylations, the Thorpe reaction, the Thorpe-Ziegler reaction, addition of silanes, formation of cyanohydrins, addition of HCN to C=N and C—N bonds, the Prins reaction, the benzoin condensation, addition of radicals to C=0, C=S, C=N compounds, the Ritter reaction, acylation of aldehydes and ketones, addition of aldehydes to aldehydes, the addition of isocyanates to isocyanates (formation of carbodiimides), the conversion of carboxylic acid salts to nitriles, the formation of epoxides from aldehydes and ketones, the formation of episulfides and episulfones, the formation of beta-lactones and oxetanes (e.g., the Paterno-Buchi reaction), the formation of beta-lactams, etc. Reactions involving addition to isocyanides include the addition of water to isocyanides, the Passerini reaction, the Ug reaction, and the formation of metalated aldimines.

Elimination reactions, including alpha, beta, and gamma eliminations, as well as extrusion reactions, can be performed using nucleotide-templated chemistry, although the strength of the reagents and conditions employed should be considered. Preferred elimination reactions include reactions that go by El, E2, ElcB, or E2C mechanisms. Exemplary reactions include, for example, reactions in which hydrogen is removed from one side (e.g., dehydration of alcohols, cleavage of ethers to alkenes, the Chugaev reaction, ester decomposition, cleavage of quarternary ammonium hydroxides, cleavage of quaternary ammonium salts with strong bases, cleavage of amine oxides, pyrolysis of keto-ylids, decomposition of toluene-p-sulfonylhydrazones, cleavage of sulfoxides, cleavage of selenoxides, cleavage of sulformes, dehydrogalogenation of alkyl halides, dehydrohalogenation of acyl halides, dehydrohalogenation of sulfonyl halides, elimination of boranes, conversion of alkenes to alkynes, decarbonylation of acyl halides), reactions in which neither leaving atom is hydrogen (e.g., deoxygenation of vicinal diols, cleavage of cyclic thionocarbonates, conversion of epoxides to episulfides and alkenes, the Ramberg-Backlund reaction, conversion of aziridines to alkenes, dehalogenation of vicinal dihalides, dehalogenation of alpha-halo acyl halides, and elimination of a halogen and a hetero group), fragmentation reactions (i.e., reactions in which carbon is the positive leaving group or the electrofuge, such as, for example, fragmentation of gamma-amino and gamma-hydroxy halides, fragmentation of 1,3-diols, decarboxylation of beta-hydroxy carboxylic acids, decarboxylation of (3-lactones, fragmentation of alpha-beta-epoxy hydrazones, elimination of CO from bridged bicyclic compounds, and elimination of $CO_2$ from bridged bicyclic compounds), reactions in which C=N or C=N bonds are formed (e.g., dehydration of aldoximes or similar compounds, conversion of ketoximes to nitriles, dehydration of unsubstituted amides, and conversion of N-alkylformamides to isocyanides), reactions in which C=0 bonds are formed (e.g., pyrolysis of beta-hydroxy alkenes), and reactions in which N=N bonds are formed (e.g., eliminations to give diazoalkenes). Extrusion reactions include, for example, extrusion of $N_2$ from pyrazolines, extrusion of $N_2$ from pyrazoles, extrusion of $N_2$ from triazolines, extrusion of CO, extrusion of $CO_2$, extrusion of $SO_2$, the Story synthesis, and alkene synthesis by twofold extrusion.

Rearrangements, including, for example, nucleophilic rearrangements, electrophilic rearrangements, prototropic rearrangements, and free-radical rearrangements, can also be performed using stage 1 and stage 2 synthesis schemes. Both 1,2 rearrangements and non-1,2 rearrangements can be performed. Exemplary reactions include, for example, carbon-to-carbon migrations of R, H, and Ar (e.g., Wagner-Meerwein and related reactions, the Pinacol rearrangement, ring expansion reactions, ring contraction reactions, acid-catalyzed rearrangements of aldehydes and ketones, the dienone-phenol rearrangement, the Favorskii rearrangement, the Arndt-Eistert synthesis, homologation of aldehydes, and homologation of ketones), carbon-to-carbon migrations of other groups (e.g., migrations of halogen, hydroxyl, amino, etc.; migration of boron; and the Neber rearrangement), carbon-to-nitrogen migrations of R and Ar (e.g., the Hofmann rearrangement, the Curtius rearrangement, the Lossen rearrangement, the Schmidt reaction, the Beckman rearrangement, the Stieglits rearrangement, and related rearrangements), carbon-to-oxygen migrations of R and Ar (e.g., the Baeyer-Villiger rearrangement and rearrangment of hydroperoxides), nitrogen-to-carbon, oxygen-to-carbon, and sulfur-to-carbon migration (e.g., the Stevens rearrangement, and the Wittig rearrangement), boron-to-carbon migrations (e.g., conversion of boranes to alcohols (primary or otherwise), conversion of boranes to aldehydes, conversion of boranes to carboxylic adds, conversion of vinylic boranes to alkenes, formation of alkynes from boranes and acetylides, formation of alkenes from boranes and acetylides, and formation of ketones from boranes and acetylides), electrocyclic rearrangements (e.g., of cyclobutenes and 1,3-cyclohexadienes, or conversion of stilbenes to phenanthrenes), sigmatropic rearrangements (e.g., (1,j) sigmatropic migrations of hydrogen, (1,j) sigmatropic migrations of carbon, conversion of vinylcyclopropanes to cyclopentenes, the Cope rearrangement, the Claisen rearrangement, the Fischer indole synthesis, (2,3) sigmatropic rearrangements, and the benzidine rearrangement), other cyclic rearrangements (e.g., metathesis of alkenes, the di-n-methane and related rearrangements, and the Hofmann-Loffler and related reactions), and non-cyclic rearrangements (e.g., hydride shifts, the Chapman rearrangement, the Wallach rearrangement, and dybtropic rearrangements).

Oxidative and reductive reactions may also be performed using stage 1 and stage 2 synthesis schemes. Exemplary reactions may involve, for example, direct electron transfer, hydride transfer, hydrogen-atom transfer, formation of ester intermediates, displacement mechanisms, or addition-elimination mechanisms. Exemplary oxidations include, for example, eliminations of hydrogen (e.g., aromatization of six-membered rings, dehydrogenations yielding carbon-carbon double bonds, oxidation or dehydrogenation of alcohols to aldehydes and ketones, oxidation of phenols and aromatic amines to quinones, oxidative cleavage of ketones, oxidative cleavage of aldehydes, oxidative cleavage of alcohols, ozonolysis, oxidative cleavage of double bonds and aromatic rings, oxidation of aromatic side chains, oxidative decarboxylation, and bisdecarboxylation), reactions involving replacement of hydrogen by oxygen (e.g., oxidation of methylene to carbonyl, oxidation of methylene to OH, $CO_2R$, or OR, oxidation of arylmethanes, oxidation of ethers to carboxylic esters and related reactions, oxidation of aromatic hydrocarbons to quinones, oxidation of amines or nitro compounds to aldehydes, ketones, or dihalides, oxidation of primary alcohols to carboxylic acids or carboxylic esters, oxidation of alkenes to aldehydes or ketones, oxidation of amines to nitroso compounds and hydroxylamines, oxidation of primary amines, oximes, azides, isocyanates, or nitroso compounds, to nitro compounds, oxidation of thiols and other sulfur compounds to sulfonic acids), reactions in which oxygen is added to the substrate (e.g., oxidation of alkynes to alpha-diketones, oxidation of tertiary amines to amine oxides, oxidation of thioesters to sulfoxides and sulfones, and oxidation of carboxylic adds to peroxy acids, and oxidative coupling reactions (e.g., coupling involving carbanoins, dimerization of silyl enol ethers or of lithium enolates, and oxidation of thiols to disulfides).

Exemplary reductive reactions include, for example, reactions involving replacement of oxygen by hydrogen {e.g., reduction of carbonyl to methylene in aldehydes and ketones, reduction of carboxylic acids to alcohols, reduction of amides to amines, reduction of carboxylic esters to ethers, reduction of cyclic anhydrides to lactones and acid derivatives to alcohols, reduction of carboxylic esters to alcohols, reduction of carboxylic adds and esters to alkanes, complete reduction of epoxides, reduction of nitro compounds to amines, reduction of nitro compounds to hydroxylamines, reduction of nitroso compounds and hydroxylamines to amines, reduction of oximes to primary amines or aziridines, reduction of azides to primary amines, reduction of nitrogen compounds, and reduction of sulfonyl halides and sulfonic adds to thiols), removal of oxygen from the substrate {e.g., reduction of amine oxides and azoxy compounds, reduction of sulfoxides and sulfones, reduction of hydroperoxides and peroxides, and reduction of aliphatic nitro compounds to oximes or nitriles), reductions that include cleavage {e.g., de-alkylation of amines and amides, reduction of azo, azoxy, and hydrazo compounds to amines, and reduction of disulfides to thiols), reductive coupling reactions {e.g., bimolecular reduction of aldehydes and ketones to 1,2-diols, bimolecular reduction of aldehydes or ketones to alkenes, acyloin ester condensation, reduction of nitro to azoxy compounds, and reduction of nitro to azo compounds), and. reductions in which an organic substrate is both oxidized and reduced {e.g., the Cannizzaro reaction, the Tishchenko reaction, the Pummerer rearrangement, and the Willgerodt reaction).

Examples of cleavable linkers/protecting groups that may be cleaved in order to transfer molecule fragments as described above, or may be used to protect and de-protect functional groups during the synthesis of the library of bi-functional molecules, and conditions mediating the cleavage of these linkers/protecting groups, are shown in FIG. 8. Cleavable linkers can be cleaved in any number of ways, e.g., by photolysis or increased temperature, or by the addition of acid, base, enzymes, ribozymes, other catalysts, or any other agents.

The linkers of the present invention may for example be chosen from the following list: Carbohydrates and substituted carbohydrates, polyvinyl, acetylene or polyacetylene, aryl/hetaryl and substituted aryl/hetaryl, ethers and polyethers such as e.g. polyethylenglycol and substituted polyethers, amines, polyamines and substituted polyamines, single- or double-stranded oligonucleotides, and polyamides and natural and unnatural polypeptides.

To maintain a physical link between the identifier and the encoded molecule (in the case of stage 2 synthesis, the template and the encoded molecule), at least one non-cleavable linker is needed. The non-cleavable linker may of course be cleavable under certain conditions, but is non-cleavable under the conditions that lead to the bi-functional molecule employed in the screening. This non-cleavable linker is preferably flexible, enabling it to expose the encoded molecule in an optimal way. Preferably the length of the flexible linker is in the range of 1-50 Å, more preferably 5-30 Å, most preferably 10-25 Å. Preferably the linker is both flexible and inert; polyethylene glycol (PEG) is an appropriate linker.

Under certain conditions it may desirable to be able to cleave the linker after the screening of the library of bi-functional molecules has been done, for example in order to perform a mass spectrometric analysis of the encoded molecule without the identifier attached, or to perform other types of assays on the free encoded molecule.

In an alternative embodiment, the linker contains an oligonucleotide moiety which may serve as an annealing site for an oligonucleotide that carries a reagent, catalyst or molecule fragment. The annealing of the reagent-, catalyst- or molecule fragment-oligonucleotide will serve to provide the reagent, catalyst or molecule fragment in a high local concentration, thereby improving the efficiency of the desired reaction.

Alternative Methods for Templated Synthesis Using Bi-Functional Carrier Molecules:

Alternative methods (to the example shown in FIG. 2) can be envisioned for carrying out the template directed reactions set in stage 2 of the invention. The alternative methods provide different ways of bringing together and reacting the bi-functional carrier molecules provided by stage 1. Some examples of such alternative methods are shown in FIG. 4. Any of these methods could be used to carry out stage 2 of the invention.

Example 1

See Example 1, FIG. 4

This is identical to the example provided in FIG. 2, except that the carriers are ligated together before reaction. X and Y represent the two different repertories of carrier molecules from stage 1 used in the example of FIG. 2. Once the oligonucleotide identifiers of the carriers have annealed to the template, they are ligated to each other and the acyl transfer reaction is hereafter carried out (the acyl transfer could also be carried out prior to the ligation step). The ligation step may be performed by a ligase, or may be performed in absence of an enzyme.

Example 2

See Example 2, FIG. 4

In example 2, the molecule fragments are attached to the ends of the oligonucleotide identifiers that are distal to each other after annealing to the template. After ligation of the oligonucleotide identifiers of the carriers, the molecule fragments are brought in contact for reaction by denaturing the duplex DNA (ligated carriers annealed to template) and removal of the template (in order to have increased flexibility of the now single stranded DNA sequence that carries the molecule fragments). The correct juxtaposition of the molecule fragments can be further ensured by including complementary sequences in the ends of the oligonucleotide identifiers that are proximal to the molecule fragments before transfer.

After reaction of the molecule fragments the single stranded DNA can be made double stranded by a standard extension reaction using a DNA polymerase and a primer annealing to the end of the DNA.

Example 3

See Example 3, FIG. 4

Example 3 shows how the oligonucleotide identifier of the carrier that carries the combined molecule fragments can be ligated to the template. This is achieved by including a region of self-complementary sequence on the template that after annealing will juxtapose the ends of the carrier oligo and the template.

As in example 2 it may also in this example be desirable to perform an extension reaction, using a primer that anneals to one of the ends of the DNA strand that is attached to the encoded molecule and a DNA polymerase. The resulting double stranded DNA, where the encoded molecule is displayed at the end, is shown in the figure of the example.

Example 4

See Example 4, FIG. 4

In this example of the reaction in stage 2 of the invention, the carriers employed carry double-stranded oligonucleotide identifiers (generated for example by ligation of double-stranded oligonucleotide identifiers during the Stage 1 synthesis). Thus, these carriers are brought together and reacted without the use of a template. The oligonucleotides of the carrier are constructed so that the resulting double stranded DNA of one repertoire of carriers (e.g. X) has a "sticky" end (a 3' or 5' overhang), which is complementary to a corresponding "sticky" end of another repertoire of carriers (e.g. Y). Any two carrier molecules from each repertoire can therefore be combined by annealing using the sticky ends of the double stranded DNA oligos. The carriers are hereafter ligated and reacted like in the other examples. The identifier DNA sequence of the combined molecules will, in addition to the 48-mer coding sequence, contain a "sticky" end derived sequence that will be identical for all molecules. One advantage of this method is that synthesis of long templates is avoided.

After reaction of the molecule fragments the single stranded DNA can be made double stranded by a standard extension reaction using a DNA polymerase and a primer annealing to the end of the DNA.

In examples 1-4 it may be desirable to include primer binding sites, either at the ends of the template DNA strand, or as part of the identifier (one primer binding site per carrier) when stage 2 involves a ligation of two carriers to each other, to form a complementary template. These primer binding sites can be used for amplification of the template (or complementary strand), allowing generation of more copies of the encoded molecules.

Example 5

See Example 5, FIG. 4

Carrier molecules with double-stranded oligonucleotide identifiers, as provided in example 4, can also be ligated into a circular double stranded DNA molecule, by digestion of the double stranded DNA molecule with restriction enzymes, which creates "sticky ends", and ligation to corresponding "sticky ends" on the double-stranded oligonucleotide identifiers. The double stranded DNA molecule used for ligation of the oligonucleotide identifiers can be a plasmid having a replication origin, which enables it to be transformed into cells, e.g. bacteria, for amplification. The double stranded DNA molecule can also be a non-functional piece of DNA only used to make circular DNA molecules containing the double-stranded oligonucleotide identifiers.

In the first step the carrier molecules from one repertoire of synthesis in stage 1 are ligated into the circular DNA. In the second step, the carrier molecules from another repertoire of synthesis in stage 1 are ligated into the double-stranded DNA molecule, adjacent to where the carrier molecules from the first step were inserted. The carrier molecules are hereafter reacted as in the other examples.

Figure 5:
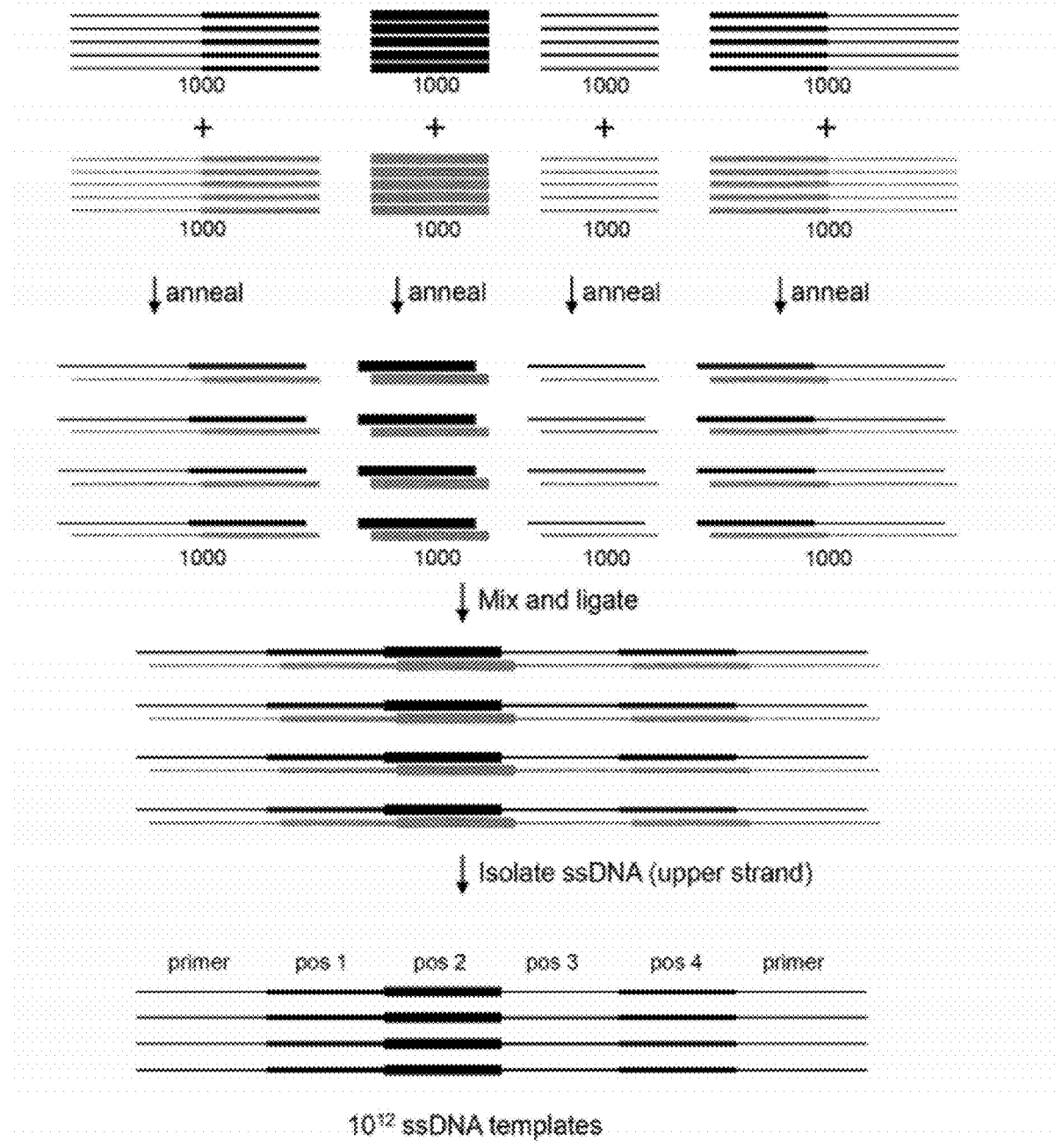

Synthesis of the Template:

$10^{12}$ different templates are required in order to generate a library of $10^{12}$ encoded molecules. In the example shown in FIGS. 1 and 2, the library consists of tetrameric polypeptides that are encoded by a 48-mer template sequence. Each of the four amino acid units in an encoded molecule is encoded by a 12-mer sequence-unit of the DNA template. In the examples, the number of different amino acids that are encoded by the 12-mer sequence-units is 1000. A simple and efficient way of synthesising the $10^{12}$ DNA templates in the example is thus by synthesising the 1000 different 12-mer oligonucleotides, corresponding to the first position of the template. This set of position 1 oligonucleotides are then incubated with a corresponding set of position 2, 3 and 4 oligonucleotides, and ligated, to form templates comprising four 12-nucleotide sequence units. A practical approach to this is suggested in FIG. 5:

i) Four sets of double-stranded DNA fragments are generated, with overhangs at both ends. The overhangs may be of any length, for example one-nucleotide overhangs. Thus, for each of the four sets, each of 1000 different 13-nt DNA oligo sequences are incubated with a partially complementary 13-nt DNA oligo. 12 of 13 nucleotides are complementary, and therefore duplex DNA with one-nucleotide overhangs at both ends is generated.

ii) Then the 4 sets each of 1000 duplex DNA fragments are incubated, and ligated together by a DNA ligase to form $10^{12}$ different DNA templates, each comprising four sequence-units of 12 base pairs. A set of primer annealing sequences can subsequently be ligated to the ends of the templates, in order to obtain templates that can easily be amplified by PCR using primers complementary to the flanking sequences. Alternatively, as shown in FIG. 5, the primer-annealing-sites may be carried by the terminal sequence units (in this example comprising position 1 and position 4 sequence-units). The primer binding sites also allow sequencing of the templates.

iii) Single-stranded template is generated by removing the upper or lower strand, for example by including biotinylated position 1 upper strand oligos. Streptavidin beads may be added, which will immobilise the double stranded templates on the beads. Then alkaline conditions are employed to melt the DNA duplexes, which releases the lower strand from solid support. The single stranded DNA templates may now be used in the Stage 2 DNA-templated synthesis reactions. Alternatively, the DNA-templated synthesis may be performed using the immobilised upper strand as template, and thus performing the reactions on solid support. This should allow the DNA-templated reactions to be performed under aqueous conditions as well as in organic solvents.

The library of DNA templates may be generated in other ways. For example, $10^{12}$ different templates may be generated by standard oligonucleotide synthesis of fully random oligonucleotides, or oligonucleotides with constant, partly randomised, and/or fully randomised positions. Alternatively, the template may be generated by split and mix synthesis, as described below.

The Nucleic Acid Component of Bi-Functional Molecules Generated in Stage 1 and Stage 2 Synthesis.

The present invention involves oligonucleotide identifiers of three different uses. Thus, "unit identifier" is the smallest unit, and typically describes the part of the final encoded molecule that is added and becomes attached to the nascent bi-functional molecule as the result of a synthesis round during stage 1 synthesis. "Carrier identifier" describe the oligonucleotide that anneals to the template during a stage 2 synthesis round. Finally, "template identifier" or "identifier template" describes the encoding oligonucleotide of the bi-functional molecule. Thus, in the example described in FIGS. 1 and 2, there are 4 unit identifiers that are linked two and two to generate 2 carrier identifiers. Then, the two carrier identifiers are hybridised to 1 identifier template carrying four identifiers complementary to the identifier portions of the carriers. In this example, the encoded molecule is attached to the identifier template non-covalently by annealing of the oligonucleotide that carries the encoded molecule to the identifier template.

In most of the examples, two molecule fragments and two unit identifiers are used to generate a carrier molecule, but the number of molecule fragments and unit identifiers used to synthesise a carrier can also be 1, 3, 4, 5, 6, 7 or higher. The resulting molecules are termed carrier molecules, where a given carrier molecule contains molecule fragments that are linked together, and where the linked molecule fragments are also linked to the identifiers that have also been linked together.

The number of carriers that bind to the same template may be 1, 2, 3, 4, 5, 6, 7 or more.

The identifiers of carrier molecules must be capable of hybridising to the template in a sequence- or partly sequence-specific way. Thus, in a preferred embodiment the template is a nucleic acid or nucleic acid analogue, and the identifiers of the carrier molecules consist of DNA, RNA, PNA, LNA, or other oligonucleotide analogues capable of sequence specific hybridisation through base pairing. The resulting structure may be a double or triple helix.

The templates employed during stage 2 synthesis likewise must be capable of hybridising to the carriers in a sequence-specific or partly sequence-specific way. Thus, the templates preferably consist of DNA, RNA, PNA, LNA, or other oligonucleotide analogues capable of sequence specific hybridisation through base pairing. In a preferred embodiment, the template is amplifiable (i.e. can be amplified through the use of a polymerase, such as is used in a PCR-reaction, or by repeated replication such as in a cell). Example amplifiable templates are DNA and RNA, and unnatural DNA- or RNA, capable of being used as a template in a polymerase-based transcription or replication process.

The carrier identifiers preferably anneal sequence specifically to the templates. Therefore, the carrier identifiers should be of a length and composition that allows a relatively strong and specific interaction between template and carrier under the hybridisation step. Preferably, the length of the carrier identifier is in the range of 3-50 nucleotides, more preferably 7-25 nucleotides, and most preferably 8-20 nucleotides. In order to ensure specific annealing of the carriers, i.e. to ensure that the correct carrier anneal to a given template, the set of carrier identifiers should be chosen such that the overlap between identifiers of different carriers is as insignificant as possible. In other words, the design of the set of carrier identifiers should ensure a high degree of non-identity among any carrier identifier in the set. Likewise, the templates should be designed so that interaction with undesired carrier identifiers is minimised.

Preferably, less than 30% of the nucleotides of a given carrier identifier sequence should be complementary to a non-desired hybridisation sequence of the template. Less preferably, less than 50%, and even less preferably, less than 70%, and the least preferably, less than 90%, of the nucleotides of a given carrier identifier sequence should be complementary to a non-desired hybridisation sequence of the template. This will ensure a high degree of specificity during the annealing step in the templated synthesis, and hence, ensure that the desired carriers bind to the template, and hence, ensure that the desired encoded molecules are generated. In principle, even where two carrier identifiers are different only at one nucleotide position, the stage 1 and stage 2 synthesis and encoding/decoding should work. However, the more different any two identifiers in a library are, the more robust the encoding, selection and characterisation will be.

In addition, the more different the identifier template sequences are, the less sensitive the system will be to errors introduced during the chemical reactions or PCR amplifications performed. For example, if all unit identifier pairs have different nucleotides at more than 5 positions, two nucleotide substitutions introduced during PCR will still allow the correct identification of the unit identifier. Therefore, the non-identity preferences that are described above for carrier identifiers also applies to unit identifiers employed during stage 1 synthesis, also if no stage 2 synthesis is performed to generate the bi-functional molecules employed in the screening step.

In order to obtain efficient attachment of the incoming identifier and the nascent bi-functional molecule during stage 1 synthesis, it is preferable to use oligonucleotide identifiers that have constant regions, i.e. a portion of the identifier is the same for all of the identifiers in the library. In the stage 1 synthesis, this region could be relatively long (e.g., 20 nucleotides), to ensure efficient annealing to a complementary oligonucleotide, and hence, efficient ligation. However, if the bi-functional molecule produced in this way is to be used as a carrier molecule in a subsequent stage 2 synthesis, the constant regions should be as short as possible, in order to ensure high annealing specificity among the different carrier molecules being used in the stage 2 synthesis. An appropriate compromise between these two opposing factors is to include constant regions (for mediating the ligation of unit identifiers) that are preferably between 1 and 10 nucleotides long, less preferably 1-20 and least preferably 1-50 nucleotides long. Most preferably, the constant region is 2, 3, 4, 5, or 6 nucleotides long. In order to ensure efficient annealing and thus ligation, but to reduce the length of the constant region, the constant region may include unnatural oligonucleotides such as e.g. LNA, which provides a higher affinity than natural DNA.

Variations and specifications to the general scheme described above for the generation of bi-functional molecules: A number of methods by which to generate carriers exist. In principle, any number of methods exist by which to perform the templated reactions. Almost any combination of methods for carrier generation and templated synthesis can be applied to the generation of bi-functional molecules. Below specific approaches to carrier generation have been outlined (Sub-procedures 1-X) and specific approaches to templated synthesis have been outlined (Sub-processes A-Z). Individual processes 1-X and A-Z, as well as combinations 1A, 1B, ... 1Z, 2A, 2B, XA, XB, XZ can be applied to the generation of bi-functional molecules.

Specific enablements of stage 1 synthesis, or generation of carriers, include but is not limited to:

1. This is a variation of bi-functional molecule formation described in (Lerner et al., EP 0643778 B1, Encoded combinatorial chemical libraries), but any embodiment of bi-functional molecule synthesis described in said patent is applicable for stage 1 synthesis. Two alternating parallel combinatorial syntheses are performed so that a genetic tag is chemically linked to a polypeptide or other type of organic molecule being synthesised; in each case, the addition of one amino acid residue (or other type of molecule fragment with at least one reactive group) to the structure is followed by the addition of an oligonucleotide sequence, which is defined to code for that amino acid (or molecule fragment), i.e., to function as an identifier for the structure of the amino acid residue (or molecule fragment). The library is built up by the repetition of this process after pooling and division. During the process, therefore, a bi-functional molecule is being formed, consisting of a polypeptide (or other organic molecule) attached to an identifier tag that encodes the synthetic history of the encoded molecule, and hence, encodes the expected chemical structure of the encoded molecule. Thus, the process is an example of a split-and-mix DNA tagging process.

In a related process, also described in (Lerner et al., EP 0643778 B1, Encoded combinatorial chemical libraries), a method is described for preparing tagged molecules or libraries of tagged molecules, where each molecule is attached to a solid support. The method comprises a solid support, being dispersible in aqueous solution, a first linkage unit coupled to the solid support, a second linkage unit coupled to the first linkage unit, a bi-functional unit coupled to the second linkage unit, wherein the bi-functional unit (or "linker") has two reactive groups, one of which is employable for oligonucleotide synthesis (i.e., may be used as an initiator-functionality for oligonucleotide synthesis), and one of which is employable for polypeptide- (or other organic molecule-) synthesis.

2. This is a variation of bi-functional molecule formation described in (Dower et al., EP 0604552 B1), but any embodiment of bi-functional molecule synthesis described in said patent is applicable for stage 1 synthesis. Organic molecules are synthesized in a component by component fashion (i.e. by a split-and-mix-like process) on solid support or particles. During the synthesis of the organic molecule, a tag is simultaneously synthesised which becomes linked to the organic molecule via a linker. The organic molecule-oligonucleotide tag complex may be released from these supports to provide a soluble library of bi-functional molecules.

3. This is a variation of bi-functional molecule formation described in (Freskgård et al., WO 2004/039825 A2), but any embodiment of bi-functional molecule synthesis described in said patent application is applicable for stage 1 synthesis. A bi-functional carrier molecule is generated as follows: A nascent bi-functional complex comprising a reactive group and a priming site for enzymatic addition of an oligonucleotide identifier is reacted at the reactive group with one or more molecule fragments, and provided with respective identifier(s) identifying the molecule fragments at the priming site using one or more enzymes. The enzyme used may be a DNA ligase, and the priming site may be a 3'-OH group on a nucleic acid to which an oligonucleotide tag carrying a 5'-phosphate can be attached. In a preferred embodiment, the ligation of identifiers does not involve an enzyme. Enzymes, including the DNA ligase, are in general substrate specific, entailing that the enzymatic addition of a tag to the priming site is not likely to interfere with the display molecule being formed. Generally, the bi-functional carrier molecule is formed by more than a single round of reaction between one or more molecule fragments and the reactive group. In a certain aspect of the invention, the nascent bi-functional complex reacted with one or more molecule fragment(s) and provided with respective oligonucleotide identifier(s) is reacted further one or more times with one or more molecule fragment(s) and is provided with respective identifier(s) to produce an encoded molecule as one part of the bi-functional carrier molecule and an encoding part comprising identifiers which codes for the identity of the molecule fragments which have participated in the formation of the encoded molecule. The reaction at the reactive group and the addition of identifiers may occur in any order, i.e. the reaction may occur subsequent to, simultaneously with, or previous to the identifier addition. The choice of order may among other things be dependent on the enzyme type, the reaction conditions, and the type of reactant. The encoding part of the nascent bi-functional complex is formed by addition of at least one unit identifier to a priming site using one or more enzymes. Further unit identifiers may be attached to a previous unit identifier so as to produce a linear or branched encoding part. As long as at least one unit identifier is attached by an enzymatic catalysed reaction, further unit identifiers may be provided using chemical means or enzymatic means at the discretion of the experimenter. The identifier can be added to the priming site using any appropriate enzyme. In a certain embodiment, an identifier is provided at the priming site of the nascent bi-functional complex utilizing an enzymatic extension reaction. The extension reaction may be performed by a polymerase or a ligase or a combination thereof. The extension using a polymerase is suitably conducted using a complementary oligonucleotide that hybridises to the previous unit identifier, and carries a sequence complementary to the unit identifier; the unit identifier is then synthesized by e.g. a polymerase by using the complementary oligonucleotide as template, and the end of the previous unit identifier as starting point for the extension. Typically, the previous unit identifier would carry a 3'-OH at the end, and a polymerase would extend from this 3'-OH, using dNTPs or NTPs. Examples of suitable enzymes for the addition of unit identifiers to the nascent bi-functional molecule include DNA polymerase, RNA polymerase, Reverse Transcriptase, DNA ligase, RNA ligase, Taq DNA polymerase, Pfu polymerase, Vent polymerase, HIV-1 Reverse Transcriptase, Klenow fragment, or any other enzyme that will catalyze the incorporation of complementing elements such as mono-, di- or polynucleotides. Polymerases that allow mismatch extension can also be used, such as for example DNA polymerase r\ (Washington et al., (2001) JBC 276: 2263-2266), DNA polymerase i (Vaisman et al., (2001) JBC 276: 30615-30622), or any other enzyme that allow extension of mismatched annealed base pairs. In another aspect, when ligases are used, suitable examples include Taq DNA ligase, T4 DNA ligase, T4 RNA ligase, T7 DNA ligase, and *E coli* DNA ligase. The choice of the ligase depends to a certain degree on the design of the ends to be joined together. Thus, if the ends are blunt, T4 RNA ligase may be preferred, while a Taq DNA ligase may be preferred for a sticky end ligation.

4. This is another variation of bi-functional molecule formation described in (Freskgård et al., WO 2004/039825 A2). In this approach, molecule fragments are attached to the unit identifier or an oligonucleotide that is complementary to the unit identifier. Using this approach, the synthesis of a library of many different bi-functional carrier molecules can be conducted in a single vessel, in contrast to the split-and-mix synthesis, where the reaction and unit identifier addition must be carried out in separate compartments. Thus, this variation entails a method comprising the steps of i) providing a nascent bi-functional complex comprising a reactive group and an oligonucleotide identifier region, ii) providing a molecule fragment-oligonucleotide conjugate comprising an oligonucleotide sufficient complementary to the oligonucleotide identifier to allow for hybridisation, a transferable molecule fragment, and a complementary anti-codon identifying the functional entity, iii) mixing the nascent bi-functional molecule and the molecule fragment-oligonucleotide conjugate under hybridisation conditions to form a hybridisation product, iv) transferring the molecule fragment of said conjugate to the nascent bi-functional molecule through a reaction involving the reactive group of the nascent bi-functional complex, and v) enzymatically extending the oligonucleotide identifier to obtain a unit identifier attached to the bi-functional molecule having received the molecule fragment. The enzymatic extension may occur subsequent to or simultaneously with the transfer of the functional entity or even prior to the transfer.

5. This is a variation of bi-functional molecule formation described in (Lerner et al., EP 0643778 B1, "Encoded combinatorial chemical libraries" and Dower et al., EP 0604552 B1). In this method, a stage 1 synthesis is performed in which identifiers are ligated together in the absence of an enzyme, but with the aid of a nucleic acid that brings the identifiers into close proximity, and hence increases ligation efficiency this way (see FIG. 12). An identifier that must be ligated must comprise, e.g. at one end of the identifier oligonucleotide, a chemical group that can react with a chemical group on the identifier that it will be ligated to. As an example, the nucleic acid may be complementary to a part of the sequence of both identifiers. In a preferred embodiment a nucleic acid is added that is complementary to the ends of the identifiers. Hybridisation of this bridging nucleic acid to the two identifiers brings the two chemical groups, one from each identifier, into close proximity, thereby improving the ligation reaction efficiency. The bridging nucleic acid can be any type of nucleic acid or nucleic acid analog, or any other type of molecule or solid support that brings the two identifiers into proximity and thereby increases the efficiency of ligation.

The complementary nucleic acid brings the ends of the two identifiers into close proximity; the ends of the identifiers have been modified to make them prone to reaction under these conditions. As an example of such chemical ligation, one of the identifiers may carry a 3'-hydroxyl group, and the other identifier carry a 2-methylimidazole-activated phosphate at its 5'-end. When brought into proximity by hybridisation to a complementary nucleic acid, the 3'-OH and the 5' activated phosphate will react to generate a native phosphodiester bond between the identifiers. This and other types of chemical ligation reactions that can be used to ligate identifiers together chemically are described in more detail above. Practically, any two reactive groups that may react to form a bond between the two identifiers can be used, as long as the ligation conditions do not modify the identifiers to an extent that abolishes efficient hybridisation of the carriers in the stage 2 synthesis that follows carrier synthesis. Thus, as an example, the reactive groups and the reactions listed in FIGS. 6 and 7 may be used for ligation of identifiers as well.

The encoded molecule formed using this approach, and the reactive groups and types of reactions that may be used to generate the encoded molecule, are the same as those mentioned for general stage 1 synthesis (and stage 2 synthesis), and thus include reactions and reactive groups listed in FIGS. 6, 7 and 8.

6. This variation of combinatorial chemistry combines the combinatorial chemical synthesis of molecule fragments with a tagging of each molecule synthesized. Combinatorial chemistry is employed to synthesize a library of molecule fragments, whereafter the molecule fragments are attached to oligonucleotides, to produce bi-functional molecules, that may be used as carriers in templated synthesis. In this approach, combinatorial chemistry is applied to the generation of a library of molecule fragments. Any type of combinatorial chemistry may be used, for example split-and-mix synthesis on beads (see review by Abelson (1996) Methods in Enzymology, vol. 267, p. 211-221; Lebl et al. (2000) U.S. Pat. No. 6,090,912; Lebl et al. (1998) U.S. Pat. No. 5,840,485), followed by the release from the bead to produce multiple solutions (e.g. in separate wells), each containing a specific molecule fragment, or the library may be generated in an array format, for example on glass or pins (Dapremont et al. (1995) Physiol. Chem. Phys. & Med. NMR, 27: 339-343, "Multiple synthesis using the multipin method"), before it is eventually released from solid support, to produce multiple solutions (e.g. in separate wells), where each well contain a specific molecule fragment. Any other means of generating a library of compounds can be applied, including the embodiments of (Still et al. (1998) U.S. Pat. No. 5,721,099; Dower et al. (1991) US 1991000762522; Boger et al. (2001) U.S. Pat. No. 6,194,612 B1; Cook et al. (2001) U.S. Pat. No. 6,191,273; Gustafson et al. (2000) U.S. Pat. No. 6,140,361; Graybill et al. (2000) U.S. Pat. No. 6,127,191; Dervan et al. (2000) U.S. Pat. No. 6,090,947; Baindur et al. (1999) U.S. Pat. No. 5,891,737; Baindur et al. (1997) U.S. Pat. No. 5,646,285). Once the library of molecule fragments is generated, each specific molecule fragment is attached a specific oligonucleotide. As a result, a library of bi-functional molecules have been generated, where specific molecule fragments are attached to specific oligonucleotides that thus encode the structure of the molecule fragment generated by combinatorial chemistry. The bi-functional molecules may be used as carriers in a templated synthesis.

In a preferred embodiment, the oligonucleotides are prepared by combinatorial synthesis, either before or after their addition to the solutions containing the specific molecule fragments. Thus, for the tagging of $n^2$ molecule fragments, n oligonucleotides of length 12 nt are pairwise attached, for example by chemical ligation, to n oligonucleotides of length 13 nt, to produce $n^2$ oligonucleotides of length 25 nt that is then attached to the $n_2$ molecule fragments, for example by an acylation reaction involving an amino group on one of the ends of the oligonucleotides, and a carboxylic acid of the molecule fragment. For example, if a library of $10^6$ different molecule fragments have been prepared, one may generate $10^6$ different oligonucleotides by pairwise ligation of two sets of $10^3$ oligonucleotides.

7. This is a variation of the principle described immediately above, where combinatorial chemical synthesis is replaced by any synthetic method that produces a library of more than one hundred, one thousand, or ten thousand molecule fragments. In this variation it is thus not a requirement that a combinatorial approach is employed for the synthesis of the library of molecule fragments. Again, the bi-functional molecules are generated by attachment of specific oligonucleotides to each of the molecule fragments, and again, the oligonucleotides can be attached to the molecule fragments directly, or after a combinatorial ligation of a smaller set of oligonucleotides has produced a larger set of oligonucleotides that may then be attached to the molecule fragments. Again, the combinatorial ligation of oligonucleotides can also be performed after attachment of the first oligonucleotide to the molecule fragment.

8. This is a variation of any of the other stage 1 synthesis principles, or formation of carrier molecules (1-8), in which identifiers are linked by a non-covalent bond. As an example, the identifiers may contain complementary oligonucleotide sequences. In a preferred embodiment, a strong, non-covalent association of the identifiers by extended complementarity may allow hybridisation of the hybridised identifiers (the carrier molecule) to a template in a subsequent templated synthesis.

9. This is a variation of Morgan et al., 2005, WO 2005/058479. Any embodiment of bi-functional molecule synthesis described in said patent application is applicable for stage 1 synthesis The invention provides a method of synthesising libraries of molecules which include an encoding oligonucleotide tag. The method utilises a "split and pool" strategy in which a solution comprising an initiator (similar to the linker molecules described in this patent application), comprising a first building block linked to an encoding oligonucleotide, is divided into multiple fractions. In each fraction, the initiator is reacted with a second, unique, building block and a second, unique oligonucleotide which identifies the second building block (the oligonucleotides are reacted through the use of an enzyme, e.g. a ligase). These reactions can be simultaneous or sequential and, if sequential, either reaction can precede the other. The dimeric molecules produced in each of the fractions are combined and then divided again into multiple fractions. Each of these fractions is then reacted with a third unique building block and a third unique oligonucleotide which encodes the building block (the oligonucleotides are reacted through the use of an enzyme). The number of unique molecules present in the product library is a function of the number of different building blocks used at each step of the synthesis, and the number of times the pooling and dividing process is repeated.

10. This is a variation of Harbury and Halpin (WO 00/23458). Any embodiment of bi-functional molecule synthesis described in said patent application is applicable for the synthesis of bi-functional carrier molecules. The method involves the synthesis of a plurality of compounds, comprising a) forming a first group of subsets of identifier templates, where the templates in each subset each has a selected one of a plurality of different first hybridisation sequences, a mixture of different second hybridisation sequences, and a reactive group, b) reacting the reactive group in each of the subsets formed in (a) with a selected molecule fragment, thereby to form a molecule fragment-specific compound intermediate on the associated sequence in each subset, c) forming a second group of subsets of the reacted templates, where the templates in each subset each have a selected on of a plurality of a plurality of different second hybridisation sequences, and a mixture of different first hybridisation sequences; and d) reacting the compound intermediates in the sequences in each of the subsets formed in (c) with a selected molecule fragment.

The method may be performed on solid support, for example by sorting the templates according to the sequence of e.g. the first hybridisation sequence by annealing to beads, each of which carry a specific oligonucleotide that is complementary to a specific first hybridisation sequence, to allow the formation of different subsets of templates, where each subset of templates have a specific hybridisation sequence. The method thus provides subsets of nucleic acid templates, generated by base-specific duplex formation between each different first hybridisation sequence and a complementary oligonucleotide. The reactive group in each of the subsets are reacted with a selected molecule fragment to form a molecule fragment-specific compound intermediate (i.e., a bi-functional molecule comprising a specific molecule fragment). The end result thus is, after grouping the templates into subsets each comprising a particular first hybridisation sequence, and reacting each subset with a specific molecule fragment, and repeating this process for the second, third, fourth, etc. hybridisation sequence, a number of bi-functional molecules, comprising an encoded molecule (comprising n linked molecule fragments) and an encoding template identifier, comprising n hybridisation sequences (here called unit identifiers).

The templates employed can carry 1, 2, 3, 4, 5, 6, 7 or more hybridisation sequences, and thus, the bi-functional molecules generated by this approach can carry 1, 2, 3, 4, 5, 6, 7 or more molecule fragments. The number of different molecule fragments in a given round can be from 2 to 10.000. The template may be amplifiable or non-amplifiable by polymerases such as Taq polymerase The method, as described above, as well as the embodiments described in (Harbury and Halpin, WO 00/23458) may be performed using the chemistries and protecting groups described in this patent application, including chemistries and protecting groups shown in table 6, 7 and 8, and using any type, composition and length of oligonucleotides described in this patent application.

Specific enablements of stage 2 synthesis (templated synthesis of bi-functional molecules) include but is not limited to:

A. This is a variation of the principle described in (Bruick et al., Chemistry and Biology, January 1996, 3: 49-56, "Template-directed ligation of peptides to oligonucleotides"). In this approach a number of identifier templates are incubated with two (or more) sets of carrier molecules. One set of carriers comprise a molecule fragment comprising a reactive group A (for example an activated ester of a carboxylic acid, for example a thioester), and one set of carriers comprise a reactive group B that can react with A (B can be for example a primary or secondary amine, capable of reacting with the thioester). Upon template/carrier complex formation, an acylation reaction takes place, leading to the transfer of the molecule fragment comprising the reactive group A (e.g. thioester) onto the molecule fragment comprising the reactive group B (e.g. the amine). Thus, the templated reaction leads to formation of an encoded molecule consisting of two molecule fragments, linked by an amide bond.

Any type of reactive groups may be used in this method, including reactive groups mentioned in this patent application, including table 6, 7, and 8. For amine acylations, thioesters, N-hydroxysuccinimide esters, and phenol esters are particularly well suited for the direct transfer of one molecule fragment onto another. Alternatively, an indirect acylation between a carboxylic acid and an amine may be mediated by EDC, EDC/NHS, DMT/MM and other reagents that activate the acid for nucleophilic attack. After covalent linkage of the two molecule fragments, one of the linkers is cleaved, to transfer one molecule fragment onto the other molecule fragment, associated with the same template. In addition, many other reactions may be used to link two molecule fragments in an oligonucleotide-templated fashion. Thus, this principle may be applied to the generation of encoded molecules as listed in the present invention, and may involve reactive groups mentioned in the present invention, including those listed in FIGS. 6, 7, and 8.

B. This is a variation of the principle described in (Walder et al. (1979) Proc. Natl. Acad. Sci. USA, 76: p. 51-55), and also is closely related to the principle described immediately above. In this approach, the formation of an amide bond between two molecule fragments is facilitated by the juxtaposition of these by hybridisation of two oligonucleotides, each carrying one molecule fragment, to a complementary template. An oligonucleotide, in the present invention termed a carrier identifier, to which a carboxylic acid of a molecule fragment is attached through ester linkage, is hybridised to a template, which is also hybridised to a second oligonucleotide carrying a molecule fragment comprising an amino group. The duplex DNA is designed so as to bring the ester and the amine into close proximity. Because of this proximity, a reaction between the ester and the amine takes place; this leads to formation of an amide bond between the two molecule fragments, and the ester is cleaved to allow transfer of the ester-bound molecule fragment onto the molecule fragment comprising the amino group. An ester linkage is thus used to allow direct transfer of the molecule fragment; in principle any substitution-labile acyl linkage should allow the direct transfer of one molecule fragment onto the other in this scheme. In addition, many other reactions may be used to link two molecule fragments in an oligonucleotide-templated fashion. Thus, this principle may be applied to the generation of encoded molecules as listed in the present invention, and may involve reactive groups mentioned in the present invention, including those listed in FIGS. 6, 7, and 8.

C. This is a variation of (Liu et al. (2002), WO 02/074929 A2, "Evolving new molecular function"). Any embodiment of bi-functional molecule synthesis described in said patent application is applicable for the stage 2 synthesis of bi-functional molecules. In a preferred embodiment of this application, the method comprises first providing one or more nucleic acid templates, which one or more nucleic acid templates optionally have a reactive unit associated therewith. The nucleic acid template is then contacted with one or more transfer units designed to have a first moiety, an anticodon, which hybridises to a sequence of the nucleic acid, and is associated with a second moiety, a reactive unit, which includes a building block of the compound to be synthesised. Once these transfer units have hybridised to the nucleic acid template in a sequence-specific manner, the synthesis of the chemical compound can take place due to the interaction of reactive moieties present on the transfer units and/or the nucleic acid template. Significantly, the sequence of the nucleic acid can later be determined to decode the synthetic history of the attached compound and thereby its structure. The method allows the synthesis of large numbers of molecules using combinatorial methods. The principle may be applied to the generation of encoded molecules as listed in the present invention, and may involve reactive groups mentioned in the present invention, including those listed in FIGS. 6, 7, and 8.

D. This is a variation of the templated synthesis described in (Pedersen et al. (2002) WO 02/103008 A2, "Templated molecules and methods for using such molecules"). Any embodiment of bi-functional molecule synthesis described in said patent application is applicable for the stage 2 synthesis of bi-functional molecules. This variation involves the generation of a library of bi-functional molecules, where the individual bi-functional molecule synthesis comprises the steps of i) providing at least one identifier template comprising a sequence of n coding elements, complementary to n carrier identifiers, ii) providing a plurality of carriers, wherein each carrier comprises a) at least one carrier identifier oligonucleotide capable of recognising a predetermined coding element, b) at least one molecule fragment with at least one reactive group, and c) at least one linker separating the at least one molecule fragment from the at least one carrier identifier, iii) contacting each of said coding elements with a carrier identifier capable of recognising said coding element, and iv) obtaining a bi-functional molecule comprising covalently or non-covalently linked molecule fragments by linking, by means of a reaction involving reactive groups, two or more molecule fragments, wherein the bi-functional molecule is linked by means of a linker to the identifier template or the complementary template that templated the synthesis of the bi-functional molecule.

The principle may be applied to the generation of encoded molecules as listed in the present invention, and may involve reactive groups mentioned in the present invention, including those listed in FIGS. 6, 7, and 8.

E. This is a variation of the principle described in (Pedersen et al. (2003) WO03/078625 A2, "An improved method for synthesizing templated molecules"). Any embodiment of bi-functional molecule synthesis described in said patent application is applicable for the stage 2 synthesis of bi-functional molecules. The variation provides a method for synthesising a bi-functional molecule, said method comprising the steps of: a) providing at least one identifier template comprising one or more codons (i.e., oligonucleotide sequences complementary to carrier identifiers), b) providing a first carrier molecule comprising a zipping domain, said zipping domain comprises a first part of a molecule pair, being capable of reversible interaction with a second part of the molecule pair, c) providing one or more second carriers, comprising a zipping domain comprising the second part of said molecule pair and capable of reacting with the first carrier, d) contacting the components of step a), b), and c) with each other under conditions allowing specific hybridisation of the carriers to the template(s) and dimerization of the two parts of the molecule pair, e) allowing the reactive groups of the first carrier to react with the reactive groups of the second carrier(s), f) optionally, cleaving one or more linkers, provided that at least one linker remains to connect the molecule fragments (i.e., the encoded molecule) with the template or the complementary template, g) obtaining a bi-functional molecule where the identifier template directed the synthesis of the encoded molecule.

The principle may be applied to the generation of encoded molecules as listed in the present invention, and may involve reactive groups mentioned in the present invention, including those listed in FIGS. 6, 7, and 8.

F. This is another variation of the principle described in (Liu et al. WO 2004/016767 A2, Evolving New Moelcular Function). Here, the templated synthesis is performed with a template that has an "omega" or "O" type architecture. This type of template permits distance-dependent nucleic acid-templated reactions to be encoded by bases far removed from the associated reactive unit. The method involves providing (i) a template comprising a first reactive unit associated with a first oligonucleotide comprising a codon and (ii) a transfer unit comprising a second reactive unit associated with a second oligonucleotide comprising an anti-codon that is capable of annealing to the codon. The codon and/or the anti-codon include first and second regions spaced apart from one another. The oligonucleotides then are annealed together to bring the reactive units into reactive proximity. When the oligonucleotides anneal to one another, the codon (or anti-codon) with the spaced-apart regions produce a loop of oligonucleotides not annealed to the corresponding anti-codon (or codon). A covalent bond-forming reaction then is induced between the reactive units to produce the reaction product, the "encoded molecule".

G. These approaches are alternative methods for the templated stage 2 synthesis, and are described in the FIGS. 2-8, 11 and 13, and are described in detail elsewhere in this application.

H. This is a variation of the approach for stage 2 synthesis, in which the template and the carrier molecules do not have to be associated (hybridized) during the reaction of the molecule fragments (Franch et al., WO 2004/083427, "Ligational encoding of small molecules"). In the course of the encoding process, a single-stranded product is generated, including both the template and some or all of the carrier molecules. Thus, the molecule fragments, and the reactive groups that react during the stage 2 synthesis step, are covalently associated with the template, which allows e.g. a higher temperature to be employed during the reaction step. This may be an advantage for reactions that are particularly enthalpy-driven.

Bi-functional molecule formation (i.e. formation of carriers for use in a templated synthesis or formation of the final encoded molecule): The above methods for carrier synthesis and templated synthesis can be combined in any way. As an example, 3A (subprocess 3: formation of bi-functional carrier molecules, as described by any of the embodiments of (Freskgård et al., WO 2004/039825 A2), for example through enzymatic ligation of identifiers; followed by direct transfer acylation stage 2 synthesis as described in (Bruick et al., Chemistry and Biology, January 1996, 3: 49-56), can be applied to the generation of bi-functional molecules.

In a preferred embodiment, a one-to-one relationship exists between the identifiers and molecule fragments. Thus, one specific identifier identifies (encodes) one specific molecule fragment. However, it is not essential for the invention that such one-to-one relationship exists. For example, during stage 1 synthesis different identifiers may be added to the same well, wherefore more than one identifier will encode one molecule fragment. It is still possible, however, to identify the molecule fragment directly from the sequence of the identifier. Likewise, it is possible to add several molecule fragments to the same well during stage 1 synthesis. In this case, however, the identity of the molecule fragment cannot be deduced directly from the sequence of the attached identifier, but must be deduced by other means, for example mass spectrometry. Finally, it is also possible to add the same identifier to several wells, or the same molecule fragment to several wells. In the former case, however, it is not possible to identify the molecule directly from the sequence of the identifier.

Screening Methods Employing Bi-Functional Molecules.

Once the bi-functional molecules have been generated, the desired molecules may be identified in any way possible. Thus, a number of screening methods exist, for the identification of organic molecules with desired characteristics. Different types of selection or screening protocols are described in (Liu et al. (2002), WO 02/074929 A2; Pedersen et al. (2002) WO 02/103008 A2; Pedersen et al. (2003) WO03/078625 A2; Lerner et al., EP 0643778 B1, Encoded combinatorial chemical libraries; Dower et al., EP 0604552 B1; Freskgård et al., WO 2004/039825 A2; Morgan et al., 2005, WO 2005/058479; Harbury and Halpin, WO 00/23458).

Specific screening methods employing bifuntional molecules for the identification of organic molecules with desired characteristics include but are not limited to:

i) Affinity selection on immobilised target molecules. In this approach the target molecules (e.g., DNA, RNA, protein, peptide, carbohydrate, organic or inorganic molecule, supramolecular structure or any other molecule), is immobilized covalently or non-covalently to a solid support such as beads, the bottom of a well of a microtiter plate, a reagent tube, a chromatographic column, or any other type of solid support. A library of bi-functional molecules are now incubated with the immobilized target molecule, excess non-bound bi-functional molecules are washed off by replacing the supernatant or column buffer with buffer not containing bi-functional molecules one or more times. After washing the bound bi-functional molecules are released from solid support by addition of reagents, specific ligands or the like that results in the elution of the bi-functional molecule, or the pH is increased or decreased to release the bound bi-functional molecules, or the identifier of the bi-functional molecule is cleaved off from the encoded molecule with a reagent, pH change or light-induced cleavage. The recovered identifiers can now optionally be amplified by PCR, and cloned and sequenced to reveal the structure of the ligands encoded by the identifier, or alternatively, be amplified and taken through an additional round of templated synthesis. As an alternative, the identifiers or bi-functional molecules comprising identifiers, are not released from solid support, but rather the identifiers are optionally amplified by PCR directly while still immobilised on solid support.

ii) Affinity selection on target molecules in solution, followed by any means of isolation of the bi-functional molecules bound to the target, e.g. by immunoprecipitation of the target-bi-functional molecule complexes. A library of bi-functional molecules are incubated with target molecules (e.g. a protein). After complex formation of bi-functional molecules with target, the complex is isolated from non-complexes, for example by the addition of polyvalent antibodies against the target molecule and precipitation of antibody-target-bi-functional molecule complexes, or is precipitated by the addition of beads that bind the target molecules. The latter may for example be by addition of streptavidin-coated beads that bind to pre-biotinylated targets. The identifiers recovered by precipitation can now be characterised or amplified, e.g., by PCR, as described in (i). The sequence of the identifiers will reveal the identity of the encoded molecules that bind the target molecules.

iii) Affinity selection on target molecules in solution, followed by gel retardation, chromatographic separation e.g. size exclusion chromatography, or separation by centrifugation e.g. in a $CsCl_2$-gradient. A library of bi-functional molecules are incubated with target molecules (e.g. a protein). After complex formation of bi-functional molecules with target, the complex is isolated from non-complexes, for example by gel electrophoresis or size exclusion chromatography, or any other chromatographic or non-chromatographic method that separates the target-bi-functional molecule complexes from non-complexed bi-functional molecules, for example based on the difference in size and/or charge. The identifiers of the bi-functional molecules of the column fraction or band on the gel that comprises target-bi-functional molecule complexes are now characterised or amplified, e.g., by PCR, as described above. The sequence of the identifiers will reveal the identity of the encoded molecules that bind the target molecules.

iv) Affinity selection on surfaces. Particles, preferably small particles, of solid material, e.g., metal particles, metal oxide particles, grinded plastic, wood, preformed carbon nanotubes, clay, glass, silica, bacterial biofilm or biofilm of other microorganism, cement, solid paint particles, laminate, stone, marble, quartz, textile, paper, skin, hair, cell membranes, industrial membranes, epiderm, or the like, is added to a solution comprising a library of bi-functional molecules. After incubation, one or more washing steps are performed, to remove unbound bi-functional molecules. Then, the bi-functional molecules bound to the surface, or the identifiers of the bi-functional molecules bound to the surface, are released as described above, and the identifiers characterised and/or amplified as described above.

v) Selection for intracellularisation. Bi-functional molecules are incubated with cells or micelles, or on one side of a lipid membrane, or on one side of a cell monolayer (e.g. CaCo2 cell monolayer), in order to allow the bi-functional molecule to pass or become immobilized into the membranes. Then, a number of washing steps are performed in order to remove bi-functional molecules that have not become immobilized or have passed the membrane. Identifiers from bi-functional molecules that have become immobilized or have passed the membrane are now amplified and/or characterised as described above. The encoded molecule of bi-functional molecules that have either become immobilized in the membrane or have passed the membrane, represent potential transporters for intracellularization, i.e. by attaching these encoded molecules (without the oligonucleotide tag) to e.g. non-oral drugs these may become orally available, because the transporter mediate their transport across the cell.

vi) Selection by phase partitioning. A two- or three phase system may be set up, wherein the bi-functional molecules will partition out according (at least in part) to the characteristics of the encoded molecules. Therefore, the principle allows the identification of encoded molecules that have particular preference for a certain kind of solvent. Again, the identifiers of the isolated bi-functional molecules can be amplified and/or characterised after the selection has occurred. It may be necessary to coat the nucleic acid component of the bi-functional molecule with e.g. DNA binding proteins, in order to ensure that the partitioning of the bi-functional molecule is significantly correlated with the characteristics of the encoded molecule of the bi-functional molecule.

vii) Selection for induced dimerisation of target molecules. In a preferred embodiment, encoded molecules are sought that induce the dimerization of target molecules. For example, small molecules with the potential to induce dimerization of protein receptors in the cell membrane may be applicable as therapeutics. Thus, a selection protocol for encoded molecules with the potential to induce dimerization of proteins A and B is a s follows: A library of bi-functional molecules are incubated with proteins A and B. After incubation, the solution is applied to gel electrophoresis, ultracentrifugation (e.g. CsCl-centrifugation), size exclusion chromatography, or any other kind of separation that separates the protein A-protein B-bi-functional molecule-complex from un-complexed protein A and B, and other undesired complexes, such as protein A-protein B-complex. Bi-functional molecules from the band or fraction corresponding to the size and/or charge of the protein A-protein B-bi-functional molecule-complex is recovered, and template identifiers are then amplified and/or characterised as described above. In this case, the encoded molecule would be resynthesized, and tested in a protein dimerisation assay for its effect on the dimerisation of protein A and B.

viii) Selection by iterative rounds of binding and elution. This is a modification of the methods reported previously (Doyon et al. (2003), J. Am. Chem. Soc., 125, 12372-12373). Bi-functional molecules are incubated with e.g. immobilised target molecule, e.g. a biotinylated enzyme immobilised on streptavidin beads. After washing one or more times, the bound bi-functional molecules are released from solid support by a change in pH, or by addition of an excess of ligand that binds the target molecule (the ligand can be e.g. a small molecule, peptide, DNA aptamer or protein that is known to bind the target molecule). Alternatively, the bi-functional molecules may be released by degradation of the immobilised target (e.g. by nuclease or protease), denaturation of target or induced conformational changes in target structure or the like. The recovered bi-functional molecules are now re-applied to e.g. immobilised target molecule, optionally after removal or degradation of the ligand or reagent used for elution in the previous step. Again, washing is performed, and the bound bi-functional molecules eluted. The process of incubation and binding, washing and elution can be repeated many times, until eventually only bi-functional molecules of high affinity remains. Then the identifiers of the bi-functional molecules are amplified and/or characterised. Using this kind of iterative binding and elution, enrichment factors higher than 100.000-fold can be obtained.

Targets may be immobilised on columns, on beads (batch selection), on the surface of a well, or target and ligands may interact in solution, followed by immunoprecipitation of the target (leading to immunoprecipitation of ligands bound to target).

ix) Screening in compartments. A library of template identifiers are incubated with lipids, bi-functional carrier molecules, primers, nucleotides and other components necessary for micelle formation and PCR amplification, transcription, stage 2 templated synthesis, and assay. The lipids are allowed to assemble into micelles; the number of input templates are adjusted so that on average every fifth micelle contains a template after micelle formation. A PCR reaction is performed, to generate multiple copies of the same template in each micelle. Then transcription is performed, in order to generate many copies of the corresponding single-stranded RNA. The carriers now hybridise to the RNA, and reaction between reactive groups of the carriers take place, to form the same encoded molecule in multiple copies in a given micelle. Finally, the assay is performed (for example, an enzyme assay that examines the ability of the encoded molecule to inhibit enzyme activity). Positive micelles are picked by hand under microscope, or sorted using e.g. a FACS sorting machine. Then the identifiers contained within the positive micelles are amplified and/or characterised as described above. Encoded molecules identified in this way represent potential inhibitors of the enzyme; after resynthesis of the free encoded molecule, the encoded molecule can be examined for its inhibitory effect on enzyme activity in standard inhibition assays.

x) Whole organism selection. A library of bi-functional molecules, optionally modified by e.g. coating proteins, is injected into a dead or living animal, for example a mouse. After incubation for a period of time (e.g two hours) in the animal, specific tissue or organs are recovered, and the bi-functional molecules associated with specific organs can be characterised, by e.g. PCR amplification and/or sequencing of the corresponding identifiers. As a specific example, a mouse carrying a tumor can be injected with a library of bi-functional molecules. After incubation, the tumor can be isolated from the animal. The bi-functional molecules associated with the tumor are potential therapeutics or diagnostics for that cancer.

xi) Any other kind of selection or screening which may be performed employing libraries of bi-functional molecules.

The abovementioned target molecules may be any supramolecular structure (e.g. nanoclusters, multiprotein complex, ribosomes), macromolecule (e.g. DNA, RNA, protein, polymers such as carbohydrates, thiophenes, fibrin), or low molecular weight compound (e.g. cAMP, small peptide hormones, chelates, morphine, drug).

After having performed any of the selections above, the identifiers of the output bi-functional molecules can be amplified, and taken through one more round of stage 2 synthesis. Then, the same or another selection protocol can be performed. This process can be repeated until an appropriately small number of different bi-functional molecules are recovered.

Any combination of stage 1 and stage 2 synthesis may be employed in the generation of bi-functional molecules. Moreover, any screening method may be combined with any combination of stage 1 and stage 2 synthesis schemes. Thus, referring to the numbering above for stage 1 synthesis procedures (1, 2, 3, . . . X) and stage 2 synthesis procedures (A, B, . . . Z) and screening methods (i, ii, iii, . . . n), the following combinations may be employed during the generation and use of bi-functional molecules: 1Ai, 1Aii, 1An, 1Bi, 1Bii, . . . 1Bn, . . . 2Ai, XZn Furthermore, any sequence of encoding and screening schemes may be applied:
1Ai+1Ai, 1Ai+1Aii, . . . , XAn+XAn, 1Bi+1Bi, . . . XZn+XZn (all of which represent two rounds of library generation and screening), and
1Ai+1Ai+1Ai, 1Ai+1Ai+1Aii, . . . , XZn+XZn+XZn (all of which represent three rounds of library generation and screening), and
any sequence of, and any number of, library generation and screening rounds.

Finally, in each of the stage 1, stage 2 and screening steps, one or more approaches may be employed. For example, carriers may be generated during stage 1 synthesis, by any combination of approaches 1-X. The carriers may likewise be employed in any combination of stage 2 synthesis approaches. Finally, the bi-functional molecules generated may be screened by any combination of screening approaches i-n. Again, any sequence of encoding and screening schemes may be applied.

In a preferred embodiment, the stage 1 carrier synthesis is only performed once, whereas the stage 2 synthesis is performed any number of times. In this case, each of the stage 2 syntheses may employ the carriers synthesised in the beginning. Thus, a preferred sequence of stage 1 library synthesis, stage 2 library synthesis and library screening is as follows:

$5Ai+Ai$, where first carrier synthesis is performed according to (5) above, where the identifiers are ligated together chemically, followed by templated synthesis as described in (A) above, and using the carriers generated immediately above, followed by
screening of the library generated immediately above, by affinity selection on the target molecule as described in (i) above, followed by PCR amplification of the DNA part of the bi-functional molecules recovered from this affinity selection, followed by
templated synthesis as described in (A) above, using the PCR product generated immediately above as DNA templates, and using the carriers synthesised in the first part of the process, and finally followed by
screening of the library generated immediately above, by affinity selection on the target molecule as described in (i) above,
to identify bi-functional molecules with affinity for the target molecule.

Finally, the encoded molecules with the desired characteristics (affinity for the target molecule) may be identified, by PCR amplification and sequencing of the DNA templates of the recovered bi-functional molecules.

In another preferred embodiment, three rounds of library synthesis is performed, where the first library is generated solely by stage 1 synthesis, the second library is made through a combination of carrier synthesis and templated synthesis, and the third library is made through templated synthesis using carriers synthesised in the previous round of library synthesis. One such sequence of library syntheses and screening is 5iv+5Aiv+Aiv: First a library of bi-functional molecules is made where four molecule fragments are linked together to form the encoded molecule, and four identifiers are chemically ligated together to form the DNA template, as described in (5) above, followed by affinity selection on a surface (for example a suspension of metal-oxide particles in aqueous buffer) as described in (iv) above, followed by
Carrier synthesis as described in (5) above, where two molecule fragments are linked together and two identifiers are ligated together, to form carrier molecules consisting of two molecule fragments and two identifiers, followed by
Templated synthesis, where first the DNA templates of the recovered bi-functional molecules from the screening (iv) above are PCR-amplified, and the templates used in a templated synthesis using the carriers generated immediately above. The choice of identifiers and molecule fragments must ensure that an encoded molecule recovered from the first screening round is amplified and turned into a number of copies of the same encoded molecule, attached to a DNA template, even though different methods are used in the first and second round of library generation (i.e., 5 and 5A, respectively). Thus, the final bi-functional molecules generated either initially or after the amplification of recovered templates, contain identical encoded molecules, but may carry different DNA templates. Library generation is followed by Affinity selection on a surface (in this example, a suspension of metal-oxide particles in aqueous buffer) as described in (iv) above, followed by Templated synthesis, where first the DNA templates of the recovered bi-functional molecules from the screening (iv) immediately above are PCR-amplified, and the templates used in a templated synthesis using the carriers generated above, followed by Affinity selection on a surface (in this example, a suspension of metal-oxide particles in aqueous buffer) as described in (iv) above.

Finally, the encoded molecules with the desired characteristic (affinity for the surface) may be identified, by PCR amplification and sequencing of the DNA templates of the recovered bi-functional molecules.

Reactive groups may be protected and de-protected at various steps during the synthesis of the encoded molecules, in order to ensure that the reactions proceed in the desired order, and links desired molecule fragments in the desired way. Also, before, during or after linkage of the molecule fragments, individual parts of the encoded molecule may be made cyclic, by reaction of reactive groups of different molecule fragments, or by reaction of reactive groups within a molecule fragment.

After or during stage 1 or stage 2 synthesis, the encoded molecule may be modified, for example by hydrogenation, reduction/oxidation, or by reaction with any chemical moiety. If the modification is done on the pool of bi-functional molecules, the modification is typically not encoded (i.e., no identifiers are added). As for the stage 1 and stage 2 syntheses, it is important that the conditions and reagents of the chemical reaction on the encoded molecule does not modify the template or complementary template to such an extent that the template or complementary template cannot be amplified and/or sequenced. Examples of reactions and reagents that may be applied for the modification of the encoded molecule are shown in FIGS. 6 and 7.

The split and mix process (Stage 1) that leads to the formation of bi-functional carrier molecules may involve any number of rounds. Preferably the number of rounds is between 1 and 10. Likewise, the DNA-templated synthesis (Stage 2) may involve templates, each of which that hybridise to any number of carrier molecules. Preferably, a template can hybridise to 1-10 carrier molecules simultaneously. Any template, however, has a given maximum of carriers that it can bind. The carriers may be annealed to the template and reacted two at a time, three at a time, four at a time, more than four at a time, or all at once, or one carrier may be reacted with a reactive group on the template (i.e. the carriers are annealed and reacted one at a time, when the nascent encoded molecule is linked to the template). Any combination of hybridisations and reactions may be used until the reactive groups have reacted and the encoded molecule formed.

During stage 1 synthesis, a repertoire of molecule fragments can contain different kinds of reactive groups that participate in different coupling reactions. As an example, the first molecule fragment reacted with the functionality on the linker L may be an amino acid.

After coupling to the linker, an amine $NH_2$ functionality may be available for reaction with the incoming molecule fragment. Thus, the incoming molecule fragment must contain a reactive group capable of reacting with the amine. Example reactive groups of the incoming molecule fragment are carboxylic acid COOH (reacts through an acylation reaction with the amine by addition of e.g. EDC/NHS), aldehyde CHO (reductive amination reaction with amine), sulfonate (alkylation reaction with amine), sulfonoyl chloride (sulphonamide formation with amine), and substituted aromates (nucleophilic aromatic substitution). During stage 1 synthesis each molecule fragment is added to a specific well, and therefore, the reaction conditions that are ideal for a particular reaction may be employed in that specific well.

Likewise, during stage 2 synthesis, carriers carrying a variety of different molecule fragments can be employed. For example, if a library of templates all bind one carrier containing an amine reactive group, the other carrier can contain for example a COOH, CHO, sulfonoyl chloride or a substituted aromate. The reactions of stage 2 synthesis may not be separated in separate wells, and therefore, the molecule fragments must be compatible with the reaction conditions and reagents/catalysts used for all reactions performed. The reactions can be performed simultaneously if the reactions can be performed under the same conditions, or the reactions may be performed sequentially if the reactions require different conditions and reagents/catalysts.

For both stage 1 and stage 2 synthesis, the number of reactive groups X on the linker, or the number of reactive groups on the nascent bi-functional molecule can vary. If the linker has one reactive group, the molecule fragment that becomes attached to the linker must have at least one reactive group in order to attach further molecule fragments to the nascent bi-functional molecules. If all molecule fragments contain two reactive groups, one reactive group can react with the nascent bi-functional molecule, and one may react with the next molecule fragment that is attached. The resulting structure is a linear structure, like beads on a string. Alternatively, if the nascent bi-functional molecule carries three or more reactive groups, one reactive group may be used for attachment to the nascent bi-functional molecule, and the remaining reactive groups may be attached to different molecule fragments (in the same or in different synthesis rounds), and the resulting structure is branched. Molecule fragments containing more than two reactive groups are termed scaffolds; the structure generated (where at least two encoded molecule fragments in addition to the nascent bi-functional molecule become attached directly to the same molecule fragment) is termed a scaffolded or branched molecule. Typical scaffolds include aromatic structures, benzodiazepines, hydantoins, piperazines, indoles, furans, thiazoles, steroids, diketopiperazines, morpholines, tropanes, coumarines, qinolines, pyrroles, oxazoles, amino acid precursors, cyclic or aromatic ring structures, and many others, all of which must contain at least three reactive groups in order to be considered scaffolds.

If two or more reactive groups of a molecule fragment react directly with the nascent bi-functional molecule, a cyclic structure results.

The molecule fragment repertoires of different rounds of stage 1 synthesis may be of different size, i.e. a different number of molecule fragments may be employed in different rounds. The identifiers added in different wells or different rounds of stage 1 synthesis may be of different length and/or composition. In a preferred embodiment one well contains one specific identifier and one specific molecule fragment. However, in another preferred embodiment more than one molecule fragment is added to each well. This will result in relaxation of the one-template/one-encoded molecule relationship that exist between template sequence and encoded molecule, and can therefore only be pursued to a limited extent. Likewise, in another preferred embodiment more than one identifier sequence is added to each well. If the same identifier is added to different wells containing different molecule fragments, this will also result in relaxation of the one-template/one-encoded molecule relationship.

Under certain circumstances, the templated synthesis (Stage 2) may be repeated using the bi-functional molecules generated in the templating process as carriers in a second or third templating process. As an example, a templated synthesis reaction is employed that involves ligation of the two carrier molecules, to form a bi-functional molecule in which all the sequence-units identifying the molecule fragments are covalently linked, and where the encoded molecule remains attached to the DNA portion (for an example, see FIG. 4, example 2). Then the bi-functional molecule resulting from the templated reaction (in FIG. 4, example 2, the DNA template attached to the encoded molecule XY), may be used in a next templated reaction, using a template that carries two sequence units, one of which is complementary to the DNA portion of the bi-functional molecule generated in the first templated reaction.

Under certain circumstances, it may be desirable to i) generate the bi-functional molecules used in the screening process through split and mix synthesis only, e.g. exclude the stage 2 templating process in the initial bi-functional molecule generation. If desired, recovered bi-functional molecules from the screen may then be amplified using a combination of split and mix synthesis (stage 1) and templated synthesis (stage 2)(see for example FIG. 2), using the template generated during the bi-functional molecule synthesis described in i) above.

In i) above, a template is generated using a split and mix procedure, involving also the synthesis of an encoded molecule. However, a simpler version of this split and mix approach can be applied to the generation of a library of DNA templates. As an example, to make a library of $n^3$ DNA templates where each DNA template carries 3 codons, and where each of the 3 positions can contain any of n different codons, perform the following steps: i) Add an aliquot of a mixture of n position1 codon DNA duplexes to each of n wells, ii) To each well, add a specific position2 codon duplex DNA, iii) Ligate the position 1 codon DNA duplex and the position2 codon DNA duplex (f. ex. by the use of a DNA ligase, or an activated phosphate (e.g. Imidazole-phosphatexxxxx, see ref . . . ), iv) Mix the contents of all wells, v) Add an aliquot of the mixture of ligated position1-position2 DNA duplexes to each of n wells, vi) To each of the n wells, add a specific position3 codon DNA duplex, vii) Ligate the position3 duplex to the position1position2 duplexes, viii) Mix the contents of all wells.

The resulting pool contains $n^3$ different DNA templates, carrying n different codons at each of 3 codon positions. The DNA duplexes carrying position1 or position3 codons may also carry primer binding sites, to allow amplification by PCR of the generated templates. The nucleic acid carrying the codons may be RNA, DNA or any other type of nucleic acid or nucleic acid derivative, and it could be single- or double-stranded.

It may be desirable, after the synthesis of the bi-functional molecules but before the bi-functional molecules are used in a selection or screening experiment, to make the template double-stranded. This may be done by annealing a primer to the template strand (or its complementary strand), and extend for example using sequenase. This will form a double stranded oligonucleotide template, which is expected to be more inert in the selection experiment than the corresponding single-stranded oligonucleotide, because of the single-stranded oligonucleotide's ability to bind the target as an aptamer.

In a preferred embodiment, the carrier molecules are immobilised during their synthesis. For example, the following types of solid support may be employed for the immobilisation: Sepharose beads with functionalities like —SH, —COOH or —NH$_2$ groups (where the identifiers or templates are covalently coupled by e.g. disulfide formation, acylation, and acylation, respectively); tentagel beads with functional groups e.g. —SH, —COOH or —NH$_2$ groups; streptavidin coated beads (where the carriers or templates are covalently coupled to biotin, which in turn can be non-covalently bound to streptavidin); and many other types of supports and functionalities (e.g. polystyrene, polypropylene, agarose (e.g. Hispanagar); diol functionalities, ester functionalities; amide functionalities, glyoxal functionalities). Advantages of immobilisation of carriers or templates include the easy isolation of single-stranded carriers or single-stranded templates (for use in stage 2 synthesis), easy removal of excess reagents (molecule fragments, identifiers, catalysts, reactants), the ability to conveniently change solvent (for example, change to organic solvent prior to the reaction of the molecule fragments), removal of protection groups, etc.

Finally, the molecule fragments may be immobilised prior to reaction with the growing carrier molecule. This allows for the purification of growing carriers that have reacted with the immobilised molecule fragments. This in turn allows purification of full-length carriers (i.e., carriers that contain the desired molecule fragments), which will lead to a more efficient stage 2 synthesis.

The carriers and/or templates may be released from the solid support by hydrolysis (e.g. high pH), proteolysis (of a peptide linker), thiol mediated cleavage of disulfide bond, nuclease-mediated cleavage, etc.

Types of Encoded Molecules:

Different kinds of molecules may be generated and attached to the DNA template that encodes it. Molecules that may be generated by the present invention include small compact molecules, linear structures, polymers, polypeptides, poly-ureas, polycarbamates, scaffold structures, cyclic structures, natural compound derivatives, alpha-, beta-, gamma-, and omega-peptides, mono-, di- and tri-substituted peptides, L- and D-form peptides, cyclohexane- and cyclopentane-backbone modified beta-peptides, vinylogous polypeptides, glycopolypeptides, polyamides, vinylogous sulfonamide peptide, Polysulfonamide conjugated peptide (i.e., having prosthetic groups), Polyesters, Polysaccharides, polycarbamates, polycarbonates, polyureas, poly-peptidylphosphonates, Azatides, peptoids (oligo N-substituted glycines), Polyethers, ethoxyformacetal oligomers, polythioethers, polyethylene, glycols (PEG), polyethylenes, polydisulfides, polyarylene sulfides, Polynucleotides, PNAs, LNAs, Morpholinos, oligo pyrrolinone, polyoximes, Polyimines, Polyethyleneimine, Polyacetates, Polystyrenes, Polyacetylene, Polyvinyl, Lipids, Phospholipids, Glycolipids, polycycles, (aliphatic), polycycles (aromatic), polyheterocycles, Proteoglycan, Polysiloxanes, Polyisocyanides, Polyisocyanates, polymethacrylates, Monofunctional, Difunctional, Trifunctional and Oligofunctional open-chain hydrocarbons.

Figure 13:
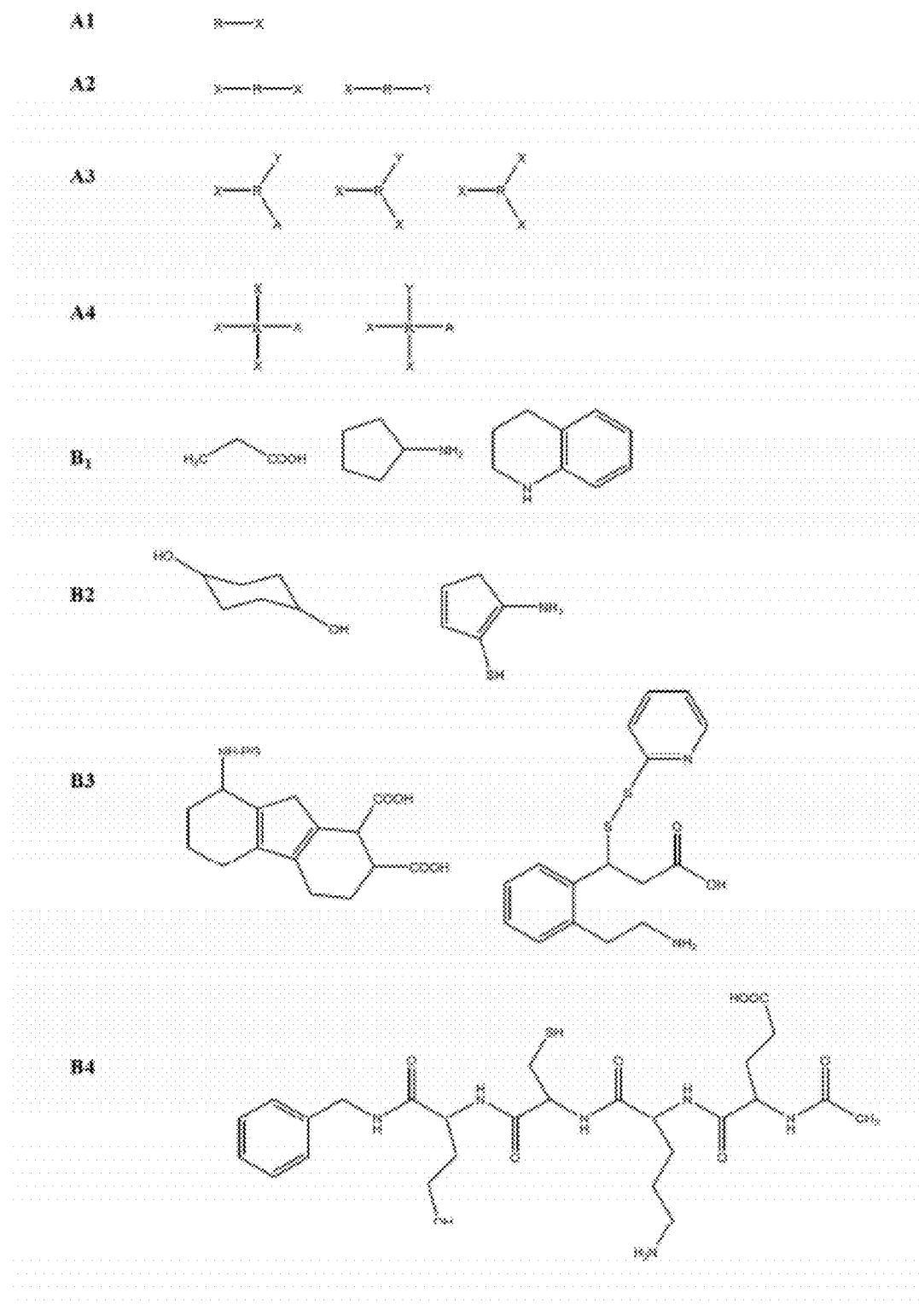
Figure 13:
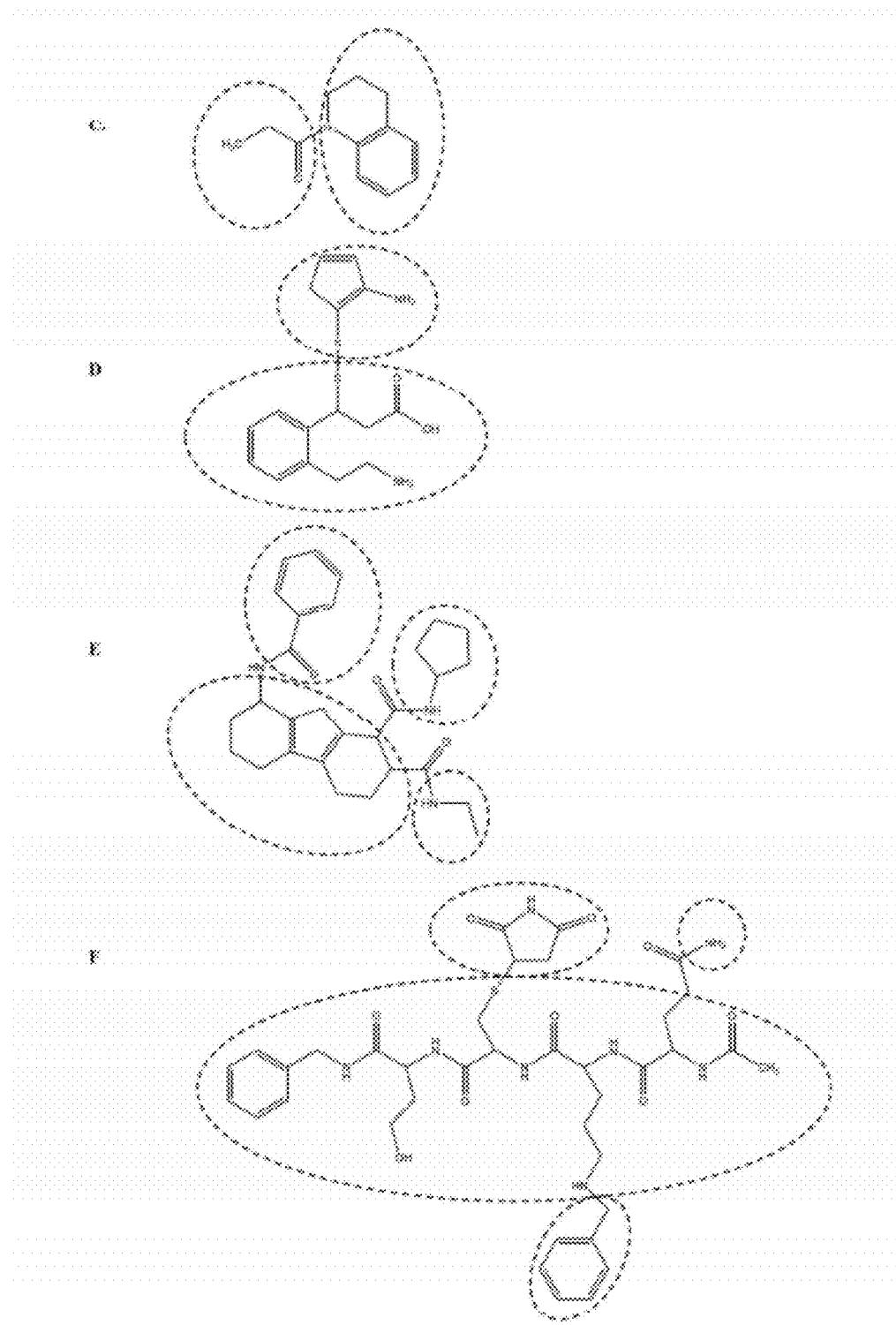

Monofunctional, Difunctional, Trifunctional and Oligofunctional Nonaromat Carbocycles, Monocyclic, Bicyclic, Tricyclic and Polycyclic Hydrocarbons, Bridged Polycyclic Hydrocarbones, Monofunctional, Difunctional, Trifunctional and Oligofunctional Nonaromatic, Heterocycles, Monocyclic, Bicyclic, Tricyclic and Polycyclic Heterocycles, bridged Polycyclic Heterocycles, Monofunctional, Difunctional, Trifunctional and Oligofunctional Aromatic Carbocycles. Monocyclic, Bicyclic, Tricyclic and Polycyclic Aromatic Carbocycles
Monofunctional, Difunctional, Trifunctional and Oligofunctional Aromatic Hetero-cycles. Monocyclic, Bicyclic, Tricyclic and Polycyclic Heterocycles. Chelates, fullerenes, and any combination of the above and many others. A non-comprehensive list of example generic and specific structures generated by the present invention is shown in (FIG. 13). Each of the molecule fragments linked together during the process may be prepared by any kind of synthetic protocol, including standard organic synthesis, prior to the library generation process. Therefore, any type of chemical moiety can be included in a molecule or library of molecules of the present invention. The linkages (bonds) between the molecule fragments (the linkages that are generated during the library generation process) must be compatible with the presence of the DNA.

The types of bonds that may be generated must be compatible with the presence of the oligonucleotide. Types of linkages that may be generated in the present invention include amide bonds, carbamates, sulfones, sulfoxides, phophodiester bonds, carbohydrate bonds, ureas, phosphonates, esters, and many others A non-comprehensive list of such linkage bonds is shown in (FIGS. 6 and 7), and is listed within the description below.

Following the encoded synthesis of the molecules (whereby one or more bi-functional molecules have been formed), the encoded molecules may be modified in a non-encoded way. For example, the library of molecules may be hydrogenated, acylated, oxidised or reduced, or protection groups may be removed. It will often be necessary to protect chemical motifs that would otherwise participate in the reactions that attach molecule fragments, either through reaction with molecule fragments, reagents, or other nascent bi-functional molecules. These chemical motifs can then be generated at the end of library synthesis, by deprotection reactions after the encoding- and encoded reactions. In principle, any of the reactions listed in FIG. 6, 7 or 8 may be used after the encoded synthesis, in order to modify the encoded molecules.

Use of the method for the synthesis of specific (one or a few) different molecule species. The described methods for organic molecule synthesis may be applied to a) synthesis of compounds of high stereochemical purity, or b) synthesis of compounds without the cumbersome use of protection groups, or c) as a means to increase the yield of synthesis steps that are usually inefficient, for example because the necessary concentrations cannot be achieved in a standard organic synthesis setting.

Examples of such uses of the methods is synthesis of a sequence of saccharides, without the use of protection groups.

Use of the Library for Screening.

The bi-functional molecules generated by the present invention may be used to identify encoded molecules with particular characteristics. For example, the bi-functional molecules may be employed in affinity selection experiments, in which bi-functional molecules capable of binding to proteins, DNA, RNA, surfaces, inorganic or organic molecules, and other molecules and substances may be identified. During the affinity selection experiments bi-functional molecules interacting with these molecules or substances may be isolated, and identified by sequencing the DNA portion of the bi-functional molecules. Alternatively, the bi-functional molecules may be screened for catalytic activity, for the ability to interact with other bi-functional molecules, for the ability to become internalised into a cell, for the ability to interfere with conductance or fluorescence or any other characteristics of another molecule or substance, or for any other characteristics desired. Finally, the library may be screened for the ability to interact with library members of other types of molecules, for example phage-displayed peptides or proteins, in order to identify bi-functional molecules that interact with peptides or proteins of the phage-display library.

The DNA portion of the bi-functional molecules in these different types of screens and selections allows the easy and highly sensitive identification of the encoded small molecule component responsible for its isolation during the screen or selection. In principle, one species of a bi-functional molecule is enough to allow its identification, by first amplifying the DNA component by PCR, followed by sequencing of the DNA.

In addition, the DNA component allows several rounds of screening and amplification to be performed. Thus, after a screening round, the recovered population of bi-functional molecules may be amplified (by amplification of the DNA template, followed by Stage 1 carrier synthesis (or the original preparation of carriers may be used) and Stage 2 templated synthesis using the amplified DNA template for bi-functional molecule synthesis). The amplification generates several copies of each of the recovered bi-functional molecules without the need for identification of the recovered bi-functional molecules. The ability to perform several rounds of screening or selection allows efficient screening of very large libraries of bi-functional molecules, involving up to at least $10^{16}$ different bi-functional molecules.

Figure 9:
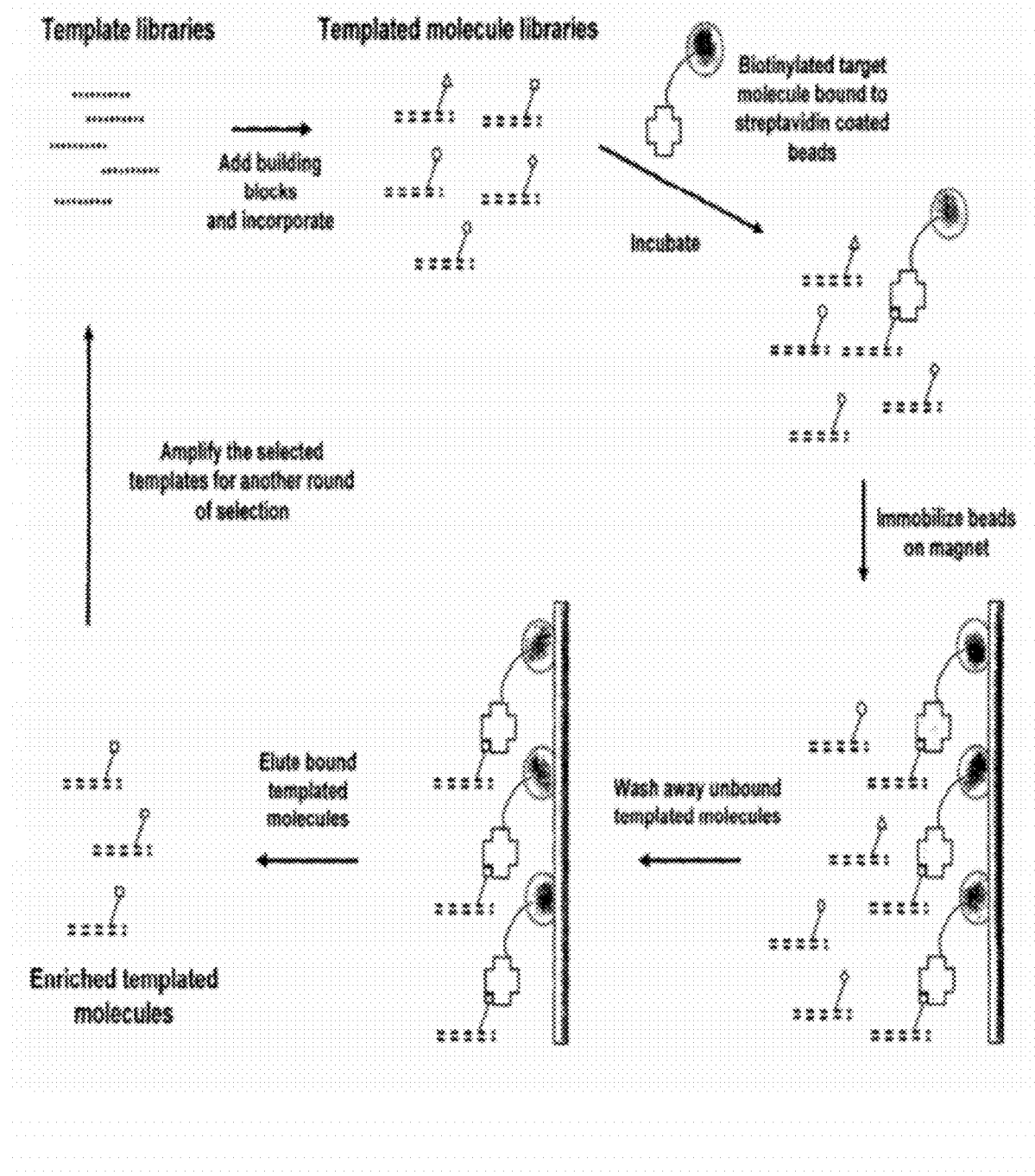

A typical selection protocol involves the addition of a population (a library) of bi-functional molecules to an affinity column, to which a certain molecular target (e.g., a receptor protein or a DNA fragment) has been immobilised. After washing the column, the binders are eluted. This eluate consists of an enriched population of bi-functional molecules with affinity for the immobilised target molecule. The enriched population may be taken through an amplification round (by first amplifying the template and then using the amplified template in a stage 2 templated synthesis of bi-functional molecules), and then be subjected to yet a selection round, where the conditions optionally may be more stringent. After a number of such selection-and-amplification rounds, an enriched population of high-affine binders are obtained. A typical selection process is illustrated in FIG. 9. Other types of selection methods that may be used include immunoprecipitation, FACS sorting, mass spectrometry, cell-surface subtraction, in vivo selection (e.g., injection of bi-functional molecules into animals and isolation of bi-functional molecules from specific tissues) and gel mobility shift assays.

Polyvalent display and other means of increasing the likelihood of identifying encoded molecules with weak characteristics.

Under certain conditions the requirements of an encoded molecule, in order to be isolated during the screening step, are too strong, and few or none of the encoded molecules of a library are expected to fulfil the requirements. Such requirements may be for example high affinity or high catalytic turn-over.

In those cases it may desirable to employ a multivalent display mode, i.e., to generate libraries of multivalent encoded molecules (either multiple encoded molecules attached to multiple identifiers, or multiple encoded molecules attached to one identifier). During a selection step in which for example an encoded molecule interacts weakly with a target protein, a multivalent encoded molecule may interact with multiple protein targets through the multiple copies of encoded molecules that it contains, and as a result, may bind with higher affinity because of the avidity effect. Likewise, in a screening or selection step for catalytic efficiency, a multivalent encoded molecule may generate more product in a given time, and may be isolated because of this.

A preferred means of generating libraries of multivalent encoded molecules each containing multiple copies of the same encoded molecule, is as follows (FIG. 11A). First, a library of templates that may be used in stage 2 synthesis is generated. The library of templates may be generated as described in FIG. 5, whereafter the libraries are then circularised (for example by ligating the two ends of a template). Alternatively the circular templates can be generated as described in FIG. 4, example 5. A rolling circle amplification is hereafter performed on the library of templates, leading to the generation of a library of templates, where each template now contains multiple copies of the sequence that may be used in stage 2 synthesis to generate an encoded molecule. Secondly, templated synthesis is performed using the templates generated (using carriers optionally generated by stage 1 synthesis, or generated by any other means), leading to multivalent encoded molecules each containing multiple copies of an encoded molecule. Multivalent encoded molecules containing multiple copies of two different encoded molecules may be generated by ligating together sequences two-and-two before circularisation and rolling circle amplification (i.e., ligate two templates together, circularise the ligation product, and perform rolling circle amplification). After templated synthesis on these templates, the library will consist of bi-functional molecules each with multiple copies of two different encoded molecules.

The multivalent encoded molecules can now be used in various screening or selection processes. For example, the multivalent encoded molecules may be added to an affinity column, to which target protein has been immobilised with an appropriately high density, so that multivalent encoded molecules may interact with several immobilised targets simultaneously. This will lead to the isolation of bi-functional molecules that contain encoded molecules with affinity for the immobilised target protein.

Divalent encoded molecules (bi-functional molecules containing two copies of an encoded molecule) may be generated in several different ways. In a stage 1 synthesis where the linker molecule contains two reactive groups, the stage 1 synthesis may lead to the formation of two encoded molecules (FIG. 11B). Hereafter, the divalent carrier molecules can be used in a templated stage 2 synthesis scheme, for generating a library of divalent template encoded molecules (FIG. 11C). These principles for the formation of divalent encoded molecules may of course be applied to the generation of trivalent and higher valency encoded molecules, by employing linkers during stage 1 carrier synthesis that carry three or more, respectively, reactive groups.

The divalent encoded molecules generated may be used in screening or selection experiments. For example, a library of divalent encoded molecules may be added to beads to which a target molecule has been coupled with appropriately high density, and an affinity selection experiment performed, leading to the isolation of divalent encoded molecules which contain encoded molecules with affinity for the target molecule. Divalent encoded molecules may be particularly advantageous to use when selecting for affinity to a homodimeric target molecule, or any other target that contains two or more identical binding sites. Relevant targets include membrane proteins such as the Epo-receptor, p53, HER2, Insulin Receptor, many interleukins, palindromic DNA- or RNA-sequences, or fibrin. Divalent encoded molecules containing identical encoded molecules are also appropriate for affinity selection on target molecules with one binding site, where the binding site is partly or fully symmetrical, and therefore allows two identical encoded molecules to interact.

A similar principle may be applied to the generation of bi-functional molecules that carry a helper moiety. For example, when searching for an encoded molecule with affinity for a particular nucleic acid sequence, it may be advantageous to generate a bi-functional molecule that contains a nucleic acid sequence that is complementary to the sequence next to the target nucleic acid sequence, and in this way increase the total affinity of the bi-functional molecule for the target nucleic acid (FIG. 11D). A similar approach may be applied to the isolation of encoded molecules with affinity for any target molecule with two binding sites, or a binding site that can accommodate two binding moieties. Thus, as an example, if a ligand is known for a binding site in a protein, this ligand may be coupled to the bi-functional molecule, in order to guide the encoded molecule to the target protein, and in order to increase the affinity of the bi-functional molecule (carrying the known ligand) for the target protein (FIG. 11E). A simple way of attaching the known ligand is by hybridisation, i.e. the encoded molecule is linked to the template and the known ligand is linked to an oligonucleotide that is complementary to part of the template (FIG. 11F) Similar approaches may be used for isolation of encoded molecules with affinity for a target binding site, where the binding site can be occupied by both the encoded molecule and the known ligand simultaneously (FIG. 11G). Finally, it may be desirable to increase the overall affinity of the bi-functional molecule for the target by linking a short oligonucleotide that is complementary to the template of the bi-functional molecule to the target. The short oligonucleotide will then function as a helper moiety that increases the affinity of the bi-functional molecule for the target, by hybridisation of the short oligonucleotide to the bi-functional molecule (FIG. 11H).

Selections employing such bi-functional molecules to which have been attached a helper moiety may be applied to affinity selection against all kinds of targets, including protein-heterodimers as well as protein-homodimers, and thus molecular targets include HER2, Insulin-receptor, VEGF, EGF, IL-4, IL-2, TNF-alpha, the TATA-box of eukaryotic promoter regions, and many others.

Figure 14:
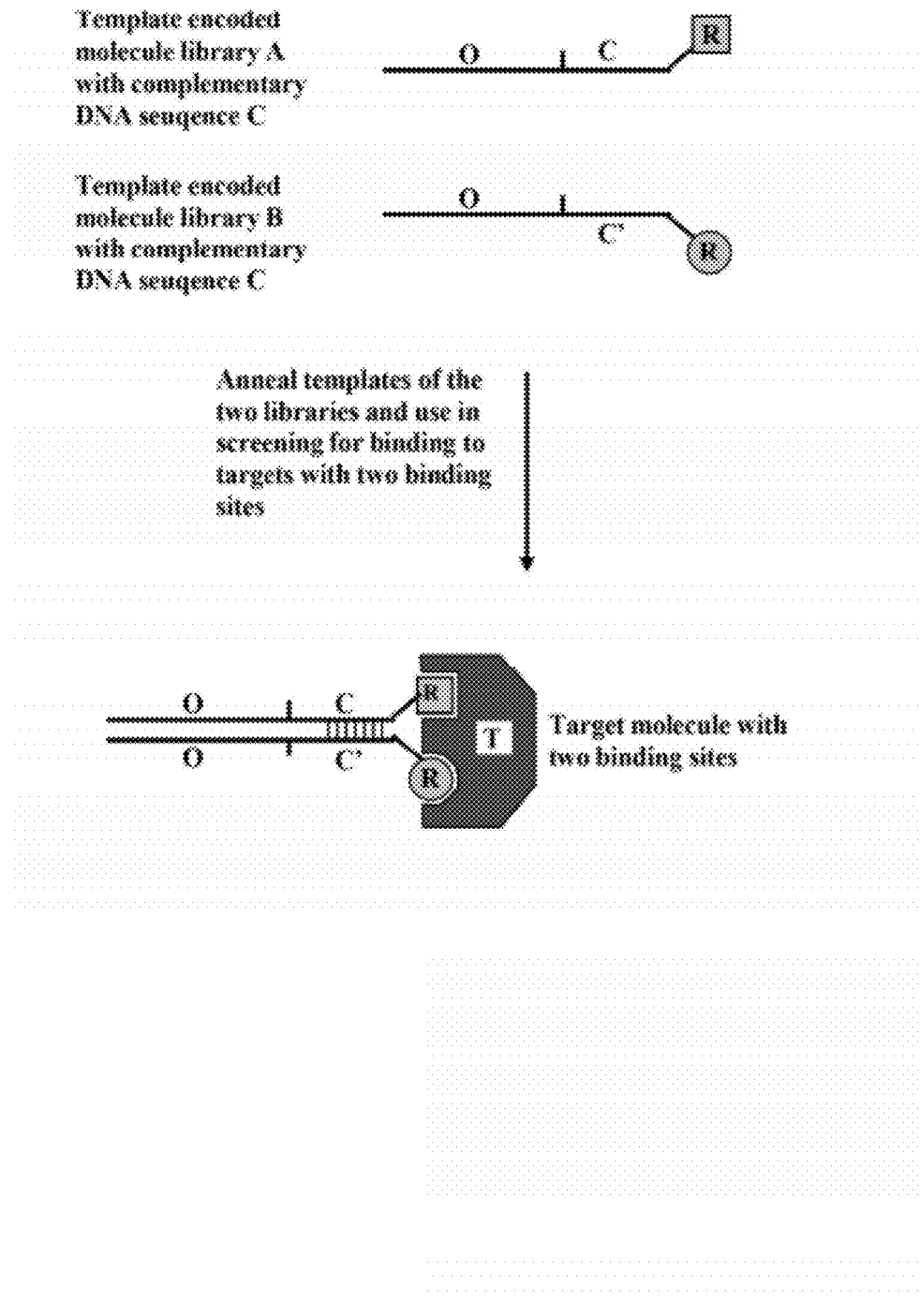

Dynamic combinatorial library of dimers or trimers of encoded molecules. The bi-functional molecules of a library may be designed in a way that leads to transient complex formation between 2, 3, or more bi-functional complexes during the screening process. This may be desirable, especially in cases where the libraries that have been generated are relatively small, or in cases where it is desirable to screen a large number of combinations of encoded molecules for synergistic effects. In order to generate transient complexes, the bi-functional molecules may be designed so as to comprise half of a transient interaction pair. For example, a short single stranded oligonucleotide region may be included in the design of the identifiers of the bi-functional molecules that result from the present invention; if some of the bi-functional molecules carry a molecular entity "A" and some other bi-functional molecules of the library carry another molecular entity "B" that interacts transiently, i.e. forms a short-lived complex with, "A", then the two sets of bi-functional molecules of the library will form transient dimers of bi-functional molecules. These transient dimers may then be exposed to a screening process, for example affinity selection, where the dimers are then examined for ability to bind to a certain target. As an example, for each of the species of bi-functional molecules, half of the generated bi-functional molecules carry the oligo sequence 3'-ATGC-5' in the proximity of the encoded molecule, and the other half of the generated bi-functional molecules carry the oligo sequence 3'-GCTA-5'. When all the generated bi-functional molecules are incubated at appropriately low temperature, different combinations of dimers will transiently form, and allow for a feature displayed by the combination of the corresponding two encoded molecules to be selected for. This feature could be the binding of the two encoded molecules of the dimer to bind simultaneously to a target molecule. If appropriately designed, trimers may be (transiently) formed, by formation of triplex DNA between three bi-functional molecules. In this way, all the possible dimers (or trimers) of a pool of bi-functional molecules may be screened for the desired feature. See (FIG. 14).

Molecular Biological Methods Applicable to Bi-Functional Molecules.

As the present invention involves the templated synthesis of encoded molecules, most in vitro molecular biological techniques may be applied to the DNA-, RNA- or any other oligonucleotide-portion of the template, and as a result of the encoding by this template, indirectly may be applied to the encoded molecule. Examples of such molecular biological techniques applicable to the encoded molecules of this invention are listed in FIG. 10.

Characterisation of Encoded Molecules Identified During a Screening of a Library of Bi-Functional Molecules.

Once the screening of a library of bi-functional molecules have been done, the isolated bi-functional molecules may be identified by cloning of the oligonucleotide portion, and sequencing. The sequencing may be done by any means, including Sanger sequencing, mass spectrometry-based sequencing, single molecule sequencing, or sequencing by hybridisation to oligonucleotide arrays. The characteristics of the encoded molecules thus identified may now be analyzed, either in its free form (after resynthesis by organic chemistry or after generation of the bi-functional molecule followed by cleavage of the linker that connects the encoded molecule and its identifier) or in its oligonucleotide-linked form (as a bi-functional molecule). In order to analyze the bi-functional molecule carrying the specific encoded molecule, individual templates of the bi-functional molecules isolated during the screening may be cloned (by dilution and PCR in separate wells, or by cloning into vectors and propagation in e.g. *E. coli*), and then amplified by PCR, to produce many copies of the template that encoded the recovered organic molecule. When the encoding process (Stage 2 templated process) is then performed, many identical copies of bi-functional molecules carrying the specific encoded molecule is generated The characteristics of the specific encoded molecule, when linked to its identifier template, may then be examined. Example assays used for the analysis of the encoded molecules (in their free form or attached to identifiers) include:
Enzyme inhibition assays
Affinity-determination by competition assays and/or ELISA
Cell-based receptor binding assays
Cell-based activity assays, based on the interaction of the encoded molecule with molecular targets on the surface of the cells
Biacore-measurements of molecule-ligand or surface-ligand interactions
Affinity and specificity/selectivity determination using arrays of immobilized targets (e.g. array of 100 immobilized phosphatases), onto which the specific encoded molecule (in free- or oligonucleotide-associated form) is added
Affinity and specificity/selectivity determination on many specific encoded molecules simultaneously, by immobilization of e.g. 1000 different bi-functional molecules to an array of oligonucleotides, followed by addition of a specific fluorescent protein.

Example assays used for the analysis of the encoded molecules (in their free form) include:
CaCo2-cell-based analysis of membrane permeability
In vivo determination of animal toxicity, bioavailability of the compounds, and other ADMET characteristics.
Solubility of encoded molecule.
Water-octanol partitioning measurements
Metabolic stability measurements.

In one embodiment, the reactive groups of a molecule fragment of each of two or more bi-functional molecules hybridized to the same template are reacted. Alternatively, the reactive group of a molecule fragment of one bi-functional molecule is reacted with a reactive group associated with the template to which it is hybridized. Preferably the template is an oligonucleotide template.

In a further embodiment of the invention the number of wells in step a) is m and the number of wells in step f) is n, and may be the same or different for each repetition of steps b) to f) in step g) n; and
the structure of the encoded (bifunctional) molecule is

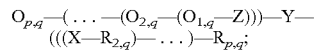

wherein
X, Y and Z are components of the linker molecule, L, X being adapted for reaction with a molecule fragment, Z being adapted for reaction with an oligonucleotide and Y being a flexible linker connecting X and Z;
$O_{p,q}$ is the oligonucleotide identifier added in repetition number (p−1) of steps b) to f) in well number q;
$R_{p,q}$ is the molecule fragment added in repetition number (p−1) of steps b) to f) in well number q;
p is an integer of at least 1;
m and n are integers of at least 5, such as at least 10, preferably at least 15, more preferably at least 20, and most preferably at least 50; and
for $O_{1,q}$ and $R_{1,q}$, q is in the range 1 to m, for $O_{p,q}$ and $R_{p,q}$ where p is greater than 1, q is in the range 1 to n.

In another embodiment of the present invention the number of wells in step a) is m and the number of wells in step f) is n, and n may be the same or different for each repetition of steps b) to f) in step g); and
the structure of the encoded (bifunctional) molecule is

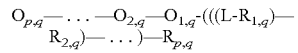

wherein
$O_{p,q}$ is the oligonucleotide identifier added in repetition number (p−1) of steps b) to f) in well number q;
$R_{p,q}$ is the molecule fragment added in repetition number (p−1) of steps b) to f) in well number q;
p is an integer of at least 2;
m and n are integers of at least 5, such as at least 10, preferably at least 15, more preferably at least 20, and most preferably at least 50; and
for $O_{1,q}$ and $R_{1,q}$, q is in the range 1 to m, for $O_{p,q}$ and $R_{p,q}$ where p is greater than 1, q is in the range 1 to n.

In the formula above the bond to a residue inside a parenthesis ( ) signifies that the bond may be to any part of said residue, e.g. $(L-R_{1,q})-R_{2,q}$ means that $R_{2,q}$ may be bound to either of L and $R_{1,q}$).

In an equally important aspect the present invention provides a method for synthesizing an encoded molecule or one or more encoded molecules comprising the steps of:

a) Dispensing aliquots of a nascent linker molecule L into each of m reaction wells;
b) Dispensing into each of said m reaction wells a corresponding aliquot of an $m^{th}$ molecule fragment, $R_{1,m}$ and a corresponding aliquot of an $m^{th}$ oligonucleotide, $O_{1,m}$;
c) Combining all of the nascent bi-functional molecules from all m reaction wells to produce an admixture of nascent bi-functional molecules;
d) Optionally, Dispensing said admixture of nascent bi-functional molecules into n reaction wells
e) Optionally, dispensing into each of the n reaction wells of step d) a corresponding aliquot of an $m^{th}$ molecule fragment, $R_{p,q}$, and a corresponding aliquot of an $m^{th}$ oligonucleotide or oligonucleotide identifier, $O_{p,q}$;
f) Optionally, combining all of the nascent bi-functional molecules from all n reaction wells in step e) to produce an admixture of nascent bi-functional molecules;
g) Optionally repeating steps d) to f) one or more times;
h) contacting a resulting bi-functional molecule of step f) or g) with one or more templates, said one or more templates optionally being associated with a reactive group, under conditions to allow for hybridization of each of the templates to one or more of said nascent bi-functional molecule generated in step f) or g);
i) Optionally, reacting reactive groups of a molecule fragment of two or more nascent bi-functional molecules hybridized to the same template, or reacting the reactive group of a molecule fragment of one nascent bi-functional molecule with the reactive group associated with the template to which it is hybridized;

the linker molecule L contains at least one reactive group capable of reacting with a reactive group in the molecule fragment and at least one reactive group capable of reacting with a reactive group in the oligonucleotide;
the molecule fragments each contain at least one reactive group capable of reacting with a reactive group in the linker molecule L or a reactive group in another molecule fragment, and the reactive groups of each molecule fragment may be the same or different; the oligonucleotide identifiers each contain at least one reactive group capable of reacting with a reactive group in the linker L or a reactive group in another oligonucleotide identifier, and the reactive groups of each oligonucleotide identifier may be the same or different;
the oligonucleotide identifier added to each well in step b) and e) identifies the molecule fragment added to the same well in the respective step;
the steps a) and b) as well as the steps d) and e) may be performed in any order;
the steps d) and e) in step f) may also be performed in any order.

It is to be understood that the encoded molecule may be a bi-functional molecule with an encoded part comprising one or more molecule fragments, R, and a coding part comprising one or more oligonucleotide identifiers, O.

In steps b) and e) of the above process the molecule fragment as well as the oligonucleotide is reacted with the linker to produce a nascent bi-functional molecule.

In step h) the said bi-functional molecule may be viewed as a carrier or a carrier molecule and as mentioned above the template in step i) is preferably an oligonucleotide template.

Again, the process outlined above may be seen as a combination of a step 1 synthesis and a step 2 synthesis, wherein the step 1 synthesis comprises the steps a) to g) and the step 2 synthesis is carried out in step h.

In one embodiment of the method described in the preceding paragraphs the number of wells in step a) is m and the number of wells in step f) is n, and for each repetition of steps b) to f) in step g) n may be the same or different; and the structure of the encoded (bifunctional) molecule is

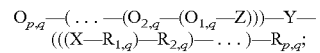

wherein
X, Y and Z are components of the linker molecule, L, X being adapted for reaction with a molecule fragment, Z being adapted for reaction with an oligonucleotide and Y being a flexible linker connecting X and Z;
$O_{p,q}$ is the oligonucleotide identifier added in repetition number (p−1) of steps d) to f) in well number q;
$R_{p,q}$ is the molecule fragment added in repetition number (p−1) of steps d) to f) in well number q;
p is an integer of at least 2;
m and n are integers of at least 5, such as at least 10, preferably at least 15, more preferably at least 20, and most preferably at least 50; and
for $O_{1,q}$ and $R_{1,q}$, q is in the range 1 to m, for $O_{p,q}$ and $R_{p,q}$ where p is greater than 1, q is in the range 1 to n.

In another embodiment the method n may for each repetition of steps d) to f) in step g) be the same or different; and the structure of the encoded (bifunctional) molecule is

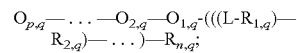

wherein
$O_{p,q}$ is the oligonucleotide identifier added in repetition number (p−1) of steps d) to f) in well number q;
$R_{p,q}$ is the molecule fragment added in repetition number (p−1) of steps d) to f) in well number q;
p is an integer of at least 1;
m and n are integers of at least 5, such as at least 10, preferably at least 15, more preferably at least 20, and most preferably at least 50; and
for $O_{1,q}$ and $R_{1,q}$, q is in the range 1 to m, for $O_{p,q}$ and $R_{p,q}$ where p is greater than 1, q is in the range 1 to n. Again, the bond to a residue inside a parenthesis ( ) signifies that the bond may be to any part of said residue, e.g. (L-$R_{1,q}$)—$R_2$, means that $R_{2,q}$ may be bound to either of L and $R_{1,q}$).

In a further embodiment of the above described method, the structure of the nascent bi-functional molecules resulting from step b is

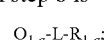

and the structure of the nascent bi-functional molecule obtained after repeating the process steps defined in step g) p−1 times is

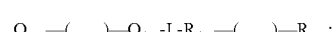

wherein p is greater than or equal to 1.

It is preferred that the number of reaction wells in step a) and/or the number of reaction wells in step f) is at least 2, such as at least 5, at least 10, at least 25, at least 50, at least 100, at least 200, at least 500, at least 1000, at least 10,000, at least 100,000 at least 1,000,000, at least $10^7$, or at least $10^8$. For certain applications m must be 100,000 or more, such as $10^6$, $10^7$, or $10^8$ in step b and c, if the process steps d) to f) are not repeated. If said steps are repeated, however, m may be as low as 10,000 in steps b) and c).

Accordingly it may be preferred to repeat the process steps defined in step g) at least once, such as at least twice, such as at least three times, such as at least four times or more.

In certain embodiments unique identification of the molecule fragments may be preferred. Accordingly, in these embodiments the oligonucleotide identifier, $O_{p,q}$, added in reaction well number q in repetition number (p−1) of the steps specified in step g) uniquely identifies the molecule fragment, $R_{p,q}$, added in reaction well number q in repetition number (p−1) of the steps specified in g). In other embodiments, however, identical oligonucleotide identifiers, $O_{p,q}$, are added in two or more reaction wells in the same repetition number (p−1) of the steps specified in g).

Furthermore, yet other embodiments of the invention involves addition of identical molecule fragments, $R_{p,q}$, in two or more wells in the same repetition number (p−1) of the steps specified in g).

Also, it may be preferred to add two or more oligonucleotide identifiers to one or more reaction wells in a repetition of the steps specified in step g). Most preferably, however 1 oligonucleotide identifier is added per well, but it should be recognised that it will be possible to add 2, 3, 4, oligonucleotide identifier per well.

Furthermore the method according to the invention may involve adding two or more molecule fragments to one reaction wells in each repetition of the steps specified in g). Whereas it is preferred to add 1 molecule fragment per well, it will also be possible to add 2, 3, 4, or 5 molecule fragments per well.

In the method described above, each oligonucleotide identifier comprises a sequence of from 2 to 100, such as from 2 to 90, from 2 to 80, from 2 to 70, from 2 to 60, from 2 to 50, from 2 to 40 from 2 to 30, from 2 to 25, from 2 to 20, from 2 to 15, from 2 to 10 or from 2 to 5 nucleotides, such as at least 2, 3, 4, 5, 6, 7, 8, 9, 10, 11, 12, 13, 14, 15, 20, 25, 30, 35 40, 45, 50, 55, 60, 65, 70, 75, 80, 85, 90, 95 or 100 nucleotides.

It should be recognised that, preferably, the number of identifiers in each resulting bi-functional molecule is 2. However, each bi-functional molecule may also comprise 1, 3, 4, or 5 identifiers.

It should likewise be recognised that each template is preferably capable of hybridising with 2 carriers. Whereas this is preferred, the template may also be capable of hybridising with 1, 3, 4, 5, 6 or 7 carrier molecules.

It will for most applications be preferred that the number of nucleotides in each oligonucleotide identifier is 10-15. Other preferred numbers of nucleotides are 5-10, 5-15, 5-20, 10-30.

It should be recognised that the said one or more templates may be an amplifiable template as well as a template, which is non-amplifiable by polymerses. The one or more templates may thus comprise a sequence selected from the group consisting of: nucleotides, unnatural nucleotides, PNA, morpholinos, LNA, RNA, DNA, and other nucleotide analogs capable of base pairing with a natural oligonucleotide or unnatural oligonucleotide. Most preferably the template comprises a DNA sequence or an RNA sequence.

In preferred embodiments of the invention said one or more templates have a length of at least 40 nucleotides, such as 30-50 nucleotides, 20-60 nucleotides, 15-80 nucleotides if not considering the primer annealing sites. When these sites are included the total length is preferably approximately 80 nucleotides, such as 70-120 nucleotides, 60-100 nucleotides, 55-120 nucleotides 50-150 nucleotides or 60-175 nucleotides. In some embodiments of the invention the said one or more templates may even comprise up to 250 nucleotides or even up to 500 nucleotides.

As for the nature of the oligonucleotide sequences each oligonucleotide identifier and/or a sequence of two or more of the oligonucleotide identifiers may comprise a sequence of oligonucleotides, the complementary sequence of which is at least 20% identical, such as at least 30%, such as at least 40%, such as at least 50%, such as at least 55%, such as at least 60%, such as at least 65%, such as at least 70%, such as at least 75%, such as at least 80%, such as at least 85%, such as at least 90% or such as at least 95% identical to the part of said template that hybridises to the identifier. It is to be understood that the templates when used in the method according to the present invention may be comprised of coding regions separated by spacer regions.

In some preferred embodiments of the present invention the linker, L, is selected from the group consisting of flexible linkers such as Polyethylen glycol, polypeptide, polysaccharide, oligonucleotide, $C_8$, $C_6$, $C1_2$. In further preferred embodiments of the invention the linker, L, is a cleavable linker. For example the linker may be cleavable by base, acid, light, reagent, heat)

In further applications of the method according to the invention the method may involve using the bi-functional product molecule resulting directly from the process steps presented above, that is steps a) to h), as a carrier molecule in a second round of step 2 synthesis. Accordingly, the method may also comprise a further step comprising contacting the bi-functional molecule resulting from step h) with one or more nascent bi-functional molecules and one or more templates each capable of recognizing at least two of the oligonucleotide identifiers present in the bi-functional molecule. The nascent bi-functional are generated through steps a) through f) and the optional steps, g)). It is further to be understood that the identifiers may be covalently or non-covalently linked to each other, and that the identifiers may be double- or single-stranded identifier oligonucleotides, with overhang or blunt-ended.

In a preferred embodiment two or more oligonucleotide identifiers may be covalently linked together, optionally in the presence of a ligase or isomerase enzyme. Alternatively two or more oligonucleotide identifiers are linked by templated extension by enzymes (polymerases).

In some embodiments of the invention two or more oligonucleotide identifiers are ligated by chemical ligation or by a combination of enzymatic and chemical ligation. By a combination of enzymatic and chemical ligation one may understand that two or more oligonucleotide identifiers are ligated by enzymatic ligation in one process step and chemical ligation in a preceding or subsequent process step. For chemical ligation of the oligonucleotide identifiers the following reactions and pairs of reactive groups are the preferred ones:

| reaction | reactive group reacts w/ | reactive group |
|---|---|---|
| phophodiester formation | 3'-OH | Imidazole-activated 5'-phosphate |
| acylation | amine | ester |
| acylation | amine | carboxylic acid |
| disulfide formation | SH | pyridyl-disulfide |
| reductive amination | amine | aldehyde |
| phosphodiester formation | 3'-OH | pyrophosphate-activated 5'- |
| phosphate tosyl displacement reaction | | |

It is to be understood that the linker of at least one bi-functional molecule may be cleaved simultaneously with or subsequently to hybridisation of the oligonucleotide identifier of said nascent bi-functional molecule to the template.

In the method according to the invention said reactive groups of molecule fragments of the bi-functional molecules or of molecule fragments of the bi-functional molecules and of the template may be reacted in a reaction selected from the group consisting of: acylation, reductive amination, alkylhalide alkylation, Wittig reaction, sulphonoylation, isocyanate addition, Suzuki coupling, nucleophilic aromatic substitution, thiourea bond formation, carbamate formation, Heck coupling, HWE reaction, 1,3-dipolar cycloaddition, Michael addition, nitro aldol condensation.

In some embodiments of the invention the resulting encoded molecule has a linear structure and is selected from the group consisting of: dimers, trimers, tetramers, pentamers, multimers, and polymers.

In further preferred embodiments at least one molecule fragment having more than one reactive groups has been used in the preparation of the resulting encoded molecule. It is to be understood that the number of reactive groups pr molecule fragment may be 1, 2, 3, 4, 5 or 6. It is further to be understood that, in the final product, the reactive groups of said at least one molecule fragment has reacted with other molecule fragments. The resulting molecule is thus a branched or scaffolded structure selected from the group of molecules comprising a scaffold with two substituents, scaffolds with three substituents, scaffolds with four substituents, and scaffolds with five substituents. In this context the term "substituent" means a molecule fragment that has been reacted at the substituent position of the scaffold.

In another main aspect the invention provides a method for identifying a molecule with desired characteristics, said method comprising synthesizing a library of encoded molecules by a method as described above.

In some embodiments the method further comprises a step of subjecting the library to a partitioning or enrichment procedure, to identify encoded molecules with desired characteristics. In still other embodiments the method further comprises screening a plurality of encoded molecules in a process to identify and optionally increase the relative amount of an encoded molecule having one or more desired characteristics. Various means and methods for carrying out enrichment procedures and screening are described in the present specification which may be applied to the process.

In some preferred embodiments the method comprises identifying the encoded molecule by determining the oligonucleotide sequence(s) of the attached identifiers.

In yet another main aspect of the invention a library of encoded molecules or bi-functional molecules is obtained. Said encoded or bi-functional molecules may be obtained or may be obtainable by a method according to any of claims.

In the library the number of different compounds or compound species may be at least 100, such as at least 1000, at least 10,000, at least 100,000, at least 106, at least $10^7$, at least $10^8$, at least $10^9$, at least $10^{10}$, at least $10^{11}$, at least $10^{12}$, at least $10^{13}$ or at least $10^{14}$.

Additional aspects and embodiments of the invention are described in brief in the following:

a) A method for synthesising one or more encoded molecules, comprising the following steps:

step 1: dispensing aliquots of a nascent linker molecule L comprising the components X, Y, and Z, where X is adapted for reaction with a molecule fragment, Z is adapted for reaction with an oligonucleotide and Y is a flexible linker connecting X and Z, into each of m reaction wells; then step 2: dispensing into each of the m reaction wells of said step 1 a corresponding aliquot of the $m^{th}$ molecule fragment $R_{1,m}$ and a corresponding aliquot of the $m^{th}$ oligonucleotide identifier $O_{1,m}$ to allow for reaction between the molecule fragment and X of the linker, and reaction between the oligonucleotide and Z of the linker, to produce a product bi-functional molecule $R_{1,m}$-L-$O_{1,m}$ where the produced bi-functional molecule comprises a reactive group; then step 3: combining all of the nascent bi-functional molecules from all m reaction wells produced in said step 2 for producing an admixture of nascent bi-functional molecules; then step 4: dispensing equal aliquots of the admixture of nascent bi-functional molecules from the prior step into each of m reaction wells, then step 5: dispensing into each of the m reaction wells of said step 4 a corresponding aliquot of the $m^{th}$ molecule fragment represented by $R_{n,m}$ and a corresponding aliquot of the $m^{th}$ identifier molecule represented by $O_{n,m}$ for producing a nascent bi-functional molecule represented by:

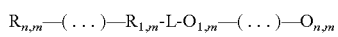

$$R_{n,m}-(\ldots)-R_{1,m}\text{-L-}O_{1,m}-(\ldots)-O_{n,m}$$

wherein n is greater than or equal to 2; then step 6: combining all of the elongated nascent bi-functional molecules from all m reaction wells of step 5 for producing an admixture of elongated nascent bi-functional molecules; then step 7: repeating steps 4-6 until the desired bi-functional carrier molecules, each formed from the reaction of n molecule fragments and n oligonucleotide identifiers, are produced, and where each bi-functional carrier molecule generated comprises one or more reactive units; then step 8: providing one or more templates, which one or more templates optionally have a reactive unit associated therewith; then step 9: contacting one or more carrier molecules of step 7 with said one or more templates under conditions to allow for specific hybridisation of the oligonucleotide identifiers of the one or more carrier molecules to the one or more templates; then step 10: reacting the reactive units of the molecule fragments of at least two carrier molecules hybridised to the same template, or reacting the reactive unit of a carrier molecule with the reactive unit associated with the template to which it is hybridised, to generate one or more encoded molecules.

b) The method as described in a), wherein the oligonucleotide identifiers of two or more carrier molecules are covalently linked together prior to, during or after step 9 or 10.

c) The method as described in b), wherein the oligonucleotide identifiers are covalently linked together after step 9 but before step 10, by a ligase enzyme.

d) The method of b), wherein the oligonucleotide identifiers are covalently linked together after step 9 but before step 10, in the absence of a ligase enzyme.

e) The method of a) to d), wherein the template is dissociated from the carrier molecules prior to reaction between said reactive units.

f) The method of a) to e), wherein more than one molecule fragment is added to the same reaction well in steps 2 or 5, to allow for a multiple component reaction to take place.

g) The method of a) to f) where m does not have the same value in different repetitions of step 5.

h) The method of a) to g), where in step 2 or 5 the oligonucleotide identifiers are linked to the nascent bi-functional molecule by a ligase enzyme.

i) The method of a) to h), where in step 2 or 5 the oligonucleotide identifiers are linked to the nascent bi-functional molecule without the use of a ligase enzyme.

j) The method of a) to i), wherein a library of more than one bi-functional molecule is generated, the method further comprising enriching for library members comprising an encoded molecule displaying a desired property.

k) The methods of a) to j) wherein steps 4-7 have been eliminated.

l) The methods of a) to k), wherein steps 8-10 have been eliminated.

m) The library of two or more bi-functional molecules generated by the method of a) to l).

n) The library of $10^6$ or more bi-functional molecules generated by the method of a) to l).

o) The library of $10^{10}$ or more bi-functional molecules generated by the method of a) to l).

With respect to the above description of the various aspects of the present invention and of the specific embodiments of these aspects it should be understood that any feature and characteristic described or mentioned above in connection with one aspect and/or one embodiment of an aspect of the invention also apply by analogy to any or all other aspects and/or embodiments of the invention described.

When an object according to the present invention or one of its features or characteristics is referred to in singular this also refers to the object or its features or characteristics in plural. As an example, when referring to "a cell" it is to be understood as referring to one or more cells.

Throughout the present specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

FIGURE LEGENDS

FIG. 1. Reactions in Stage 1 of the Method in the Invention

Schematic representation of an example of the synthesis steps of stage 1. Two rounds of "split and mix" synthesis are shown leading to the generation of bi-functional carrier molecules each carrying a different di-peptide and a unique 24-mer oligonucleotide that encodes the di-peptide. Each round of synthesis adds an amino acid and an identifier oligonucleotide. (m) represents the number of different molecule fragments in each of the two different repertoires employed. (m) can have a different values for different repertoires.

The split and mix synthesis shown in the example includes the following steps:
Add linker molecule to wells 1-m
Add amino acids $R_{1(1-m)}$ to wells 1-m, and react with linker.
Add oligonucleotides $O_{1(1-m)}$ to wells 1-m, and react with the linker.
Mix content of wells 1-m and split into 1-m wells on a new plate.
Add amino acids $R_{2(1-m)}$ to wells 1-m and react with reactive group of $R_{1(1-m)}$
Add oligonulceotides $O_{2(1-m)}$ to wells and react with $O_{1(1-m)}$.
Mix content of wells 1-m FIG. 2. Reactions in Stage 2 of the Method in the Invention Example of the synthesis steps of stage 2. In the illustrated example the bi-functional carrier molecules generated in the example in FIG. 1 are combined by a template directed method. Tetra-peptide bi-functional carrier molecules with 48-mer identifier oligonucleotides are therefore generated in the example. (m) represents the number of different molecule fragments in each of the four different repertoires, i.e., in the example m=1000 for all four repertoires. (M) represents the total number of (encoded) molecules generated. Here, $M=(1000)^4=10^{12}$.

The synthesis in the example comprise the following steps:
Add bi-functional carrier molecule from stage 1
Add DNA templates that bind the carriers through their complementary oligo's Acyl transfer reaction where the amino group of di-peptide in one carrier attacks the peptidyl ester of the di-peptide in the other carrier
The synthesis is complete FIG. 3. Types of Molecule Fragment Transfer from One Carrier to Another:

Direct transfer reaction: The reaction between reactive groups leads directly to the transfer of a molecule fragment. The mechanism is shown schematically ("generic") as well as for a specific case ("example"). Other types of reactions allowing direct transfer are shown in FIG. 6.

Indirect transfer reaction. Reaction between reactive groups leads to the formation of a linkage between the two reactive groups. Thereafter a molecule fragment is cleaved off from one carrier, mediating its transfer to another carrier. "Clv" indicates a cleavable moiety, i.e. a part of the linker that is cleavable, for example by acid, base, electromagnetic radiation, light, heat, or by specific reagents or catalysts. Long horizontal line symbolises a template. Short horizontal line symbolises oligonucleotide identifier.

FIG. 4. Alternative Methods for the Reactions in Stage 2

Examples of alternative methods for carrying out the reactions of stage 2 are shown. A number of templates (long horizontal line) is mixed with sets of carriers (short horizontal line). In the examples, two sets of carriers are employed. The first example is identical to the example shown in FIG. 2, except that in this example the two carriers are ligated together before reaction of the reactive groups of the two carriers. The next two examples show variations of the template directed reactions illustrated in the first example. In Example 2, the identifiers of the two carriers are ligated together prior to reaction of the reactive groups of X and Y, and the duplex structure denatured, to generate single-stranded complementary template. The single-stranded structure improves the likelihood of X and Y reacting. The reaction efficiency of the reactive groups of X and Y may be increased by including complementary sequences next to X and Y. This will lead to stable duplex formation proximal to X and Y, positioning X and Y in close proximity, and thereby increasing the reaction efficiency. In Example 3, one of the carriers is ligated to the template through its oligonucleotide identifier moiety. The ligation of carrier to template may be stimulated by including a hair-pin structure in the template, as shown in the figure, and then ligating together the template and carrier by use of for example a ligase or chemical ligation. Example 4 shows a template-free method of carrying out the reactions in stage 2. The carriers of the example are double-stranded, allowing for efficient ligation of their overhangs. Ligation of the carriers lead to the formation of a complementary template. Before reaction of X with Y, the duplex structure is denatured, allowing a more efficient reaction of X and Y. As in example 3, the efficiency of reaction may be increased by including complementary sequences proximal to X and Y, respectively.

The library of encoded molecules that results from each of the examples can be of the same kind; however, the examples describe different set-ups that may allow different chemical reactions to be performed. In a preferred embodiment, the template of the bifunctional molecules are turned into double-stranded DNA before selection or screening is performed, in order to eliminate potential interaction from the single-stranded regions. Thus, in examples 2 and 4, it may be advantageous to add a terminal oligonucleotide that anneals to the DNA template that carries the encoded molecule; by extension, e.g. by a polymerase such as Sequenase, a double-stranded DNA will be generated, carrying the encoded molecule at one end.

The lower strand of the duplexes symbolises the template (long horizontal line); short horizontal lines symbolise oligonucleotide identifiers; after ligating the oligonucleotide identifiers together, a complementary template is formed, symbolised by a long horizontal line. X and Y are molecule fragments, each containing at least one reactive group.

FIG. 5. Template Generation:

An example of a DNA library generation process for the synthesis of a library of $10^{12}$ DNA templates. Four sets of 1000 DNA oligos are mixed individually with their complementary sequences, to form for example 12 nt duplex DNA, with an overhang of one nucleotide at both ends. In the example each oligo carries a region complementary to an identifier sequence (a "codon" sequence). In addition, the oligos of the two distal sets of oligos contain constant regions. These constant regions may be used at a later stage for PCR-amplification, sequencing or polymerase extension. This is followed by a ligation step in which the overhangs mediate the ligation of the 4000 duplex DNA complexes, to form $10^{12}$ ($=1000^4$) different duplex DNA complexes. Ligation may be by a ligase or by chemical ligation. Optionally, the templates may be amplified by e.g. PCR using primers that anneal to the constant regions at the ends of the template, or by any other molecular biological technique that allows amplification. Finally, one of the strands is isolated in order to be used in a templating process (stage 2 templated synthesis). The isolation of single stranded templates can be done in a number of ways, including asymmetric PCR on the ligated product (which leads to excess of one of the strands), or by including a biotinylated PCR-primer that anneals to one end of the template and thus leads to incorporation of biotin into one of the strands of the duplex; by immobilisation of the biotin on streptavidin-coated solid support, and denaturation of the duplex template, one may recover the non-biotinylated strand from the supernatant, or the biotinylated strand immobilised on solid support.

In the example, the configuration of each of the $10^{12}$ single-stranded templates thus is as follows: "Constant sequence-codon1-codon2-codon3-codon4-Constant sequence". Each of the codon positions contain one specific of the 1000 possible sequences, i.e., each template carries its specific combination of a codon1-, codon2-, codon3-, and codon4 sequence.

Templates may also be generated by stage 1 split and mix synthesis, in which optionally the reaction of molecule fragments with the carrier is excluded. To generate a DNA template library as the one described in this example, 4 sets of 1000 different duplex DNA molecules must be ligated, employing 1000 wells in each of four rounds of split and mix synthesis. This will generate the same DNA template library of $10^{12}$ molecules as described above.

FIG. 6. Direct Transfer: Reactive Groups and Bonds Formed Upon Reaction:

A number of reactions are shown that mediate the direct transfer of molecule fragments from one carrier to another. In the left part of the figure the two carriers (the donor- and the acceptor carrier) are shown. The oligonucleotide identifiers of the carriers are indicated by a short horizontal line. The templates to which the carriers bind are indicated by long horizontal lines. The carriers carry molecule fragments containing reactive groups that upon reaction lead to the transfer of a molecule fragment from one carrier onto the other. The reactions that allow direct transfer include acylation (formation of amide, pyrazolone, isoxalone, pyrimidine, coumarine, quinolon, phtalhydrazide, diketopiperazine, hydantoin, benzodiazepinone, etc), alkylation (including reductive amination not shown in figure), vinylation, disulfide formation, addition to carbon-hetero multiple bonds, such as Wittig/Wittig-Horner-Emmon (formation of substituted alkenes), transition metal catalysed reactions such as arylation (formation of biaryl, vinylarene), alkylation, nucleophilic substitution using activation of nucleophiles, such as condensations, and cycloadditions. All of these reactions may be used for indirect transfer as well. The reactions may also be used during stage 1 synthesis. FIG. 6 is adapted from (Pedersen et al. (2002) WO 02/103008 A2, "Templated molecules and methods for using such molecules").

FIG. 7. Indirect Transfer: Reactive Groups and Bonds Formed Upon Linking Reaction:

Indirect transfer involves first the coupling reaction between the reactive groups of carrier molecules, followed by a cleavage that releases one molecule fragment from its carrier molecule. This figure shows examples of reactive groups that may for example be used in the coupling reaction. The coupling reaction may be nucleophilic substitution, aromatic nucleophilic substitution, transition metal catalysed reactions, addition to carbon-carbon multiple bonds, cycloaddition to multiple bonds, and addition to carbon-hetero multiple bonds. In FIG. 8 a number of example cleavable linkers that may be combined with these coupling reactions in order to obtain efficient indirect transfer are shown. The reactions may also be used during stage 1 split and mix synthesis. FIG. 7 is adapted from (Pedersen et al. (2002) WO 02/103008 A2, "Templated molecules and methods for using such molecules").

FIG. 8. Cleavable Linkers and Protection Groups, Cleaving Agents and Cleavage Products:

Cleavable linkers and protection groups that may be used to release molecule fragments in an indirect transfer reaction, or can be used as protecting groups, are shown. The cleavable linkers may be combined with reactive groups from FIG. 7, in order to indirectly transfer molecule fragments from one carrier to another. Linkers may be cleaved by acid, base, electromagnetic radiation, light, heat, by specific reagents or catalysts such as LiOH, $PdCl_2$, TCEP, $NaIO_4$, etc. FIG. 8 is adapted from (Pedersen et al. (2002) WO 02/103008 A2, "Templated molecules and methods for using such molecules").

FIG. 9. A Typical Affinity Selection Process:

An example affinity selection process is shown. First a DNA template library is generated, for example as described in FIG. 5. Then, stage 2 templated synthesis is performed using the carriers generated in stage 1 (not shown), which generates a library of bi-functional molecules. The target may be biotinylated, allowing its immobilisation on magnetic beads coated with streptavidin. The beads are immobilised on a magnet and washed. The bound ligands are then eluted, and the DNA of the eluted bi-functional molecules are amplified, for example by PCR, where after this amplified DNA can be used in yet another round of bi-functional molecule library synthesis, or may be sequenced in order to identify the ligand structures that bound to the target.

FIG. 10. Molecular Biological Techniques Applicable to Bi-Functional Molecules:

A number of molecular biological techniques are listed that allow small molecule engineering, analogous to protein engineering through modification of the DNA encoding the protein. Using bi-functional molecules, one may here modify the encoded small molecule through modifications of the DNA encoding the small molecule. Shuffling of the DNA templates (and hence, the small molecules), can be done efficiently by e.g. restriction endonuclease cleavage of the DNA template in the spacer that separates the codons. Other techniques such as DNA arrays of bi-functional molecules are also suggested.

FIG. 10 is modified from (Pedersen et al. (2002) WO 02/103008 A2, "Templated molecules and methods for using such molecules").

FIG. 11. Polyvalent Display and Other Approaches to the Identification of Molecules with Weak Binding Characteristics.

Polyvalent display by rolling circle amplification of templates before templated reaction. DNA template molecules are circularised by ligation of the ends. Specific primers are annealed and extended by rolling circle amplification resulting in templates having multiple copies of the specific binding sites for carrier molecules. The multiple copy templates are thereafter used for templated synthesis with carrier molecules resulting in polyvalent display of encoded molecules.

Stage 1 Synthesis of Divalent Bi-Functional Carrier Molecules.

Split and mix synthesis is carried out as in the example describing stage 1 synthesis, but the linker molecule (L) employed in the first step of the synthesis has, in this example, two reactive ends to which molecule fragments ($R_{1-n}$) can be coupled. This results in the generation of divalent bi-functional carrier molecules having two encoded molecules attached to a linker that is attached to a single oligonucleotide identifier ($O_{1-n}$).

Stage 2 Templated Synthesis Employing Divalent Bi-Functional Carrier Molecules (Generated in Example B Above).

The divalent carrier molecules from example B can be used for templated synthesis employing the method described for stage 2 of the present invention. As a result a library of divalent encoded molecules are generated. Each molecule consists of two encoded molecules ($R_{1-n}$) attached to a linker that is attached to one oligonucleotide identifier ($O_{1-n}$).

Template Assisted Binding to Target DNA Molecule.

For screening of a library of encoded molecules for binding to target DNA sequences, hybridisation of complementary DNA sequences (C and C') on the bi-functional molecule and the target DNA, can increase the overall affinity and help in the identification of molecules in the library with low affinity for the target DNA.

Use of Known Ligand for Assisted Target Binding.

A library of encoded divalent bi-functional molecules, each containing a known ligand (L) and an encoded molecular entity, (R), is used for screening for molecules with two binding sites, of which one of these is specific for the known ligand. Binding of the known ligand to its site on the target molecule (T), assists the binding of the encoded molecular entity to the other binding site.

Use of Known Ligand for Assisted Target Binding—Hybridisation of Known Ligand to Template.

This example uses the same principle as illustrated above in FIG. 11F, but in this example the known ligand is hybridised to the bi-functional molecule through hybridisation of complementary DNA sequences (C' and C) carried by the known ligand and the template DNA. Hybridisation of the known ligand to the template DNA of the bi-functional molecule creates functionally divalent molecules that can be used for screening for target with two binding sites, of which one is specific for the known ligand.

Use of Known Ligand for Assisted Target Binding—Binding to the Same Site.

As in the example illustrated in FIG. 11E, but in this example the known ligand (L) and the molecular entity (R) bind to the same site of the target molecule.

Use of Complementary DNA Attached to the Target Molecule to Assist Binding.

A DNA sequence, C', which is attached to the target molecule, is complementary to a DNA sequence, C, on the template DNA. Hybridisation of the complementary DNA sequences assists binding of the encoded molecules to the target (T).

FIG. 12. Example Set-Ups Allowing Improved Ligation of Identifiers.

During the stage 1 synthesis, the identifiers are ligated together. In order to make this an efficient reaction, the identifiers can be double-stranded DNA with overhangs that are complementary, and therefore bring the reactive groups of the identifiers into close proximity. Alternatively, the identifiers are single-stranded and a complementary oligonucleotide, or some other kind of molecule that binds to the identifiers and brings the reactive groups into proximity, is added in order to increase the efficiency of the chemical or enzymatic ligation.

Ligation Assisted by "Sticky" Ends of the DNA

Ligation assisted by complementary oligonucleotide

Ligation assisted by complementary oligonucleotide attached to solid support

Ligation assisted by annealing to self-complementary sequence

Ligation assisted by DNA binding molecule

FIG. 13. Example Molecule Fragments and the Encoded Molecules Resulting from Stage 1 and Stage 2 Synthesis.

A1-A4 show generic structures of molecule fragments, carrying at least 1 reactive group (A1), two reactive groups (A2), three reactive groups (A3), and four reactive groups (A4). R can be any molecular entity, and can be cyclic or non-cyclic, aliphatic or aromatic. X, Y and A are reactive groups. Molecule fragments can carry multiple reactive groups of the same kind (e.g., three X reactive groups), or can carry multiple reactive groups of different kinds (e.g., X, Y and A).

B1-B4 show specific examples of molecule fragments. B1 structures carry at least one reactive group (here: carboxylic acid or amine). B2 structures carry at least two reactive groups (hydroxyl, amine, thiol). B3 structures carry at least three reactive groups (amine, disulfide, carboxylic acid). B4 carry at least four reactive groups (hydroxyl, amine, thiol, carboxylic acid).

C, D, E, and F show examples of molecules generated by stage 1 and/or stage 2 synthesis, i.e., by covalently coupling molecule fragments through their reactive groups. The stipled circles indicate molecule fragments that have been linked together during the stage 1 and/or stage 2 synthesis.

During stage 1 synthesis the molecule fragments become attached to the linker molecule L via reaction of a reactive group of the molecule fragment with a reactive group of the linker. In this example, the hydroxyl of the encoded molecule of (F) could have been attached to a carboxylic acid-modified oligonucleotide, thus linking the encoded molecule to the linker.

FIG. 14. Dynamic Combinatorial Library of Dimers or Trimers of Encoded Molecules.

A library, A, of encoded bi-functional molecules carries, in addition to its oligonucleotide identifier, O, an oligonucleotide sequence, C, that is complementary to a corresponding oligonucleotide sequence carried by another library, B, of encoded bi-functional molecules. The two libraries are hybridised, thus creating functionally divalent bi-functional molecules that can be used in screening for targets with two binding sites. If appropriately designed, trimers may be formed instead of dimers, thus creating a library of functionally trivalent encoded molecules.

Figure 15:
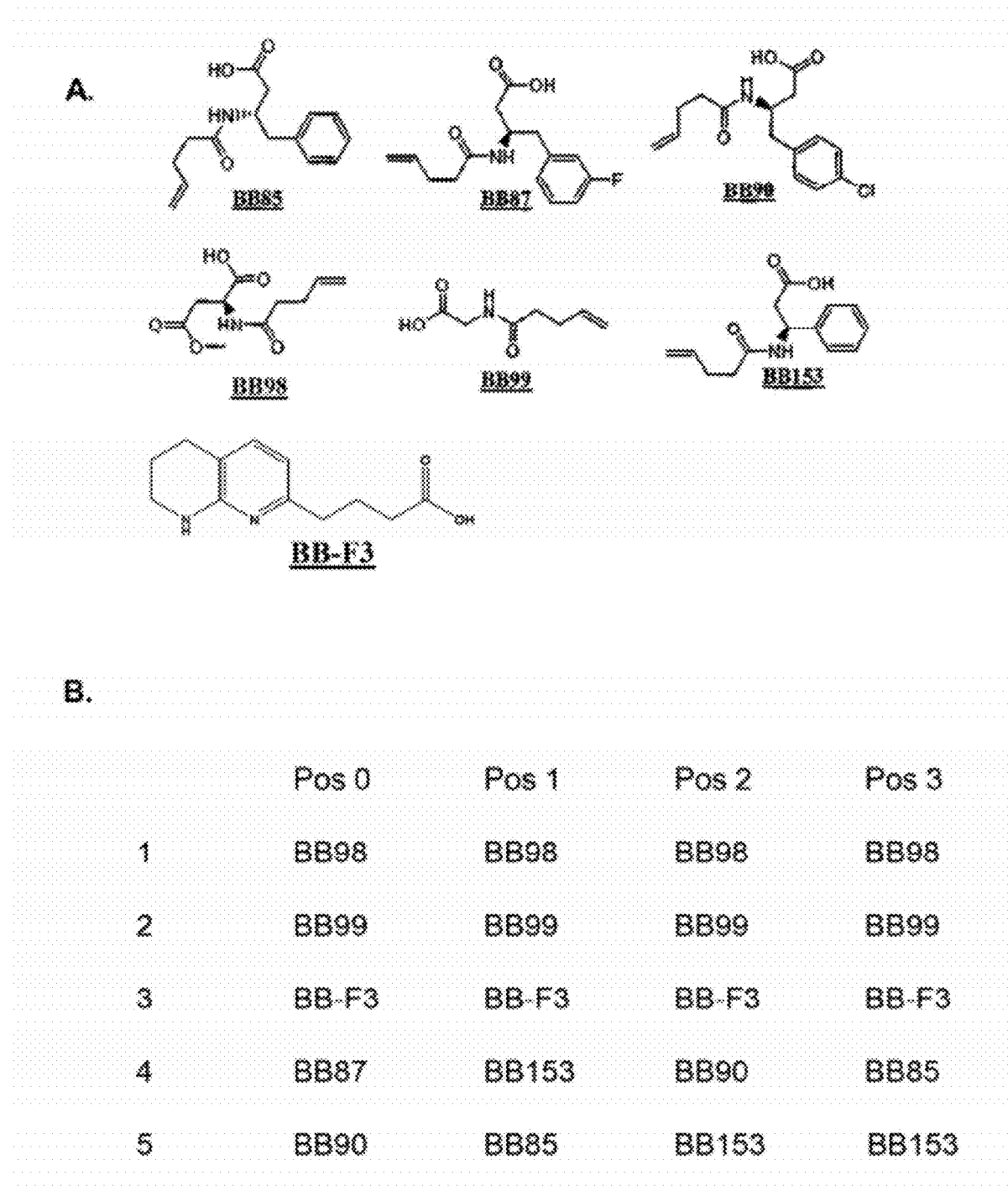

FIG. 15. Molecule Fragments Used in Example 1.

A). Molecule fragments employed in example X1 are shown.

B). List of the molecule fragments used at positions 0, 1, 2, and 3 in the library generation process of example X1.

EXAMPLES

Example 1

Formation of a Library of Bifunctional Molecules and Affinity Selection Against the Protein Target Integrin AlphaV/Beta3 Receptor, Employing Subprocesses 3, 5, A and i (First Synthesis-Selection-Amplification Round), and A and i (Second Synthesis-Selection-Round) (See Above), Using Amine Acylations for the Coupling of Molecule Fragments to Generate the Encoded Molecules The human integrin receptor $a_v/\beta 3w$ is implicated in many biological functions such as inflammatory responses and thrombus formation as well as cellular migration and metastatic dissemination. The natural ligands for alphaV/beta3 integrin receptor contain an RGD tri-peptide consensus motif that interacts with the receptor binding pocket. Consequently, much medical research have focused on the synthesis and identification of small molecule RGD-mimetics with increased affinity for the alphaV/beta3 receptor. One mimetic, Feuston 5 (Feuston et al., *J Med. Chem.* 2002 Dec. 19; 45(26):5640-8.), comprising an arginine bioisostere coupled to a GD dipeptide exhibits a ten-fold increased affinity ($K_D$=111 nM) compared to the RGD-tripeptide.

It would therefore be of interest to synthesize libraries of bifunctional molecules that include the molecule fragments that generate the Feuston 5 ligand. In the following protocols for the generation and screening of such libraries are described. First, the formation and screening of a 625-membered library is described.

Stage 1 Synthesis: Generation of Two Sets of Carriers, Using Chemical Ligation and Enzymatic Ligation, Respectively, During Stage 1 Synthesis to Generate Carrier Molecules (Subprocesses 3 and 5).

FIG. 15 shows the molecule fragments and oligonucleotides employed to generate the library.

Formation of carrier molecules, Set I: Five 14 nt oligonucleotides, each containing a 5'-terminal amino-group (Glen Research catalog #10-1905-90) linked by a Spacer-PEG18 (Glen Research catalog #10-1918-90) are synthesised by standard phosphoramidite chemistry, to give the following oligonucleotides:

O-0.1: 5'-NH2-PEG-ATGCTCGAGA<u>CGCG</u>-3' (SEQ ID NO: 1)

O-0.2: 5'-NH2-PEG-TAGCTGTAGG<u>CGCG</u>-3' (SEQ ID NO: 2)

O-0.3: 5'-NH2-PEG-AGAGCTCTGA<u>CGCG</u>-3' (SEQ ID NO: 3)

O-0.4: 5'-NH2-PEG-CGTCGTCGTA<u>CGCG</u>-3' (SEQ ID NO: 4)

O-0.5: 5'-NH2-PEG-ATCGTCGAGA<u>CGCG</u>-3' (SEQ ID NO: 5)

The sequences of these oligonucleotides are not crucial, and the sequences can be changed to increase the sequence dissimilarity or decrease the differences in annealing temperature. Each of the O-0.n oligonucleotides (position 0 in the library) are now portioned out into separate wells (i.e., each oligonucleotide is placed in a separate well, here an eppendorf tube), and loaded with a specific molecule fragment, each of which comprises a carboxylic acid and a penteneoyl-protected amine. The five molecule fragments are shown in FIG. 15; one of these molecule fragments is penteneoyl-Asp (OMe)-OH (aspartic acid, where the side chain carboxylic acid has been protected with a methyl ester). The following molecule fragment loading protocol, Protocol A, is used:

1 nmol amino-modified oligonucleotide is lyophilized and then dissolved in 20 microliter of 100 mM Na-borate buffer, pH 8.0 with 90 mM sulpho-N-Hydroxysuccinimide (sNHS, Merck). The molecule fragments are preactivated by incubation of 15 microliter of 100 mM molecule fragment in DMSO and 15 microliter of 100 mM 1-ethyl-3-(3-dimethylamino-propyl)carbodiimide hydrochloride (EDC, Merck) in DMF for 30 min at 30° C. before addition to the oligonucleotide solution. Each of the five molecule fragments are added to a specific oligonucleotide, as described in FIG. 15. Following incubation for 45 min at 30° C., an additional 30 microliter of pre-activated molecule fragment is added and the solution incubated for another 45 min at 30° C. Excess molecule fragment, activation agents, solvents and salt is removed by double gel filtration using Bio-rad microspin columns 6 and eluted in MS-grade $H_2O$. Loading is optionally verified by Electrospray-MS analysis. Subsequently, the amino-protection group is removed by addition of 0.2 volumes of 25 mM iodine in a mixture of $THF/H_2O$ (1:1) and incubated at 37° C. for 2 h. Excess iodine is quenched by 20 mM 2-mercaptoethanol before gel filtration purification using Bio-rad 6 microspin columns. From MS-analysis the efficiency of loading and deprotection can optionally be estimated. At the end of this first round of synthesis, each of the 5 oligonucleotides should be attached to their specific molecule fragment; the molecule fragment contains a reactive group, the amine, ready for reaction with the next molecule fragment that is added. The contents of the five wells are pooled, and redistributed into five new wells.

Next, 1.2 nmoles unit identifier oligonucleotides, corresponding to position 1, are added to each well, according to the scheme of FIG. 15. The five oligonucleotides carry an imidazole-activated 5'-phosphate (Visscher, J., Schwarz, A. W. Journal of Molecular Evolution (1988), 28: 3-6; Zhao, Y., Thorson, J. S. Journal of Organic Chemistry (1998), 63:7568-7572) and have the following sequences:

O-1.1: 5'-ImP-<u>CAC</u>AAGTACGAACG-3' (SEQ ID NO: 6)

O-1.2: 5'-ImP-<u>CAC</u>ATAGTCTCCTC-3' (SEQ ID NO: 7)

O-1.3: 5'-ImP-<u>CAC</u>ATACATCGTTC-3' (SEQ ID NO: 8)

O-1.4: 5'-ImP-<u>CAC</u>ATCCAGTGCAA-3' (SEQ ID NO: 9)

O-1.5: 5'-ImP-<u>CAC</u>AAGCATCACTA-3' (SEQ ID NO: 10)

1-2 nmoles of the oligonucleotide 3'-GCGCGTGT-5' is added to all wells, and an appropriate buffer of pH 8-10 is added, to a final volume of 20-50 microliter. This oligo is complementary to the ends of oligonucleotides O-0.n and O-1.n, and by hybridization of these complementary sequences the 3'-OH group of the oligonucleotides O-0.n and the Imidazole activated 5'-phosphates of the 0-1.n oligonucleotides will be juxtaposed. The solution is incubated for 1-5 hrs at 37° C. or 50° C. This results in ligation of the juxtaposed oligonucleotides, by formation of a phosphodiester bond.

Optionally, the five solutions containing the ligation products are purified individually using Biorad 6 spin columns according to manufacturer's instructions and lyophilized. Next, a specific molecule fragment is reacted with each of the five solutions of nascent bifunctional molecules, according to the scheme shown in FIG. 18, using loading protocol A described above. Excess free reactant, reagents and buffer is removed by gelfiltration. The eluates are pooled, lyophilized and resuspended in 40 ul of $H_2O$ before addition of 10 ul of 25 mM iodine
(in $THF/H_2O$, ratio 1:1) for deprotection. The reaction is incubated at 37° C. for 2 h. Excess Iodine is quenched by addition of 1 ul of 1 M 2-mercaptoethanol and left at ambient temperature for 5 min before purification of the sample using spin-gelfiltration (Bio-rad 6). The solution now contains 25 carrier molecules, where 25 different carrier identifier oligonucleotides each is attached to a specific one of 25 different dimers of molecule fragments. The carriers contain a free amino group, for reaction in the templated synthesis (see below).

Formation of carrier molecules, Set II: The five 15 nt oligonucleotides, corresponding to position 2 of the library:

```
O-2.1: 3'-SH-GAGCAGGACCACCAG-5' P   (SEQ ID NO: 11)
O-2.2: 3'-SH-CTCGACCACTACCAG-5' P   (SEQ ID NO: 12)
O-2.3: 3'-SH-CGTGCTTCCTACCAG-5' P   (SEQ ID NO: 13)
O-2.4: 3'-SH-CCTGGTGTCGACCAG-5' P   (SEQ ID NO: 14)
O-2.5: 3'-SH-CTCGACGAGGACCAG-5' P   (SEQ ID NO: 15)
``` each carrying a 3'-terminal thiol-group, linked to the oligonucleotide through a flexible linker, and a 5'-terminal phosphate group, and each portioned out into one of five separate wells, are each linked through a thioester bond to a specific one of the five molecule fragments listed in FIG. 15 by the following Protocol B (Bruick et al., (1996), *Current biology* 3:49-56):

Five N-protected molecule fragments (see FIG. 15) carrying a free carboxylic acid are first converted by standard procedures to the corresponding thioacids. After lyophilization, 1.2 equivalents of Ellmanns Reagent (5,5'-dithiobis(2-nitrobenzoic acid)) is incubated with the thioacid at pH 6.5 for 1 h, to produce the corresponding 5-thio-2-nitrobenzoic acid ester. Optionally, the desired compounds are purified and characterized by HPLC and mass spectrometry.

1 nmol of each of the five oligonucleotides O-2.n are now incubated in separate wells with an excess of one of the five 5-thio-2-nitrobenzoic acid esters, according to the scheme of FIG. 15, at 25° C. or 37° C., at pH 8 for 1-5 h. Optionally, 2 mM spermidine may be added to improve the efficiency of the reaction. Optionally, the formation of the correct oligonucleotide-thioester-molecule fragment product can be verified by mass spectrometry. Finally, the five modified oligonucleotides are pooled.

Excess molecule fragment, activation agents, solvents and salt is removed by double gel filtration using Bio-rad microspin columns 6 and eluted in MS-grade $H_2O$, Subsequently, the amino-protection group is removed by addition of 0.2 volumes of 25 mM iodine in a mixture of $THF/H_2O$ (1:1) and incubated at 37° C. for 2 h. Excess iodine is quenched by 20 mM 2-mercaptoethanol before gel filtration purification using Bio-rad 6 microspin columns. Alternatively, the oligonucleotides are precipitated with ethanol to remove the iodine. From MS-analysis the efficiency of loading and deprotection can optionally be estimated. At the end of this first round of synthesis, each of the 5 oligonucleotides should be attached to their specific molecule fragment through a thioester bond; the molecule fragment contains a free amine, ready for reaction with the next molecule fragment that is added. The contents of the five wells are pooled, and redistributed into five new wells.

Next, 1.2 nmoles unit identifier oligonucleotides, corresponding to position 3, are added to the wells, according to the scheme of FIG. 15. The five oligonucleotides have the following sequences:

```
O-3.1:   3'-CCTTAGTACGAACG-5'   (SEQ ID NO: 16)
O-3.2:   3'-CCTTACACGGAAAG-5'   (SEQ ID NO: 17)
O-3.3:   3'-CCTTGCTACTAGCT-5'   (SEQ ID NO: 18)
O-3.4:   3'-CCTTGGAATTCCGA-5'   (SEQ ID NO: 19)
O-3.5:   3'-CCTTGTACCATGGA-5'   (SEQ ID NO: 20)
```

1-2 nmoles of the oligonucleotide 5-TGGTCGGAA-3', complementary to the ends of oligonucleotides O-2.n and O-3.n, is added to all wells. Then, the oligos are ligated in a volume of 20 ul using ligation buffer (30 mM Tris-HCl (pH 7.9), 10 mM $MgCl_2$, 10 mM DTT, 1 mM ATP) and 10 units T4-DNA ligase at ambient temperature for 1 hour. Subsequently, the 5 solutions of ligation products are purified individually using Biorad 6 spin columns, and the oligonucleotides lyophilized.

Next, a specific molecule fragment is reacted with the nascent bifunctional molecule according to the scheme shown in FIG. 18 using loading protocol A described above. Excess free molecule fragment, reagents and buffer are then removed by gelfiltration. The eluate is pooled, lyophilized and resuspended in 40 ul $H_2O$.

The BB—F3 molecule fragment does not react efficiently using protocol A, due to poor solubility of BB—F3 in organic solvent. Consequently, BB—F3 is reacted using Protocol C instead: The ligated and lyophilized sample is dissolved in 35 microliter 100 mM Na-borate buffer (pH 8.0) before addition of 10 microliter 100 mM BB—F3 in water and 5 microliter of 500 mM 4-(4,6-dimethoxy-1,3,5-triazin-2-yl)-4 methylmorpholinium chloride (DMT-MM, carboxylic acid activator) and incubated at 25° C. for 2 h. Following the coupling reaction, excess molecule fragment, reagent and salt is removed by gelfiltration as described in protocol A.

The two solutions are pooled, and the resulting solution now contains 25 carrier molecules, all of which contain a thioester bond linking the molecule fragments to the carrier identifiers.

Stage 2 synthesis: Generation of bifunctional molecules by DNA-templated synthesis as described by (Bruick et al., (1996), Current biology 3:49-56) (subprocess A, see above). Single-stranded DNA template library generation. First, four sets of duplex DNAs with overhangs are produced, by standard oligonucleotide synthesis followed by hybridization of appropriate oligonucleotide pairs, corresponding to the four encoded positions in the library. Each set of duplex DNA in this library contains five different dsDNAs, corresponding to the 5 different identifier sequences at each position, encoding 5 different molecule fragments at each positions. All dsDNA 0.n carry a biotin as indicated below for the dsDNA 0.1. When employing more molecule fragments, the number of dsDNAs in each set must be increased accordingly. An example of dsDNAs is shown below for the O-0.1, O-1.1, O-2.1, and O-3.1 identifiers:

```
dsDNA 0.1:
5'-ATGCTCGAGACGCG-3'              (SEQ ID NO: 21)
```

-continued

```
3'-GTACGAGCTCT-5'                              (SEQ ID NO: 22)

dsDNA 1.1:
5'-CACAAGTACGAACGTATGCGTTGGCCAAA               (SEQ ID NO: 23)
CACTG-3'

3'-GCGCGTGTTCATGCTTGCATACGCAACCG               (SEQ ID NO: 24)
GXTTGTGAC-5' dsDNA 2.1:
5'-GACCACCAGGACGAGC-3'                         (SEQ ID NO: 25)

3'-AAGGCTGGTGGTCCTGCTC-5'                      (SEQ ID NO: 26)

dsDNA 3.1:
5'-TTGGTTGACTAGAGACGAGCGCAAGCATG               (SEQ ID NO: 27)
ATTCC-3'

3'-AACCAACTGATCTCTGCTCGCGTTCGTACT-             (SEQ ID NO: 28)
5'
```

Underlined sequences are priming sites for PCR amplification. All 5'-ends are phosphorylated (contain phosphates). Overhang sequences can be extended in order to allow more efficient ligation in the preparation of the templates described below. The X in dsDNA 1.1 denotes a T that carries a biotin group.

The four sets of dsDNAs are incubated, to allow for hybridization between overhang, and ligated as a mixture using ligation buffer (30 mM Tris-HCl (pH 7.9), 10 mM MgCl$_2$, 10 mM DTT, 1 mM ATP) and T4-DNA ligase at ambient temperature for 1 hour. Thus, a total of 5×5×5×5=625 templates are generated. As an example, we have aligned the four dsDNAs corresponding to the O-0.1, O-1.1, O-2.1, and O-3.1 identifiers immediately below; open spaces highlight the complementary overhangs that hybridize during the ligation reaction:

```
          dSDNA 3.1                 dsDNA 2.1          dsDNA 0.1          dsDNA 1.1
-TTGGTTGACTAGAGACGAGCGCAAGCATGATTCC GACCACCAGGACGAGC ATGCTCGAGACGCG CACAAGTACGAACGTATGCGTTGGCCAAACACTG-
3

-AACCAACTGATCTCTGCTCGCGTTCGTACT AAGGCTGGTGGTCCTGCTC GTACGAGCTCT GCGCGTGTTCATGCTTGCATACGCAACCGGTTTGTGAC-
5
```

The ligation product (the template) that results from the ligation of the above sequences is indicated immediately below:

```
          dsDNA 3.1                 dsDNA 2.1          dsDNA 0.1          dsDNA 1.1
5'-TTGGTTGACTAGAGACGAGCGCAAGCATGATTCCGACCACCAGGACGAGCATGCTCGAGACGCGCACAAGTACGAACGTATGCGTTGGCCAAACACTG-
3' (SEQ ID NO: 81)

3'-AACGAACTGATCTCTGCTCGCGTTCGTACTAAGGCTGGTGGTCCTGCTCGTACGAGCTCTGCGCGTGTTCATGCTTGCATACGCAACCGGXTTGTGAC-
5' (SEQ ID NO: 82)
use the gap bulletin per instructions from pto
```

Thus, the sequence of identifier sequences in the 625 templates is: (primer annealing site)-O-3-O-2-O-0-O-1-(primer annealing site). Optionally, more copies of the templates can be produced by PCR amplification using primers that anneal to underlined sequences. One of the primers should carry a T with biotin, as indicated. Thus, the ligation product and the PCR product contains a biotinylated lower strand.

The biotinylated double stranded product is now incubated with streptavidin-coated beads, and the upper strand removed by alkaline denaturation of the strands, and the pH is neutralized with an appropriate buffer to produce immobilized, single stranded template.

Hybridisation of carriers and template, and templated reaction between reactive groups Bruick et al., (1996), Current biology 3:49-56): 1-100 pmol immobilized templates are mixed with an excess of Set I and Set II carriers obtained above, in an appropriate buffer at pH 8. Optionally, the temperature is kept at 50° C. for 2 min., then lowered to 37° C. The temperature is now kept at 37° C. for 24 h. The carrier molecules anneal to the template under these conditions; the close proximity of the amino group of carriers of Set I, and the thioester of carriers of Set II, leads to amide formation, in effect transferring the molecule fragment of the thioester carrier onto the amine carrier. At this point, 625 different bifunctional molecules have been generated.

Optionally, a DNA loop that can be ligated to the carrier molecule with the 0.n and 1.n identifiers (to the right in the figure above) and to the template, and thus covalently attaches the carrier molecule to the template, can be added. Thus, optionally, to the bifunctional molecule that results from the templated synthesis immediately above, add an oligonucleotide with the sequence 5'-TATGCGTTGGCCAAACACTG-GCAGATA-GAGGTCTGC-3' (SEQ ID NO 29), where the stem sequences are underlined, and where the 5'-terminus is phosphorylated (carries a phosphate). Add ligation buffer (30 mM Tris-HCl (pH 7.9), 10 mM MgCl$_2$, 10 mM DTT, 1 mM ATP) and T4-DNA ligase at ambient temperature for 1 hour, to covalently attach the right-ward carrier molecule (carrying the encoded molecule that results from the templated synthesis) to the template.

Optional amine and carboxylic acid deprotection. Optionally, to the solution of the previous step is now added 0.2 volumes of 25 mM iodine (in THF/H$_2$O, ratio 1:1) for deprotection of the penteneoyl-protected amines. Excess Iodine is quenched by addition of 1 ul of 1 M 2-mercaptoethanol and left at ambient temperature for 5 min before optional purification of the sample using spin-gelfiltration (Bio-rad 6). Then, optionally, NaOH is added to 25 mM, at 80° C. for 5 minutes, to deprotect methylester-protected carboxylic acids. Then increase pH to 12.5 for one min Optionally, the sample is purified using spin-gelfiltration (Bio-rad 6).

Selection on Immobilised Target (Subprocess i).

Immobilisation and selection: Maxisorp ELISA wells (NUNC A/S, Denmark) is coated with each 100 microliter 2 ug/mL integrin alphaV/beta3 (Bachem) in PBS buffer (2.8 mM NaH$_2$PO$_4$, 7.2 mM Na$_2$HPO$_4$, 0.15 M NaCl, pH 7.2) overnight at 4° C. Then the integrin solution is substituted for 200 microliter blocking buffer (TBS, 0.05% Tween 20 (Sigma P-9416), 1% bovine serum albumin (Sigma A-7030), 1 mM MnCl$_2$) and incubated for 1 hour at room temperature. Then the wells are washed 2 times with 250 microliter blocking buffer, and 200 microliter blocking buffer, containing the library of bifunctional molecules generated above, is added to the wells. Following 2 hours incubation at room temperature the wells are washed with 20×250 microliter blocking buffer.

After the final wash the wells are cleared with washing buffer and the bound bifunctional molecules eluted with MeOH, glycine pH 5, or an appropriate buffer of pH 11-13. The pH is adjusted to 7. The eluted fraction contains potential integrin alphaV/beta3 receptor ligands.

PCR amplification of the DNA templates of the isolated bifunctional molecules, and cloning and characterization: The templates of the eluted fraction is now amplified by PCR, and then either cloned and sequenced for characterization, or is taken through one more round of single-stranded template preparation, and stage 2 synthesis. For characterization, 5 ul eluted bifunctional molecules are used for PCR in a 25 ul reaction using 10 ul Eppendorf hotmastermix 2.5× and 10 pmol each of forward and backwards primers that anneal to the underlined sequences depicted above. The PCR product is then ligated into suitable plasmid and transformed into e.g. *E. coli*, whereafter individual clones are sequenced by standard means (see for example below). From the DNA sequences the identity of the recovered encoded molecules can be deduced.

Template amplification, single-stranded template preparation, stage 2 synthesis (e.g. subprocess 5) and selection (e.g. subprocess i). Instead of amplifying the recovered identifiers from the selection step above, and cloning and sequencing, the bifunctional molecules can be amplified and taken through one more round of selection. To this end, amplify the recovered identifiers with forwards and backwards primers, where the backwards primer carries a biotin (as indicated above). Isolate single-stranded DNA-template, add carriers generated above, and perform stage 2 synthesis as indicated above. Finally, the selection is performed, as indicated above, or by any other means that lead to identification of integrin alphaV/beta3 ligands. Finally, the identifiers recovered are PCR amplified, cloned, and sequenced (see for example below), to reveal the identity of the encoded molecules responsible for binding to the integrin receptor.

Identification and Characterisation.

To obtain the sequences of the DNA templates, and thereby deduce the chemical structure of the encoded molecules, the double stranded PCR-product is cloned into e.g. an *E. coli* vector, propagated in *E. coli*, and individual clones sequenced. Each of the clones represent an identifier sequence of a bifunctional molecule in the pool isolated by the selections; from the sequence of the DNA the corresponding encoded molecule (that was attached to the identifier of the same bifunctional molecule) can be deduced. The TOPO-TA (Invitrogen Cat#K4575-J10) ligation is reacted with 4 ul PCR product, 1 ul salt solution, 1 ul vector. The reaction is incubated at RT for 30 min. Heat-shock competent TOP10 *E. coli* cells are thawed and put on ice. 5 ul ligation reaction is added. Following 30 min on ice, the cells are heat-shocked at 42° C. water for 30 sec, then put on ice. 250 ul SOC is added and the cells incubated 1 h at 37° C., before spreading on LB-ampicillin plates followed by incubation ON at 37° C. Individual *E. coli* clones are picked and transferred to PCR wells containing 50 ul water. Colonies are incubated at 94° C. for 5 minutes and 20 ul is used in a 25 ul PCR reaction with 5 pmol of each TOPO primer M13 forward & M13 reverse and Ready-To-Go PCR beads (Amersham) using the following PCR program: 94° C. 2 min, then 30×(94° C. 4 sec, 50° C. 30 sec, 72° C. 1 min) then 72° C. 10 min. Primers and free nucleotides are degraded by adding 1 ul EXO/SAP mixture 1:1 to 2 ul PCR product. Incubation is at 37° C. for 15 min and then 80° C. for 15 min. 5 pmol T7 primer is added and water to 12 ul. Subsequently, 8 ul DYE-namic ET cycle sequencing Terminator Mix is added followed by PCR-cycling using 30 rounds of (95° C. 20 sec, 50° C. 15 sec, 60° C. 1 min). Purification is done using seq96 spinplates (Amersham), followed by analysis on a MegaBace sequenzer.

To verify that the isolated encoded molecules indeed represent ligands to the target protein (integrin alphaV/beta3), individual bifunctional molecules may be prepared, by preparation of single stranded DNA of that bifunctional molecule, and performing the templated synthesis, to generate multiple copies of that specific bifunctional molecule. The ability of the bifunctional molecule (and, expectably, the ability of the encoded molecule) to bind the protein target (integrin alphaV/beta3) is then tested by e.g. immobilising the protein target in the well of a microtiter plate, adding the bifunctional molecule, washing off unbound bifunctional molecule, and then determine the amount of bound bifunctional molecule.

Alternatively, the identified encoded molecule may be synthesized in its free form, by standard chemical synthesis protocols, and then examined in e.g. competition binding experiments.

The directionality of the oligonucleotides used in the example may be changed, so as for example to include a thiol at the 5'-end rather than the 3'-end, or the sequences of the oligonucleotides may be changed in order to obtain highest possible mismatch ("sequence difference") among the different unit identifiers and carrier identifiers, while keeping the annealing temperatures relatively similar. This will increase the fidelity of the hybridization of carriers to the template during stage 2 synthesis, and will also increase the fidelity of the deconvolution step, since sequencing errors will be less of a problem if the identifiers have fewer identical nucleotide positions.

In the example a thioester was employed as the reactive group of Set II carriers. The activated ester can be any other type of activated ester (e.g., N-hydroxide succinimide ester, nitrophenyl-ester, nitrobenzyl-ester), or the ester may be a regular carboxyester. These activated esters are prepared by standard organic synthesis methods.

In the example, only the Set I carriers contain a long, flexible PEG linker. It may be advantageous that both carrier sets contain a PEG linker, to obtain high flexibility of the molecule fragments that must react.

In the example, the order of reactions between molecule fragments, and ligation of identifiers during stage 1 synthesis, is "reaction-ligation-reaction". This order can be changed, to be reaction-reaction-ligation, if desired.

The constant regions of the unit identifier oligonucleotides are 4 or 5 nt in the example. The constant regions are complementary to the third oligonucleotide added; the third oligonucleotide brings the two unit identifiers into close proximity, and thus mediates the ligation of the unit identifiers. The overlap region between the identifier and the third oligonucleotide can be extended (to allow for a more efficient ligation during stage 1 synthesis), or shortened (to allow for more specific annealing of the carrier molecule during the stage 2 synthesis that follows; annealing is more specific because the sequence similarity with other carriers employed during the stage 2 templated synthesis will be smaller when the constant regions are shorter.

The recovered sequences from the selection experiment of example X1 will contain an abundance of the identifier sequences encoding the molecule fragments BB98, BB99, and BB—F3, as these are the molecule fragments that generate the known integrin alphaV/beta3 receptor ligand, Feuston 5.

The stage 1 synthesis protocol, stage 2 synthesis protocol, screening protocol, and characterization protocol, can be employed as modular units, as long as each of the four protocols are finalized by a purification to remove salts, reagents, unreacted molecule fragments, and the like. Often, an appropriate purification is spin-gelfiltration (Bio-rad 6); in order to obtain very efficient purification, two spin-gelfiltrations may be performed.

The following examples describe protocols for individual stage 1 synthesis, stage 2 synthesis, screening/selection, and characterization. As mentioned, these may be combined in any desired way, as long as each of the protocols are finalized with an appropriate purification step. Obviously, the length and composition of the identifiers must be designed so as to mediate specific and efficient annealing of the carriers to the template during templated synthesis.

Example 2

Formation of Five Different Libraries of Bifunctional Molecules, i.e., Libraries Containing 16, $1.6 \times 10^5$, $6.25 \times 10^6$, $10^8$, or $10^{12}$ Bi-Functional Molecules and Affinity Selection Against the Protein Target Integrin AlphaV/Beta3 Receptor, Employing Subprocesses 3), 5), A) and i), Using Amine Acylations for the Coupling of Molecule Fragments to Generate the Encoded Molecules This example describes the generation of libraries of five different libraries, i.e, libraries of 16, $1.6 \times 10^5$, $6.25 \times 10^6$, $10^8$, or $10^{12}$ bi-functional molecules, and the use of these libraries for selection against the integrin alphaV/beta3 receptor.

The protocol described in example X1 is followed, except that the sets of molecule fragments are now changed so as to include 2, 20, 50, 100, or 1000 molecule fragments at each of the four positions, leading to the formation of libraries of $2 \times 2 \times 2 \times 2 = 16$, $20 \times 20 \times 20 \times 20 = 1.6 \times 10^5$, $50 \times 50 \times 50 \times 50 = 6.25 \times 10^6$, $100 \times 100 \times 100 \times 100 = 10^8$, or $1000 \times 1000 \times 1000 \times 1000 = 10^{12}$ bifunctional molecules. The molecule fragments carry the same N-protecting group (N-penteneoyl) and a free carboxylic acid, wherefore the protocol described in example X1 can be used, except that an appropriate number of wells are used, corresponding to the number of molecule fragments. A number of unit identifier oligonucleotides are used that correspond to the number of molecule fragments. Because of the size of these libraries, novel ligands not strongly related to the Feuston 5 ligand, will be identified from the bigger libraries. This is particularly true for the libraries of $10^8$ or $10^{12}$ bifunctional molecules. For library sizes larger than $10^8$ encoded molecules, ligands will be identified that do not contain all three molecule fragments BB98, BB99, and BBF3, yet have dissociation constants lower than 100 micromolar.

Example 3

Covalent Attachment of a Carrier to the Template Employed in the Stage 2 Synthesis The structure of the identifier template of the bifunctional molecule generated by stage 2 synthesis, and employed in the selections, can be varied. For example, before, during or after the templated reaction, one of the carriers may be ligated to the template by a DNA ligase, if the template for example loops back on itself, as described in FIG. 4, example 3. Optionally, an extension reaction involving a primer that anneals to the other end of the template may be performed, in order to generate a duplex DNA where the encoded molecule is displayed at the end of the dsDNA. This may be done by annealing 1 nmol of a primer that is complementary to the end of the template that is not looping back on itself, and adding sequenase buffer containing 200 micromolar deoxy-ribonucleotides (dNTP) in a total volume of 100 microliter before addition of 20 units of sequenase and incubation at 30° C. for 1 h. Following extension the reaction mixture is used in the selection step without further purification.

Example 4

Disulfide Formation During Stage 1 Synthesis, Employed to Attach a Scaffold Molecule Fragment Comprising Three Reactive Groups This is an example of a reaction that attaches a molecule fragment to another molecule fragment, or to the linker molecule L, through formation of a disulfide bond (Freskgård et al., WO 2004/039825 A2, example 1, p. 106-108). The protocol may be used in stage 1 synthesis. Similar reaction conditions can be employed in a stage 2 synthesis. An amino-modifier C6 5'-labeled oligo (5'-X-CGTAACGACTGAATGACGT-3') (SEQ ID NO 30), wherein X may be obtained from Glen research, cat. #10-1039-90) was loaded with a peptide (Cys-Phe-Phe-Lys-Lys-Lys, CFFKKK) using SPDP activation (see below). The SPDP-activation of amino-oligo was performed using 160 uL of 10 nmol oligo in 100 mM Hepes-KOH, pH=7.5, and 40 uL 20 mM SPDP and incubation for 2 h at 30° C. The activated amino-oligo was extracted 3 times with 500 uL EtOAc, dried for 10 min in a speedvac and purified using micro bio-spin column equilibrated with 100 mM Hepes-KOH. The loading of peptide was then performed by adding 10 uL of 100 mM attachment entity and incubating overnight at 30° C. The loaded identifier oligo was precipitated with 2 M NH$_4$OAc and 2 volume 96% ethanol for 15 min at 80° C. and then centrifuged for 15 min at 4° C. and 15.000 g. The pellet was re-suspended in water and the precipitation was repeated. Wash of the oligo-pellet was done by adding 100 uL of 70% ethanol and then briefly centrifuged. The oligo was re-dissolved in 50 uL H$_2$O and analysed by MS. After incubation the resin was removed by centrifugation and 15 uL of the supernatant was mixed with 7 uL of water, 2 uL of piperidine and imidazole (each 625 mM) and 24 uL acetonitrile. The sample was analysed using a mass spectroscopy instrument (Bruker Daltonics, Esquire 3000plus). The observed mass was 7244.93 Da, which correspond well with the calculated mass, 7244.00 Da. This experimental data exemplify the possibility to load a molecule fragment onto oligonucleotides through the formation of a disulfide bond. This particular molecule fragment (peptide) harbours three reactive groups, i.e. the amine groups of the lysine side chains, and therefore represents a scaffold with the ability to be reacted with one, two, or three other molecule fragments that are capable of reacting with the amine groups (e.g. carboxylic acids).

Example 5

Stage 1 Acylation Reaction

This is an example of a stage 1 acylation reaction that attaches a molecule fragment to another molecule fragment coupled to an oligonucleotide, or to a reactive group of an oligonucleotide. Similar conditions can be applied for a stage 2 acylation reaction, except that the incoming molecule fragment must be at high concentration, e.g. 10-100 mM. The experiment is described in (Freskgård et al., WO 2004/039825 A2, p. 129-137).

EDC-based acylation protocol: 10 uL triethanolamine (TEA) (0.1 M in DMF) was mixed with 10 uL molecule fragment (here called "Building Block (BB)"). The building blocks that were tested all carry a carboxylic acid and a Pent-4-enal amine protecting group; the concentration of the building block was 0.1 M in DMSO. From this mixture 6.7 uL was taken and mixed with 3.3 uL EDC (1-Ethyl-3-(3-Dimethylaminopropyl) carbodiimide Hydrochloride) (0.1 M in DMF) and incubated 30 minutes at 25° C. 10 uL of the Building block-EDC-TEA mixture was added to 10 uL of an amino modified oligonucleotide (here termed "amino oligo") (in 0.1 M HEPES buffer ((4-(2-Hydroxyethyl)-1-piperazineethanesulfonic acid, SIGMA), pH 7.5 and incubated for 30 minutes. During this half hour, another 6.7 uL of BB-TEA mix was mixed with 3.3 uL EDC (0.1M in DMF) and incubated for 30 minutes at 25° C. 10 uL of this second BB-EDC-TEA mixture was then added to the amino oligo mixture together with 10 uL of 0.1 M HEPES buffer to maintain a 1:1 ratio of DMSO/DMF:H$_2$O. Then the mixture was incubated for 30 minutes. During this half hour, another 6.7 uL of BB-TEA mix was mixed with 3.3 uL EDC (0.1 M in DMF) and incubate for 30 minutes at 25° C. 10 uL of this third BB-EDC-TEA mixture was then added to the amino oligo mixture together with 10 uL of 0.1 M HEPES buffer to maintain a 1:1 ratio of DMSO/DMF:H$_2$O. Then the mixture was incubated for 30 minutes. The oligonucleotide, linked to the molecule fragment (here termed "loaded oligo") was then purified by gel filtration with columns (Biospin P-6, Bio-Rad) equilibrated with water. The pent-4-enal amine protection group was then removed by addition of 0.25 volumes 25 mM I$_2$ in 1:1 water:tetrahydrofuran (THF) and incubation at 37° C. for 2 hours. The mixture was then purified by gel filtration with spin columns (Biospin P-6, BioRad) equilibrated with water. Loaded oligos were analyzed by ES-MS. Molecule fragments tested included aliphatic as well as aromatic compounds, and all were attached efficiently through amide bond formation, as evidenced by mass spectrometric data within a few Daltons of the expected mass. See (Freskgård et al., WO 2004/039825 A2, p. 129-137).

DMT-MM-based acylation protocol: 10-15 nmol of carrier oligo 2 was lyophilized and redissolved in 27.5 ul H$_2$O. To this was added 7.5 ul 1 M HEPES pH 7.5, 10 ul of 2-aminopent-4-enal protected (allyl-glycine) building block (0.1 M in dimethyl sulfoxide), and 5 ul DMT-MM (4-(4,6-dimethoxy-1,3,5-thiazin-2-yl)-4-methylmorpholinium chloride) (0.5 M in water). The mixture was incubated 4-16 hours at 25-30° C. The oligo was purified by gel filtration (Biospin P-6, Bio-Rad). To convert the methyl ester moiety of the building block to a carboxylic acid, 5 ul 0.4 M NaOH was added and the mixture was incubated 20 min at 80° C. The mixture was then neutralized by adding 10 ul 0.5 M HEPES pH 7.5 and 5 ul 0.4 M HCl. The loaded building block oligo was purified by gel filtration Biospin P-6, BioRad) and analyzed by ES-MS. Aliphatic as well as aromatic building blocks were attached to the amine modified oligonucleotide efficiently, as evidenced by the MS-data which showed good correlation between expected and observed mass. See (Freskgård et al., WO 2004/ 039825 A2, p. 129-137).

Example 6

Stage 1 Enzymatic Ligation of Oligonucleotides Carrying Molecule Fragments

This is an example of a stage 1 enzymatic ligation that attaches one oligonucleotide, carrying a molecule fragment, to another oligonucleotide through covalent phosphodiester bond formation. The experiment is described in (Freskgård et al., WO 2004/039825 A2, p. 137-143).

500 pmol loaded carrier oligo (oligonucleotide carrying a molecule fragment), 5'-phosphorylated, was mixed with 750 pmol anti-codon oligo (not carrying any molecule fragment) and 750 pmol splint oligo (comprising complementary sequences to both the carrier oligo and the anti-codon oligo). See figure immediately below, showing an example pair of carrier oligo and anti-codon oligo, as well as the splint oligo. Note that the anti-codon oligo comprises Inosines (allowing annealing to several different bases, here C and A. The mixture was lyophilized and redissolved in 15 ul water. Oligos were annealed by heating and slowly cooling to 20° C. 15 ul TaKaRa ligase mixture (Takara Bio Inc) was added and the reaction was incubated at 20° C. for 1 hour. The mixture was purified by gel filtration (Biospin P-6, BioRad) and the efficiency of the ligation was checked by running an aliquot on a Novex TBE-UREA gel (Invitrogen). Both oligonucleotides carrying aliphatic and aromatic compounds were tested; different sequences around the ligation point was examined as well. All oligonucleotides tested were ligated with more than 95% efficiency. See (Freskgård et al., WO 2004/039825 A2, p. 137-143).

```
Loaded carrier Oligo
3'-2GGAGTCGACACATAGCTCGCp         (SEQ ID NO: 31)
Anti-codon oligo
CGTCGIIIIIGCAGCCAATAGTCGT-X       (SEQ ID NO: 32)
Splint oligo
TCGAGCG--GCAGCCA
```

Example X7

Stage 1 Synthesis of a 484-Member Library of Bifunctional Molecules (Subprocess 4), and Selection by Affinity Selection on Immobilized Target (Subprocess i)

This is an example of a stage 1 synthesis employing subprocess 4. Three rounds of encoding are employed, involving 4, 11 and 11 molecule fragments, thus generating a total of 484 bifunctional molecules that may be used as carriers in a templated stage 2 synthesis. The three rounds of encoding involve acylation reactions. (Freskgård et al., WO 2004/ 039825 A2, p. 143-148).

First encoding round. 2 pmol of loaded identifier oligo 1.1 (i.e, a particular molecule fragment attached to the identifier oligonucleotide) was combined with 200 pmol of each loaded identifier oligo 1.2, 1.3, and 1.4. (602 pmol loaded identifier oligos in total). These were mixed with 0.7 pmol building block oligo 3.1.3. (i.e., a particular molecule fragment attached to an oligonucleotide, capable of hybridizing with the identifier oligonucleotide), and 72.7 pmol each of 10 different other first round building block oligos (eg. 3.1.1 and 3.1.2; 727 pmol loaded building block oligos in total). The oligos were lyophilized and redissolved in 50 ul extension buffer (EX) (20 mM HEPES, 150 mM NaCl, 8 mM MgCl$_2$). The mixture was heated to 80° C. and slowly cooled to 20° C. to allow efficient annealing of identifier and building block oligos. 5 ul of 0.5 M DMT-MM in water was added and the mixture was incubated at 37° C. for 4 hours. Extension of the identifier oligo on the building block oligo identifier was performed by adding 3 ul of a 10 mM mixture of each deoxynucleotide triphosphate (dATP, dGTP, dCTP, dTTP) and 3 uL of 13 units/ul Sequenase (Amersham Biosciences). The mixture was subsequently incubated at 30° C. overnight. Then 3 pi of 2M NaOH was added and the mixture was incubated for 80° C. for 10 minutes followed by neutralization by addition of 3 pi 2M HCl. The mixture was then purified by passing through a gel filtration column (Biospin P-6, BioRad). 0.25 volumes of 25 mM $I_2$ in 1:1 THF:water was added, mixed and incubated at 37° C. for 2 hours. 60 ul binding buffer (BF) (100 mM HEPES, 150 mM NaCl) and water ad 300 ul was added. The mixture was added to streptavidin-sepharose beads (Amersham Biosciences) pre-washed 3 times in BF buffer and incubated at room temperature for 10 minutes, followed by incubation on ice for 10 minutes with gentle stirring. The beads were then washed three times with water. Extended identifier oligos were stripped from the building block oligos bound to the streptaviding-sepharose beads by applying 100 ul NH3 1:1 in water and incubating at room temperature for 5 minutes.

Second encoding round. To the eluate was added 0.36 pmol second round loaded building block oligo 3.2.2 and 36.4 pmol each of 10 different other second round building block oligos (eg. 3.2.1 and 3.2.3; 364 pmol loaded second round building block oligos in total) and the mixture was lyophilized and redissolved in 50 ul EX buffer. The encoding was performed essentially as described under above.

Final extension. The eluted identifier oligo were lyophilized and dissolved in 50 ul EX buffer. Then 200 pmol primer E38 (5'-XTTTTAGATGGCAGAT-3\ X=CXS Biotin) was added. Annealing was performed by heating the mixture to 80° C. and slowly cooling to 20° C. Extension of the identifier oligo was performed by adding 3 ul of a 10 mM mixture of each deoxynucleotide triphosphate (dATP, dGTP, dCTP, dTTP) and 3 ul of 13 units/ul Sequenase. The mixture was subsequently incubated at 30° C. for 2 hours. The mixture was then purified by passing through a gel filtration column (Biospin P-6, BioRad). This eluate was used for selection. An aliquot was removed for analysis of the input in the selection procedure.

General procedure 5: affinity selection on immobilized protein target. Maxisorp ELISA wells (NUNC A/S, Denmark) were coated with each 100 uL 2 ug/mL integrin $\alpha_v\beta_3$ (Bachem) in PBS buffer (2.8 mM $NaH_2PO_4$, 7.2 mM $Na_2HPO_4$, 0.15 M NaCl, pH 7.2) overnight at 4° C. Then the integrin solution was substituted for 200 pi blocking buffer (TBS, 0.05% Tween 20 (Sigma P-9416), 1% bovine serum albumin (Sigma A-7030), 1 mM $MnCl_2$) which was left on for 3 hours at room temperature. Then the wells were washed 10 times with blocking buffer and the encoded library was added to the wells after diluting it 100 times with blocking buffer. Following 2 hours incubation at room temperature the wells were washed 10 times with blocking buffer. After the final wash the wells were cleared of wash buffer and subsequently inverted and exposed to UV light at 300-350 nm for 30 seconds. Then 100 ul blocking buffer without Tween-20 was immediately added to each well, the wells were shaken for 30 seconds, and the solutions containing eluted identifiers were removed for PCR analysis.

Analysis of selection input and output. PCR was performed on the input and output of the selection, using primers corresponding to the 5' end of the identifier oligos and the E38 primer. PCR was performed using Ready-To-Go (RTG) PCR beads (Amersham Biosciences) and 10 pmol each primer in a reaction volume of 25 ul. The PCR reaction consisted of an initial denaturation step of 94° C. for 2 minutes followed by 30-45 cycles of denaturation at 94° C. for 30 seconds, annealing at 58° C. for 1 minute and extension at 72° C. for 1 minute. A final extension step of 2 minutes at 72° C. was included. The PCR products were resolved by agarose gel electrophoresis and the band corresponding to the expected size was cut from the gel and purified using QIAquick Gel Extraction Kit (QIAGEN). To sequence individual PCR fragments the purified PCR products were cloned into the pCR4-TOPO vector (Invitrogen) according to the manufacturer's instructions. The resulting mixture was used for transformation of TOP10 E. coli cells (Invitrogen) using standard procedures. The cells were plated on growth medium containing 100 ug/ml ampicillin and left at 37° C. for 12-16 hours. Individual E. coli clones were picked and transferred to PCR wells containing 50 ul water. These wells were then boiled for 5 minutes and 20 ul mixture from each well was used in a PCR reaction using RTG PCR beads and 5 pmol each of M13 forward and reverse primers according to the manufacturer's instructions. A sample of each PCR product was then treated with Exonuclease I (USB) and Shrimp Alkaline Phosphatase (USB) to remove degrade single stranded DNA and dNTPs and sequenced using the DYEnamic ET cycle sequencing kit (Amersham Biosciences) according to the manufacturer's instructions and the reactions were analyzed on a MegaBace 4000 capillary sequencer (Amersham Biosciences). Sequence outputs were analyzed with ContigExpress software (Informax Inc.). A overview of molecule fragments used for library generation is shown in (Freskgård et al., WO 2004/039825 A2, p. 146-147).

Theoretically, the integrin aVp3 ligand A (Molecule 7 in Feuston B. P. et al., Journal of Medicinal Chemistry 2002, 45, 5640-5648) is present in 1 out of $3 \times 10^8$ bifunctional molecules in this library. The codon combination compatible with encoding of ligand A was not found in 28 sequences derived from the encoded library before selection (input) in agreement with the expected low abundance of this codon combination (1 in $3 \times 10^8$). A codon combination compatible with encoding of ligand A was found in 5 out of 19 sequences derived from the encoded library after selection in integrin $\alpha_v\beta_3$-coated wells. These numbers thus correspond to an apparent enrichment factor of $(3 \times 10^8/(19/7))=8 \times 10^7$.

For more detailed date see (Freskgård et al., WO 2004/039825 A2, p. 143-148).

Example 8

Selection of Bifunctional Molecules Using Size-Exclusion Chromatography

This is an example of subprocess iii), although a real library of bifunctional molecules are not screened. A protocol for selection employing size-exclusion chromatography is presented. The experiment is taken from (Freskgård et al., WO 2004/039825 A2, p. 148-150).

This example illustrates the possibility to use column separation to perform selection on complexes against various targets. In this example, size-exclusion chromatography (SEC) is used, but other types of chromatography can be used where target-bound complexes are separated from the non-bound complexes. The complex is exemplified in this example by a biotin molecule attached to an oligonucleotide sequence with a predetermined sequence (see below). Thus, the nucleotide sequence of the identifier specifies the identity of the synthetic molecule as biotin. The encoding sequence can have any length and be divided into discrete regions for encoding various building blocks as discussed elsewhere herein. Also, the displayed molecule can have a linear or scaffold structure. Biotin-AATTCCGGAACATACTAGT-CAACATGA (SEQ ID NO 33) Biotin is known to bind to streptavidin. The binding of biotin to streptavidin will link the identifier to the target molecule and therefore change the identifiers physical and chemical properties, such as e.g. the apparent molecular weight. This change is possible to detect using e.g. size-exclusion chromatography: 78 pmol of the complex molecule was loaded on a Superdex 200, PC 3.2/30 column (AKTA-FPLC, AmershamPharmaciaBiotech) and analysed in PBS buffer with a flow rate of 0.050 ml/min. As may be seen from the spectrogram, the complex molecules retention-time was approximately 35 minutes. When the target (83 pmol streptavidin) was analysed under identical conditions, the retention-time was approximately the same. The low absorption of the target molecules is due to the wavelength (260 nm) used in the measurement. At this wavelength, the extinction coefficient is high for the nucleotides in the complexes but low for the protein target.

However, when the complex molecules was premixed with the target molecules (78 pmol complex and 83 pmol target incubated for about 1 h in PBS buffer) to allow binding and then analysed under identical conditions, the retention-time change significantly (28 minutes). The change is due to the increase in molecular weight (or hydrodynamic volume) due to the binding of the complex to the target. This will allow the separation of the target-bound complexes from the non-bound complexes. The fraction that contains the complexes and the target molecules are pooled and amplified using appropriate primers. The amplified identifiers can then be used to decode the structures of the enriched displayed molecules. The strategy of performing column-selection of libraries of bifunctional complexes has two major advantages. First, the enriched (target-bound) complexes are eluted before the non-bound complexes, which will drastically reduce the background from the non-bounded complexes. Secondly, the enrichment on the column will be extensive due to all the separation steps in the pores in the matrix. The separation of the target-bound complexes using this approach will be dependent on the molecular weight of the complexes but predominantly of the molecular weight of the target. The molecular weight of the target can be adjusted by linking the target to a support that increases the apparent molecular weight. The increased molecular weight will enhance the separation by reducing the retention-time on the column. This can be done using for example a fusion protein, antibody, beads, or cross-linking the target in multimeric form. Thus, the target protein can be expressed as a fusion protein or a specific antibody can be use to increase the molecular weight. The target can be immobilized on small beads that permit separation and the target can be cross-linked using standard reagents to form multimers or cross-linked to a carrier molecule, for example another protein. Preferably, the molecular weight is increased so the target molecules elute in the void volume of the column.

Examples of other types of column separation that can be used are affinity chromatography, hydrophobic interaction chromatography (HIC), and ion-exchange chro-matography. Examples of column media, other than Superdex, that can be used in size-exclusion chromatography are: Sephacryl, Sepharose or Sephadex.

Example 9

Encoded Multiple Component Reaction (MCR) During a Stage 1 Synthesis

This is an example of a stage 1 synthesis that involves the reaction of multiple different encoded molecule fragments in the same well; this is an example of an UGI reaction. The experiment is described in (Freskgård et al., WO 2004/039825 A2, p. 157-162).

Preparation of aldehyde-comprising scaffold-oligo, using 4-carboxybenzaldehyde. A solution of 4-carboxybenzaldehyde (scaffold) in DMF (25 uL, 150 mM) was mixed with 25 uL of a 150 mM solution of EDC in DMF. The mixture was left for 30 min at 25° C. 50 uL aminooligo (10 nmol) in 100 mM HEPES buffer pH 7.5 was added and the reaction mixture was left for 20 min at 25° C. Excess scaffold was removed by extraction with EtOAc (500 uL) and remaining EtOAc was removed in vacuo by spinning 10 min in a speedvac. The mixture was then purified by gel filtration with spin columns (Biospin P-6, BioRad) equilibrated with water. The loaded oligo were analyzed by ES-MS.

Multi-component reaction. A solution of the Benzaldehyde loaded oligo prepared above (200 pmol) was lyophilized and redissolved in 10 uL $H_2O$. 2-Methoxy ethylamine in methanol (10 uL, 40 mM), 3-furan-2-yl-acrylic acid in methanol (10 uL, 40 mM), and cyclohexyl isocyanide in methanol (10 uL, 40 mM) was added and incubated overnight at 37° C. The reaction mixture was diluted with 40 uL $H_2O$ and purified by gel filtration with spin columns (Biospin P-6, BioRad) equilibrated with water. MCR-product on oligo was analyzed by ES-MS. The starting benzaldehyde loaded oligo was identified in the MS-spectrum together with the UGI product.

Multi-component reaction. A solution of benzaldehyde loaded oligo (320 pmol) was lyophilized and redissolved in 10 uL $H_2O$. 2-Amino ethanol in methanol (10 uL, 40 mM), 3-Methoxy-propionic acid in methanol (10 uL, 40 mM), and ethyl isocyanoacetate in methanol (10 uL, 40 mM) was added and incubated overnight at 37° C. The reaction mixture was diluted with 40 uL $H_2O$ and purified by gel filtration with spin columns (Biospin P-6, BioRad) equilibrated with water. MCR-product on oligo was analyzed by ES-MS. The starting benzaldehyde loaded oligo was identified in the MS-spectrum together with three products, Diketopiperazine, UGI product and the Amine product.

Encoding. Excess reactants, activation agents, solvents and salt was removed by double gel-filtration using Bio-rad microspin columns 6 and eluted in MS-grade $H_2O$ and loading was verified by Electrospray-MS (Bruker Inc) analysis before the displayed molecule attached to the oligonucleotide was encoded. The benzaldehyde loaded oligonucleotide, that has been reacted with the other three components to form the displayed molecule as described above was mixed with the codon oligonucleotides L2, L3 and L4 together with the splint oligonucleotides S1, S2 and S3 (sequences shown below) and ligated using a ligase (T4 DNA ligase). The ligation was performed using the following conditions. The double stranded oligonucleotide was achieved by mixing the encoding strands (L1, L2, L3 and L4) with the splint oligonucleotides (S1, S2 and S3) to form a 7 oligonucleotide hybridisation product (for efficient annealing and ligation). About 50 pmol of each specific oligonucleotide was used and the oligonucleotides was ligated in a volume of 20 uL using ligation buffer (30 mM Tris-HCl (pH 7.9), 10 mM $MgCl_2$, 10 mM DTT, 1 mM ATP) and 10 units T4-DNA ligase at ambient temperature for 1 hour.

```
L1:  5'-CGATGGTACGTCCAGGTCGCA-3'    (SEQ ID NO: 34)

S1:  5'-ATCGTGCTGCGACCT-3'          (SEQ ID NO: 35)

L2:  5'-GCACGATATGTACGATACACTGA-3'  (SEQ ID NO: 36)

S2:  5'-GTGCCATTCAGTGT-3'           (SEQ ID NO: 37)

L3:  5'-ATGGCACTTAATGGTTGTAATGC-3'  (SEQ ID NO: 38)

S3:  5'-TGTATGCGCATTAC-3'           (SEQ ID NO: 39)

L4:  5'-GCATACAAATCGATAATGCAC-3'    (SEQ ID NO: 40)
```

The identifier comprising the tags was amplified using a forward (FP) and reverse (RP) primer using the following conditions: 5 uL of the ligated identifier oligonucleotide was used for PCR in a 25 uL reaction using 10 uL Eppendorph hotmastermix 2.5× and 10 pmol each of AH361 & Frw-27. PCR was run: (ENRICH30): 94° C. 2 min, then 30 cycles of (94° C. 30 sec, 58° C. 1 min, 72° C. 1 min), then 72° C. 10 min.

```
                                        (SEQ ID NO 41)
FP: 5'-CGATGGTACGTCCAGGTCGCA-3'

(SEQ ID NO 42)
RP: 5'-GTGCATTATCGATTTGTATGC-3'.
```

The amplified identifier oligonucleotide was cloned to verify that the assembled oligonucleotides contained the codon region (CGTCC, GTACG, AATGG and TCGAT). The TOPO-TA (Invitrogen Cat#K4575-J10) ligation was reacted with 4 ul PCR product, 1 ul salt solution, 1 ul vector. The reaction was incubated at RT for 30 min. Heat-shock competent TOP10 $E.$ $coli$ cells was thawed and put on ice. 5 ul ligation reaction was added. Following 30 min on ice, the cells were heat-shocked at 42° C. water for 30 sec, and then put on ice. 250 ul SOC was added and the cells incubated 1 h at 37° C., before spreading on LB-ampicillin plates followed by incubation ON at 37° C. Individual $E.$ $coli$ clones were picked and transferred to PCR wells containing 50 uL water. Colonies were incubated at 94° C. for 5 minutes and 20 uL was used in a 25 uL PCR reaction with 5 pmol of each TOPO primer M13 forward & M13 reverse (AH365/AH366) and Ready-To-Go PCR beads (Amersham) using PCR program: 94° C. 2 min, then 30×(94° C. 4 sec, 50° C. 30 sec, 72° C. 1 min) then 72° C. 10 min.

Primers and free nucleotides were degraded by adding 1 pi EXO/SAP mixture 1:1 to 2 uL PCR product. Incubation was at 37° C. for 15 min and then 80° C. for 15 min. 5 pmol T7 primer (AH368) was added and water to 12 uL. Subsequently, 8 uL DYE-namic ET cycle sequencing Terminator Mix was added followed by PCR-cycling using 30 rounds of (95° C. 20 sec, 50° C. 15 sec, 60° C. 1 min). Purification was done using seq96 spinplates (Amersham), followed by analysis on a MegaBace sequenizer.

Example 10

Stage 1 "Click" Reaction

This is an example of stage 1 synthesis, using the "click" reaction. Similar conditions can be applied to stage 2 "click" reactions. The experiment is described in (U.S. patent application 60/588,672, p. 34-35.)

General procedure. An alkyne-containing DNA conjugate is dissolved in pH 8.0 phosphate buffer at a concentration of ca. 1 mM. To this mixture is added 10 equivalents of an organic azide and 5 equivalents each of copper (II) sulfate, ascorbic acid, and the ligand (tris-((1-benzyltriazol-4-yl)methyl)amine) all at room temperature. The reaction is followed by LCMS, and is usually complete after 1~2 h. The resulting triazole-DNA conjugate can. be isolated by ethanol precipitation.

Preparation of Azidoacetyl-Gly-Pro-Phe-Pra-NH$_2$. Using 0.3 mmol of Rink-amide resin, the indicated sequence was synthesized by automated synthesis with Fmoc-protected amino acids and HATU as activating agent (Pra=C-propargylglycine). Azidoacetic acid was used to cap the tetxapeptide. The peptide was cleaved from the resin with 20% TFA/DCM for 4 h. Purification by RP HPLC afforded product as a white solid (75 mg, 51%). $^1$H NMR (DMSO-d$_6$, 400 MHz): 8.4-7.8 (m, 3H), 7.4-7.1 (m, 7H), 4.6-4.4 (m, 1H), 4.4-4.2 (m, 2H), 4.0-3.9 (m, 2H), 3.74 (dd, 1H, J=6 Hz, 17 Hz), 3.5-3.3 (m, 2H), 3.07 (dt, 1H, J=5 Hz, 14 Hz), 2.92 (dd, 1H, J=5 Hz, 16 Hz), 2.86 (t, 1H, J=2 Hz), 2.85-2.75 (m, 1H), 2.6-2.4 (m, 2H), 2.2-1.6 (m, 4H). IR (mull) 2900, 2100, 1450, 1300 cm$^{-1}$. ESIMS 497.4 ((M+H), 100%), 993.4 ((2M+H), 50%). ESIMS with ion-source fragmentation: 519.3 ((M+Na), 100%), 491.3 (100%), 480.1 ((M−NH$_2$), 90%), 452.2 ((M-NH$_2$—CO), 20%), 424.2 (20%), 385.1 ((M-Pra), 50%), 357.1 ((M-Pra-CO), 40%), 238.0 ((M-Pra-Phe), 100%).

Cyclization of Azidoacetyl-Gly-Pro-Phe-Pra-NH$_2$: The azidoacetyl peptide (31 mg, 0.62 mmol) was dissolved in MeCN (30 mL). Diisopropylethylamine (DIEA, 1 mL) and Cu(MeCN)JPF$_6$ (1 mg) were added. After stirring for 1.5 h, the solution was evaporated and the resulting residue was taken up in 20% MeCN/H$_2$O. After centrifugation to remove insoluble salts, the solution was subjected to preparative reverse phase HPLC. The desired cyclic peptide was isolated as a white solid (10 mg, 32%). $^1$H NMR (DMSO-d$_6$, 400 MHz): 8.2S (t, 1H, J=5 Hz), 7.77 (s, 1H), 7.2-6.9 (m, 9H), 4.98 (m, 2H), 4.48 (m, 1H), 4.28 (ra, 1H), 4.1-3.9 (m, 2H), 3.63 (dd, 1H, J=5 Hz, 16 Hz), 3.33 (m, 2H), 3-0 (m, 3H), 2.48 (dd, 1H, J=11 Hz, 14 Hz), 1.75 (m, 1H0, 1.55 (m, 1H), 1.32 (m, 1H), 1.05 (m, 1H). IR (mull) 2900, 1475, 1400 cm$^{-1}$. ESIMS 497.2 ((M+H), 100%), 993.2 ((2M+H), 30%), 1015.2 ((2M+Na), 15%). ESIMS with ion-source fragmentation: 535.2 (70%), 519.3 ((M+Na), 100%)· 497.2 ((M+H), 80%), 480.1 ((M-NH$_2$), 30%), 452.2 ((M-NH$_2$—CO), 40%), 208.1 (60%).

Example 11

A Stage 1 Synthesis Involving Aromatic Nucleophilic Substitution

This is an example of an aromatic nucleophilic substitution reaction employed in a stage 1 synthesis. Similar conditions may be used in stage 2 synthesis. The experiments are described in (U.S. patent application 60/588,672, p. 36)

General Procedure for Arylation of DNA-linker with Cyanuric Chloride: DNA-Linker is dissolved in pH 9.5 borate buffer at a concentration of 1 mM. The solution is cooled to 4° C. and 20 equivalents of cyanuric chloride is then added as a 500 mM solution in MeCN. After 2 h, complete reaction is confirmed by LCMS and the resulting dichlorotriazine-DNA conjugate is isolated by ethanol precipitation.

Procedure for Amine Substitution of Dichlorotriazine-DNA: Dichlorotriazine-DNA is dissolved in pH 9.5 borate buffer at a concentration of 1 mM. At room temperature, 40 equivalents of an aliphatic amine is added as a DMF solution. The reaction is followed by LCMS and is usually complete after 2 h. The resulting monochlorotriazine-DNA conjugate is isolated by ethanol precipitation.

Procedure for Amine Substitution of Monochlorotriazine-DNA: (Alkylamino)-monochlorotriazine-DNA is dissolved in pH 9.5 borate buffer at a concentration of 1 mM. At 42° C., 40 equivalents of a second aliphatic amine is added as a DMF solution. The reaction is followed by LCMS and is usually complete after 2 h. The resulting diaminotriazine-DNA conjugate is isolated by ethanol precipitation.

Example 12

A Stage 1 Synthesis (Subprocess 9) and Characterization of a Library of 10$^5$ Members This is an example of a stage 1 synthesis, involving five synthesis rounds (here termed "cycles"), employing acylation reactions for the coupling of molecule fragments (here termed "building blocks"). Similar conditions can be used in stage 2 synthesis. The experiments are described in (U.S. patent application 60/588,672, p. 26-34). The synthesis of a library comprising on the order of $10^5$ distinct members was accomplished using the following reagents:

Compound 1: An approximately 19 bp duplex DNA, where the two strands at one end has been covalently linked, and where that end includes a PEG linker and a teminal amino group; and where the 5'-end of one strand at the other end carries a 5'-phophate. Building block precursors: 12 compounds, each of which contains a Fmoc-protected amino group and a free carboxylic acid. The compounds include aliphatic as well as aromatic compounds and aliphatic cyclic structures.

Oligonucleotide tags: A total of 60 duplex DNAs, with 7 central base pairs and 2 nt overhangs at both ends, and 5'-phosphates at both ends, are included. The 60 duplex DNAs correspond to 5 cycles where 12 tags are added, one per building block precursor, in each round.

1× ligase buffer: 50 mM Tris, pH 7.5; 10 mM dithiothreitol; 10 mM $MgCl_2$; 2.5 mM ATP; 50 mM NaCl.

10× ligase buffer: 500 mM Tris, pH 7.5; 100 mM dithiothreitol; 100 mM $MgCl_2$; 25 mM ATP; 500 mM NaCl Cycle 1

To each of twelve PCR tubes was added 50 uL of a 1 mM solution of Compound 1 in water; 75 uL of a 0.80 mM solution of one of Tags 1.1-1.12; 15 uL 10× ligase buffer and 10 uL deionized water. The tubes were heated to 95° C. for 1 minute and then cooled to 16° C. over 10 minutes. To each tube was added 5,000 units T4 DNA ligase (2.5 uL of a 2,000,000 unit/mL solution (New England Biolabs, Cat. No. M0202)) in 50 ul 1× ligase buffer and the resulting solutions were incubated at 16° C. for 16 hours.

Following ligation, samples were transferred to 1.5 ml Eppendorf tubes and treated with 20 uL 5 M aqueous NaCl and 500 ul cold (−20° C.) ethanol, and held at −20° C. for 1 hour. Following centrifugation, the supernatant was removed and the pellet was washed with 70% aqueous ethanol at −20° C. Each of the pellets was then dissolved in 150 uL of 150 mM sodium borate buffer, pH 9.4.

Stock solutions comprising one each of building block precursors BB1 to BB12, N,N-diisopropylethanolamine and 0-(7-azabenzotriazol-1-yl)-1,1,3,3-tetramethyluronium hexafluorophosphate, each at a concentration of 0.25 M, were prepared in sodium phosphate buffer, pH 8.0, and incubated at room temperature for 20 minutes. Each solution (6 uL) was diluted with 30 uL $N_5N$,-dimethylformamide and added to the appropriate eppendorf tube. Two additional 6 uL aliquots of building block precursor stock solution were added after 20 minutes and 40 minutes, respectively, for a final ratio of 30:1 building block precursor to tag. The tubes were gently shaken for 2 hours at 4° C. The tags and corresponding building block precursors used in Round 1 are set forth in Table 1, below.

TABLE 1

| Building Block Precursor | Tag |
|---|---|
| BB1 | 1.11 |
| BB2 | 1:6 |
| BB3 | 1.2 |
| BB4 | 1-8 |
| BB5 | 1.1 |
| BB6 | 1.10 |
| BB7 | 1.12 |

TABLE 1-continued

| Building Block Precursor | Tag |
|---|---|
| BB8 | 1.5 |
| BB9 | 1.4 |
| BB10 | 1.3 |
| BB11 | 1.7 |
| BB12 | 1.9 |

Following acylation, the 12 reaction mixtures were pooled and the resulting mixture was lyophilized to yield a dry residue, which was dissolved in 1.7 mL water. Two volumes of cold 100% ethanol were added and the mixture was allowed to stand at −20° C. for at least one hour. The mixture was then centrifuged for 15 minutes at 14,000 rpm in a 4° C. microcentrifuge. Following centrifugation, as much supernatant as possible was removed with a 1 mL micropipet; the mixture was then centrifuged again, and the remainder of the supernatant was removed with a 200 jiL pipet. Cold 70% ethanol (200 uL) was then added to the rube, and the mixture was centrifuged for 5 minutes at 4° C.

The supernatant was then removed with a 200 uL pipet; and the remaining ethanol was allowed to evaporate at room temperature over 5 to 10 minutes. The remaining pellet was suspended in 2 mL water and purified by HPLC with a 50 mM aqueous triethylammonium acetate mobile phase at pH 7.5. The fractions containing the library were collected, pooled and lyophilized. The resulting residue was redissolved in 2.5 mL aqueous $Na_2HPO4$ and 100 uL piperidine was added, resulting in the formation of a precipitate. The precipitate was separated from the supernatant by centrifugation and washed with 200 uL water. The wash and the supernatant were combined and used for Cycle 2.

Cycles 2-5

For each of these cycles, the combined solution resulting from the previous cycle was divided into 12 equal aliquots of 50 ul each and placed in PCR tubes. To each tube was added a solution comprising a different tag, and ligation, purification and acylation were performed as described for Cycle 1, except that for Cycles 3-5, the HPLC purification step described for Cycle 1 was omitted. The correspondence between tags and building block precursors for Cycles 2-5 is presented in Table 2.

The products of Cycle 5 were ligated with the closing primer shown below, using the method described above for ligation of tags.

```
5'-PO3-GGCACATTGATTTGGGAGTCA    (SEQ ID NO: 43)

GTGTAACTAAACCCTCAGT-PO3-5'      (SEQ ID NO: 44)
```

TABLE 2

| Building Block Precursor | Cycle 2 Tag | Cycle 3 Tag | Cycle 4 Tag | Cycle 5 Tag |
|---|---|---|---|---|
| BB1 | 2.7 | 3.7 | 4.7 | 5.7 |
| BB2 | 2.8 | 3.8 | 4.8 | 5.8 |
| BB3 | 2.2 | 3.2 | 4.2 | 5.2 |
| BB4 | 2.10 | 3.10 | 4.10 | 5.10 |
| BB5 | 2.1 | 3.1 | 4.1 | 5.1 |
| BB6 | 2.12 | 3.12 | 4.12 | 5.12 |
| BB7 | 2.5 | 3.5 | 4.5 | 5.5 |
| BB8 | 2.6 | 3.6 | 4.6 | 5.6 |
| BB9 | 2.4 | 3.4 | 4.4 | 5.4 |

TABLE 2-continued

| Building Block Precursor | Cycle 2 Tag | Cycle 3 Tag | Cycle 4 Tag | Cycle 5 Tag |
|---|---|---|---|---|
| BB10 | 2.3 | 3.3 | 4.3 | 5.3 |
| BB11 | 2.9 | 3.9 | 4.9 | 5.9 |
| BB12 | 2.11 | 3.11 | 4.11 | 5.11 |

Results:

The synthetic procedure described above has the capability of producing a library comprising $12^5$ (about 249,000) different structures. The synthesis of the library was monitored via gel electrophoresis of the product of each cycle. The gel electrophoresis shows that each cycle results in the expected molecular weight increase and that the products of each cycle are substantially homogeneous with regard to molecular weight.

Example 13

Direct Transfer Acylation Reaction

This is an example of a stage 2 synthesis direct transfer reaction, involving the reactive group NH2, and an activated ester, N-hydroxysuccinimide ester. Similar reaction conditions can be applied to the stage 1 acylation reaction, except that the concentration of the incoming molecule fragment must be higher (e.g., 100 mM incoming molecule fragment in a stage 1 synthesis). The example is taken from (Freskgård et al., WO 2004/039825 A2, example 3, p. 111-116.

The molecule fragment, in the following called "attachment entitiy (AE)" is in the following experiments either a scaffold molecule fragment, e.g. the peptide, CFFKKK, attached to an oligonucleotide, in the following called "identifier", or a molecule fragment, in the following called "recipient reactive group" exemplified by an amino modified oligonucleotide. These molecule fragments allow transfer of three or one molecule fragments, respectively. The identifier used in this experiment is an oligonucleotide coupled to the peptide CFFKKK as described in Example 4. The molecule fragment, in the following called "functional entity (FE)", is in this experiment 4-Pentynoic acid, which is attached to an oligonucleotide. The identifier oligonucleotide, coupled to the CFFKKK scaffold, is annealed to the oligonucleotide carrying the 4-pentynoic acid, thereby bringing the two molecule fragments into close proximity. The annealing is directed by the complementarity of the two oligonucleotides. The annealing was performed using 600 pmol of the 4-pentynoic acid oligonucleotide and 400 pmol identifier oligonucleotide in 0.1 M MES buffer at 25° C. in a shaker for 2 hours. After annealing and subsequent reaction between the two molecule fragments, the sample was purified by micro-spin gel filtration and analyzed by MS. The observed mass was 7323.45 Da, which correspond well with the calculated mass, 7324.00 Da. Thus, the MS shows a mass corresponding to the transfer of the molecule fragment (4-pentenoic acid) onto the amino group of the identifier oligonucleotide through formation of an amide bond. Another example of transfer of a molecule fragment is shown below using the amine-modified oligonucleotide directly as the AE on the identifier molecule. The functional entity on the building block molecule used in this experiment was 4-pentynoic acid.

The annealing was performed using 500 pmol of either carrier molecule in 0.1 M MES buffer and incubating the mixture at 25° C. in a shaker for 2 hours. The molecule fragment (4-pentenoic acid) was transferred to the amino group on the identifier molecule during the annealing (see below). After annealing and transfer the sample was purified by micro-spin gel filtration and analyzed by MS. The observed mass was 6398.04 Da, which correspond well with the calculated mass, 6400.00 Da. Thus, the MS spectra of the identifier molecule after transfer of the functional entity show a mass corresponding to the transferred molecule fragment, 4-pentenoic acid, onto the identifier molecule, by formation of an amide bond. Another example of direct transfer of a molecule fragment by acylation uses the amine modified oligo directly as the identifier molecule. The functional entity used in this experiment was Hexynoic acid. The annealing was performed using 500 pmol of either carrier molecule in 0.1 M MES buffer incubated at 25° C. in a shaker for 2 hours. The hexynoic acid molecule fragment was transferred to the amino group on the identifier molecule through formation of an amide bond (see below). After annealing and transfer the sample was purified by micro-spin gel filtration and analyzed by MS. The observed mass was 6411.96 Da, which correspond well with the 15 calculated mass, 6414 Da. Thus, the MS spectra show a mass corresponding to the transfer of hexynoic acid onto the amine of the identifier oligo through amide bond formation.

Example 14

Multi-Step Stage 2 Synthesis Using Different Types of Cleavable Linkers

This is an example of a multistep, stage 2 synthesis involving several carriers hybridizing to different positions of the same template, and the use of three different types of cleavable linkers, employed in indirect transfer reactions. Also described is a templated Wittig reaction, a direct transfer reaction. The description of the experiment is taken from (Liu et al., WO 2004/016767 A2, example 3, p. 112-117). The figures referred to are from the same patent application.

Three distinct strategies have been developed to link chemical reagents (reactive units) with their decoding DNA oligonucleotides, and to purify product after any DNA-templated synthetic step. When possible, an ideal reagent-oligonucleotide linker for DNA-templated synthesis positions the oligonucleotide as a leaving group of the reagent. Under this "autocleaving" linker strategy, the oligonucleotide-reagent bond is cleaved as a natural chemical consequence of the reaction (see WO 2004/016767 A2, FIG. 28A).

As the first example of this approach applied to DNA-templated chemistry, a dansylated Wittig phosphorane reagent (WO 2004/016767 A2, compound (1)) was synthesized in which the decoding DNA oligonucleotide was attached to one of the aryl phosphine groups (Hughes (1996) TETRAHEDRON LETT. 37: 7595). DNA-templated Wittig olefination with aldehyde-linked template 2 resulted in the efficient transfer of the fluorescent dansyl group from the reagent to the template to provide olefin 3 (WO 2004/016767 A2, FIG. 28A). As a second example of an autocleaving linker, DNA-linked thioester 4 (WO 2004/016767 A2), when activated with Ag(I) at pH 7.0 (Zhang et al. (1999) J. AM. CHEM. SOC. 121: 3311) acylated amino-terminated template 5 to afford amide product 6 (WO 2004/016767 A2, FIG. 28B).

Ribosomal protein biosynthesis uses aminoacylated tRNAs in a similar autocleaving linker format to mediate RNA-templated peptide bond formation. To purify desired products away from unreacted reagents and from cleaved oligonucleotides following DNA-templated reactions using autocleaving linkers, biotinylated reagent oligonucleotides and washing crude reactions with streptavidin-linked magnetic beads (see WO 2004/016767 A2, FIG. 30A) were utilized. Although this approach does not separate reacted templates from unreacted templates, unreacted templates can be removed in subsequent DNA-templated reaction and purification steps.

Reagents bearing more than one functional group can be linked to their decoding DNA oligonucleotides through second and third linker strategies. In the "scarless linker" approach (WO 2004/016767 A2, FIG. 28C), one functional group of the reagent is reserved for DNA-templated bond formation, while the second functional group is used to attach a linker that can be cleaved without introducing additional unwanted chemical functionality. The DNA-templated reaction then is followed by cleavage of the linker attached through the second functional group to afford desired products (WO 2004/016767 A2, FIG. 28C). For example, a series of aminoacylation reagents such as (D)-Phe derivative 7 (WO 2004/016767 A2) were synthesized in which the alpha-amine is connected through a carbamoylethylsulfone linker (Zarling et al (1980) J. IMMUNOLOGY 124: 913) to its decoding DNA oligonucleotide. The product (WO 2004/016767 A2, compound (8)) of DNA-templated amide bond formation using this reagent and an amine-terminated template (WO 2004/016767 A2, (5)) was treated with aqueous base to effect the quantitative elimination and spontaneous decarboxylation of the linker, affording product 9 containing the cleanly transferred amino acid group (WO 2004/016767 A2, FIG. 28C). This sulfone linker is stable in pH 7.5 or lower buffer at 25° C. for more than 24 hours yet undergoes quantitative cleavage when exposed to pH 11.8 buffer for 2 hours at 37 C.

In some cases it may be advantageous to introduce one or more new chemical groups as a consequence of linker cleavage. Under a third linker strategy, linker cleavage generates a "useful scar" that can be functionalized in subsequent steps (WO 2004/016767 A2, FIG. 28C). As an example of this class of linker, amino acid reagents such as the (L)-Phe derivative 10 were generated linked through 1,2-diols (Fruchart et al. (1999) TETRAHEDRON LETT. 40: 6225) to their decoding DNA oligonucleotides. Following DNA-templated amide bond formation with amine terminated template (WO 2004/016767 A2, compound (5)), this linker was quantitatively cleaved by oxidation with 50 mM aqueous sodium periodate (NaI04) at pH 5.0 to afford product 12 containing an aldehyde group appropriate for subsequent functionalization (for example, in a DNA-templated Wittig olefination, reductive amination, or nitrolaldol addition).

FIG. 29 of (WO 2004/016767 A2) shows the results of exemplary DNA-templated synthesis experiments using autocleaving linkers, scarless linkers, and useful scar linkers. The depicted reactions were analyzed by denaturing PAGE. Lanes 1-3 were visualized using UV light without DNA staining; lanes 4-10 were visualized by staining with ethidium bromide following by UV-transillumination. Conditions for 1 to 3 were: one equivalent each of reagent and template, 0.1 M TAPS buffer pH 8.5, 1 M NaCl, at 25° C. for 1.5 hours. Conditions for 4 to 6 were: three equivalents of 4,0; $1^{11}$ M. MES buffer pH 7.0, 1 M sodium nitrite (NaNO$_2$) 10 mM silver nitrate (AgNC<3), at 37° C. for 8 hours. Conditions for 8 to 9 were 0.1 M 3-(cyclohexylamino)-1-5-propanesulfonic acid (CAPS) buffer pH 11.8, 60 mM (3-mercaptoethanol (BME), at 37° C. for 2 hours. Finally, conditions for 11 to 12 were: 50 mM aqueous NaI04, at 25° C. for 2 hours. Ri=NH (CH$_2$)$_2$NH-dansyl; R$_2$=biotin.

Desired products generated from DNA-templated reactions using the scarless, or useful scar linkers can be readily purified using biotinylated reagent oligonucleotides (WO 2004/016767 A2, FIG. 30B). Reagent oligonucleotides together with desired products are first captured on streptavidin-linked magnetic beads. Any unreacted template bound to reagent by base pairing is removed by washing the beads with buffer containing 4 M guanidinium chloride. Biotinylated molecules remain bound to the streptavidin beads under these conditions. Desired product then is isolated in pure form by eluting the beads with linker cleavage buffer (in the examples above, either pH 11 or sodium periodate (NaI04)-containing buffer), while reacted and unreacted reagents remain bound to the beads.

As one example of a specific library generated as described above, three iterated cycles of DNA-templated amide formation, traceless linker cleavage, and purification with streptavidin-linked beads were used to generate a non-natural tripeptide (WO 2004/016767 A2, FIGS. 31A-B). Each 20 amino acid reagent was linked to a unique biotinylated 10-base DNA oligonucleotide through the sulfone linker described above. The 30-base amine-terminated template programmed to direct the tripeptide synthesis contained three consecutive 10-base regions that were complementary to the three reagents, mimicking the strategy that would be used in a multi-step DNA-templated small molecule library synthesis.

In the first step, two equivalents of 13 (see WO 2004/016767 A2) were activated by treatment with 20 mM EDC, 15 mM sulfo-NHS, 0.1 M MES buffer pH 5.5, and 1 M NaCl, for 10 minutes at 25° C. The template then was added in 0.1 M MOPS pH 7.5, and 1M NaCl, at 25° C. and was allowed to react for 1 hour. The free amine group in 14 (see WO 2004/016767 A2) then was elaborated in a second and third round of DNA-templated amide formation and linker cleavage to afford dipeptide and tripeptide 16 (see WO 2004/016767 A2) using the following conditions: two equivalents of reagent, 50 mM DMT-MM, 0.1 M MOPS buffer pH 7.0, 1 M NaCl, at 25° C. for 6 hours. Desired product after each step was purified by capture on avidin-linked beads and elution with 0.1 M CAPS buffer pH 11.8, 60 mM BME, at 37° C. for 2 hours. The progress of each reaction and purification was followed by denaturing polyacrylamide gel electrophoresis (WO 2004/016767 A2, FIG. 31B, bottom). Lanes 3, 6, and 9 represent control reactions using reagents containing scrambled oligonucleotide sequences.

The progress of each reaction, purification, and sulfone linker cleavage step was followed by denaturing polyacrylamide gel electrophoresis. The final tripeptide linked to template 16 (see WO 2004/016767 A2) was digested with the restriction endonuclease EcoRI and the digestion fragment containing the tripeptide was characterized by MALDI mass spectrometry. Beginning with 2 nmol (~20 ug) of starting material, sufficient tripeptide product was generated to serve as the template for more than $10^6$ in vitro selections and PGR reactions (Kramer et al. (1999) CURRENT PROTOCOLS IN MOL. BIOL. 3: 15.1) (assuming 1/10,000 molecules survive selection). No significant product was generated when the starting material template was capped with acetic anhydride, or when control reagents containing sequence mismatches were used instead of the complementary reagents (WO 2004/016767 A2, FIG. 31B).

A non-peptidic multi-step DNA-templated small molecule synthesis that uses all three linker strategies developed above was also performed (WO 2004/016767 A2, FIGS. 32A-32B). An amine-terminated 30-base template was subjected to DNA-templated amide bond formation using an aminoacyl donor reagent (WO 2004/016767 A2, compound (17)) containing the diol linker and a biotinylated 10-base oligonucleotide to afford amide 18 (WO 2004/016767 A2) (two equivalents 17 in 20 mM EDC, 15 mM sulfo-NHS, 0.1 M MES buffer pH 5.5, 1 M NaCl, 10 minutes, 25° C., then add to template in 0.1 M MOPS pH 7.5, 1M NaCl at 16° C. for 8 hours). The desired product then was isolated by capturing the crude reaction on streptavidin beads followed by cleaving the linker with NaI04 to generate aldehyde 19 (WO 2004/016767 A2). The DNA-templated Wittig reaction of 19 with the biotinylated autocleaving phosphorane reagent 20 (WO 2004/016767 A2) afforded fumaramide 21 (WO 2004/016767 A2) (three equivalents 20, 0.1 M TAPS pH 9.0, 3 M NaCl at 25° C. for 48 hours). The products from the second DNA-templated reaction were partially purified by washing with streptavidin beads to remove reacted and unreacted reagent. In the third DNA-templated step, fumaramide 21 was subjected to a DNA-templated conjugate addition (Gartner et al. (2001) J. AM. CHEM. SOC. 123: 6961) using thiol reagent 22 (WO 2004/016767 A2) linked through the sulfone linker to a biotinylated oligonucleotide (three equivalents 22, 0.1 M TAPS pH 8.5, 1 M NaCl at 25° C. for 21 hours). The desired conjugate addition product (WO 2004/016767 A2, compound (23)) was purified by immobilization with streptavidin beads. Linker cleavage with pH 11 buffer afforded final product 24 (WO 2004/016767 A2) in 5-10% overall isolated yield for the three bond forming reactions, two linker cleavage steps, and three purifications (WO 2004/016767 A2, FIGS. 32A-32B). The final product was digested with EcoRI and the mass of the small molecule-linked template fragment was confirmed by MALDI mass spectrometry (exact mass: 2568, observed mass: 2566±5). As in the tripeptide example, each of the three reagents used during this multi-step synthesis, annealed at a unique location on the DNA template, and control reactions with sequence mismatches yielded no product (WO 2004/016767 A2, FIG. 32B, bottom). In FIG. 32B, bottom lanes 3, 6, and 9 represent control reactions. As expected, control reactions in which the Wittig reagent was omitted (step 2) also did not generate product following the third step. Taken together, the DNA-templated syntheses of compounds 16 and 24 (see WO 2004/016767 A2) demonstrate the ability of DNA to direct the sequence-programmed multi-step synthesis of both oligomeric and non-oligomeric small molecules: unrelated in structure to nucleic acids.

Example 15

Stage 2 Reactions in Organic Solvents

This is an example of a stage 2 synthesis performed in organic solvents. Similar or identical conditions can be applied to stage 1 synthesis, except that the concentrations of molecule fragments must be appropriately high to obtain efficient reaction, e.g. higher concentrations of molecule fragments than 10 mM. The description of the experiment is taken from (Liu et al., WO 2004/016767 A2, example 4, p. 117-118). The figures referred to are from the same patent application.

A variety of DNA-templated reactions can occur in aqueous media. It has also been discovered that DNA-templated reactions can occur in organic solvents, thus greatly expanding the scope of DNA-templated synthesis. Specifically, DNA templates and reagents have been complexed with long chain tetraalkylammonium cations (see, Jost et al. (1989) NUCLEIC ACIDS RES. 17:2143; Melnikov et al. (1999) LANGMUIR 15: 1923-1928) to permit quantitative dissolution of reaction components in anhydrous organic solvents including $CH_2Cl_2$, CHCl3, DMF and methanol. Surprisingly, it was found that DNA-templated synthesis can indeed occur in anhydrous organic solvents with high sequence selectivity.

FIG. 33, WO 2004/016767 A2 shows DNA-templated amide bond formation reactions where the reagents and templates are complexed with dimethyldidodecylammonium cations either in separate vessels or after preannealing in water, lyophilized to dryness, dissolved in $CH_2Cl_2$, and mixed together. Matched, but not mismatched, reactions provided products both when reactants were preannealed in aqueous solution and when they were mixed for the first time in $CH_2Cl_2$ (WO 2004/016767 A2, FIG. 33). DNA-templated amide formation and Pd-mediated Heck coupling in anhydrous DMF also proceeded sequence-specifically.

These observations of sequence-specific DNA-templated synthesis in organic solvents imply the presence of at least some secondary structure within tetraalkylammonium-complexed DNA in organic media, and should permit DNA receptors and catalysts to be evolved towards stereoselective binding or catalytic properties in organic solvents. Specifically, DNA-templated reactions that are known to occur in aqueous media, including conjugate additions, cycloadditions, displacement reactions, and Pd-mediated couplings can also be performed in organic solvents.

It is contemplated that reactions in organic solvents may be utilized that are inefficient or impossible to perform in water. For example, while Ru-catalyzed olefin metathesis in water has been reported (Lynn et al. (1998) J. AM. £HEM. SOC. 120: 1627-1628; Lynn et al. (2000) J. AM. CHEM. SOC. 122: 6601-6609; Mohr et al. (1996) ORGANOMETALLICS 15: 4317-4325), the aqueous metathesis system is extremely sensitive to the identities of the functional groups. The functional group tolerance of Ru-catalyzed olefin metathesis in organic solvents, however, is significantly more robust. Some exemplary reactions to utilize in organic solvents include, but are not limited to, 1,3-dipolar cycloaddition between nitrones and olefins which can proceed through transition states that are less polar than ground state starting materials.

Example 16

Stage 2 Omega Synthesis (Subprocess F), Involving Amine Acylation, Wittig Olefination, 1,3-Dipolar Cycloaddition and Reductive Amination This is an example of a stage 2 synthesis employing the Omega DNA architecture during the templated synthesis. Also described are the conditions allowing amine acylation, Wittig olefination, 1,3-Dipolar Cycloaddition and Reductive amination reactions to proceed efficiently. The same conditions can be applied during a stage 1 synthesis involving the same reactions, except that the molecule fragments must be added at a higher concentration (e.g. 10-100 mM molecule fragment). The description of the experiments is taken from (Liu et al., WO 2004/016767 A2, example 5, p. 118-126). The figures referred to are from the same patent application.

This example discloses two different template architectures that further expand the scope of nucleic acid-templated synthesis. During a nucleic acid-templated chemical reaction a portion of a template anneals to a complementary sequence of an oligonucleotide-linked reagent, holding functional groups on the template and transfer unit in reactive proximity. Template architecture can have a profound effect on the nature of the resulting reaction, raising the possibility of manipulating reaction conditions by rationally designing template-reagent complexes with different secondary structures. It was hypothesized that the distance dependence of certain DNA-templated reactions such as 1,3-dipolar cycloadditions and reductive animation could be overcome by designing a new architecture that permits a reagent to anneal to two distinct and spatially separated regions of the template. In the "Omega" architecture (see WO 2004/016767

A2, FIG. 7), the template oligonucleotide contains a small number of constant bases at, for example, the reactive 5'-end of the template in addition to distal coding regions. The oligonucleotide of the transfer unit for the Omega architecture contains at its reactive 3'-end the bases that complement the constant region of the template followed by bases that complement a coding region anywhere on the template. The constant regions were designed to be of insufficient length to anneal in the absence of a complementary coding region. When the coding region of the template and transfer unit are complementary and anneal, the elevated effective molarity of the constant regions induces their annealing. Constant region annealing forms a bulge in the otherwise double-stranded template-reagent complex and places groups at the ends of the template and reagent in reactive proximity. This design permits distance-dependent DNA-templated reactions to be encoded by bases distal from the reactive end of the template.

The efficiency of DNA-templated synthesis using the Omega architecture was compared with that of the standard E and H architectures. The Omega architectures studied comprise (i) three to five constant bases at the 5' end of the template followed by (ii) a five- to 17-base loop and (iii) a ten-base coding region. As a basis for comparison, four different classes of DNA-templated reactions were performed that collectively span the range of distance dependence observed to date.

Amine acylation reactions are representative of distance independent reactions that proceed efficiently even when considerable distances (e.g., 30 bases) separate the amine and carboxylate groups. As expected, amine acylation (20 mM DMT-MM, pH 7.0, at 30° C. for 12 hours) proceeded efficiently (46-96% yield) in all architectures with both small and large distances between reactive groups on the reagent and template (WO 2004/016767 A2, FIG. 34, lanes 1-5; and FIG. 35A). The Omega architecture mediated efficient amine acylation with three, four, or five constant bases at the reactive ends of the template and reagent and 10 or 20 bases between annealed reactants (n=10 or 20). Importantly, control reactions in which the distal coding region contained three sequence mismatches failed to generate significant product despite the presence of the complementary three- to five-base constant regions at the ends of the template and reagent 5 (see WO 2004/016767 A2, FIG. 34, lane 5 for a representative example). The Omega architecture, therefore, did not impede the efficiency or sequence-specificity of the distance-independent amine acylation reaction.

DNA-templated Wittig olefination reactions proceed at a significantly lower rate when the aldehyde and phosphorane are separated by larger numbers of template bases, eventhough product yields typically are excellent after 12 hours or more of reaction regardless of intervening distance. After only 2 hours of reaction (pH 7.5, 30° C.) in the E or H architectures, however, yields of olefin products were three- to six-fold lower when reactants were separated by ten or more bases (n=10 or 20) than when reactants are separated by only one base (n=1) (WO 2004/016767 A2, FIG. 34, lanes 6-7, and FIG. 35B). In contrast, the Omega architecture with four or five constant bases at the reactive end resulted in efficient and sequence-specific Wittig product formation after 2 hours of reaction even when 10 or 20 bases separated the coding region and reactive end of the template (WO 2004/016767 A2, FIG. 34, lanes 8-9, and FIG. 35B). These results suggest that the constant regions at the reactive ends of the template and transfer unit in the Omega architecture permit the aldehyde and phosphorane moieties to react at an effective concentration comparable to that achieved with the E-architecture when n=1 (WO 2004/016767 A2, FIG. 34).

Among the many DNA-templated reactions studied to date, the 1,3-dipolar cycloaddition and reductive animation reactions demonstrate the most pronounced distance dependence. Both reactions proceed in low to modest efficiency (7%-44% yield) under standard reaction conditions using the E or H architectures when 10 or 20 bases separate the annealed reactive groups (WO 2004/016767 A2, FIG. 34, lanes 10-11 and 14-15, and FIGS. 35C-35D). This distance dependence limits the positions on a DNA template that can encode these or other similarly distant dependent reactions. In contrast, both 1,3-dipolar cycloaddition and reductive animation proceed efficiently (up to 97% yield) and sequence-specifically when encoded by template bases 15-25 bases away from the functionalized end of the template using the Omega architecture with four or five constant bases (WO 2004/016767 A2, FIG. 34, lanes 12-13 and 16-17, and FIGS. 35C-35D). These results demonstrate that the templates Omega architecture permits distance-dependent reactions to be efficiently directed by DNA bases far from the reactive end of the template. By overcoming the distance dependence of these reactions while preserving the efficiency of distant independent reactions, the Omega architecture may permit virtually any contiguous subset of bases in a single-stranded 30-base template to encode any viable DNA-templated reaction. Interestingly, the Omega templates with only three constant bases at their reactive ends do not consistently improve the efficiency of these reactions compared with the E-architecture (WO 2004/016767 A2, FIGS. 35C-35D), suggesting that four or five constant bases may be required in the Omega architecture to fully realize favorable proximity effects.

In order to probe the structural features underlying the observed properties of the Omega architecture, the thermal denaturation of the Omega-5 and E architectures using n=10 and n=20 reagents were characterized. For all template-reagent combinations, only a single cooperative melting transition was observed. Compared to the E architecture reagent lacking the five-base constant region, the Omega-5 reagent increased the hypochromicity upon annealing by ~50% but did not significantly affect melting temperature in either phosphate-buffered saline (PBS) or in 50 mM sodium phosphate pH 7.2 with 1 M NaCl (WO 2004/016767 A2, FIG. 36). These results are consistent with a model in which template-reagent annealing in the Omega architecture is dominated by coding region interactions even though the constant region forms secondary structure once the coding region is annealed. The entropic cost of partially ordering the loop between the coding and constant regions may, therefore, be offset by the favorable interactions that arise upon annealing of the constant region.

DNA templates of arbitrary length are easy to synthesize and undesired cross-reactivity between reactants in the same solution can be avoided using concentrations that are too low to allow non-complementary reactants to react intermolecularly. These features of DNA-templated synthesis permit more than one DNA-templated reaction to take place on a single template in one solution, saving the effort associated with additional DNA-templated steps and product purifications. Multiple DNA-templated reactions per step can be difficult using the E, H, or Omega architectures, because the reagent oligonucleotide that remains annealed to the template following the first reaction forms a relatively rigid double helix that can prevent a second reagent annealed further away along the template from encountering the reactive end of the template. To overcome this, the reactive group on the template was moved from the end of the oligonucleotide to the middle, attaching the reactive group to the non-Watson-Crick face of a base. This "T" architecture (see WO 2004/016767

A2, FIG. 7G) was designed to permit two DNA-templated reactions, one with a reagent coupled to the 5' end of the oligonucleotide of a first transfer unit and one with a reagent coupled to the 3'-end of the oligonucleotide of a second transfer unit, to take place sequence-specifically in the same solution on a single template.

To test the viability of the T-architecture in DNA-templated reactions, the efficiency of the amine acylation, Wittig olefination, 1,3-dipolar cycloaddition, and reductive amination reactions using the T architecture was studied. The T architecture sequence-specifically directed these four reactions with efficiencies comparable to or greater than those of the E or H architectures (WO 2004/016767 A2, FIG. 37, 69-100% yield when n=1).

It can thus be concluded that it is possible to perform each of those reactions in an efficient way, providing high yields, at least for one DNA architecture.

The observed degree of distance dependence using the T architecture for each of the four reactions was consistent with the above findings (WO 2004/016767 A2, compare FIG. 37 and FIG. 35). Together these results demonstrate that the T architecture can mediate sequence-specific and efficient DNA-templated synthesis.

Once the ability of the T architecture to support efficient DNA-templated synthesis was established, the ability of the T architecture to direct two DNA-templated reactions on one template in one solution was studied. Two different two-reaction schemes using the T architecture were performed. In the first scheme, depicted in (WO 2004/016767 A2, FIG. 38A), a benzaldehyde-linked T template (WO 2004/016767 A2, (1)) was combined with a phosphine-linked reagent (WO 2004/016767 A2, (2)) and an alpha-iodoamide-linked reagent (WO 2004/016767 A2, (3)) in a single solution (pH 8.5, 1 M NaCl, at 25° C. for 1 hour). The phosphine-linked oligonucleotide complemented ten bases of the template 5' of the aldehyde (n=−4), while the iodide-linked oligonucleotide complemented ten bases 3' of the aldehyde (n=0). DNA-templated SN2 reaction between the phosphine and alpha-iodoamide generated the corresponding phosphorane, which then participated in a DNA-templated Wittig reaction to generate cinnanamide 4 (WO 2004/016767 A2) in 52% overall yield after 1 hour (FIG. 38B, lanes 9-10). Control reactions containing sequence mismatches in either reagent generated no detectable product. The additional control reaction lacking the aldehyde group on the template generated only the SN2 reaction product (FIG. 38B, lanes 3-4) while control reactions lacking either the phosphine group or the alpha-iodoamide group did not generate any detectable products (FIG. 38B, lanes 5-8). In a second two-reaction scheme mediated by the T architecture, depicted in (WO 2004/016767 A2, FIG. 38C), an amine-linked T template (WO 2004/016767 A2, (5)) was combined with a propargylglycine-linked 5'.

reagent (WO 2004/016767 A2, (6)) at n=−1 and a phenyl azide-linked 3' reagent (WO 2004/016767 A2, (7)) at n=1. The addition of 20 mM DMT-MM at pH 7.0 to induce amide formation followed by the addition of 500 uM copper(n) sulfate and sodium ascorbate to induce the recently reported Sharpless-modified Huisgen 1,3-dipolar cycloaddition provided 1,4-disubstituted triazoyl alanine adduct 8 (WO 2004/016767 A2) in 32% overall yield. Taken together, these observations show that the T architecture permits two sequence-specific DNA-templated reactions to take place on one template in one solution. Importantly, the T architecture templates described above were accepted as efficient templates for both a single cycle of primer extension as well as standard PCR amplification using Taq DNA polymerase, consistent with the known tolerance of several DNA polymerases for modifications to the non-Watson-Crick face of DNA templates. In addition to reducing the number of separate DNA-templated steps needed to synthesize a target structure, this architecture may also permit three-component reactions commonly used to build structural complexity in synthetic libraries to be performed in a DNA-templated format.

In summary, the Omega and T architectures significantly expand the scope of DNA-templated synthesis. By enabling distance-dependent DNA-templated reactions to be encoded by bases far away from the reactive end of the template, the Omega architecture expands the types of reactions that can be encoded anywhere on a DNA template. The T architecture permits two DNA-templated reactions to take place on a single template in one step.

Materials and Methods

Oligonucleotide synthesis. Unless otherwise specified, DNA oligonucleotides were synthesized and functionalized as previously described using 2-(2-(4-monomethoxytrityl)aminoethoxy)ethyl-(2-cyanoethyl)-N,N-diisopropyl-phosphoramidite (Glen Research, Sterling, Va., USA) for S-functionalized oligonucleotides, and using (2-dimethoxytrityloxymethyl-6-fluorenylmethoxycarbonylamino-hexane-1-succinoyl)-long chain alkylamino-CPG (Glen Research, Sterling, Va., USA) for 3'-functionalized oligonucleotides (Calderone et al. (2002) ANGEW. CHEM. INT. ED. ENGL. 41:4104; (2002) ANGEW. CHEM. 114: 4278). In the case of templates for the T architecture, amine groups were added using 5'-dimethoxytrityl-5-(N-(trifluoroacetylamino-hexyl)-3-acrylimido)-2'-deoxyuridine-3$^1$-((2-cyanoethyl)-(N,N-diisopropyl))-phosphoramidite (Glen Research, Sterling, Va., USA) and then acylated as reported previously (Calderone et al. (2002) supra).

Amine Acylation. Amine-labeled and carboxylic acid-labeled DNA were combined in aqueous 100 mM MOPS buffer, 1 M NaCl, pH 7.0 (60 nM in template DNA, 120 nM in reagent DNA) in the presence of 20 mM DMT-MM. Reactions proceeded for 12 hours at 25° C.

Wittig Olefin ation. Aldehyde-labeled and phosphorane-labeled DNA were combined in aqueous 100 mM MOPS, 1 M NaCl, pH 7.5 (60 nM in template DNA, 120 nM in reagent DNA). Reactions proceeded for 2 hours at 30° C.

1,3-Dipolar Cycloaddition. Dialdehyde-labeled DNA was incubated in 260 mM N-methylhydroxylamine hydrochloride for 1 hour at room temperature (Gartner et al. (2002) J. AM. CHEM. SOC. 124: 10304). It was subsequently combined with succinimide-labeled DNA in aqueous 50 mM MOPS, 2.8 M NaCl, pH 7.5. (final concentrations of N-methylhydroxylamine hydrochloride 0.75 mM, 60 nM in template DNA and 9.0 nM in reagent DNA). Reactions proceeded for 12 hours at 37° C.

Reductive Animation. Amine-labeled and aldehyde-labeled DNA were combined in aqueous 100 mM MES buffer, 1 M NaCl, pH 6.0 (60 nM in template DNA, 120 nM in reagent DNA). Sodium cyanoborohydride was added as a 5 M stock in 1 M NaOH to a final concentration of 38 mM, and reactions proceeded for 2 hours at 25° C. Reactions were quenched by ethanol precipitation in the presence of 15 mM methylamine.

T Architecture-mediated Conversion of Compound 1 to 4. The 5'-phosphine-linked oligonucleotide (WO 2004/016767 A2, (2)) was generated by coupling N-succinimidyliodoacetate (SIA) to the amine derived from 12-(4-monomethoxytritylamino) dodecyl-(2-cyanoethyl)-(N,N-diisopropyl)-phosphoramidite (Glen Research, Sterling, Va., USA) using the T (n=−4) oligonucleotide listed below, followed by treatment with 4-diphenylphosphinobenzoic acid as described previously (Gartner et al. (2002) supra). The 3'-omega-iodoamide-linked reagent (WO 2004/016767 A2, (3)) was prepared by reacting the T (n=1) oligonucleotide (see below) with SIA as described previously (Gartner et al. (2001) supra). Aldehyde-labeled template (WO 2004/016767 A2, (1)) was prepared by reacting the "T template" oligonucleotide (see below) with para-formyl benzoic acid N-hydroxysuccinimidyl ester as described previously (Gartner et al. (2002) ANGEW. CHEM. INT. ED. 41: 1796; (2002) ANGEW. CHEM. 114:1874). Template 1 was combined with reagents 2 and 3 (WO 2004/016767 A2) in aqueous 200 mM N-(2-hydroxyethyl)piperazine-N'-(2-ethanesulfonic acid) (HEPES) buffer at pH 8.5 with 1 M NaCl, (63 nM template and 125 nM of each reagent). Reactions proceeded for up to 1 hour at 25° C.

The results of denaturing polyacrylamide gel electrophoresis analysis of these reactions is shown in (WO 2004/016767 A2, FIG. 38B). The 30-base T architecture template (WO 2004/016767 A2, (1)) containing an aldehyde group was present in lanes 1-2 and lanes 5-10. A template lacking the aldehyde group but otherwise identical to (1) was present in lanes 3 and 4. DNA-linked phosphine reagent (WO 2004/016767 A2, (2)) was present in lanes 3-6 and lanes 9-10. DNA-linked alpha-iodoamide reagent (WO 2004/016767 A2, (3)) was present in lanes 3-4 and lanes 7-10. Lanes 1, 3, 5, 7 and 9 show reactions after 30 minutes. Lanes 2, 4, 6, 8, and 10 show reactions after 1 hour.

T Architecture-mediated Conversion of Compound 5 to 8. The 5'-propargylglycine linked oligonucleotide (WO 2004/016767 A2, (6)) was generated by combining the corresponding T (n=−1) 5'-amine-linked reagent oligonucleotide (see below) with 2 mg/mL bis(sulfosuccinimidyl)suberate in 9:1 200 mM sodium phosphate pH 7.2:DMF for 10 minutes at 25° C., followed by treatment with 0.3 vol of 300 mM racemic propargylglycine in 300 mM NaOH for 2 hours at 25° C. The 3'-azido linked oligonucleotide (WO 2004/016767 A2, (7)) was generated by combining the T (n=1) amine-linked reagent oligonucleotide (see below) with 2 mg/mL (N-15 hydroxysuccinimidyl)-4-azidobenzoate in 9:1 200 mM sodium phosphate pH 7.2: DMF for, 2 hours at 25° C. Reagents 6 and 7 (WO 2004/016767 A2) were purified by gel filtration and reverse-phase HPLC. Template 5 and reagents 6 and 7 were combined in aqueous 100 mM MOPS pH 7.0 in the presence of 1 M NaCl and 20 mM DMT-MM for 12 hours (60 nM template, 120 nM reagents) at 25° C. Copper (II) sulfate pentahydrate and sodium ascorbate were then added to 500 uM each. After 1 hour at 25° C., reactions were quenched by ethanol precipitation.

DNA Oligonucleotide Sequences Used. E or Omega template: 5'-H$_2$N-GGT ACGAAT TCG ACT CGG GAA TAC CAC CTT (SEQ ID NO 45). H template: 5'-H$_2$N-CGC GAG CGT ACG CTC GCG GGT ACG AAT TCG ACT CGG GM TAC CAC CTT (SEQ ID NO 46). T template: 5'-GGT ACG AAT TCG AC(dT-NH$_2$) CGG GAA TAC CAC CTT (SEQ ID NO 47). E or H reagent (n=1): 5'-AAT TCG TAC C—NH$_2$ (SEQ ID NO 48). E or H reagent (n=10): 5'-TCC CGA GTC G-NH$_2$ (SEQ ID NO 49). E or H reagent (n=20): 5'-AAG GTG GTA T-NH$_2$ (SEQ ID NO 50). Mismatched E or H reagent: 5'-TCC CTG ATC G—NH$_2$ (SEQ ID NO 51). Omega-3 reagent (ra=10): 5'-TCC CGA GTC GAC C—NH$_2$ (SEQ ID NO 52). Omega-4 reagent (ra=10): 5'-TCC CGA GTC GTA CC-NH$_2$ (SEQ ID NO 53). Omega-5 reagent (n=10): 5'-TCC CGA GTC GGT ACC-NH$_2$(SEQ ID NO 54). Omega-3 reagent (n=20): 5'-AAG GTG GTA TAC C—NH$_2$ (SEQ ID NO 55). Omega-4 reagent (n=20): 5'-AAG GTG GTA TTA CC-NH$_2$ (SEQ ID NO 56). Omega-5 reagent (n=20): 5'-AAG GTG GTA TGT ACC-NH$_2$ (SEQ ID NO 57). Mismatched Omega-3 reagent: 5'-TCC CTG ATC GAC C—NH$_2$ (SEQ ID NO 58). Mismatched Omega-4 reagent: 5'-TCC CTG ATC GTA CC—NH$_2$ (SEQ ID NO 59). Mismatched Omega-5 reagent: 5'-TCC CTG ATC GGT ACC: NH$_2$ (SEQ ID NO 60). T reagent (n=1): 5'-GGT '5 ATT CCC G-NH$_2$ (SEQ ID NO 61). T reagent (n=2): 5'-TGG TAT TCC C—NH$_2$ (SEQ ID NO 62). T reagent (n=3): 5'-GTG GTA'TTC C—NH$_2$ (SEQ ID NO 63). T reagent, \n=4): 5'-GGT GGT ATT C—NH$_2$ (SEQ ID NO 64). T reagent (n=5): 5'-AGG TGG TAT T-NH$_2$ (SEQ ID NO 65). T reagent (n=−1): 5'—NH$_2$-GTC GAA TTC G (SEQ ID NO 66), T reagent (n=−4) for 2: 5'-(C$_{12}$-amine linker)-AAT TCG TAG C (SEQ ID NO 67).

Reaction yields were quantitated by denaturing polyacrylamide gel electrophoresis followed by ethidium bromide staining, UV visualization, and CCD-based densitometry of product and template starting material bands. Yield calculations assumed that templates and products were denatured and, therefore, stained with comparable intensity per base; for those cases in which products are partially double-stranded during quantitatidn, changes in staining intensity may result in higher apparent yields. Representative reaction products were characterized by MALDI mass spectrometry in addition to denaturing polyacrylamide gel electrophoresis.

Melting curves were obtained on a Hewlett-Packard 8453 UV-visible spectrophotometer using a Hewlett-Packard 89090A Peltier thermocontroller. Absorbances of template-reagent pairs (1.5 uM each) at 260 nm were measured every 1° C. from 20° C. to 80° C. holding for 1 minute at each temperature in either phosphate-buffered saline ("PBS," 137 mM NaCl, 2.7 mM potassium chloride, 1.4 mM potassium phosphate, 10 mM sodium phosphate, pH 7.4) or in high salt phosphate buffer ("HSB," 50 mM sodium phosphate pH 7.2, 1 M NaCl).

Example 18

Functionalisation of Oligonucleotides

This is an example of how oligonucleotides may be functionalized for their further manipulation in stage 1 or stage 2 synthesis schemes. It also describes a stage 1 amine acylation reaction. The description of the experiment is taken from (Liu et al., WO 2004/016767 A2, p. 131). The figures referred to are from the same patent application.

2-bromopropionamide-NHS esters. 200 mg JV-hydroxysuccinimide (Pierce, Rockford, Ill., USA) was dissolved in anhydrous CH$_2$Cl$_2$ together with 1.1 equivalents of a 2-bromopropionic acid (either racemic, (R)-, or (5)-) and 2 equivalents of 1-(3-dimethylaminopropyl)-3-ethylcarbodiimide (EDC) (Aldrich). The 2-bromopropionic acid enantiomers were >95% enantiopure as judged by chiral HPLC (5% isopropanol in hexanes, (R,R) WHELK 01 chiral phase, detection at 220 nm). The reaction was maintained at room temperature and complete after 1.5 hours as judged by TLC (EtOAc). The crude reaction mixture was extracted with 2.5% sodium hydrogen sulfate (NaHSO$_4$ to remove the excess EDC. The organic phase was washed with brine, dried over magnesium sulfate (MgSO$_4$), and concentrated in vacuo. The residue was dried and used directly for DNA functionalization.

5'-functionalization of oligonucleotides. An NHS ester prepared as described above was dissolved in DMSO. Up to 150 ug of a 5'-amino DNA oligonucleotide was combined with 3 mg/mL NHS ester (final reaction=10% DMSO) in 200 mM sodium phosphate (pH=7.2) at room temperature for 2 hours. The functionalized oligonucleotides were purified by gel filtration and reverse-phase HPLC, and were characterized by denaturing PAGE and MALDI-TOF mass spectrometry.

3'-thiol modified oligonucleotides. The 3' thiol group was incorporated by standard automated DNA synthesis using 3'-disulfide-linked CPG (Glen Research, Sterling, 20 Va., USA). Following oligonucleotide synthesis, the disulfide was cleaved with 50 mM DTT, 1M TAPS (pH=8.0) at room temperature for 1 hour and purified by gel filtration before being used in DNA-templated reactions.

Example 19

One-Pot Simultaneous Stage 2 Synthesis Involving Amine Conjugate Addition, Thiol Conjugate Addition, Nitro-Michael Addition, Reductive Amination, Amine Acylation, and Wittig Olefination This is an example of a number of templated reactions that are executed simultaneously in one solution, giving high yields of all reaction types tested. The same reaction conditions may be applied to stage 1 synthesis, except that the molecule fragments must be added in higher concentrations (preferably 10-100 mM). The description of the experiments is taken from (Liu et al., WO 2004/016767 A2, example 7, p. 137-142). The figures referred to are from the same patent application.

This example demonstrates that oligonucleotides can simultaneously direct several different synthetic reaction types within the same solution, even though the reactants involved would be cross-reactive and, therefore, incompatible under traditional synthesis conditions. These findings also demonstrate that it is possible to perform a one-pot diversification of synthetic library precursors into products using multiple, simultaneous and not necessarily compatible reaction types.

The ability of DNA templates to mediate diversification using different reaction types without. spatial separation was initially tested by preparing three oligonucleotide templates of different DNA sequences (Ia-3a)(WO 2004/016767 A2) functionalized at their 5' ends with maleimide groups and three oligonucleotide reagents (4a-6a) (WO 2004/016767 A2) functionalized at their 3' ends with an amine, thiol, or nitroalkane group, respectively (WO 2004/016767 A2, FIG. 46). The DNA sequences of the three reagents each contained a different 10-base annealing region that was complementary to ten bases, near the 5' end of each of the templates. Combining 1a with 4a, 2a with 5a, or 3a with 6a in three. separate vessels at pH 8.0 resulted in the expected DNA-templated amine conjugate addition, thiol conjugate addition, or nitro-Michael addition products 7-9 (WO 2004/016767 A2, FIG. 46, lanes 1-3).

To distinguish the nine possible reaction products that could be generated upon combining 1a-6a, the lengths of template oligonucleotides were varied to include 11, 17, or 23 bases and the lengths of reagent oligonucleotides were varied to include 14, 16, or 18 bases. Differences in oligonucleotide length were achieved using extensions distal from the reactive groups that did not significantly affect the efficiency of DNA-templated reactions. This design permitted all nine possible reaction products (linked to 25, 27, 29, 31, 33, 35, 37, 39, or 41 bases of DNA) to be distinguished by denaturing polyacrylamide gel electrophoresis.

A solution containing all three templates (Ia-3a) was combined with a solution containing all three reagents (4a-6a) at pH 8.0. The resulting reaction exclusively generated the three desired products 7, 8, and 9 of lengths 25, 33, and 41 bases indicating that only the three reactions corresponding to the complementary template-reagent pairs took place (WO 2004/016767 A2, FIG. 46, lane 4). Formation of the other six possible reaction products was not detected by densitometry (<5% reaction). In contrast, individually reacting templates and reagents containing the same, rather than different, 10-base annealing regions permitted the formation of all possible products (WO 2004/016767 A2, FIG. 46, lane 5). This result demonstrates the ability of DNA-templated synthesis to direct the selective one-pot transformation of a single functional group into three distinct types of products (in this example, maleimide into secondary amine, thioether, or a-branched nitroalkane).

To test the ability of this diversification mode to support one-pot reactions requiring non-DNA-linked accessory reagents, an analogous experiment was conducted with two aldehyde-linked reagents either 14 or 16 bases in length (WO 2004/016767 A2, (4b) or (5b), respectively) and a complementary 11-base amine-linked template (WO 2004/016767 A2, (Ib)) or a 17-base phosphorane-linked template (WO 2004/016767 A2, (2b)). Combining Ib and 4b at pH 8.0 in the presence of 3 mM NaBH$_3$CN resulted in the DNA-templated reductive amination product 10 (WO 2004/016767 A2), while 2b and 5b under the same conditions generated Wittig olefination product 11 (WO 2004/016767 A2, FIG. 46). Mixing all four reactants together in one pot resulted in an identical product distribution as the combined individual Wittig olefination or reductive animation reactions (WO 2004/016767 A2, FIG. 46). No reaction between amine 1b and aldehyde 5b or between phosphorane 2b and aldehyde 4b was detected (WO 2004/016767 A2, FIG. 46, lane 8 versus lane 9).

The generality of this approach was explored by including multiple reaction types that required different accessory reagents. Three amine-linked templates (Ic-3c) (WO 2004/016767 A2) of length 11, 17, or 23 bases were combined with an aldehyde-, carboxylic acid-, or maleimide-linked reagent (4c-6c) (WO 2004/016767 A2) 14, 16, or 18 bases in length, respectively, at pH 8.0 in the presence of 3 mM NaBH$_3$CN, 10 mM 1-(3-dimethyl-aminopropyl)-3-ethylcarbodiimide (EDC), and 7.5 mM N-hydroxylsulfosuccinimide (sulfo-NHS). The reactions containing all six reactants afforded the same three reductive animation, amine acylation, or conjugate addition products (12-14) (WO 2004/016767 A2) that were generated from the individual reactions containing one template and one reagent and did not produce detectable quantities of the six possible undesired products arising from non-DNA-templated reactions (WO 2004/016767 A2, FIG. 46, lanes 10-14). Collectively, these results indicate that DNA-templated synthesis can direct simultaneous reactions between several mutually cross-reactive groups in a single pot to yield only the sequence-programmed subset of many possible products.

The above three examples each diversified a single functional group (maleimide, aldehyde, or amine) into products of different reaction types. A more general format for the one-pot diversification of a DNA-templated synthetic library into products of multiple reaction types would involve the simultaneous reaction of different functional groups linked to both reagents and templates. To examine this possibility, six DNA-linked nucleophile templates (15-20) (WO 2004/016767 A2) and six DNA-linked electrophile reagents (21-25) (WO 2004/016767 A2) collectively encompassing all of the functional groups used in the above three examples (amine, aldehyde, maleimide, carboxylic add, nitroalkane, phosphorane, and thiol) were prepared (WO 2004/016767 A2, FIG. 47). These twelve DNA-linked reactants could, in theory, undergo simultaneous amine conjugate addition, thiol, conjugate addition, nitro-Michael addition, reductive amination, amine acylation, and Wittig olefination in the same pot, although the apparent second order rate constants of these six reactions vary by more than 10-fold.

Determining the outcome of combining all twelve reagents and templates in a single pot by using oligonucleotides of varying lengths; is difficult due the large number (at least 28) of possible products that could be generated. Accordingly, the length of the reagents as 15, 20, 25, 30, 35, or 40 bases were varied but the length of the templates was fixed at 11 bases (WO 2004/016767 A2, FIG. 47). Each of the six complementary template-reagent pairs when reacted separately at pH 8.0 in the presence of 3 mM $NaBH_3CN$; 10 mM EDC, and 7.5 mM sulfo-NHS generated the expected amine conjugate addition, thiol conjugate addition, nitro-Michael addition, reductive amination, amine acylation, or Wittig olefination products (WO 2004/016767 A2, FIG. 47). Reaction efficiencies were greater than 50% relative to the corresponding individual reactions despite having to compromise between differing optimal reaction conditions. Templates 15-20 (WO 2004/016767 A2) were also prepared in a 3'-biotinylated form. The biotinylated templates demonstrated reactivities indistinguishable from those of their non-biotinylated counterparts (WO 2004/016767 A2, FIG. 47).

Six separate reactions each containing twelve reactants then were performed at pH 8.0 in the presence of 3 mM $NaBH_3CN$, 10 mM EDC, and 7.5 mM sulfo-NHS (WO 2004/016767 A2, FIG. 48). Each reaction contained a different biotinylated template (15, 16, 17, 18, 19, or 20) together with five non-biotinylated templates (from 15-20) (WO 2004/016767 A2) and six reagents (21-25) (WO 2004/016767 A2). These reactions were initiated by combining a solution containing 15-20 with a solution containing 21-25. The products that arose from each biotinylated template were captured with streptavidin-coated magnetic beads and identified by denaturing gel electrophoresis. Because the six reagents in each reaction contained oligonucleotides of unique lengths, the formation of any reaction products involving the biotinylated templates and any of the reagents could be detected. In all six cases, the biotinylated template formed only the single product programmed by its DNA sequence (WO 2004/016767 A2, FIG. 48) despite the possibility of forming up to five other products in each reaction. Taken together, these findings indicate that reactions of significantly different rates requiring a variety of non-DNA-linked accessory reagents can be directed by DNA-templated synthesis in the same solution, even when both templates and reagents contain several different cross-reactive functional groups. The ability of DNA templates to direct multiple reactions at concentrations that exclude non-templated reactions from proceeding at appreciable rates mimics, in a single solution, a spatially separated set of reactions.

Compared to the use of traditional synthetic methods, generating libraries of small molecules by DNA-templated synthesis is limited by several factors including the need to prepare DNA-linked reagents, the restriction of aqueous, DNA-compatible chemistries, and the reliance on characterization methods such as mass spectrometry and electrophoresis that are appropriate for molecular biology-scale (pg to ug) reactions. On the other hand, DNA-templated synthesis (i) allows the direct in vitro selection (as opposed to screening) and amplification of synthetic molecules with desired properties, (ii) permits the preparation of synthetic libraries of unprecedented diversity, and (iii) requires only minute quantities of material for selection and identification of active library members. In addition, this example demonstrates that potentially useful modes of reactivity not possible using current synthetic methods can be achieved in a DNA-templated format. For example, six different types of reactions can be performed simultaneously in one solution, provided that required non-DNA-linked accessory reagents are compatible. This reaction mode permits the diversification of synthetic small molecule libraries using different reaction types in a single solution.

Materials and Methods
Synthesis of Templates and Reagents

Oligonucleotides were synthesized using standard automated solid-phase techniques. Modified phosphoramidites and controlled-pore glass supports were obtained from Glen Research, Sterling, Va., USA. Unless otherwise noted, functionalized templates and reagents were synthesized by reacting 5'-$H_2N(CH_2O)_2$ terminated oligonucleotides (for templates) or 3'-$OPO_3$—$CH_2CH(CH_2OH)(CH_2)_4NH_2$ terminated oligonucleotides (for reagents) in a 9:1 mixture of aqueous 200 mM pH 7.2 sodium phosphate buffer:DMF containing 2 mg/mL of the appropriate N-hydroxysuccinimide ester (Pierce, Rockford, Ill., USA) at 25° C.

For the aldehyde and nitroalkane-linked oligonucleotides (4b, 4c, 5b, 6a, 17, 24, and 26, FIGS. 46 and 47, WO 2004/016767 A2) the NHS esters were generated by combining the appropriate carboxylic acid (900 mM in DMF) with equal volumes of dicyclohexylcarbodiimide (900 mM in DMF) and NHS (900 mM in DMF) for 90 minutes. Phosphorane-linked oligonucleotides (2b and 20, FIGS. 46 and 47, WO 2004/016767 A2) were prepared by a 90 minute reaction of the appropriate amino-terminated oligonucleotide with 0.1 volumes of a 20 mg/mL DMF solution of the NHS ester of iodoacetic acid (SIA, Pierce, Rockford, Ill., USA) in pH 7.2 buffer as above, followed by addition of 0.1 volumes of a 20 mg/mL solution of 4-diphenylphosphinobenzoic acid in DMF.

Thiol-linked template 16 was synthesized by reacting ethylene glycol bis(succinimidylsuccinate) (EGS, Pierce, Rockford, Ill., USA) with the appropriate oligonucleotide for 15 minutes, followed by addition of 0.1 volumes of 300 mM 2-aminoethanethiol. Reagent 5a was synthesized using 3'-$OPO_3$—$(CH_2)_3SS(CH_2)_3$ODMT functionalized controlled-pore glass (CPG) support and reduced prior to use according to the manufacturer's protocol.

The 3'-biotinylated oligonucleotides were prepared using biotin-TEG[1] CPG (Glen Research, Sterling, Va., USA). Products arising from biotinylated templates were purified by mixing with 1.05 equivalents of streptavidin-linked magnetic beads (Roche), washing twice with 4 M guanidinium hydrochloride, and eluting with aqueous 10 mM Tris pH 7.6 with 1 mM biotin at 80° C.

Synthesis of Linkers

Linkers between DNA oligonucleotides and the functional groups in 1a-6c are as follows. Ib and Ic: DNA-5'—$NH_2$; Ia, 2a-2c, 3a, and 3c: DNA-5'-$O(CH_2)_2O(CH_2)_2$—NH—; 5a: DNA-3'-O-$(CH_2)_3$SH; 4a-4c, 5b, 5c, 6a, and 6c: DNA-3'-O-$CH_2CH(CH_2OH)(CH_2)_4$NH—. Oligonucleotide sequences used to generate all possible products in (WO 2004/016767 A2, FIG. 46, lanes 5, 9, and 14), with annealing regions underlined: R-TATCTACAGAG-3' (SEQ ID NO 83) (Ia-Ic); R-TATCTACAGAGTAGTCT-3' (SEQ ID NO 84) (2a-2c); R-TATCTACAGAGTAGTCTAATGAC-3' (SEQ ID NO 85) (3a-3c); 5'-CAGCCTCTGTAGAT-R (SEQ ID NO 86) (4a-4c); 5'-CTCAGCCTCTGTAGAT-R (SEQ ID NO 87) (5a-5c); 5'-GGCTCAGCCTCTGTAGAT-R (SEQ ID NO 88) (6a-6c). Functionalized templates and reagents were purified by gel filtration (Sephadex G-25) followed by reverse-phase HPLC (0.1 M triethylammonium acetate/acetonitrile gradient).

Representative functionalized templates and reagents were further characterized by MALDI mass spectrometry.

Reaction Conditions

All reactions were performed by dissolving reagents and templates in separate vessels in pure water before combining them into a solution of 50 mM aqueous TAPS buffer, pH 8.0, 250 mM NaCl at 25° C. for 16 hours with DNA-linked reactants at 60 nM (WO 2004/016767 A2, FIG. 47) or at 12.5 nM (WO 2004/016767 A2, FIGS. 47 and 48). NaBH$_3$CN, EDC, and sulfo-NHS were present when appropriate as described. Products were analyzed by denaturing polyacrylamide gel electrophoresis using ethidium bromide staining and UV transillumination: Differences in charge states, attached functional groups, and partial secondary structure resulted in modest variations in gel mobility for different functionalized oligonucleotides of the same length (FIGS. 46-48).

Example 20

Selection for Bifunctional Molecules Capable of Binding to a Macromolecular Target This is an example of a selection against 6 protein targets, by affinity selection on immobilized protein (subprocess i). The experiments are described in detail in the patent application (Liu et al., WO 2004/016767 A2, example 11, p. 171-182).

Six proteins, GST, Carbonic anhydrase, Papain, Trypsin, Chymotrypsin, and Strepavidin, were immobilized on NHS-activated Sepharose 4 fast flow beads. For each of the proteins, a known ligand was prepared and linked to a unique DNA sequence. Solutions containing DNA-linked protein ligands and DNA-linked negative controls were used to simulate libraries of bifunctional molecules. The selections were performed by first incubating the DNA-linked ligands with immobilized protein, then beads were washed, and finally the DNA of the DNA-linked ligands that bound to the beads was amplified by PCR, to reveal the efficiency of the model selection experiment. All proteins were enriched more than 50-fold.

Example 21

Iterated Selection on Immobilized Target (Subprocess Viii)

This is an example of iterated rounds of selection and elution without intervening amplification of the bifunctional molecule (subprocess viii, above). The description of the experiments is taken from (Liu et al., WO 2004/016767 A2, example 11, p. 173). The figures referred to are from the same patent application.

Selections can be iterated to multiply the net enrichment of desired molecules. To test this possibility with DNA-linked synthetic molecules, a 1:1,000 mixture of DNA-linked phenyl sulfonamide (3):DNA-linked N-formyl-Met-Leu-Phe (2) (WO 2004/016767 A2) was subjected to a selection for binding carbonic anhydrase. The molecules surviving the first selection were eluted and directly subjected to a second selection using fresh immobilized carbonic anhydrase. PCR amplification and restriction digestion revealed that the first round of selection yielded a 1:3 ratio of (3):(2), representing a 3.30-fold enrichment for the DNA-linked phenyl sulfonamide. The second round of selection further enriched (3) by more than 30-fold, such that the ratio of (3):(2) following two rounds of selection exceeded 10:1 (>10$^4$-fold net enrichment). Similarly, three rounds of iterated selection were used to enrich a 1:10$^6$ starting ratio of (3):DNA-linked biotin (4) by a factor of 5×10$^6$ into a solution containing predominantly DNA-linked phenyl sulfonamide (3) (see WO 2004/016767 A2, FIG. 81). These findings demonstate that enormous net enrichments for DNA-linked synthetic molecules can be achieved. through iterated selection, and suggest that desired molecules represented as rarely as 1 part in 10$^6$ within DNA-templated synthetic libraries may be efficiently isolated in this manner.

Example 22

Stage 2 Reactions: Reductive Amination, Amine Acylation, Carbon-Carbon Forming Reactions, and Organometallic Coupling Reactions This is an example of reactions that can be employed in a stage 2 synthesis. By maintaining a high concentration of molecule fragments (e.g. 10-100 mM), the conditions applied to the templated synthesis hereunder, can be applied to stage 1 synthesis as well, using the same reaction types. The description of the experiments is taken from (Liu et al., WO 2004/016767 A2, example 2, p. 107-112). The figures referred to are from the same patent application.

As described in detail herein, a variety of chemical reactions for example, DNA-templated organometallic couplings and carbon-carbon bond forming reactions can be utilized to construct small molecules.

The ability of DNA-templated synthesis to direct reactions that require a non-DNA-linked activator, catalyst or other reagent in addition to the principal reactants has also been demonstrated herein. To test the ability of DNA-templated synthesis to mediate such reactions without requiring structural mimicry of the DNA-templated backbone, DNA-templated reductive animations between an amine-linked template (1) (WO 2004/016767 A2) and benzaldehyde- or glyoxal-linked reagents (3) (WO 2004/016767 A2) with millimolar concentrations of sodium cyanoborohydride (NaBH$_3$CN) at room temperature in aqueous solutions can be performed (see WO 2004/016767 A2, FIG. 23A). Significantly, products formed efficiently when the template and reagent sequences were complementary, while control reactions in which the sequence of the reagent did not complement that of the template, or in which NaBH$_3$CN was omitted, yielded no significant product (see WO 2004/016767 A2, FIGS. 23A-23D and 24). Although DNA-templated reductive aminations to generate products closely mimicking the structure of double-stranded DNA have been previously reported (see, for example, Li et al. (2002) J. AM. CHEM. SOC. 124: 746 and Gat et al. (1998) BIOPOLYMERS 48:19), these results demonstrate that reductive animation to generate structures unrelated to the phosphoribose backbone can take place efficiently and sequence-specifically.

Referring to (WO 2004/016767 A2, FIGS. 25A-25B, DNA-templated amide bond formations between amine-linked templates 4 and 5 and carboxylate-linked reagents 6-9 mediated by 1-(3-dimethylaminopropyl)-3-ethylcarbodiimide (EDC) and N-hydroxylsulfosuccinimide (sulfo-NHS) generated amide products in good yields at pH 6.0, 25° C. Product formation was (i) sequence-specific, (ii) dependent on the presence of EDC, and (iii) insensitive to the steric encumbrance of the amine or carboxylate. Efficient DNA-templated amide formation was also mediated by the water-stable activator 4-(4,6-dimethoxy-1,3,5-trizin-2-yl)-4-methylmorpholinium chloride (DMT-MM) instead of EDC and sulfo-NHS (WO 2004/016767 A2, FIGS. 24 and 25A-25B). The efficiency and generality of DNA-templated amide bond formation under these conditions, together with the large number of commercially available chiral amines and carboxylic acids, make this reaction an attractive candidate in future DNA-templated syntheses of structurally diverse small molecule libraries.

Carbon-carbon bond forming reactions are also important in both chemical and biological syntheses and thus several such reactions can be utilized in a nucleic add-templated format. Both the reaction of nitroalkane-linked reagent (10) (WO 2004/016767 A2) with aldehyde-linked template (11) (WO 2004/016767 A2) (nitro-aldol or Henry reaction) and the conjugate addition of 10 to maleimide-linked template (12) (WO 2004/016767 A2) (nitro-Michael addition) proceeded efficiently and with high sequence specificity at pH 7.5-8.5, 25° C. (WO 2004/016767 A2, FIGS. 23A and 24). In addition, the sequence-specific DNA-templated Wittig reaction between stabilized phosphorus ylide reagent 13 (WO 2004/016767 A2) and aldehyde-linked templates 14 or 11 (WO 2004/016767 A2) provided the corresponding olefin products in excellent yields at pH 6.0-8.0, 25° C. (WO 2004/016767 A2, FIGS. 23B and 24). Similarly, the DNA templated 1,3-dipolar cycloaddition between nitrone-linked reagents 15 and 16 (WO 2004/016767 A2) and olefin-linked templates 12, 17 or 18 also afforded products sequence specifically at pH 7.5, 25° C. (WO 2004/016767 A2, FIGS. 23B, 23C arid 24).

In addition to the reactions described above, organometallic coupling reactions can also be utilized in the present invention. For example, DNA-templated Heck reactions were performed in the presence of water-soluble Pd precatalysts. In the presence of 170 mM $Na_2PdCl_4$, aryl iodide-linked reagent 19 (WO 2004/016767 A2) and a variety of olefin-linked templates including maleimide 12, acrylamide 17, vinyl sulfone 18 or cinnamamide 20 (WO 2004/016767 A2) yielded Heck coupling products in modest yields at pH 5.0, 25° C. (WO 2004/016767 A2, FIGS. 23D and 24). For couplings with olefins 17, 18 and 20, adding two equivalents of $P(p-SO_3C_6H_4)_3$ per equivalent of Pd prior to template and reagent addition typically increased overall yields by 2-fold.'. Control reactions containing sequence mismatches or lacking Pd precatalyst yielded no product.

In order to evaluate the ability of the DNA-templated reactions to take place efficiently when reactants are separated by distances relevant to library encoding, the yields of reductive animation, amide formation, nitro-aldol addition, nitro-Michael addition, Wittig olefination, dipolar cycloaddition, and Heck coupling reactions were compared when either zero {n~0) or ten (n=10) bases separated the annealed reactive groups. Among the reactions described here, amide bond formation, nitro-aldol
addition, Wittig olefination, Heck coupling, conjugate addition of thiols to maleimides and $S_N2$ reaction between thiols and alpha-iodo amides demonstrate comparable product formation when reactive groups are separated by zero or ten bases (WO 2004/016767 A2, FIG. 26B). FIG. 26B shows the results of denaturing polyacrylamide gel electrophoresis of a DNA-templated Wittig olefination between complementary 11 and 13 with either zero bases (lanes 1-3) or ten bases (lanes 4-6) separating the annealed reactants. Product yields after 13 hours at both distances were nearly quantitative.

Control reactions containing sequence mismatches yielded no detectable product. These findings indicate that these reactions can be encoded during synthesis by nucleotides that are distal from the reactive end of the template without significantly impairing product formation.

In addition to the DNA-templated $S_N2$ reaction, conjugate addition, vinyl sulfone addition, amide bond formation, reductive animation, nitro-aldol (Henry reaction), nitro Michael, Wittig olefination, 1,3-dipolar cycloaddition and Heck coupling reactions described above, a variety of additional reagents can also be utilized in the method of the present invention. For example, as depicted in (WO 2004/016767 A2, FIG. 27), powerful aqueous DNA-templated synthetic reactions including, but not limited to, the Lewis acid-catalysed aldol addition, Mannich reaction, Robinson annulation reactions, additions of allyl indium, zinc and tin to ketones and aldehydes, Pd-assisted allylic substitution, Diels-Alder cycloadditions, and hetero-Diels-Alder reactions can be utilized efficiently in aqueous solvent and are important complexity-building reactions.

Taken together, these results expand considerably the reaction scope of DNA-templated synthesis. A wide variety of reactions can proceed efficiently and selectively when the corresponding reactants are programmed with complementary sequences. By augmenting the repertoire of known DNA-templated reactions to include carbon-carbon bond forming and organometallic reactions (nitro-aldol additions, nitro-Michael additions, Wittig olefinations, dipolar cycloadditions, and Heck couplings, in addition to previously reported amide bond formation (see, Schmidt et al (1997) NUCLEIC ACIDS RES. 25:4792; Bruick et al. (1996) CHEM. BIOL. 3: 49), imine formation (Czlapinski: ˆ al. (2001) J. AM. CHEM. SOC. 123: 8618), reductive aminatiori (Li et al. (2002) J. AM. CHEM. SOC. 124: 746; Gat et al. (1998) BiOPOLYMERS 48:19), $S_N2$ reactions (Gartner et al. (2001) J. AM. CHEM. SOC. 123: 6961; Xu et al. (2001) NAT. BIOTECHNOL. 19: 148; Herrlein et al. (1995) J. AM. CHEM. SOC. 117: 10151), conjugate addition of thiols (Gartner et al. (2001) J. AM. CHEM. SOC. 123: 6961), and phosphoester or phosphonamide formation (Orgel et al. (1995) Ace. CHEM. RES. 28: 109; Luther et al. (1998) NATURE 396: 245), these results may permit the, sequence-specific translation of libraries of DNA into libraries of structurally and functionally diverse synthetic products.

Because minute quantities of templates encoding desired molecules can be amplified by PCR, the yields of DNA-templated reactions arguably are less critical than the yields of traditional synthetic transformations. Nevertheless, many of the reactions discussed in this example proceed efficiently.

Materials and Methods

Functionalized templates and reagents were typically prepared by reacting 5'—$NH_2$ terminated oligonucleotides (for template 1), 5'—$NH_2$—$(CH_2O)_2$ terminated oligonucleotides (for all other templates) or 3'-$OP0_3$—$CH_2CH(CH_2OH)$ $(CH_2)_4NH_2$ terminated nucleotides (for all reagents) with the appropriate NHS esters (0.1 volumes of a 20 mg/mL solution in DMF) in 0.2 M sodium phosphate buffer, pH 7.2, 25° C., for 1 hour to provide the template and reagent structures shown in (WO 2004/016767 A2, FIGS. 23A-23D and 25A-25B). For amino acid linked reagents 6-9,3'-$OP0_3CH_2CH$ $(CH_2OH)(CH_2)_4NH_2$ terminated oligonucleotides in 0.2 M sodium phosphate-buffer, pH 7.2 were reacted with 0.1 volumes of a 100 mM bis(2-(succinimidyloxycarbonyloxy) ethyl)sulfone (BSOCOES, Pierce, Rockford, Ill., USA) solution in
DMF for 10 minutes at 25° C., followed by 0.3 volumes of a 300 mM amino acid in 300 mM sodium hydroxide (NaOH) for 30 minutes at 25° C.

Functionalized templates and reagents were purified by gel filtration using Sephadex G-25 followed by reverse-phase HPLC (0.1 triethylammonium acetate-acetonitrile gradient) and characterized by MALDI mass spectrometry. For the DNA templated reactions described in (WO 2004/016767 A2, FIGS. 23A-23D) reactions were conducted at 25° C. with one equivalent each of template and reagent at 60 nM final concentration unless otherwise specified. Conditions: (a) 3 mMNaBH$_3$CN, 0.1 M/V-(2-morpholinoethane) sulfonic acid (MES) buffer pH 6.0, 0.5 M NaCl, 1.5 hours; b) 0.1 M N-tris(hydroxymethyl)methyl-3-aminopropanesulfonic acid (TAPS) buffer pH 8.5, 300 mM NaCl, 12 hours; c) 0.1 M pH 8.0 TAPS buffer, 1 M NaCl, 5° C., 1.5 hours; d) 50 mM MOPS buffer pH 7.5, 2.8 M NaCl, 22 hours; e) 120 nM 19, 1.4 mM Na$_2$PdCl$_4$, 0.5 M NaOAc buffer pH 5.0, 18 hours; (f) Premix NaaPdCL} with two equivalents of P(p-SO$_3$CeH$_4$)$_3$ in water for 15 minutes, then add to reactants in 0.5 M NaOAc buffer pH 5.0, 75 mM NaCl, 2 hours (final (Pd)=0.3 mM, (19)=120 nM). The olefin geometry of products from 13 and the regiochemistries of cycloaddition products from 14 and 16 are presumed but not verified (WO 2004/016767 A2, FIGS. 23A-23D). Products were characterized by denaturing polyacrylamide gel electrophoresis and MALDI mass spectrometry. For all reactions under the specified conditions, product yields of reactions with matched template and reagent sequences were greater than 20-fold higher than that of control reactions with scrambled reagent sequences.

The conditions for the reactions described in (WO 2004/016767 A2, FIGS. 25A-25B) were: 60 nM template, 120 nM reagent, 50 mM DMT-MM in 0.1 M MOPS buffer pH 7.0, 1 M NaCl, for 16 hours at, 25° C.; or 60 nM template, 120 nM reagent, 20 mM EDC, 15 mM sulfo-NHS, 0.1 M MES buffer pH 6.0, 1 M NaCl, for 16 hours at 25° C. In each row of the table in (WO 2004/016767 A2, FIGS. 25A-25B), yields of DMT-MM-mediated reactions between reagents and templates complementary in sequence were followed by yields of EDC and sulfo-NHS-mediated reactions. In all cases, control reactions with mismatched reagent sequences yielded little or no detectable product and products were characterized by denaturing polyacrylamide gel electrophoresis and MALDI mass spectrometry.

(WO 2004/016767 A2, FIG. 24) depicts the analysis by denaturing polyacrylamide gel electrophoresis of representative DNA-templated reactions listed in (WO 2004/016767 A2, FIGS. 23A-23D and 25A-25B). The structures of reagents and templates correspond to the numbering in FIGS. 23A-23D and 25A-25B. Lanes 1, 3, 5, 7, 9, 11: reaction of matched (complementary or "M") reagents and templates under conditions listed in FIGS. 23A-23D and 25A-25B (the reaction between 4 and 6 was mediated by DMT-MM). Lanes 2, 4, 6, 8, 10, 12: reaction of mismatched (non-complementary or "X") reagents and templates under conditions identical to those in lanes 1, 3, 5, 7, 9 and 11, respectively.

The sequences of oligonucleotide templates and reagents are as follows (5' to 3' direction, n refers to the number of bases between reactive groups when template and reagent are annealed as shown in (WO 2004/016767 A2, FIG. 26A).

```
1:                          TGGTACGAATTCGACTCGGG;     (SEQ ID NO: 68)

2 and 3 matched:            GAGTCGAATTCGTACC;         (SEQ ID NO: 69)

2 and 3 mismatched:         GGGCTCAGCTTCCCCA;         (SEQ ID NO: 70)

4 and 5:                    GGTACGAATTCGACTCGG-       (SEQ ID NO: 71)
                            GAAT
                            ACCACCTT;

6-9 matched (n = 10):       TCCCGAGTCG;               (SEC ID NO: 72)

6 matched (n = 0):          AATTCGTACC;               (SEQ ID NO: 73)

6-9 mismatched:             TCACCTAGCA;               (SEQ ID NO: 74)

11, 12, 14, 17, 18, 20:     GGTACGAATTCGACTCGCGA;     (SEQ ID NO: 75)

10, 13, 16, 19 matched:     TCCCGAGTCGAATTCGTACC;     (SEQ ID NO: 76)

10, 13, 16, 19 mismatched:  GGGCTCAGCTTCCCCATAAT;     (SEQ ID NO: 77)

15 matched:                 AATTCGTACC;               (SEQ ID 20 NO: 78)

15 mismatched:              TCGTATTCCA;               (SEQ ID NO: 79)

template for n 10 vs. n =   TAGCGATTACGGTACGAAT-      (SEQ ID NO: 80)
                            TCG
0 comparison:               ACTCGGGA.
```

Reaction yields were quantitated by denaturing PAGE followed by ethidium bromide staining, UV visualization, and charge-coupled device (CCD)-based densitometry of product and template starting material bands. Yield calculations assumed that templates and 25 products stained with equal intensity per base; for those cases in which products were partially double-stranded during quantitation, changes in staining intensity may have resulted in higher apparent yields.

Example 23

Different Stage 1 and Stage 2 Synthesis Schemes Employed in a Given Series of Experiments Because of the modular nature of the stage 1, stage2 and selection/screening protocols, it is perfectly possible to generate a first generation library using e.g. subprocess (1, i.e., no templated synthesis involved), then select (e.g. using subprocess i), and then perform a second round of library generation, and this time use the recovered templates as templates, and therefore, perform a stage 2 synthesis to make the enriched second generation library. Obviously, it is important to keep the same code for the same molecule fragments, It may also be advantageous to select against immobilized target in the first round, and then in the second round perform in solution selection experiments for example, or some other selection experiment that share few of the same features as the first selection assay.

Example 24

Carrier Preparation by Several Different Routes

Because of the modular nature of the stage 1 synthesis procedures, the carrier that are employed in a stage 2 synthesis can be prepared by different synthetic routes. As an example, in order to make e.g. 2,000 identifiers, with the ability to make 1,000,000 different template-encoded molecules, one could synthesize 625 carriers by two step Lerner-like stage 1 synthesis (subprocess 1), using acylation reactions to link the molecule fragments; synthesize 1000 carriers using the DNA-routing approach by Harbury (subprocess 10), for example employing reductive amination and nucleophilic aromatic substitution reactions; synthesize 375 compounds by combinatorial chemistry and attach these to identifiers. Then use this pool of 2000 carriers in a stage 2 synthesis to generate 1,000,000 bifunctional molecules.

Example 25

Stage 1 Synthesis Employing the Harbury and Halpin Method (Subprocess 10)

Subprocess 10 stage 1 synthesis involves a DNA sorting step, in which the identifiers to be linked to the molecule fragments are sorted according to their DNA sequences. Once the DNA has been sorted, the molecule fragments can be linked under conditions identical to the conditions described in the present invention, in particular, as described in all of the above examples. Thus, the preferred reactions, reductive amination, Wittig reaction, acylation, alkylhalide alkylation, nucleophilic aromatic substitution, Heck coupling, cycloaddition reactions, sulfonoylation, isocyanide addition, Michael addition and others, may be executed in exactly the same way as described here.

Applications of the Present Invention.

The methods of the present invention provide for the identification of organic and inorganic molecules that are catalysts useful for the synthesis of complex molecules from simple substrates, inorganic compounds with useful properties as materials, may be used in the degradation of plastics, animal feed processing, etc. Also, the methods can be applied to identification of compounds with high affinity or selectivity for targets and surfaces, including protein targets, DNA, and other macromolecular structures, metal surfaces, plastics, etc. Such compounds may be useful as additives to paint, cement, textiles, and other substances where improved rigidity, strength, flexibility or stability is desired. New materials may be identified in this way, including superconductors and nanosensors. Compounds that bind with high affinity and/or selectivity to protein, RNA, DNA, polysaccharides, or other molecules of an organism, may be used in diagnostics or as therapeutics.

REFERENCES

Baindur et al., U.S. Pat. No. 5,891,737
Baindur et al., U.S. Pat. No. 5,646,285
Boger et al., U.S. Pat. No. 6,194,612 B1
Cook et al., U.S. Pat. No. 6,191,273
Dervan et al., U.S. Pat. No. 6,090,947;
Dower et al. US1991000762522
Dower et al. EP 0604552 B1
Franch et al., WO 2004/083427
Freskgård et al., WO 2004/039825 A2
Graybill et al., U.S. Pat. No. 6,127,191
Gustafson et al., U.S. Pat. No. 6,140,361
Harbury and Halpin, WO 00/23458
Lebl et al., U.S. Pat. No. 6,090,912
Lebl et al., U.S. Pat. No. 5,840,485
Lerner, R. et al., EP 0643778 B1
Liu et al., WO02/074929A2
Liu et al., WO 2004/016767 A2
Morgan et al., WO 2005/058479
Pedersen et al., WO02/103008A2
Pedersen et al., WO03/078625 A2
Still et al. (1998) U.S. Pat. No. 5,721,099;
Abelson (1996) *Methods in Enzymology*, 267; 211-221;
Alvarez et al. (1999), *Journal of Organic Chemistry*, 64; 6319-28;
Ashley, G. W., Kushlan, D. M. (1991), *Biochemistry*, 30; 2927-2933
Bruick et al. (1996), *Chem. Biol.* 3; 49
Calderone et al. (2002), *Angew. Chem. Int. Ed. Engl.*, 41; 4104;
Czlapinski et al. (2001), *J. Am. Chem. Soc.*, 123; 8618
Dapremont et al. (1995) *Physiol. Chem. Phys. & Med. NMR*, 27; 339-343,
Dolinnaya, N. G. et al. (1993), *Nucl. Acids. Res.*, 21; 5403-5407
Dolinnaya, N. G., et al. (1994), *Nucleosides Nucleotides* 13; 2169-2183
Doyon et al. (2003), *J. Am. Chem. Soc.*, 125; 12372-12373
Feuston et al. (2002), *J. Med. Chem.*, 45; 5640-8
Fruchart et al. (1999), *Tetrahedron Lett.*, 40; 6225
Gao, H., et al. (1994), *Bioconjugate Chem.*, 5; 445-453
Gartner et al. (2001), *J. Am. Chem. Soc.* 123; 6961
Gartner et al. (2002), *Angew. Chem. Int. Ed.* 41, 1796
Gat et al. (1998), *Biopolymers*, 48; 19
Goodwin, J. T., and Lynn, D. G. (1992), *J. Am. Chem. Soc.*, 114; 9197-9198)
Herrlein et al. (1995), *J. Am. Chem. Soc.*, 117; 10151
Hughes (1996), *Tetrahedron Lett.*, 37; 7595
Kool, E. T. (1991), *J. Am. Chem. Soc.*, 113; 6265-6266
Kramer et al. (1999), *Current Protocols in Mol. Biol.*, 3; 15.1
Jost et al. (1989), *Nucleic Acids Res.*, 17; 2143
Li et al. (2002), *J. Am. Chem. Soc.*, 124; 746
Luebke, et al. (1991), *J. Am. Chem. Soc.*, 113; 7447-7448
Luebke et al. (1992), *Nucl. Acids Res.*, 20; 3005-3009
Luther et al. (1998), *Nature*, 396; 245
Lynn et al. (1998), *J. Am. Chem. Soc.*, 120; 1627-1628
Lynn et al. (2000), *J. Am. Chem. Soc.*, 122; 6601-6609
Melnikov et al. (1999), *Langmuir*, 15; 1923-1928
Mohr et al. (1996) *Organometallics*, 15; 4317-4325
Orgel et al. (1995), *Ace. Chem. Res.*, 28; 109
Pirrung et al. (1998), *Journal of Organic Chemistry*, 63; 241-46
Rohatgi, R., et al. (1996), *J. Am. Chem. Soc.*, 118; 3332-3339
Schmidt et al (1997), *Nucleic Acids Res.*, 25; 4792
Shabarova, Z. A. (1988), *Biochemie*, 70; 1323-1334;
Sokolova, N. I. et al. (1988), *FEBS Letters*, 232; 153-155;
Vaisman et al., (2001) *J. Biol. Chem.*, 276; 30615-30622
Visscher, J., Shwartz, A. W. (1988), *Journal of Molecular Evolution*, 28; 3-6
Walder et al. (1979), *Proc. Natl. Acad. Sci.*, 76; 51-55
Wang, E., Yanagawa, H. (1986), *Biochemistry*, 25; 7423-7430
Washington et al., (2001) *J. Biol. Chem.*, 276; 2263-2266
Yanzheng, X., and Kool, E. T. (1997), *Tetrahedron Letters*, 38; 5595-5598
Xu et al. (2001), *Nat. Biotechnol.*, 19; 148
Zhang et al. (1999), *J. Am. Chem. Soc.* 121; 3311
Zhao et al, (1998), *Journal of Organic Chemistry*, 63; 7568-7572
Zarling et al., (1980), *J. Immunol.*, 124; 913

The invention claimed is:

1. A method for synthesizing an encoded molecule comprising the steps of:
   a) Adding a linker molecule L to one or more reaction wells;
   b) Adding a molecule fragment to each of said reaction wells;
   c) Adding an oligonucleotide identifier to each of said reaction wells;
   d) Subjecting said wells to conditions sufficient to allow said molecule fragments and said oligonucleotide identifiers to become attached to said linker molecule, or conditions sufficient for said molecule fragments to bind to other molecule fragments and sufficient for said oligonucleotide identifiers to bind to other oligonucleotide identifiers, so as to form bi-functional molecules consisting of an encoded molecule and an oligonucleotide;
   e) Combining the contents of said one or more reaction wells, to produce an admixture of said bi-functional molecules;
   f) Optionally, distributing the combined product to one or more new reaction wells;
   g) Optionally, repeating steps b) to f) one or more times; and
   h) Contacting the resulting bifunctional molecule(s) of step e) or g) with one or more templates each capable of hybridizing to at least one of the oligonucleotide identifiers added in step c);
   wherein
   the linker molecule L contains at least one reactive group capable of reacting with a reactive group in the molecule fragment and at least one reactive group capable of reacting with a reactive group in the oligonucleotide;
   the molecule fragments each contain at least one reactive group capable of reacting with a reactive group in the linker molecule L or a reactive group in another molecule fragment, and the reactive groups of each molecule fragment may be the same or different;
   the oligonucleotide identifiers each contain at least one reactive group capable of reacting with a reactive group in the linker L or a reactive group in another oligonucleotide identifier, and the reactive groups of each oligonucleotide identifier may be the same or different;
   the region of the oligonucleotide identifier added to each well in step c) which hybridizes to said template identifies the molecule fragment added to the same well in step b);
   the steps a) to d) may be performed in any order;
   the steps b) to d) in step g) may also be performed in any order;
   the number of wells in steps a) and f) may be the same or different; and
   the oligonucleotide template optionally is associated with a reactive group.

2. A method according to claim 1, wherein reactive groups of a molecule fragment of each of two or more bi-functional molecules hybridized to the same template are reacted, or wherein the reactive group of a molecule fragment of one bi-functional molecule is reacted with a reactive group associated with the template to which it is hybridized.

3. The method according to claim 1, wherein the number of wells in step a) is m and the number of wells in step f) is n, and wherein for each repetition of steps b) to f) in step g) n may be the same or different; and
   the structure of the encoded molecule is

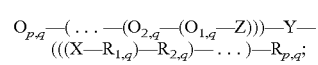

wherein

X, Y and Z are components of the linker molecule, L, X being adapted for reaction with a molecule fragment, Z being adapted for reaction with an oligonucleotide and Y being a flexible linker connecting X and Z;

$O_{2,q}$ is the oligonucleotide identifier added in repetition number 1 of steps b) to f) in well number q;

$O_{p,q}$ is the oligonucleotide identifier added in repetition number (p−1) of steps b) to f) in well number q;

$R_{2,q}$ is the molecule fragment added in repetition number 1 of steps b) to f) in well number q;

$R_{p,q}$ is the molecule fragment added in repetition number (p−1) of steps b) to f) in well number q;

p is an integer of at least 2;

m and n are integers of at least 5; and for $O_{1,q}$, $O_{2,q}$, $R_{1,q}$, and $R_{2,q}$, q is in the range 1 to m, for $O_{p,q}$ and $R_{p,q}$ where p is greater than 1, q is in the range 1 to n.

4. The method according to claim 1, wherein the number of wells in step a) is m and the number of wells in step f) is n, and wherein for each repetition of steps b) to f) in step g) n may be the same or different; and the structure of the encoded molecule is

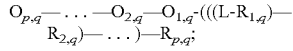

$$O_{p,q}-\ldots-O_{2,q}-O_{1,q}-(((L-R_{1,q})-R_{2,q})-\ldots)-R_{p,q};$$

wherein $O_{p,q}$ is the oligonucleotide identifier added in repetition number (p−1) of steps b) to f) in well number q;

$O_{2,q}$ is the oligonucleotide identifier added in repetition number 1 of steps b) to f) in well number q;

$R_{2,q}$ is the molecule fragment added in repetition number 1 of steps b) to f) in well number q;

$R_{p,q}$ is the molecule fragment added in repetition number (p−1) of steps b) to f) in well number q;

p is an integer of at least 1;

m and n are integers of at least 5; and for $O_{1,q}$, $O_{2,q}$, $R_{1,q}$, and $R_{2,q}$, q is in the range 1 to m, for $O_{p,q}$ and $R_{p,q}$ where p is greater than 1, q is in the range 1 to n.

5. A method for synthesizing an encoded molecule comprising the steps of:

a) Dispensing aliquots of a nascent linker molecule L into each of m reaction wells;

b) Dispensing into each of said m reaction wells a corresponding aliquot of an $m^{th}$ molecule fragment, $R_{1,m}$ and a corresponding aliquot of an $m^{th}$ oligonucleotide, $O_{1,m}$ identifier;

c) Combining all of the nascent bi-functional molecules from all m reaction wells to produce an admixture of nascent bi-functional molecules;

d) Optionally, dispensing said admixture of nascent bi-functional molecules into n reaction wells;

e) Optionally, dispensing into each of the n reaction wells of step d) a corresponding aliquot of an $m^{th}$ molecule fragment, $R_{p,q}$ and a corresponding aliquot of an $m^{th}$ oligonucleotide identifier, $O_{p,q}$;

f) Optionally, combining all of the nascent bi-functional molecules from all n reaction wells in step e) to produce an admixture of nascent bi-functional molecules;

g) Optionally repeating steps d) to f) one or more times;

h) contacting a resulting bi-functional molecule of step f) or g) with one or more templates, said one or more templates optionally being associated with a reactive group, under conditions to allow for hybridization of each of the templates to one or more of said nascent bi-functional molecule generated in step f) or g); and i) Optionally, reacting reactive groups of a molecule fragment of two or more nascent bi-functional molecules hybridized to the same template, or reacting the reactive group of a molecule fragment of one nascent bi-functional molecule with the reactive group associated with the template to which it is hybridized;

Wherein:

the linker molecule L contains at least one reactive group capable of reacting with a reactive group in the molecule fragment and at least one reactive group capable of reacting with a reactive group in the oligonucleotide;

the molecule fragments each contain at least one reactive group capable of reacting with a reactive group in the linker molecule L or a reactive group in another molecule fragment, and the reactive groups of each molecule fragment may be the same or different;

the oligonucleotide identifiers each contain at least one reactive group capable of reacting with a reactive group in the linker L or a reactive group in another oligonucleotide identifier, and the reactive groups of each oligonucleotide identifier may be the same or different;

the oligonucleotide identifier added to each well in step b) and e) identifies the molecule fragment added to the same well in the respective step;

the steps a) and b) as well as the steps d) and e) may be performed in any order; and the steps d) and e) in step g) may also be performed in any order, wherein $O_{p,q}$ is the oligonucleotide identifier added in repetition number (p−1) of steps b) to f) in well number q, and $R_{p,q}$ is the molecule fragment added in repetition number (p−1) of steps b) to f) in well number q.

6. The method according to claim 5, wherein the number of wells in step a) is m and the number of wells in step e) is n, and wherein for each repetition of steps d) to f) in step g) n may be the same or different; and the structure of the encoded molecule is

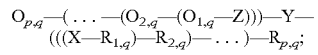

$$O_{p,q}-(\ldots-(O_{2,q}-(O_{1,q}-Z)))-Y-(((X-R_{1,q})-R_{2,q})-\ldots)-R_{p,q};$$

wherein

X, Y and Z are components of the linker molecule, L, X being adapted for reaction with a molecule fragment, Z being adapted for reaction with an oligonucleotide and Y being a flexible linker connecting X and Z;

$O_{p,q}$ is the oligonucleotide identifier added in repetition number (p−1) of steps b) to f) in well number q;

$O_{2,q}$ is the oligonucleotide identifier added in repetition number 1 of steps b) to f) in well number q;

$R_{2,q}$ is the molecule fragment added in repetition number 1 of steps b) to f) in well number q;

$R_{p,q}$ is the molecule fragment added in repetition number (p−1) of steps b) to f) in well number q;

p is an integer of at least 2;

m and n are integers of at least 5; and for $O_{1,q}$, $O_{2,q}$, $R_{1,q}$, and $R_{2,q}$, q is in the range 1 to m, for $O_{p,q}$ and $R_{p,q}$ where p is greater than 1, q is in the range 1 to n.

7. The method according to claim 5, wherein for each repetition of steps d) to f) in step g) n may be the same or different; and the structure of the encoded molecule is

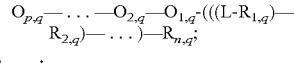

$$O_{p,q}-\ldots-O_{2,q}-O_{1,q}-(((L-R_{1,q})-R_{2,q})-\ldots)-R_{n,q};$$

wherein $O_{p,q}$ is the oligonucleotide identifier added in repetition number (p−1) of steps b) to f) in well number q;

$O_{2,q}$ is the oligonucleotide identifier added in repetition number 1 of steps b) to f) in well number q;

$R_{2,q}$ is the molecule fragment added in repetition number 1 of steps b) to f) in well number q;

$R_{p,q}$ is the molecule fragment added in repetition number (p−1) of steps b) to f) in well number q;

p is an integer of at least 1;

m and n are integers of at least 5; and for $O_{1,q}$, $O_{2,q}$, $R_{1,q}$, and $R_{2,q}$, q is in the range 1 to m, for $O_{p,q}$ and $R_{p,q}$ where p is greater than 1, q is in the range 1 to n.

8. The method according to claim 5, wherein the structure of the nascent bi-functional molecules resulting from step b is:

$O_{1,q}$-L-$R_{1,q}$;

and the structure of the nascent bi-functional molecule obtained after repeating the process steps defined in step g) p−1 times is:

$O_{p,q}$—(...)—$O_{1,q}$-L-$R_{1,q}$—(...)—$R_{n,q}$;

and wherein p is greater than or equal to 1.

9. The method according to claim 5, wherein the number of reaction wells in step a) and/or the number of reaction wells in step f) is at least 2, at least 5, at least 10, at least 25, at least 50, at least 100, at least 200, at least 500, at least 1000, at least 10,000, at least 100,000, at least 1,000,000, at least $10^7$, or at least $10^8$.

10. The method according to claim 5, wherein the process steps defined in step g) are repeated at least once, at least twice, at least three times, or at least four times.

11. The method according to claim 3, wherein the oligonucleotide identifier, $O_{p,q}$, added in reaction well number q in repetition number (p−1) of the steps specified in step g) uniquely identifies the molecule fragment, $R_{p,q}$, added in reaction well number q in repetition number (p−1) of the steps specified in g).

12. The method according to claim 3, wherein identical oligonucleotide identifiers, $O_{p,q}$, are added in two or more reaction wells in repetition number (p−1) of the steps specified in g).

13. The method according to claim 3, wherein identical molecule fragments, $R_{p,q}$, are added in two or more wells in repetition number (p−1) of the steps specified in g).

14. The method according to claim 3, wherein two or more oligonucleotide identifiers are added to one or more reaction wells in a repetition of the steps specified in g).

15. The method according to claim 1, wherein two or more molecule fragments are added to one reaction well in each repetition of the steps specified in g).

16. The method according to claim 1, wherein each oligonucleotide identifier comprises a sequence of at least 2, 3, 4, 5, 6, 7, 8, 9, 10, 11, 12, 13, 14, 15, 20, 25, 30, 35 40, 45, 50, 55, 60, 65, 70, 75, 80, 85, 90, 95, or 100 nucleotides.

17. The method according to claim 1, wherein the number of identifiers in each resulting bi-functional molecule is 2, 3, 4 or 5.

18. The method according to claim 1, wherein each template is capable of hybridising with 2, 3, 4, 5, 6 or more carriers.

19. The method according to claim 1, wherein said one or more templates comprise a sequence selected from the group consisting of: nucleotides, unnatural nucleotides, PNA, morpholinos, LNA, RNA, DNA, and other nucleotide analogs capable of base pairing with a natural oligonucleotide or unnatural oligonucleotide.

20. The method according to claim 1, wherein each oligonucleotide identifier or a sequence of two or more of the oligonucleotide identifiers comprises a sequence of oligonucleotides, the complementary sequence of which is at least 20% identical to the encoding part of said template.

21. The method according to claim 1, wherein said linker, L, is selected from the group consisting of: Polyethylene glycol, polypeptide, polysaccharide, and oligonucleotide.

22. The method according to claim 1, wherein said linker, L, is a cleavable linker.

23. The method according to claim 1, wherein a further step is added comprising contacting the bi-functional molecule resulting from step h) with one or more nascent bi-functional molecules and one or more templates each capable of recognizing at least two of the oligonucleotide identifiers present in the bi-functional molecule.

24. The method according to claim 1, wherein two or more oligonucleotide identifiers are covalently linked together, optionally in the presence of a ligase or isomerase enzyme.

25. The method according to claim 1, wherein two or more oligonucleotide identifiers are linked by templated extension by enzymes.

26. The method according to claim 1, wherein two or more oligonucleotide identifiers are ligated by chemical ligation or by enzymatic ligation in one process step and chemical ligation, in a preceding or subsequent process step.

27. The method according to claim 1, wherein the linker of at least one bi-functional molecule is cleaved simultaneously with or subsequently to hybridisation of the oligonucleotide identifier of said nascent bi-functional molecule to the template.

28. The method according to claim 1, wherein said reactive groups are reacted in a reaction selected from the group consisting of: acylation, reductive amination, alkylhalide alkylation, Wittig reaction, sulphonoylation, isocyanate addition, Suzuki coupling, nucleophilic aromatic substitution, thiourea bond formation, carbamate formation, Heck coupling, HWE reaction, 1,3-dipolar cycloaddition, Michael addition, and nitro aldol condensation.

29. The method according to claim 1, wherein the resulting encoded molecule has a linear structure and is selected from the group consisting of: dimers, trimers, tetramers, pentamers, multimers, and polymers.

30. The method according to claim 1, wherein at least one molecule fragment having more than one, two, three, four, five, or six reactive groups has been used in the preparation of the resulting encoded molecule.

31. A method according to claim 1, said method comprising identifying the encoded molecule by determining the oligonucleotide sequence(s) of the attached identifiers.

32. A library of encoded molecules obtained by a method according to claim 1.

33. A library according to claim 32, wherein the number of different compounds is at least 100.

34. The method according to claim 1, wherein in step b) the molecule fragment is made by combinatorial chemistry.

35. The method according to claim 1, wherein said encoded molecule is a divalent or multivalent encoded molecule.

36. The method according to claim 1, wherein a library of encoded molecules is generated, comprising at least 100 compounds.

37. The method according to claim 1, wherein steps b) to f) are repeated one or more times.

38. The method according to claim 1, wherein steps b) to f) are not repeated and the library comprises at least 1,000 molecules.

39. The method according to claim 1, wherein steps b) to f) are not repeated and the library comprises at least 10,000 molecules.

40. The method according to claim 38, wherein the molecule fragments are generated by combinatorial chemistry.

41. The method according to claim 38, wherein the oligonucleotide identifiers are generated by combinatorial chemistry.

42. The method according to claim 1, wherein the one or more templates have been made by a split and mix procedure.

43. The method according to claim 42, wherein a library of nx DNA templates is generated by a process comprising the steps of:
  i) Adding an aliquot of a mixture of n position 1 codon DNA duplexes to each of n wells,
  ii) To each well, adding a specific position 2 codon duplex DNA,
  iii) Ligating the position 1 codon DNA duplex and the position 2 codon DNA duplex,
  iv) Mixing the contents of all wells to obtain a mixture of ligated DNA duplexes,
  v) Adding an aliquot of the mixture of ligated DNA duplexes to each of n wells,
  vi) Adding to each of the n wells a specific codon DNA duplex,
  vii) Ligating the ligated DNA duplexes and the specific codon DNA duplex,
  viii) optionally repeating steps iv) to vii) one or more times;
  wherein x is the number of codons in each DNA template and the codon at each position 1 to x is selected from n different codons.

44. The method according to claim 1, wherein said oligonucleotide identifiers are ligated by chemical ligation in step d) and in each repetition of step d).

45. The method according to claim 1, wherein said bi-functional molecules are hybridized to said one or more templates and subsequently ligated together prior to reaction of reactive groups of a molecule fragment of each of two or more bi-functional molecules.

46. The method according to claim 1, wherein said template comprises all the codons and/or oligo identifiers and/or encoding regions that encode the final molecule, prior to reaction of any of the molecule fragments.

* * * * *